US010442763B2

(12) United States Patent
Messick et al.

(10) Patent No.: US 10,442,763 B2
(45) Date of Patent: Oct. 15, 2019

(54) EBNA1 INHIBITORS AND METHODS USING SAME

(71) Applicant: THE WISTAR INSTITUTE OF ANATOMY AND BIOLOGY, Philadelphia, PA (US)

(72) Inventors: Troy E. Messick, Upper Darby, PA (US); Garry R. Smith, King of Prussia, PA (US); Allen B. Reitz, Lansdale, PA (US); Paul M. Lieberman, Wynnewood, PA (US); Mark E. McDonnell, Lansdale, PA (US); Yan Zhang, Fort Washington, PA (US); Marianne Carlsen, Yardley, PA (US); Shuai Chen, Philadelphia, PA (US)

(73) Assignee: THE WISTAR INSTITUTE OF ANATOMY AND BIOLOGY, Philadelphia, PA (US)

( * ) Notice: Subject to any disclaimer, the term of this patent is extended or adjusted under 35 U.S.C. 154(b) by 0 days.

(21) Appl. No.: 15/571,223

(22) PCT Filed: May 14, 2016

(86) PCT No.: PCT/US2016/032574
§ 371 (c)(1),
(2) Date: Nov. 1, 2017

(87) PCT Pub. No.: WO2016/183534
PCT Pub. Date: Nov. 17, 2016

(65) Prior Publication Data
US 2018/0305312 A1  Oct. 25, 2018

Related U.S. Application Data

(60) Provisional application No. 62/161,490, filed on May 14, 2015.

(51) Int. Cl.
*C07D 209/08* (2006.01)
*C07D 403/12* (2006.01)
*C07D 405/14* (2006.01)
*C07D 401/12* (2006.01)
*C07D 405/12* (2006.01)
(Continued)

(52) U.S. Cl.
CPC .......... *C07D 209/08* (2013.01); *A61K 31/404* (2013.01); *A61K 31/41* (2013.01); *A61K 31/4155* (2013.01); *A61K 31/422* (2013.01); *A61K 31/426* (2013.01); *A61K 31/427* (2013.01); *A61K 31/433* (2013.01); *A61K 31/435* (2013.01); *A61K 31/437* (2013.01); *A61K 31/4375* (2013.01); *A61K 31/4439* (2013.01); *A61K 31/454* (2013.01); *A61K 31/4725* (2013.01); *A61K 31/496* (2013.01); *A61K 31/501* (2013.01); *A61K 31/506* (2013.01); *A61K 31/517* (2013.01); *A61K 31/519* (2013.01); *A61K 31/5377* (2013.01); *A61K 31/541* (2013.01); *A61K 31/551* (2013.01); *A61K 45/06* (2013.01); *A61P 31/20* (2018.01); *A61P 35/00* (2018.01); *C07D 277/62* (2013.01); *C07D 401/10* (2013.01); *C07D 401/12* (2013.01); *C07D 401/14* (2013.01); *C07D 403/10* (2013.01); *C07D 403/12* (2013.01); *C07D 403/14* (2013.01); *C07D 405/12* (2013.01); *C07D 405/14* (2013.01); *C07D 409/12* (2013.01); *C07D 413/10* (2013.01); *C07D 417/10* (2013.01); *C07D 417/12* (2013.01); *C07D 471/04* (2013.01); *C07D 471/08* (2013.01); *C07D 471/10* (2013.01); *C07D 487/04* (2013.01); *C07D 487/08* (2013.01); *C07D 491/107* (2013.01)

(58) Field of Classification Search
CPC ................................................... C07D 209/08
See application file for complete search history.

(56) References Cited

U.S. PATENT DOCUMENTS 4,638,002 A  1/1987 Szekely et al.
5,155,248 A  10/1992 Ullrich et al.
(Continued)

FOREIGN PATENT DOCUMENTS

CN  1634810 A  7/2005
WO  0153274 A1  7/2001
(Continued)

OTHER PUBLICATIONS

Bochkarev "Crystal Structure of the DNA-Binding Domain of the Epstein-Barr Virus Origin-Binding Protein, EBNA1, Bound to DNA" Cell, vol. 84, Mar. 8, 1996, 791-800.*
(Continued)

*Primary Examiner* — David K O'Dell
(74) *Attorney, Agent, or Firm* — Saul Ewing Arnstein & Lehr LLP; Domingos J. Silva

(57) ABSTRACT

The present invention provides EBNA1 inhibitors, and/or pharmaceutical compositions comprising the same, that are useful for the treatment of diseases caused by EBNA1 activity, such as, but not limited to, cancer, infectious mononucleosis, chronic fatigue syndrome, multiple sclerosis, systemic lupus erythematosus and/or rheumatoid arthritis. The present invention further provides EBNA1 inhibitors, and/or pharmaceutical compositions comprising the same, that are useful for the treatment of diseases caused by latent Epstein-Barr Virus (EBV) infection and/or lytic EBV infection.

5 Claims, No Drawings
Specification includes a Sequence Listing.

(51) Int. Cl.

| | | |
|---|---|---|
| C07D 409/12 | (2006.01) | |
| C07D 417/12 | (2006.01) | |
| C07D 471/08 | (2006.01) | |
| C07D 487/08 | (2006.01) | |
| A61P 35/00 | (2006.01) | |
| A61P 31/20 | (2006.01) | |
| A61K 31/404 | (2006.01) | |
| A61K 31/41 | (2006.01) | |
| A61K 31/4155 | (2006.01) | |
| A61K 31/422 | (2006.01) | |
| A61K 31/426 | (2006.01) | |
| A61K 31/427 | (2006.01) | |
| A61K 31/433 | (2006.01) | |
| A61K 31/435 | (2006.01) | |
| A61K 31/437 | (2006.01) | |
| A61K 31/4375 | (2006.01) | |
| A61K 31/4439 | (2006.01) | |
| A61K 31/454 | (2006.01) | |
| A61K 31/4725 | (2006.01) | |
| A61K 31/496 | (2006.01) | |
| A61K 31/501 | (2006.01) | |
| A61K 31/506 | (2006.01) | |
| A61K 31/517 | (2006.01) | |
| A61K 31/519 | (2006.01) | |
| A61K 31/5377 | (2006.01) | |
| A61K 31/541 | (2006.01) | |
| A61K 31/551 | (2006.01) | |
| A61K 45/06 | (2006.01) | |
| C07D 277/62 | (2006.01) | |
| C07D 401/10 | (2006.01) | |
| C07D 401/14 | (2006.01) | |
| C07D 403/10 | (2006.01) | |
| C07D 403/14 | (2006.01) | |
| C07D 413/10 | (2006.01) | |
| C07D 417/10 | (2006.01) | |
| C07D 471/04 | (2006.01) | |
| C07D 471/10 | (2006.01) | |
| C07D 487/04 | (2006.01) | |
| C07D 491/107 | (2006.01) | |

(56) References Cited

U.S. PATENT DOCUMENTS

| 5,185,454 A | 2/1993 | Bader et al. |
| 5,356,919 A | 10/1994 | Djuric et al. |
| 6,166,028 A | 12/2000 | Bloom et al. |
| 2003/0032623 A1 | 2/2003 | Ban et al. |
| 2003/0199511 A1 | 10/2003 | Li et al. |
| 2004/0044041 A1 | 3/2004 | Kuduk et al. |
| 2006/0030613 A1 | 2/2006 | Conte-Mayweg et al. |
| 2006/0258645 A1 | 11/2006 | Failli et al. |
| 2008/0153802 A1 | 6/2008 | Lessene et al. |
| 2009/0171091 A1 | 7/2009 | Thombare et al. |
| 2011/0009447 A1 | 1/2011 | Huth et al. |
| 2013/0040949 A1 | 2/2013 | Gray et al. |
| 2014/0113897 A1 | 4/2014 | Lieberman et al. |

FOREIGN PATENT DOCUMENTS

| WO | 0190101 A1 | 11/2001 | |
| WO | 2006019831 A1 | 2/2006 | |
| WO | 2006055070 A2 | 5/2006 | |
| WO | 2007002433 A1 | 1/2007 | |
| WO | 2007002587 A2 | 1/2007 | |
| WO | 2007023242 A1 | 3/2007 | |
| WO | 2010048332 A2 | 4/2010 | |
| WO | 2010092043 A1 | 8/2010 | |
| WO | 2010100475 A1 | 9/2010 | |
| WO | 2010118009 A1 | 10/2010 | |
| WO | 2010124047 A1 | 10/2010 | |
| WO | 2010127440 A1 | 11/2010 | |
| WO | 2011082098 A1 | 7/2011 | |
| WO | 2011090911 A1 | 7/2011 | |
| WO | 2012098416 A1 | 7/2012 | |
| WO | 2012162291 A1 | 11/2012 | |
| WO | 2014145022 A1 | 9/2014 | |
| WO | WO-2015073864 A1 * | 5/2015 | ........... C07C 311/08 |

OTHER PUBLICATIONS

Martin, Yvonne C. et. al. "Do Structurally Similar Molecules Have Similar Biological Activity?" Journal of Medicinal Chemistry 2002, 45, 4350-4358.*

Penning et. al. "Structure-Activity Relationship Studies on 1-[2-(4-Phenylphenoxy)ethyl]pyrrolidine (SC-22716), a Potent Inhibitor of Leukotriene A4 (LTA4) Hydrolase" Journal of Medicinal Chemistry 2000, 43, 721-735.*

PubChem. Compound Summary for: CID 1962039. Create Date: Dec. 5, 2007 [retrieved on Mar. 31, 2015]. Retrieved from the Internet: <URL: https//pubchem.ncbi.nlm.nih.gov/compound/19612039>. entire document.

STN registration file RN 1244017-13-7, 2010.

STN registration file RN 873330-62.2, 2006.

STN Registry 178742-95-5, 1996.

STN Registry RN 10601-99-7, 1984.

Crawford, et al.,The Preparation of Some Alkyl-substituted Benxoic Acids, Jan. 1, 1952—Retrieved from the Internet: URL:http://pubs.rsc.org/en/content/articlepdf/1952/jr/jr9520004443 [retrieved on Apr. 7, 2017].

Ghosh, et al.,Histone deacetylase inhibitors are potent inducers of gene expression in latent EBV and sensitize lymphoma cells to nucleoside antiviral agents., 2012, Blood 119(4):1008-1017.

Li, et al.,Discover of selective inhibitors against EBNA1 via high throughput in silico virtual screening., PLoS ONE, Apr. 12, 2010, vol. 5, No. 4, pp. e10126.

Thompson, et al.,Development of a High-Throughput Screen for Inhibitors of Epstein-Barr Virus EBNA1, Journal of Biomolecular Screening 15(9); 2010 pp. 1107-1115.

Shimakage, et al.,Significant role of macrophages in human cancers associate with Epstein-Barr virus (Review)., Oncology Reports 32:1763-1771, 2014.

Faigl, et al.,Organometallic Approach to the Functionalization of Alkyl Groups Containing 1-Phenylpyrroles., 2006, Synthetic Communications 36:2841-2849 Abstract.

Gao, et al.,Discovery and Optimization of 3-(2-(Pyrazolo[1,5-a]pyrimidin-6-yl) ethynyl)benzamides as Novel Selective and Orally Bioavailable Discoidin Domain Receptor 1 (DDR1) Inhibitors, J. Med. Chem., 2013, 56 (8), pp. 3281-3295 (Abstract).

Kim, et al.,Palladium-Catalyzed Domino Cyclization (5-exo/3-exo), Ring-Expansion by Palladium Rearrangement, and Aromatization: An Expedient Synthesis of 4-Arylnicotinates from Morita-Baylis-Hillman Adducts., 2013, Advanced Synthesis & Catalysis 355:1977-1983 Abstract.

Liu, et al.,Studies of Phenylethynyl-pyrrolo[1,2-a]pyrazine as mGluR5 Antagonists Using 3D-QSAR Method, Asian Journal of Chemistry; vol. 24, No. 1 (2012), 238-248.

Newman, et al.,The Synthesis of 6,6'-Diethynyldiphenic Anhydride., 1971, J Org Chem 36(10:1398-1401.

* cited by examiner

SEQUENCE LISTING

<160> NUMBER OF SEQ ID NOS: 1

<210> SEQ ID NO 1
<211> LENGTH: 36
<212> TYPE: DNA
<213> ORGANISM: Artificial Sequence
<220> FEATURE:
<223> OTHER INFORMATION: chemically synthesized

<400> SEQUENCE: 1
gggtagcata tgctatctag atagcatatg ctaccc    36

EBNA1 INHIBITORS AND METHODS USING SAME

CROSS-REFERENCE TO RELATED APPLICATIONS

The present application is a 35 U.S.C. § 371 national phase application from, and claims priority to, International Application No. PCT/US2016/032574, filed May 14, 2016, which claims priority under 35 U.S.C. § 119(e) to U.S. Provisional Application No. 62/161,490, filed May 14, 2015, all of which applications are incorporated by reference herein in their entireties.

STATEMENT REGARDING FEDERALLY SPONSORED RESEARCH OR DEVELOPMENT

This invention was made with government support under grant numbers 5R43AI079928 and 2R44AI09658803 awarded by National Institutes of Health (NIAID) and grant number 1R21NS063906 awarded by National Institutes of Health (NINDS). The government has certain rights in the invention.

BACKGROUND OF THE INVENTION

EBV is a human gamma-herpesvirus that infects over 90% of the adult population worldwide. In combination with known and unknown cofactors, especially immunosuppression, EBV infection constitutes a high carcinogenic risk. EBV has been classified by the World Health Organization as a class I human carcinogen because of its causal association with Burkitt's lymphoma, nasopharyngeal carcinoma, about 50% of all Hodgkin's lymphoma, gastric carcinoma, angiocentric T/NK lymphoma, and lymphoproliferative disorders of the immunosuppressed. EBV is responsible for about 1% of all human cancers, worldwide. The oncogenic potential of EBV is readily demonstrated in vitro by its capacity to immortalize primary B-lymphocytes in culture, and in vivo by its ability to drive infected B-cells into aggressive lymphoblastic lymphomas in immunocompromised hosts.

EBV, like other herpesviruses, has a latent and lytic replication cycle. While the EBV lytic cycle is essential for viral transmission and increases risk of EBV-associated malignancy, it is the latent viral infection that is oncogenic. The latent virus expresses a limited set of viral genes that stimulate cellular proliferation and survival. Clinically available inhibitors of herpesvirus DNA polymerases, including variants of acyclovir (e.g. ganciclovir) and phosphonoacetic acid (e.g. foscarnet) have at least partial inhibitory activity against EBV lytic replication. However, none of the available herpesvirus antivirals are effective at blocking the virus from progressing to a latent infection or eliminating latent infection. Primary infections with EBV can evoke a robust, sometimes debilitating immune response referred to as infectious mononucleosis (IM). Despite this robust immune reaction, the virus efficiently establishes latent infection in B-lymphocytes, where the virus can reside in long-lived memory B-cells. In some circumstances, latent infection can also be established in T-lymphocytes and epithelial cells. During latency, the virus does not produce infectious particles, and viral gene expression is limited to a subset of transcripts with growth-transforming and anti-apoptotic functions that contribute to EBV carcinogenesis. Thus, no existing anti-viral drug or immunological response can block the establishment of an EBV latent infection, which has the potential to drive lymphoid and epithelial cell oncogenic growth transformation.

Numerous studies have demonstrated that Epstein-Barr Nuclear Antigen 1 (EBNA1) is an ideal target for elimination of latent infection and treatment of EBV-associated disease. In one aspect, EBNA1 is expressed in all EBV-positive tumors. In another aspect, EBNA1 is required for immortalization of primary B-lymphocytes and for the stable maintenance of the EBV genome in latently infected cells. In yet another aspect, genetic disruption of EBNA1 blocks the ability of EBV to immortalize primary human B-lymphocytes and causes loss of cell viability in previously established EBV-positive cell lines. In yet another aspect, biochemical disruption of EBNA1 folding blocks the establishment of EBV latent infection. HSP90 inhibitors cause the selective killing of EBV$^+$ B-cells and block lymphomagenesis in mouse models. In yet another aspect. EBNA1 is a non-cellular viral oncoprotein that is functionally and structurally well characterized. The three-dimensional structure of EBNA1 bound to its cognate DNA sequence has been solved by X-ray crystallography. Analysis of the DNA binding domain reveals that EBNA1 protein is druggable, with several deep pockets and channels within the DNA binding domain that are predicted to disrupt DNA binding when bound to small molecules. In yet another aspect, targeting a non-self viral-encoded protein for inhibition mitigates the potential risk of inherent toxicity. EBNA1 has a unique structural fold that is distinct from all known cellular DNA binding and replication proteins. In yet another aspect, the EBNA1 DNA binding function is essential for all known EBNA1 functions, including genome maintenance, DNA replication, transcription regulation, and host-cell survival. These studies demonstrate that EBNA1-DNA binding domain is a validated target for inhibition of EBV-latent infection and treatment of EBV-associated malignancies.

EBV plays a causative role in the tumorigenesis for a number of cancers including nasopharyngeal carcinoma, gastric carcinomas, non-hodgkin lymphoma (anaplastic large-cell lymphoma, angioimmunoblastic T-cell lymphoma, hepatosplenic T-cell lymphoma. B-cell lymphoma. Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy), leiomyosarcomas, X-linked lymphoproliferative disease, post-transplant lymphoproliferative disorders, Hodgkin's lymphoma and breast cancer. An inhibitor of EBNA1 would change current clinical practice and be valuable for therapeutic treatment of EBV-associated diseases. Currently, nucleoside analogues (aciclovir, ganciclovir, foscarnet) can be used to treat lytic EBV infection and pathologies related to lytic EBV infection. However, these general antiviral drugs are not specific for lytic EBV infection, and carry the risk of severe adverse effects.

EBV infection and EBNA1 have also been implicated in infectious mononucleosis, chronic fatigue syndrome (CFS), multiple sclerosis, systemic lupus erythematosus, and rheumatoid arthritis. Treatment with compounds that prevent EBV infection and/or prevent lytic EBV infection and/or prevent latent EBV infection and/or inhibit EBNA1 would provide therapeutic relief to patients suffering from these diseases. To date, however, no effective specific treatments exist for lytic EBV infection and/or for pathologies related to lytic EBV infection. Further, to date, no effective treatments exist for latent EBV infection and/or pathologies related to latent EBV infection. Further, no effective treatments exist for the treatment of diseases associated with EBNA1.

There is a thus long felt need for novel compounds and methods using the same, which are useful for treating EBNA1 infection and/or diseases associated with EBNA1. Such treatments should be useful for the treatment of subjects afflicted with diseases and conditions associated with EBV infection, and/or subjects that are refractory to current treatments for infectious mononucleosis, chronic fatigue syndrome, multiple sclerosis, systemic lupus erythematosus and/or rheumatoid arthritis. The present invention addresses these needs.

BRIEF SUMMARY OF THE INVENTION

The invention provides a compound of formula (I), or an enantiomer, diastereomer, tautomer, salt and/or solvate thereof. The invention further provides a pharmaceutical composition comprising at least one compound of the invention and at least one pharmaceutically acceptable carrier. The invention further provides a method of treating and/or preventing a disease or disorder caused by EBNA1 activity in a subject. The invention further provides a method of treating and/or preventing Epstein-Barr Virus (EBV) infection, and/or a disease or disorder associated with EBV infection, in a subject. The invention further provides a method of treating and/or preventing lytic and/or latent EBV Virus infection in a subject. The invention further provides a method of making compounds of the invention.

In certain embodiments, the compound is

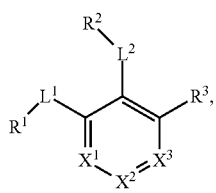

(I)

wherein: $X^1$ is selected from the group consisting of $CR^{4a}$ and N; $X^2$ is selected from the group consisting of $CR^{4b}$ and N; $X^3$ is selected from the group consisting of $CR^{4c}$ and N; $R^1$ is selected from the group consisting of

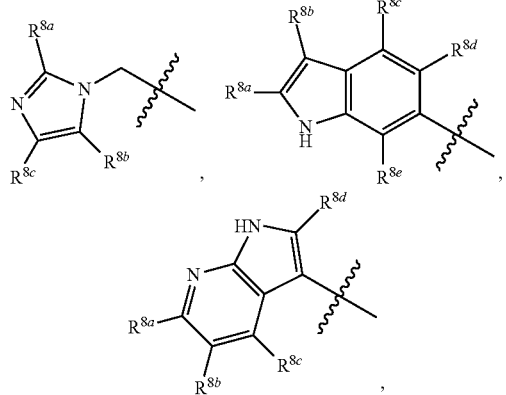

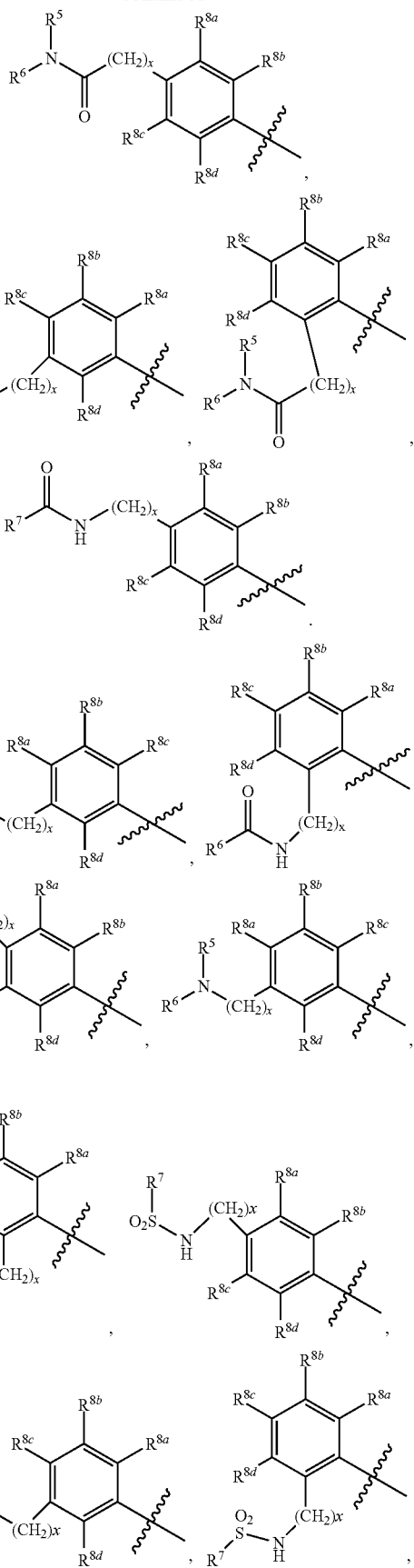

-continued
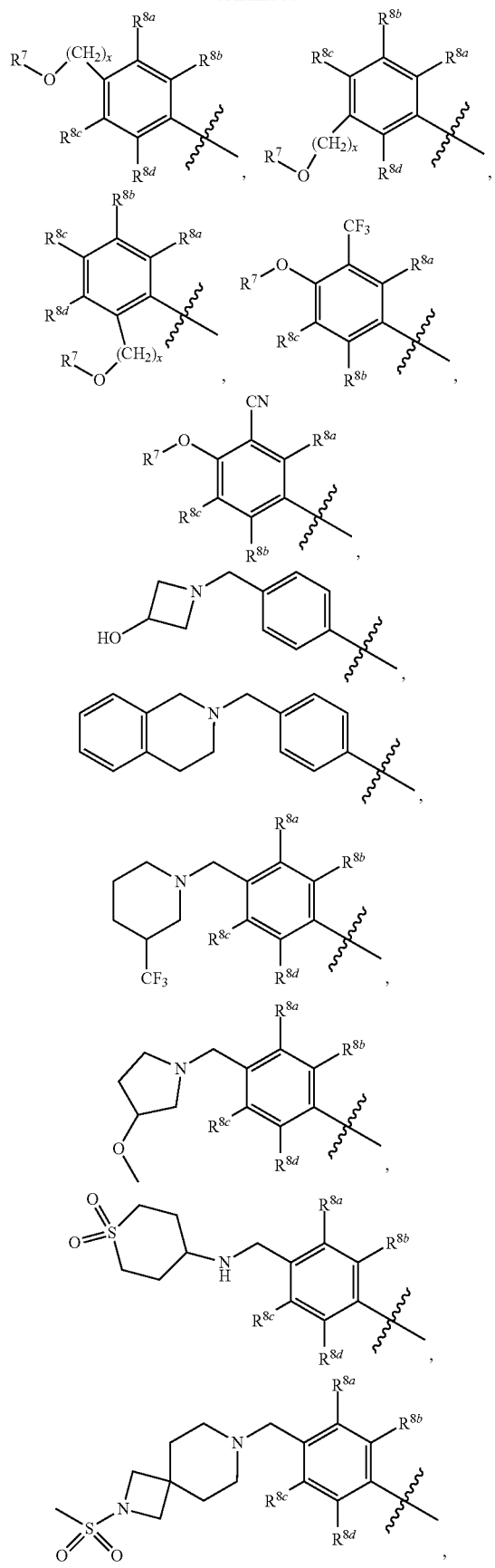
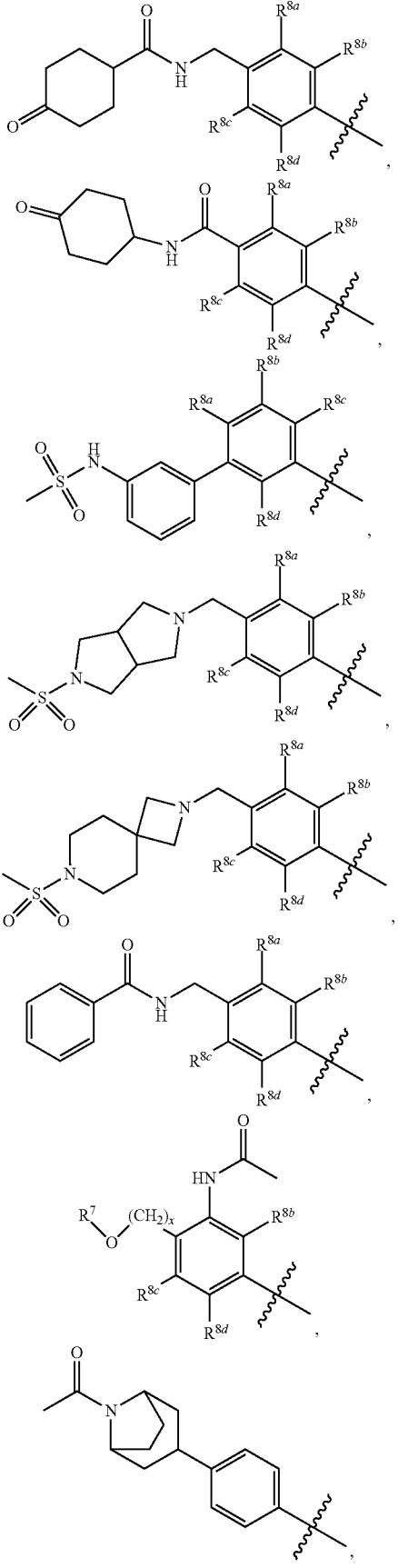

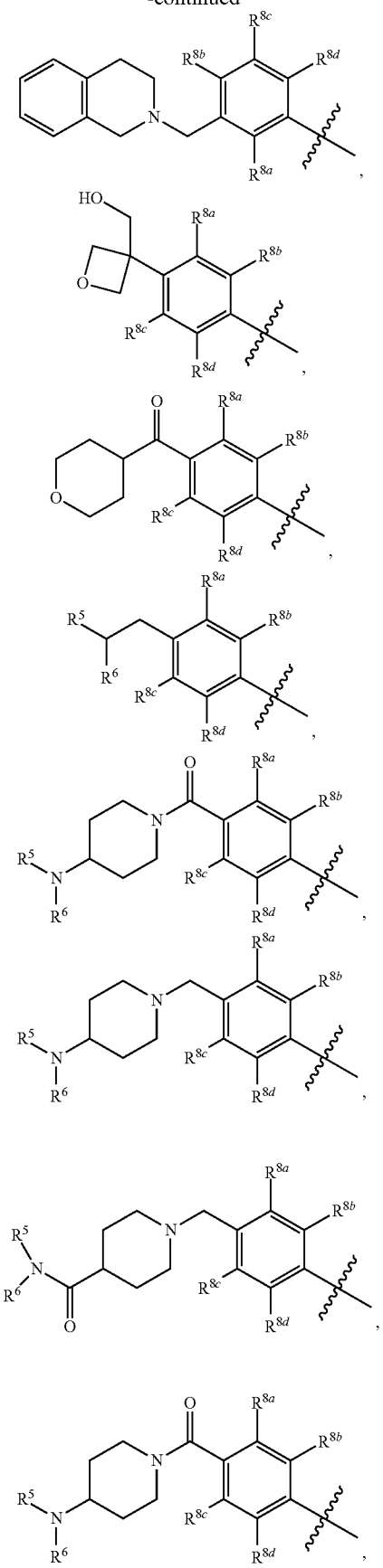
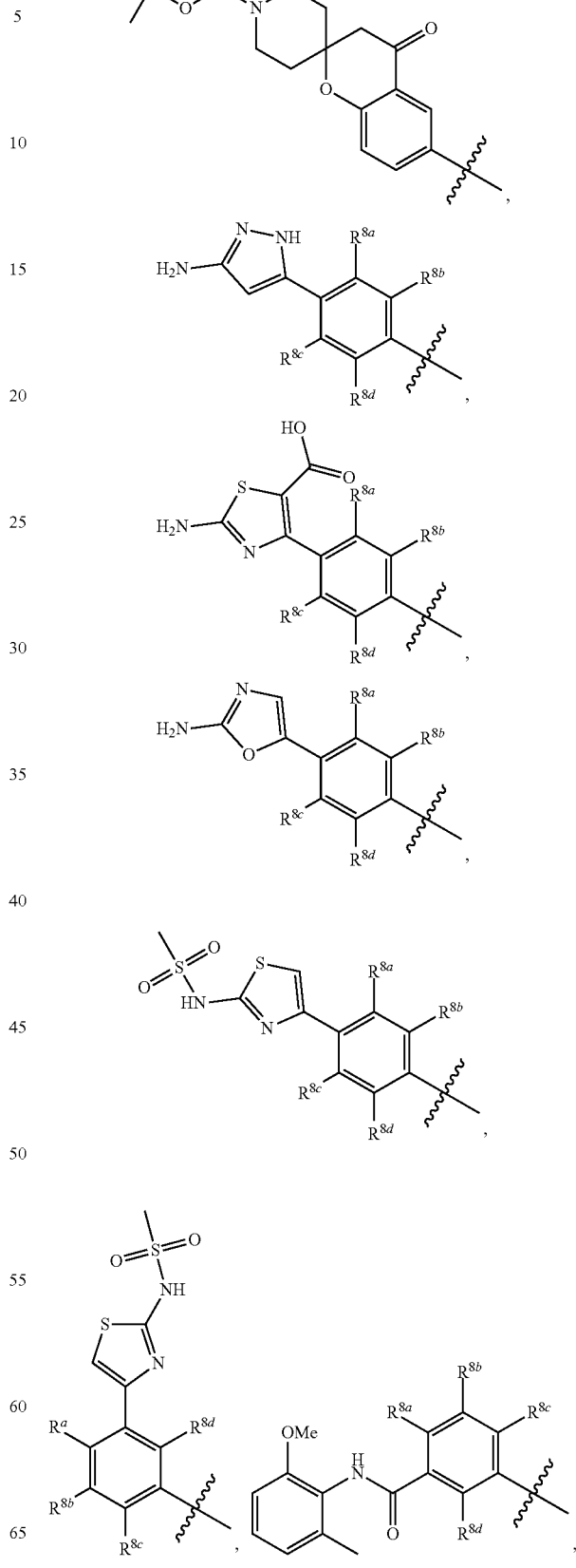

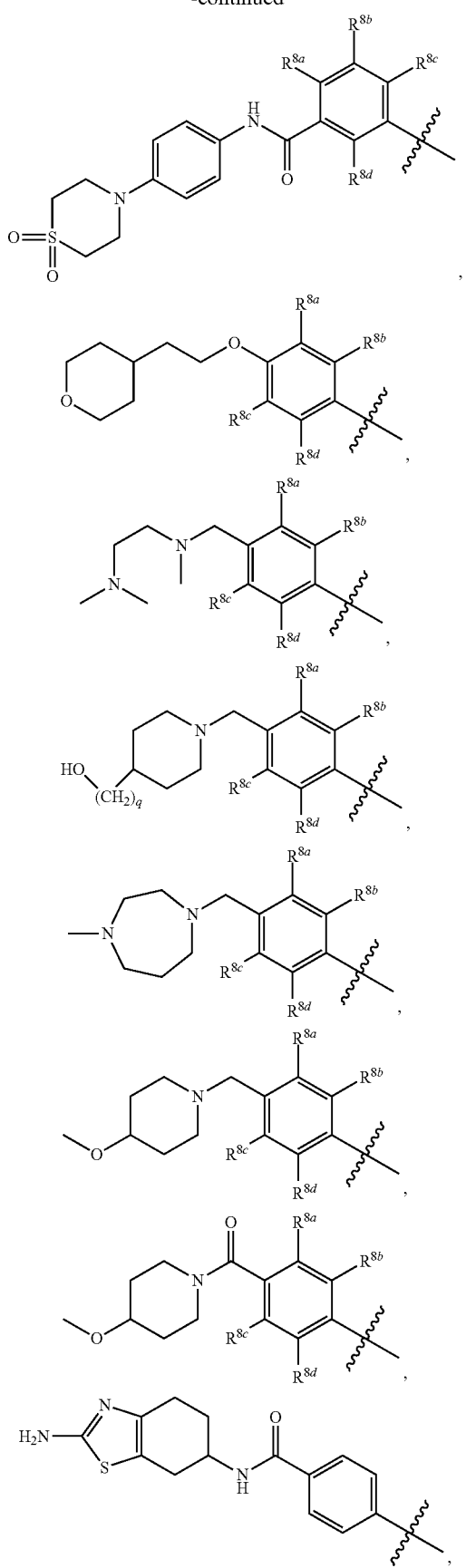
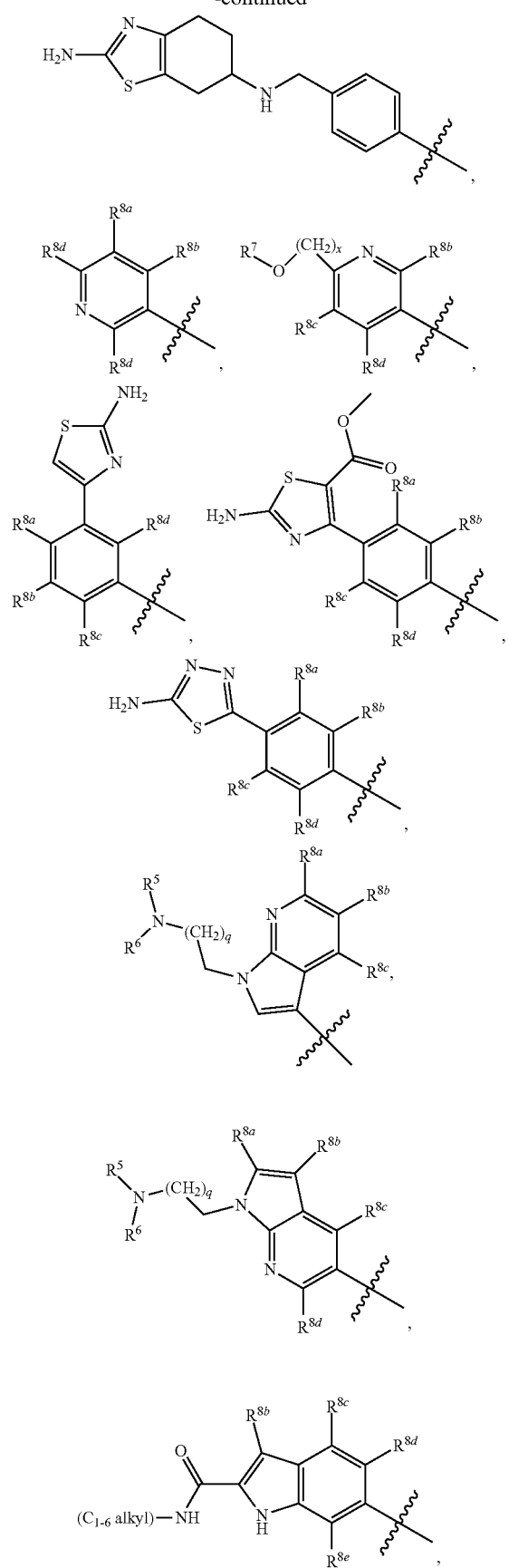

-continued
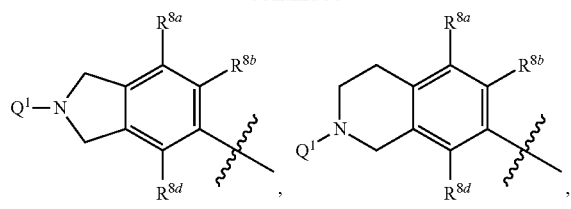
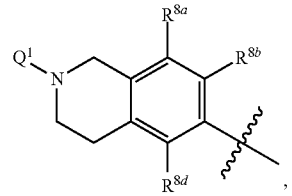
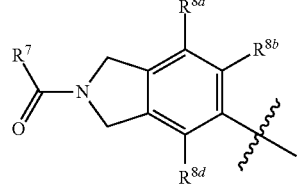
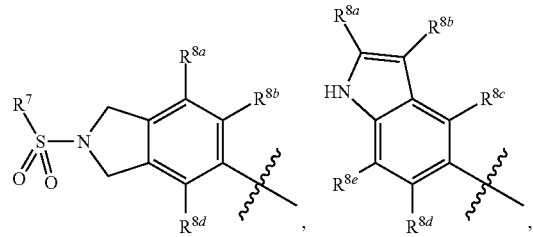
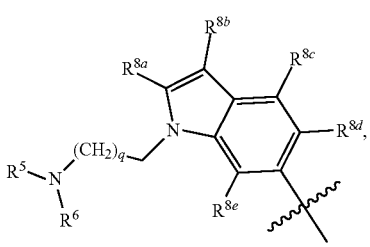
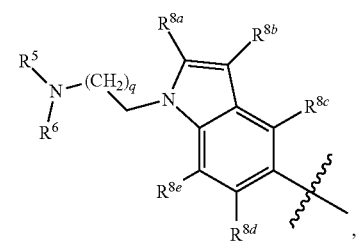
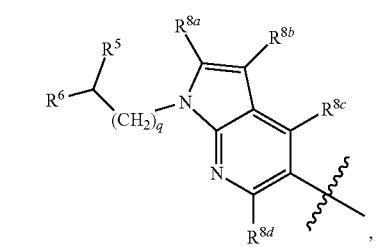
-continued
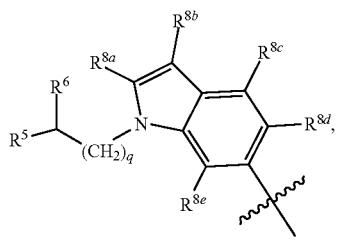
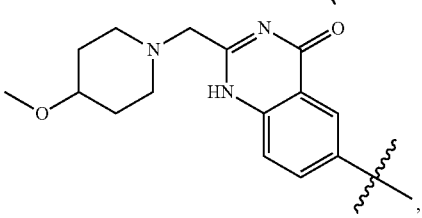
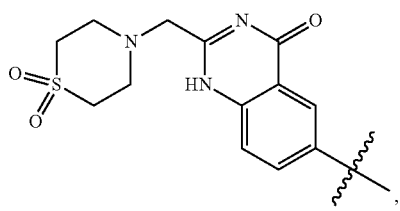
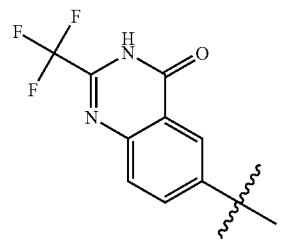
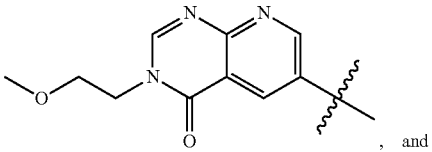
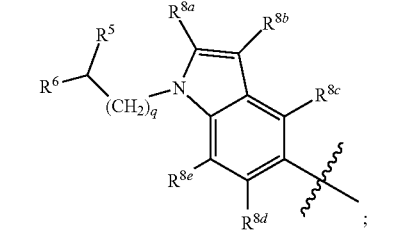
$R^2$ is selected from the group consisting of
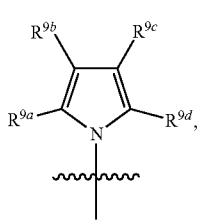 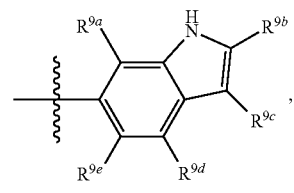

-continued

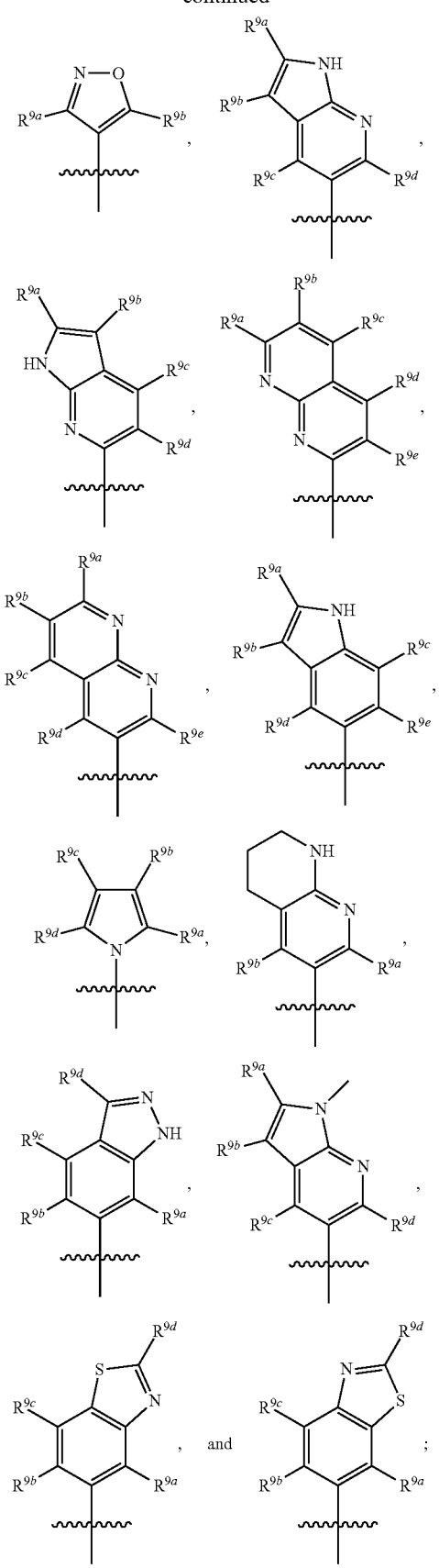

$R^3$ is selected from the group consisting of —CO$_2$R$^{4d}$, —C(=O)NH—S(=O)$_2$NR$^5$R$^6$, —S(=O)$_2$NHC(=O)R$^7$, —NHS(=O)$_2$R$^7$, and 1H-tetrazol-5-yl;

$R^{4a}$, $R^{4b}$, and $R^{4c}$ are each independently selected from the group consisting of F, Cl, Br, I, and H;

$R^{4d}$ is selected from the group consisting of H, optionally substituted C$_{1-6}$ linear alkyl, and optionally substituted C$_{3-6}$ branched alkyl;

$R^5$ is selected from the group consisting of H, optionally substituted C$_{1-6}$ linear alkyl, and optionally substituted C$_{3-6}$ branched alkyl;

$R^6$ is selected from the group consisting of H, optionally substituted C$_{1-6}$ linear alkyl, and optionally substituted C$_{3-6}$ branched alkyl; or $R^5$ and $R^6$ are taken together with the atoms to which they are connected to form a 3-, 4-, 5-, or 6-membered ring optionally containing a unit selected from the group consisting of oxygen, sulfur, SO, SO$_2$, CF$_2$, NH, N(C$_{1-6}$ alkyl), N(C$_{3-7}$ branched alkyl), N(C$_{3-6}$ cycloalkyl), N(heteroaryl), NCO(C$_{1-6}$ alkyl), NCO(C$_{1-6}$ branched alkyl), NCO(C$_{3-6}$ cycloalkyl), NCO$_2$(C$_{1-6}$ alkyl), NCO$_2$(C$_{1-6}$ branched alkyl), NCO$_2$(C$_{3-6}$ cycloalkyl), NCON(C$_{1-6}$ alkyl)$_2$, SO$_2$NH$_2$, NSO$_2$(C$_{1-6}$ alkyl), NSO$_2$(C$_{3-6}$ branched alkyl), NSO$_2$(C$_{3-6}$ cycloalkyl), and NSO$_2$Aryl;

$R^7$ is selected from the group consisting of H, optionally substituted C$_{1-6}$ linear alkyl, optionally substituted C$_{3-6}$ branched alkyl, C$_{1-6}$ haloalkyl, optionally substituted phenyl, optionally substituted pyridyl, optionally substituted heteroaryl, and —CH(R$^5$)(R$^6$);

$R^{8a}$, $R^{8b}$, $R^{8c}$, $R^{8d}$, and $R^{8e}$ are each independently selected from the group consisting of H, halogen, hydroxyl, CN, optionally substituted C$_{1-6}$ linear alkyl, optionally substituted C$_{3-6}$ branched alkyl, and C$_{1-6}$ alkoxy;

$R^{9a}$, $R^{9b}$, $R^{9c}$, $R^{9d}$, and $R^{9e}$ are each independently selected from the group consisting of H, halogen, optionally substituted C$_{1-6}$ linear alkyl, C$_{1-6}$ alkoxy, and optionally substituted C$_{3-6}$ branched alkyl;

$R^{10a}$ and $R^{10b}$ are each independently selected from the group consisting of H, optionally substituted C$_{1-6}$ linear alkyl, and optionally substituted C$_{1-6}$ branched alkyl;

$L^1$ is selected from the group consisting of —C≡C—, —CH=CH— and —(CH$_2$)$_n$—;

$L^2$ is selected from a group consisting of NH, (CH$_2$)$_m$, and

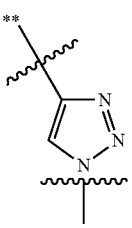

wherein "**" indicates the point of attachment for $R^2$;

$Q^1$ is selected from a group consisting of optionally substituted benzyl, —COR$^7$, —SO$_2$R$^7$

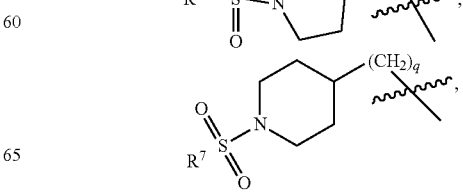

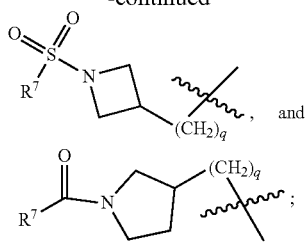, and

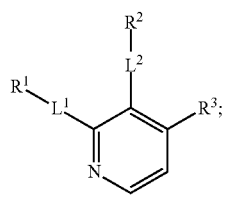;

n is 0, 1, 2, or 3; m is 0, 1, 2, or 3; q is 1, 2, 3, or 4; and x is 0, 1, 2, or 3.

In certain embodiments, the compound is at least one compound of formula selected from the group consisting of formula (II)

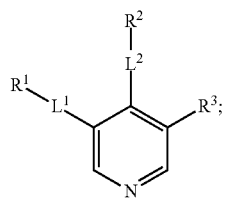

formula (III)

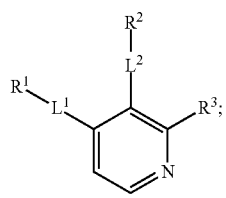

formula (IV)

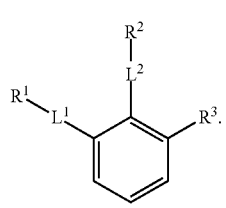

and formula (V)

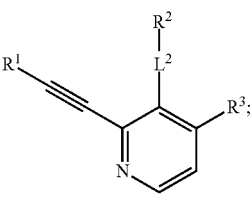

In certain embodiments, the compound is at least one compound of formula selected from the group consisting of formula (VI)

formula (VII)

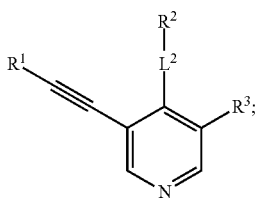

formula (VIII)

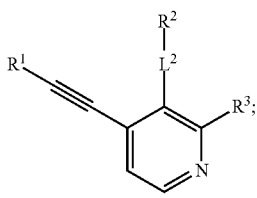

formula (IX)

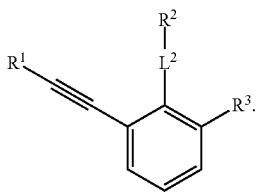

In certain embodiments, the compound is at least one compound of formula selected from the group consisting of formula (X)

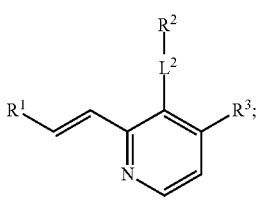

formula (XI)

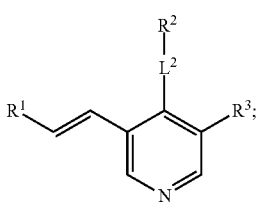

Formula (XII)

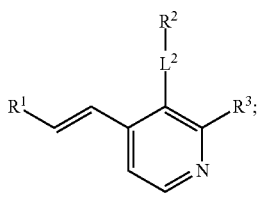

formula (XIII)

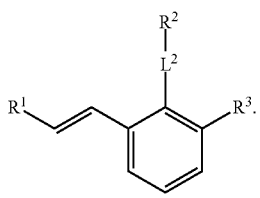

In certain embodiments, the compound is at least one compound of formula selected from the group consisting of formula (XIV)

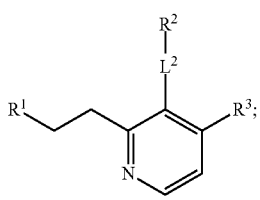

formula (XV)

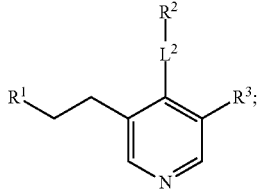

formula (XVI)

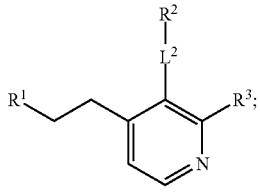

and formula (XVII)

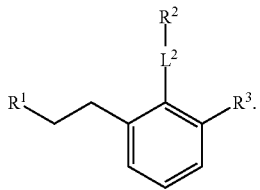

In certain embodiments, the compound is a compound of formula (XVIII)

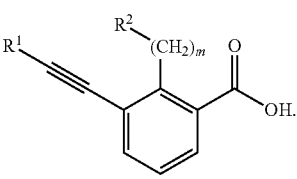

In certain embodiments, $R^1$ is at least one selected form the group consisting of 4-acetamidophenyl; 4-(aminomethyl)phenyl; 4-aminophenyl; 4-{8-azabicyclo[3.2.1]octan-3-yl}phenyl; 3-carbamoyl-5-methoxyphenyl; 4-{[(2-carboxyphenyl)formamido]methyl} phenyl; 4-{[(4-carboxyphenyl) formamido]methyl} phenyl; 4-(3-chloro-4-fluorobenzenesulfon amido) phenyl; 2,4-difluorophenyl; 4-[(4,4-difluoropiperidin-1-yl)methyl]phenyl; 4-{[2-(dimethylamino)ethyl]carbamoyl}phenyl; 4-({[2-(dimethylamino)ethyl](methyl)amino}methyl)phenyl; 1-[2-(dimethylamino)ethyl]-1H-pyrrolo[2,3-b]pyridin-3-yl; 1-[3-(dimethylamino)propyl]-1H-pyrrolo[2,3-b]pyridin-3-yl; 4-[(dimethylamino)methyl]phenyl; 4-[(1,1-dioxo-1$\lambda^6$-thian-4-yl)oxy]phenyl; 4-[(1,1-dioxo-1$\lambda^6$-thiomorpholin-4-yl)methyl] phenyl; 4-[(4-ethylpiperazin-1-yl)methyl]phenyl; 4-fluoro-3-(oxan-4-yloxy)phenyl; 4-fluorophenyl; 4-{[(2-fluorophenyl)formamido]methyl)phenyl; 4-[(3-hydroxy azetidin-1-yl)methyl]phenyl; 4-([4-(2-hydroxyethyl)piperidin-1-yl]methyl} phenyl; 4-[(4-hydroxypiperidin-1-yl)methyl]phenyl; 4-methanesulfonamidophenyl; 3-(3-methanesulfonamide phenyl)phenyl; 4-(4-methoxybenzenesulfonamido)phenyl; 4-{[(2-methoxyethyl)(methyl)amino]methyl}phenyl; 4-[(2-methoxyethyl)(methyl)carbamoyl]phenyl; 4-methoxyphenyl; 4-[(4-methoxypiperidin-1-yl)methyl]phenyl; 4-[(4-methyl-1,4-diazepan-1-yl)methyl]phenyl; 4-[(4-methylpiperazin-1-yl)methyl]phenyl; 2-methyl-4-oxo-3,4-dihydroquinazolin-7-yl; 3-(morpholin-4-ylmethyl)phenyl; 4-(morpholin-4-ylmethyl)phenyl; 1-[2-(morpholin-4-yl)ethyl]-1H-pyrrolo[2,3-b]pyridin-3-yl; 1-[3-(morpholin-4-yl)propyl]-1H-pyrrolo[2,3-b]pyridin-3-yl; 1-[2-(morpholin-4-yl)ethyl]-1H-pyrrolo[2,3-b]pyridin-5-yl; 1-[2-(dimethylamino)ethyl]-1H-pyrrolo[2,3-b]pyridin-5-yl; 1,8-naphthyridin-2-yl; 4-(oxan-4-ylmethoxy)phenyl; 4-[2-(oxan-4-yl)ethoxy]phenyl; 4-(oxan-4-yloxy)phenyl; 4-(oxan-4-yloxy)-3-(trifluoromethyl)phenyl; 4-oxo-3,4-dihydroquinazolin-7-yl; phenyl 4-[(phenylformamido)methyl] phenyl; 4-(piperazine-1-carbonyl)phenyl; 4-(pyridine-3-amido)phenyl; 2-(5,6,7,8-tetrahydro-1,8-naphthyridin-3-yl; and 4-(thiophene-2-sulfonamido)phenyl.

In certain embodiments, $R^2$ is selected from the group consisting of 1,3-benzothiazol-5-yl; 5-fluoro-indol-6-yl; 7-fluoro-indol-6-yl; Indol-6-yl; 2-methyl-1,3-benzothiazol-5-yl; 1-methyl-1H-pyrrolo[2,3-b]pyridin-6-yl; 1,8-naphthyridin-2-yl; 1,8-naphthyridin-3-yl; and 1H-pyrrolo[2,3-b]pyridine-5-yl.

In certain embodiments, the compound is at least one selected from the group consisting of 2-(1H-indol-6-yl)-3-[1-(2-morpholin-4-yl-ethyl)-1H-indol-6-ylethynyl]-benzoic acid; 3-[3-Acetylamino-4-(tetrahydro-pyran-4-yloxy)-phenylethynyl]-2-(1H-indol-6-yl)-benzoic acid; 3-[4-(8-Acetyl-8-aza-bicyclo[3.2.1]oct-3-yl)-phenylethynyl]-2-(1H-indol-6-yl)-benzoic acid; 3-[1-(2-Dimethylamino-ethyl)-1H-pyrrolo[2,3-b]pyridin-5-ylethynyl]-2-(1H-indol-6-yl)-benzoic acid; 3-[1-(3-Dimethylamino-propyl)-1H-pyrrolo[2,3-b]pyridin-5-ylethynyl]-2-(1H-indol-6-yl)-benzoic acid;

2-(1H-indol-6-yl)-3-[1-(3-morpholin-4-yl-propyl)-1H-pyrrolo[2,3-b]pyridin-5-ylethynyl]-benzoic acid; 2-(1H-indol-6-yl)-3-[1-(3-morpholin-4-yl-propyl)-1H-pyrrolo[2,3-b]pyridin-3-ylethynyl]-benzoic acid; 2-(1H-indol-6-yl)-3-[1-(2-morpholin-4-yl-ethyl)-1H-pyrrolo[2,3-b]pyridin-5-ylethynyl]-benzoic acid; 3-{2-[3-(3,3-dimethyl-2-oxoazetidin-1-yl)phenyl]ethynyl}-2-(1H-pyrrol-1-yl) benzoic acid; 3-[1-(2-Dimethylamino-ethyl)-1H-pyrrolo[2,3-b]pyridin-3-ylethynyl]-2-(H-indol-6-yl)-benzoic acid; 2-(1H-indol-6-yl)-3-[1-(2-morpholin-4-yl-ethyl)-1H-pyrrolo[2,3-b]pyridin-3-ylethynyl]-benzoic acid; 3-[1-(3-Dimethylamino-propyl)-1H-pyrrolo[2,3-b]pyridin-3-ylethynyl]-2-(1H-indol-6-yl)-benzoic acid; 3-{1-[2-(1,1-Dioxo-1λ⁶-thiomorpholin-4-yl)-ethyl]-1H-pyrrolo[2,3-b]pyridin-5-ylethynyl}-2-(1H-indol-6-yl)-benzoic acid; 2-(1H-indol-6-yl)-3-[1-(2-morpholin-4-yl-ethyl)-1H-indol-5-ylethynyl]-benzoic acid; 2-(1H-indol-6-yl)-3-[1-(3-morpholin-4-yl-propyl)-1H-indol-5-ylethynyl]-benzoic acid; 2-(1H-indol-6-yl)-3-[1-(3-morpholin-4-yl-propyl)-1H-indol-6-ylethynyl]-benzoic acid; 2-(1H-Indol-6-yl)-3-(5,6,7,8-tetrahydro-[1,8]naphthyridin-3-ylethynyl)-benzoic acid; 2-(1H-indol-6-yl)-3-[1-(tetrahydro-pyran-4-ylmethyl)-1H-pyrrolo[2,3-b]pyridin-5-ylethynyl]-benzoic acid; 2-(1H-Indol-6-yl)-3-[1-(tetrahydro-pyran-4-ylmethyl)-1H-indol-5-ylethynyl]-benzoic acid; 2-(1H-Indol-6-yl)-3-[1-(1-methanesulfonyl-piperidin-4-ylmethyl)-1H-indol-5-ylethynyl]-benzoic acid; 2-(1H-Indol-6-yl)-3-[1-(1-methanesulfonyl-piperidin-4-yl-methyl)-1H-pyrrolo[2,3-b]pyridin-5-ylethynyl]-benzoic acid; 3-[1-(1,1-Dioxo-hexahydro-1λ⁶-thiopyran-4-ylmethyl)-1H-pyrrolo[2,3-b]pyridin-5-ylethynyl]-2-(1H-indol-6-yl)-benzoic acid; 3-{1-[2-(1,1-Dioxo-1λ⁶-thiomorpholin-4-yl)-ethyl]-1H-indol-5-yl-ethynyl}-2-(1H-indol-6-yl)-benzoic acid; 3-{1-[2-(1,1-Dioxo-1λ⁶-thiomorpholin-4-yl)-ethyl]-1H-indol-6-ylethynyl}-2-(1H-indol-6-yl)-benzoic acid; 3-{1-[3-(1,1-Dioxo-1λ⁶-thiomorpholin-4-yl)-propyl]-1H-indol-5-yl-ethynyl}-2-(1H-indol-6-yl)-benzoic acid; 3-{1-[3-(1,1-Dioxo-1λ⁶-thiomorpholin-4-yl)-propyl]-1H-indol-6-yl-ethynyl}-2-(1H-indol-6-yl)-benzoic acid; 3-[4-(1,1-Dioxo-hexahydro-1λ⁶-thiopyran-4-yloxymethyl)-phenyethynyl]-2-(1H-indol-6-yl)-benzoic acid; 2-(1H-Indol-6-yl)-3-[4-(tetrahydro-pyran-4-yloxymethyl)-phenylethynyl]-benzoic acid; 2-(1H-Indol-6-yl)-3-(4-isopropoxymethyl-phenylethynyl)-benzoic acid; 2-(1H-Indol-6-yl)-3-[4-(1-oxo-hexahydro-1λ⁴-thiopyran-4-yloxy)-phenylethynyl]-benzoic acid; 2-(1H-Indol-6-yl)-3-(3-morpholin-4-ylmethyl-1H-indol-6-ylethynyl)-benzoic acid; 2-(1H-indol-6-yl)-3-[3-(4-methanesulfonyl-piperazin-1-ylmethyl)-1H-indol-6-ylethynyl]-benzoic acid; 3-[3-(1,1-Dioxo-1λ⁶-thiomorpholin-4-ylmethyl)-1H-indol-6-ylethynyl]-2-(1H-indol-6-yl)-benzoic acid; 2-(1H-indol-6-yl)-3-(2-morpholin-4-ylmethyl-1H-indol-6-ylethynyl)-benzoic acid; 3-[2-(1,1-Dioxo-1λ₆-thiomorpholin-4-ylmethyl)-1H-indol-6-ylethynyl]-2-(1H-indol-6-yl)-benzoic acid; 3-[1-(4-ethoxy-2-methyl-butyl)-6-fluoro-1H-indol-5-ylethynyl]-2-(1H-indol-6-yl)-benzoic acid; 3-[7-fluoro-1-(tetrahydro-pyran-4-ylmethyl)-1H-indol-6-ylethynyl]-2-(1H-indol-6-yl)-benzoic acid; 3-[1-(1,1-dioxo-hexahydro-1λ₆-thiopyran-4-ylmethyl)-7-fluoro-1H-indol-6-ylethynyl]-2-(1H-indol-1)-benzoic acid; 3-[1-(1,1-dioxo-hexahydro-1λ⁶-thiopyran-4-ylmethyl)-6-fluoro-1H-indol-5-ylethynyl]-2-(1H-indol-6-yl)-benzoic acid; 3-(7-fluoro-3-morpholin-4-ylmethyl-1H-indol-6-ylethynyl)-2-(1H-indol-(6-yl)-benzoic acid; 3-(6-fluoro-3-morpholin-4-ylmethyl-1H-indol-5-ylethynyl)-2-(1H-indol-6-yl)-benzoic acid; 3-((4-(2H-tetrazol-5-yl)phenyl)ethynyl)-2-(1H-indol-6-yl)benzoic acid; 3-((3-(2H-tetrazol-5-yl)phenyl)ethynyl)-2-(1H-indol-6-yl)benzoic acid; 2-(1H-indol-6-yl)-3-((4-(oxazol-5-yl)phenyl)ethynyl) benzoic acid; 2-(1H-indol-6-yl)-3-((4-(6-oxo-1,6-dihydropyridazin-3-yl)phenyl)ethynyl)benzoic acid; 2-(1H-indol-6-yl)-3-((3-methoxy-4-(morpholinomethyl)phenyl) ethynyl) benzoic acid; 3-((3-hydroxy-4-(morpholine-4-carbonyl) phenyl)ethynyl)-2-(1H-indol-6-yl)benzoic acid; 2-(1H-Indol-6-yl)-3-[3-methoxy-4-(4-morpholin-4-yl-piperidin-1-ylmethyl)-phenylethynyl]-benzoic acid; 3-((4-((4,4-difluoropiperidin-1-yl)methyl)-3-methoxyphenyl)ethynyl)-2-(1H-indol-6-yl)benzoic acid; 3-((4-((4-(dimethylcarbamoyl)piperidin-1-yl)methyl)-3-methoxyphenyl)ethynyl)-2-(1H-indol-6-yl)benzoic acid; 3-((3-hydroxy-4-(4-morpholinopiperidine-1-carbonyl)phenyl)ethynyl)-2-(1H-indol-6-yl)benzoic acid; 3-((4-(4,4-difluoropiperidine-1-carbonyl)-3-hydroxyphenyl)ethynyl)-2-(1H-indol-6-yl)benzoic acid; 2-(1H-indol-(i-yl)-3-((4-((1-(methylsulfonyl)piperidin-4-yl)methyl)phenyl)ethynyl) benzoic acid; 2-(1H-indol-6-yl)-3-((4-((1-((trifluoromethyl)sulfonyl)piperidin-4-yl)methyl) phenyl)ethynyl)benzoic acid; 2-(1H-indol-6-yl)-3-((4-((1-(isopropylsulfonyl)piperidin-4-yl)methyl)phenyl) ethynyl) benzoic acid; 3-((4-((1-acetylpiperidin-4-yl)methyl)phenyl)ethynyl)-2-(1H-indol-6-yl)benzoic acid; 3-((2-acetylisoindolin-5-yl)ethynyl)-2-(1H-indol-6-yl)benzoic acid; 2-(1H-indol-6-yl)-3-((2-(isopropylsulfonyl)isoindolin-5-yl)ethynyl)benzoic acid; 2-(1H-indol-6-yl)-3-((2-(1-(methylsulfonyl)pyrrolidin-3-yl)-1,2,3,4-tetrahydroisoquinolin-7-yl)ethynyl)benzoic acid; 2-(1H-indol-6-yl)-3-((2-((1-(meth)ylsulfonyl)piperidin-4-yl)methyl)-1,2,3,4-tetrahydroisoquinolin-6-yl)ethynyl)benzoic acid; 2-(1H-indol-6-yl)-3-((2-(1-(methylsulfonyl)azetidin-3-yl)-1,2,3,4-tetrahydroisoquinolin-6-yl) ethynyl) benzoic acid; 2-(1H-indol-6-yl)-3-((2-((1-(methylsulfonyl) pyrrolidin-3-yl)methyl)-1,2,3,4-tetrahydroisoquinolin-6-yl) ethynyl)benzoic acid; 2-(1H-indol-6-yl)-3-((2-((1-(methylsulfonyl)pyrrolidin-3-yl)methyl)-1,2,3,4-tetrahydroisoquinolin-7-yl)ethynyl)benzoic acid; 3-((2-((1-acetylpyrrolidin-3-yl)methyl)-1,2,3,4-tetrahydroisoquinolin-7-yl)ethynyl)-2-(1H-indol-6-yl) benzoic acid; 2-(1H-indol-6-yl)-3-((2-((1-(methylsulfonyl) azetidin-3-yl)methyl)-1,2,3,4-tetrahydroisoquinolin-6-yl) ethynyl)benzoic acid; 2-(1H-indol-6-yl)-3-((2-((1-(methylsulfonyl) azetidin-3-yl)methyl)-1,2,3,4-tetrahydroisoquinolin-7-yl)ethynyl)benzoic acid; 2-(1H-indol-6-yl)-3-((2-(3-(methylsulfonamido)benzyl)-1,2,3,4-tetrahydroisoquinolin-6-yl)ethynyl)benzoic acid; 2-(1H-indol-6-yl)-3-((2-(3-(methylsulfonamido)benzyl)-1,2,3,4-tetrahydroisoquinolin-7-yl)ethynyl)benzoic acid; 2-(1H-indol-6-yl)-3-((2-(1-(methylsulfonyl)pyrrolidin-3-yl) isoindolin-5-yl)ethynyl)benzoic acid; 2-(1H-indol-(6-yl)-3-((2-(1-(methylsulfonyl)azetidin-3-yl)isoindolin-5-yl) ethynyl)benzoic acid; 2-(1H-indol-6-yl)-3-((2-((1-(methylsulfonyl)pyrrolidin-3-yl)methyl)isoindolin-5-yl) ethynyl)benzoic acid; 2-(1H-indol-(6-yl)-3-((2-((1 methylsulfonyl)azetidin-3-yl)methyl)isoindolin-5-yl)ethynyl) benzoic acid; 2-(1H-indol-6-yl)-3-((2-((1-(methylsulfonyl)piperidin-4-yl)methyl)isoindolin-5-yl)ethynyl)benzoic acid; 2-(1H-indol-6-yl)-3-((2-(methylsulfonyl)-1,2,3,4-tetrahydroisoquinolin-7-yl)ethynyl)benzoic acid; 2-(1H-indol-6-yl)-3-((2-(isopropylsulfonyl)-1,2,3,4-tetrahydroisoquinolin-7-yl)ethynyl)benzoic acid; 2-(1H-indol-6-yl)-3-((2-propionyl-1,2,3,4-tetrahydroisoquinolin-7-yl)ethynyl) benzoic acid; 2-(1H-indol-6-yl)-3-((2-(methylsulfonyl)-1,2,3,4-tetrahydro-isoquinolin-6-yl)ethynyl)benzoic acid; 2-(1H-indol-6-yl)-3-((2-isopropylsulfonyl)-1,2,3,4-tetrahydroisoquinolin-6-yl)ethynyl)benzoic acid; 3-((2-acetyl-1,2,3,4-tetrahydroisoquinolin-6-yl)ethynyl)-2-(1H-indol-6-yl) benzoic acid; 2-(1H-indol-6-yl)-3-((2-propionyl-1,2,3,4-tetrahydroisoquinolin-6-yl)ethynyl) benzoic acid; 3-[4-(4- cyano-phenoxymethyl)-phenylethynyl]-2-(1H-indol-6-yl)-benzoic acid; 3-[4-(3-cyano-phenoxymethyl)-phenyl ethynyl]-2-(1H-indol-6-yl)-benzoic acid; 3-[4-(3-carbamoyl-phenoxymethyl)-phenylethynyl]-2-(1H-indol-6-yl)-benzoic acid; 2-(1H-indol-6-yl)-3-[4-(4-trifluoromethyl-phenoxymethyl)-phenylethynyl]-benzoic acid; 2-(1H-indol-6-yl)-3-[4-(3-trifluoromethyl-phenoxymethyl)-phenylethynyl]-benzoic acid; 2-(1H-indol-6-yl)-3-[4-(4-methoxy-phenoxymethyl)-phenylethynyl]-benzoic acid; 3-[4-(4-carbamoyl-phenoxymethyl)-phenylethynyl]-2-(1H-indol-6-yl)-benzoic acid; 2-(1H-indol-6-yl)-3-[4-(3-methoxy-phenoxymethyl)-phenylethynyl]-benzoic acid; 2-(1H-indol-6-yl)-3-(4-phenoxymethyl-phenylethynyl)-benzoic acid; 3-[4-(2-fluoro-phenoxymethyl)-phenylethynyl]-2-(1H-indol-6-yl)-benzoic acid; 2-(1H-indol-6-yl)-3-[4-(pyridin-3-yloxymethyl)-phenylethynyl]-benzoic acid; 3-[4-(3-chloro-phenoxymethyl)-phenylethynyl]-2-(1H-indol-6-yl)-benzoic acid; 3-[4-(3,4-dichloro-phenoxymethyl)-phenylethynyl]-2-(1H-indol-6-yl)-benzoic acid; 2-(1H-indol-6-yl)-3-[4-(2-trifluoromethyl-phenoxymethyl)-phenylethynyl]-benzoic acid; 3-[4-(2-cyano-phenoxymethyl)-phenylethynyl]-2-(1H-indol-6-yl)-benzoic acid; 2-(1H-indol-6-yl)-3-[4-(4-methanesulfonyl-phenoxymethyl)-phenylethynyl]-benzoic acid; 2-(1H-indol-6-yl)-3-[4-(pyrimidin-5-yloxymethyl)-phenylethynyl]-benzoic acid; 2-(1H-indol-6-yl)-3-[4-(2-methanesulfonyl-phenoxymethyl)-phenylethynyl]-benzoic acid; 2-(1H-indol-6-yl)-3-[4-(3-methanesulfonyl-phenoxy methyl)-phenylethynyl]-benzoic acid; 2-(1H-Indol-6-yl)-3-{2-[3-(3-methanesulfonamidophenyl) phenyl]ethynyl}benzoic acid; 2-(1H-Indol-6-yl)-3-{2-[6-(oxan-4-yloxy)pyridin-3-yl]ethynyl}benzoic acid; 2-(1H-Indol-6-yl)-3-{2-[2-(propyl-carbamoyl)-1H-indol-6-yl]ethynyl}benzoic acid; 2-(1H-Indol-6-yl)-3-{2-[3-(1,2,3,4-tetrahydroisoquinolin-2-ylmethyl)phenyl]ethynyl}benzoic acid; 3-{2-[3-Cyano-4-(oxan-4-yloxy)phenyl]ethynyl}-2-(1H-indol-6-yl)benzoic acid; 3-[2-(3-{[4-(Ethoxycarbonyl)piperazin-1-yl]methyl}phenyl)ethynyl]-2-(1H-indol-6-yl)benzoic acid; 3-(2-{4-[3-(Hydroxymethyl)oxetan-3-yl]phenyl}ethynyl)-2-(1H-indol-(6-yl)benzoic acid; 3-{2-[3-(5-Amino-1H-pyrazol-3-yl)phenyl]ethynyl}-2-(1H-indol-6-yl)benzoic acid; 2-(1H-Indol-(w-yl)-3-{2-[3-(1,3-oxazol-5-yl)phenyl]ethynyl}benzoic acid; 2-(1H-Indol-6-yl)-3-{2-[4-(oxane-4-carbonyl)phenyl]ethynyl}benzoic acid; 2-(7-Fluoro-1H-indol-6-yl)-3-phenylethynyl-benzoic acid; 2-Benzothiazol-6-yl-3-phenylethynyl-benzoic acid; 2-Benzothiazol-5-yl-3-phenylethynyl-benzoic acid; 2-(2-Methyl-benzothiazol-5-yl)-3-phenylethynyl-benzoic acid; 2-(5-Fluoro-1H-indol-6-yl)-3-phenylethynyl-benzoic acid; 2-(6-Fluoro-1H-indol-5-yl)-3-phenylethynyl-benzoic acid; 2-[1,8]Naphthyridin-3-yl-3-phenylethynyl-benzoic acid; 2-(1-Methyl-1H-pyrrolo[2,3-b]pyridin-6-yl)-3-phenylethynyl-benzoic acid; 2-[1,8]Naphthyridin-2-yl-3-phenylethynyl-benzoic acid; 3-Phenylethynyl-2-(1H-pyrrolo[2,3-b]pyridin-(3-yl)-benzoic acid; 2-(4-methoxy-1H-indol-6-yl)-3-(2-phenylethynyl)-benzoic acid; 3-(2-(4-(2-hydroxypropan-2-yl)phenyl)ethynyl)-2-(1H-indol-6-yl)-benzoic acid; 3-(2-(4-(2-aminothiazol-4-yl)phenyl)ethynyl)-2-(1H-indol-6-yl)-benzoic acid; 2-(1H-Indol-6-yl)-3-(3-sulfamoyl-phenylethynyl)-benzoic acid; 3-(4-Amino-3-sulfamoyl-phenylethynyl)-2-(1H-indol-6-yl)-benzoic acid; 2-(1H-indol-6-yl)-3-(Spiro[2H-1-benzopyran-2,1'-4-piperidine-1-t-butylcarboxylate]-4(3H)-one)ethynyl)benzoic acid; 3-(2-(3-(2-aminothiazol-4-yl)phenyl)ethynyl)-2-(1H-indol-6-yl)-benzoic acid; 3-(2-(4-(5-(methoxycarbonyl)-2-aminothiazol-4-yl)phenyl)ethynyl)-2-(1H-indol-6-yl)-benzoic acid; 3-(2-(4-(5-amino-1,3,4-thiadiazol-2-yl)phenyl)ethynyl)-2-(1H-indol-6-yl)-benzoic acid; 3-(2-(4-(3-amino-1H-pyrazol-5-yl)phenyl)ethynyl)-2-(1H-indol-6-yl)-benzoic acid; 2-Amino-4-{4-[3-carboxy-2-(1H-indol-6-yl)-phenylethynyl]-phenyl}-thiazole-5-carboxylic acid; 3-(2-(4-(2-aminooxazol-5-yl)phenyl)ethynyl)-2-(1H-indol-6-yl)-benzoic acid; 2-(1H-Indol-6-yl)-3-[4-(2-methanesulfonylamino-thiazol-4-yl)-phenylethynyl]-benzoic acid; 2-(1H-Indol-6-yl)-3-[3-(2-methanesulfonylamino-thiazol-4-yl)-phenylethynyl]-benzoic acid; 3-(2-(1,4-dihydro-2-((4-methoxypiperidin-1-yl)methyl)-4-oxoquinazolin-6-yl)ethynyl)-2-(1H-indol-6-yl)benzoic acid; 3-(2-(1,4-dihydro-2-((4-thiomorpholine-1,1dioxide-1-yl)methyl)-4-oxoquinazolin-6-yl)ethynyl)-2-(1H-indol-6-yl)benzoic acid; 3-(2-(2-(trifluoromethyl)-3,4-dihydro-4-oxoquinazolin-6-yl)ethynyl)-2-(1H-indol-6-yl)benzoic acid; 3-(2-(3,4-dihydro-3-(2-methoxyethyl)-4-oxopyrido[2,3-d]pyrimidin-6-yl)ethynyl)-2-(1H-indol-6-yl)benzoic acid; 2-(1H-Indol-6-yl)-3-[3-(2-methoxy-6-methyl-phenyl carbamoyl)-phenylethynyl]-benzoic acid; 3-{3-[4-(1,1-Dioxo-1-thiomorpholin-4-yl)-phenyl carbamoyl]-phenylethynyl}-2-(1H-indol-6-yl)-benzoic acid; 3-Phenylethynyl-2-(1H-pyrrolo[2,3-b]pyridin-5-yl)-benzoic acid; 3-(4-Fluoro-phenylethynyl)-2-(1H-pyrrolo[2,3-b]pyridin-5-yl)-benzoic acid; 3-(4-Methoxy-phenylethynyl)-2-(1H-pyrrolo[2,3-b]pyridin-5-yl)-benzoic acid; 2-(1H-Pyrrolo[2,3-b]pyridin-5-yl)-3-[4-(tetrahydro-pyran-4-yloxy)-phenylethynyl]-benzoic acid; 2-(1H-Indol-(6-yl)-3-{4-[2-(tetrahydro-pyran-4-yl)-ethoxyl]-phenylethynyl}-benzoic acid; 3-[4-(1,1-Dioxo-hexahydro-1-thiopyran-4-yloxy)-phenylethynyl]-2-(1H-indol-6-yl)-benzoic acid; 2-(1H-Indol-6-yl)-3-(4-morpholin-4-ylmethyl-phenylethynyl)-benzoic acid; 3-[4-(4-Ethyl-piperazin-1-ylmethyl)-phenylethynyl]-2-(1H-Indol-6-yl)-benzoic acid; 2-(1H-Indol-6-yl)-3-[4-(4-methyl-piperazin-1-ylmethyl)-phenylethynyl]-benzoic acid; 3-[4-(1,1-Dioxo-thiomorpholin-4-ylmethyl)-phenylethynyl]-2-(1H-indol-6-yl)-benzoic acid; 3-(4-{[(2-Dimethyl-amino-ethyl)-methyl-amino]-methyl}-phenyl ethynyl)-2-(1H-indol-6-yl)-benzoic acid; 3-(4-[4-(2-Hydroxy-ethyl)-piperidin-1-ylmethyl]-phenylethynyl)-2-(1H-indol-6-yl)-benzoic acid; 3-[4-(4-Hydroxymethyl-piperidin-1-ylmethyl)-phenylethynyl]-2-(1H-indol-6-yl)-benzoic acid; 2-(1H-Indol-6-yl)-3-[4-(4-methyl-[1,4]diazepan-1-ylmethyl)-phenylethynyl]-benzoic acid; 3-[4-(3-Hydroxy-azetidin-1-ylmethyl)-phenylethynyl]-2-(1H-indol-6-yl)-benzoic acid; 3-[4-(4-Hydroxy-piperidin-1-ylmethyl)-phenylethynyl]-2-(1H-Indol-6-yl)-benzoic acid; 2-(1H-Indol-6-yl)-3-[4-(4-methoxy-piperidin-1-ylmethyl)-phenylethynyl]-benzoic acid; 3-(4-Dimethylaminomethyl-phenylethynyl)-2-(1H-indol-(6-yl)-benzoic acid; 2-(1H-Indol-6-yl)-3-4{[(2-methoxy-ethyl)-methyl-amino]-methyl}-phenylethynyl)-benzoic acid; 3-[4-(4,4-Difluoro-piperidin-1-ylmethyl)-phenylethynyl]-2-(1H-indol-6-yl)-benzoic acid; 3-[4-(3,3-Difluoro-piperidin-1-ylmethyl)-phenylethynyl]-2-(1H-indol-6-yl)-benzoic acid; 3-[4-(3,4-Dihydro-1H-isoquinolin-2-)ylmethyl)-phenylethynyl]-2-(1H-indol-6-yl)-benzoic acid; 2-(1H-Indol-6-yl)-3-[4-(4-methane sulfonyl-piperazin-1-ylmethyl)-phenylethynyl]-benzoic acid; 2-(1H-Indol-6-yl)-3-[4-(3-trifluoromethyl-piperidin-1-ylmethyl)-phenylethynyl]-benzoic acid; 2-(1H-Indol-6-yl)-3-[4-(3-methoxy-pyrrolidin-1-ylmethyl)-phenylethynyl]-benzoic acid; 2-(1H-Indol-6-yl)-3-[4-(4-isopropyl-piperazin-1-ylmethyl)-phenylethynyl]-benzoic acid; 3-[4-(4-Cyclohexyl-piperazin-1-ylmethyl)-phenylethynyl]-2-(1H-indol-6-yl)-benzoic acid; 3-[4-(4-Cyclopropanecarbonyl-piperazin-1-yl methyl)-phenylethynyl]-2-(1H-indol-6-yl)-benzoic acid; 2-(1H-Indol-6-yl)-3-(4-piperazin-1-ylmethyl-phenylethynyl)-benzoic acid; 3-[4-(4-Benzenesulfonyl-piperazin-1-ylmethyl)-phenyl ethynyl]-2-(1H-indol-6-yl)-benzoic acid; 3-{4-[(1,1-Dioxo-hexahydro-1-thiopyran-4-ylamino)-methyl]-phenylethynyl}-2-(1H-indol-6-yl)-benzoic acid; 3-[4-(4-Cyclopentyl-piperazin-1-ylmethyl)-phenylethynyl]-2-(1H-indol-6-yl)-benzoic acid; 3-[4-(4-Dimethylcarbamoyl-piperazin-1-ylmethyl)-phenylethynyl]-2-(1H-indol-6-yl)-benzoic acid; 2-(1H-Indol-6-yl)-3-[4-(2,3,5,6-tetrahydro-[1,2']bipyrazinyl-4-ylmethyl)-phenylethynyl]-benzoic acid; 2-(1H-Indol-6-yl)-3-[4-(4-thiazol-2-yl-piperazin-1-ylmethyl)-phenylethynyl]-benzoic acid; 3-{4-[(2-Amino-4,5,6,7-tetrahydro-benzothiazol-6-ylamino)-methyl]-phenylethynyl}-2-(1H-indol-6-yl)-benzoic acid; 3-{4-[(2-Amino-4,5,6,7-tetrahydro-benzothiazol-6-ylamino)-methyl]-phenylethynyl}-2-(1H-indol-6-yl)-benzoic acid; 3-[4-(4-Methyl-piperazin-1-ylmethyl)-phenylethynyl]-2-(1H-pyrrolo[2,3-b]pyridin-5-yl)-benzoic acid; 3-[4-(4-Methoxy-piperidin-1-ylmethyl)-phenylethynyl]-2-(1H-pyrrolo[2,3-b]pyridin-5-yl)-benzoic acid; 2-(1H-Indol-5-yl)-3-[4-(4-methoxy-piperidin-1-ylmethyl)-phenylethynyl]-benzoic acid; 2-(1H-Indol-5-yl)-3-[4-(4-methanesulfonyl-piperazin-1-ylmethyl)-phenylethynyl]-benzoic acid; 3-[4-(4-Methanesulfonyl-piperazin-1-ylmethyl)-phenylethynyl]-2-(1H-pyrrolo[2,3-b]pyridin-5-yl)-benzoic acid; 3-[4-(4,4-Difluoro-piperidin-1-ylmethyl)-phenylethynyl]-2-(1H-indol-5-yl)-benzoic acid; 2-(1H-Indol-5-yl)-3-[4-(4-methyl-piperazin-1-ylmethyl)-phenylethynyl]-benzoic acid; 3-[4-(4-Ethanesulfonyl-piperazin-1-ylmethyl)-phenylethynyl]-2-(1H-indol-6-yl)-benzoic acid; 3-[4-(1,1-Dioxo-hexahydro-1-thiopyran-4-yloxy)-phenylethynyl]-2-(1H-indol-5-yl)-benzoic acid; 3-[4-(1,1-Dioxo-hexahydro-thiopyran-4-yloxy)-phenylethynyl]-2-(1H-indazol-6-yl)-benzoic acid; 3-[2-Fluoro-4-(tetrahydro-pyran-4-yloxymethyl)-phenylethynyl]-2-(1H-indol-6-yl)-benzoic acid; 3-[4-(1,1-Dioxo-hexahydro-1-thiopyran-4-)yloxymethyl)-2-fluoro-phenylethynyl]-2-(1H-indol-6-yl)-benzoic acid; 2-(1H-Indol-6-yl)-3-[4-(2-methanesulfonyl-2,7-diaza-spiro[3.5]non-7-ylmethyl)-phenyl ethynyl]-benzoic acid; 2-(1H-Indol-(6-yl)-3-[4-(5-methanesulfonyl-hexahydro-pyrrolo[3,4-c]pyrrol-2-ylmethyl)-phenylethynyl]-benzoic acid; 3-[4-(4-Cyclopropanesulfonyl-piperazin-1-ylmethyl)-phenyl ethynyl]-2-(1H-indol-6-yl)-benzoic acid; 2-(1H-Indol-(w-yl)-3-{4-[4-(propane-2-sulfonyl)-piperazin-1-ylmethyl]-phenylethynyl}-benzoic acid; 2-(1H-Indol-6-yl)-3-[4-(7-methanesulfonyl-2,7-diaza-spiro[3.5]non-2-ylmethyl)-phenylethynyl]-benzoic acid; 2-(1H-Indol-5-yl)-3-[4-(tetrahydro-pyran-4-yloxy)-phenylethynyl]-benzoic acid; N—(N,N-dimethylsulfamoyl)-2-(1H-indol-6-yl)-3-((4-(((tetrahydro-2H-pyran-4-yl)oxy)methyl)phenyl)ethynyl) benzamide; 2-(1H-indol-6-yl)-N-(methyl sulfonyl)-3-((4-(((tetrahydro-2H-pyran-4-yl)oxy)methyl)phenyl)ethynyl) benzamide; 6-[2-[4-(Tetrahydro-pyran-4-yloxymethyl)-phenylethynyl]-6-(1H-tetrazol-5-yl)-phenyl]-1H-indole; 3-[4-(Benzoylamino-methyl)-phenylethynyl]-2-(1H-indol-6-yl)-benzoic acid; 2-(1H-Indol-6-yl)-3-(4-{[(4-oxo-cyclohexanecarbonyl)-amino]-methyl}-phenylethynyl)-benzoic acid; 2-(1H-Indol-6-yl)-3-[4-(4-oxo-cyclohexylcarbamoyl)-phenylethynyl]-benzoic acid; 3-[4-(2-Amino-4,5,6,7-tetrahydro-benzothiazol-6-ylcarbamoyl)-phenylethynyl]-2-(1H-indol-6-yl)-benzoic acid; 3-[4-(2-Amino-4,5,6,7-tetrahydro-benzothiazol-6-ylcarbamoyl)-phenylethynyl]-2-(1H-indol-6-yl)-benzoic acid; 2-(1H-Indol-6-yl)-3-[4-(4-methyl-piperazine-1-carbonyl)-phenylethynyl]-benzoic acid; 2-(1H-Indol-6-yl)-3-[4-(4-methoxy-piperidine-1-carbonyl)-phenylethynyl]-benzoic acid; 2-(1H-Indazol-6-yl)-3-[4-(4-methanesulfonyl-piperazin-1-ylmethyl)-phenylethynyl]-benzoic acid; and 2-(1H-Indol-6-yl)-3-[4-(4-sulfamoyl-piperazin-1-ylmethyl)-phenylethynyl]-benzoic acid.

In certain embodiments, the pharmaceutical composition further comprises at least one additional antiviral and/or anticancer agent.

In certain embodiments, the method comprises administering to the subject a therapeutically effective amount of at least one compound and/or composition of the invention.

In certain embodiments, the disease or disorder is at least one selected from the group consisting of cancer, infectious mononucleosis, chronic fatigue syndrome, multiple sclerosis, systemic lupus erythematosus, and rheumatoid arthritis.

In certain embodiments, the cancer is at least one selected from the group consisting of nasopharyngeal carcinoma, gastric carcinomas, non-hodgkin lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma. B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas. X-linked lymphoproliferative disease, post-transplant lymphoproliferative disorders, Hodgkin's lymphoma and breast cancer.

In certain embodiments, the compound is administered to the subject by at least one route selected from the group consisting of oral, nasal, inhalational, topical, buccal, rectal, pleural, peritoneal, vaginal, intramuscular, subcutaneous, transdermal, epidural, intratracheal, otic, intraocular, intrathecal, and intravenous routes. In other embodiments, the compound is administered as part of a pharmaceutical composition further comprising at least one pharmaceutically acceptable carrier

DETAILED DESCRIPTION OF THE INVENTION

The present invention relates in part to the unexpected discovery of novel EBNA1 inhibitors, and compositions comprising the same. The compounds and compositions of the invention are useful for treating and/or preventing: diseases or disorders caused by EBNA1 activity, diseases or disorders associated with EBNA1 activity, EBV infections, diseases or disorders associated with EBV infections, lytic EBV infections, latent EBV infections, diseases or disorders associated with lytic EBV infections, and diseases or disorders associated with latent EBV infection.

Definitions

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

As used herein, unless defined otherwise, all technical and scientific terms generally have the same meaning as commonly understood by one of ordinary skill in the art to which this invention belongs. Generally, the nomenclature used herein and the laboratory procedures in organic chemistry, virology, biochemistry and pharmaceutical sciences are those well-known and commonly employed in the art.

As used herein, the articles "a" and "an" refer to one or to more than one (i.e, to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

For the purposes of the present invention the terms "compound," "analog." and "composition of matter" stand equally well for the prodrug agent described herein, including all enantiomeric forms, diastereomeric forms, salts, and the like, and the terms "compound," "analog," and "composition of matter" are used interchangeably throughout the present specification.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "EBNA1 inhibitor" refers a compound that inhibits EBNA1.

As used herein, the term "EBV" refers to Epstein-Barr virus.

As used herein, the term "$ED_{50}$" or "ED50" refers to the effective dose of a formulation that produces about 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The term "low toxicity" for a compound towards a cell or tissue, as used herein, refers to a $CC_{50}$ (concentration that is cytotoxic to 50% cells) of 50 μM or less for that compound towards that cell or tissue. In certain embodiments, these characteristics ensure that these compounds do not affect the healthy cells of the patient and permit more effective treatment.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

As used herein, a "patient" or "subject" may be a human or non-human mammal or a bird. Non-human mammals include, for example, livestock and pets, such as ovine, bovine, porcine, canine, feline and murine mammals. In certain embodiments, the subject is human.

The term "treat," "treating" or "treatment," as used herein, means reducing the frequency or severity with which symptoms of a disease or condition are experienced by a subject by virtue of administering an agent or compound to the subject.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_{1-6}$ alkyl)$_2$ amino, the alkyl groups may be the same or different.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —CF$_3$, CF$_2$CF$_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

As used herein, the term "halogen" shall mean chlorine, bromine, fluorine and iodine.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3- d]pyrimidinyl, pyrido[2,3-d]pyrimidinyl, benzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxyquinolinyl, and isoquinolinyl.

The terms "heterocyclic" and/or "heterocycle" and/or "heterocycyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrrolyl, thiophenyl, furanyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposes of the present invention, fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

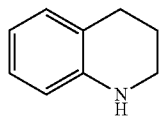

is, for the purposes of the present invention, considered a heterocyclic unit, 6,7-Dihydro-5H-cyclopentapyrimidine having the formula:

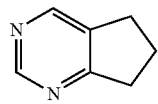

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

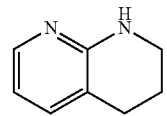

is, for the purposes of the present invention, considered a heteroaryl unit.

Whenever a term or either of their prefix roots appear in a name of a substituent, the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{11}$, —SR$^{11}$, —N(R$^{11}$)$_2$, —NR$^{11}$C(O)R$^{11}$, —SO$_2$R$^{11}$, —SO$_2$OR$^{11}$, —SO$_2$N(R$^{11}$)$_2$, —C(O)R$^{11}$, —C(O)OR$^{11}$, —C(O)N(R$^{11}$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{11}$; wherein R$^{11}$, at each occurrence, independently is H, —OR$^{12}$, —SR$^{12}$, —C(O)R$^{12}$, —C(O)OR$^{12}$, —C(O)N(R$^{12}$)$_3$, —SO$_2$R$^{12}$, —S(O)$_2$OR$^{12}$, —N(R$^{12}$)$_2$, —NR$^{12}$C(O)R$^{12}$, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{11}$ units taken together with the atom(s) to which they are bound form an optionally substituted carbocycle or heterocycle wherein said carbocycle or heterocycle has 3 to 7 ring atoms; wherein R$^{12}$, at each occurrence, independently is H, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{12}$ units taken together with the atom(s) to which they are bound form an optionally substituted carbocycle or heterocycle wherein said carbocycle or heterocycle preferably has 3 to 7 ring atoms.

In certain embodiments, the substituents are selected from the group consisting of: —OR$^{13}$; for example, —OH, —OCH$_3$, —OCH$_2$CH$_3$, —OCH$_2$CH$_2$CH$_3$; —C(O)R$^{13}$; for example, —COCH$_3$, —COCH$_2$CH$_3$, —COCH$_2$CH$_2$CH$_3$; —C(O)OR$^{13}$; for example, —CO$_2$CH$_3$, —CO$_2$CH$_2$CH$_3$, —CO$_2$CH$_2$CH$_2$CH$_3$; —C(O)N(R$^{13}$)$_2$; for example, —CONH$_2$, —CONHCH$_3$, —CON(CH$_3$)$_2$; —N(R$^{13}$)$_2$; for example, —NH$_2$, —NHCH$_3$, —N(CH$_3$)$_2$, —NH(CH$_2$CH$_3$); halogen; —F, —Cl, —Br, and —I; —CH$_e$X$_g$; wherein X is halogen, m is from 0 to 2, e+g=3, for example, —CH$_2$F, —CHF$_2$, —CF$_3$, —CCl$_3$, or —CBr$_3$; —SO$_2$R$^{13}$; for example, —SO$_2$H; —SO$_2$CH$_3$, —SO$_2$C$_6$H$_5$; C$_1$-C$_6$ linear, branched, or cyclic alkyl; Cyano; Nitro; N(R$^{13}$)C(O)R$^{13}$; Oxo (=O); Heterocycle; and Heteroaryl, wherein each R$^{13}$ is independently H, optionally substituted C$_1$-C$_6$ linear or branched alkyl (e.g., optionally substituted C$_1$-C$_4$ linear or branched alkyl), or optionally substituted C$_3$-C$_6$ cycloalkyl (e.g optionally substituted C$_3$-C$_4$ cycloalkyl); or two R$^{13}$ units can be taken together to form a ring comprising 3-7 ring atoms. In certain aspects, each R$^{13}$ is independently H, C$_1$-C$_6$ linear or branched alkyl optionally substituted with halogen or C$_3$-C$_6$ cycloalkyl or C$_3$-C$_6$ cycloalkyl.

When any variable occurs more than one time in any constituent or in any formula, its definition in each occurrence is independent of its definition at every other occurrence (e.g., in N(R$^{10}$)$_2$, each R$^{10}$ may be the same or different than the other). Combinations of substituents and/or variables are permissible only if such combinations result in stable compounds.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$, alkyl.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The EBNA1 inhibitors of the present invention include a compound of formula (I), or any enantiomer, diastereomer, tautomer, salt and/or solvate thereof:

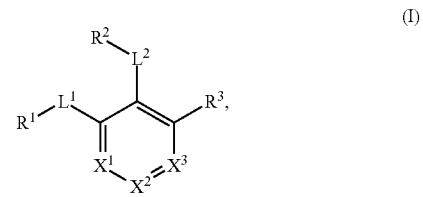

wherein:

X$^1$ is selected from the group consisting of CR$^{4a}$ and N;

X$^2$ is selected from the group consisting of CR$^{4b}$ and N;

X$^3$ is selected from the group consisting of CR$^{4c}$ and N;

R$^1$ is selected from the group consisting of

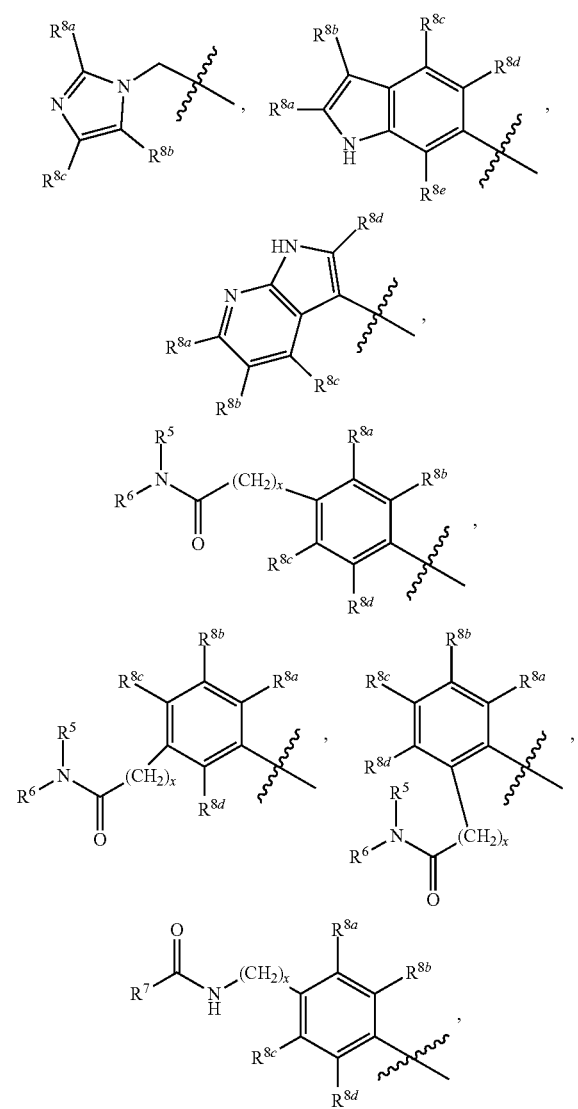

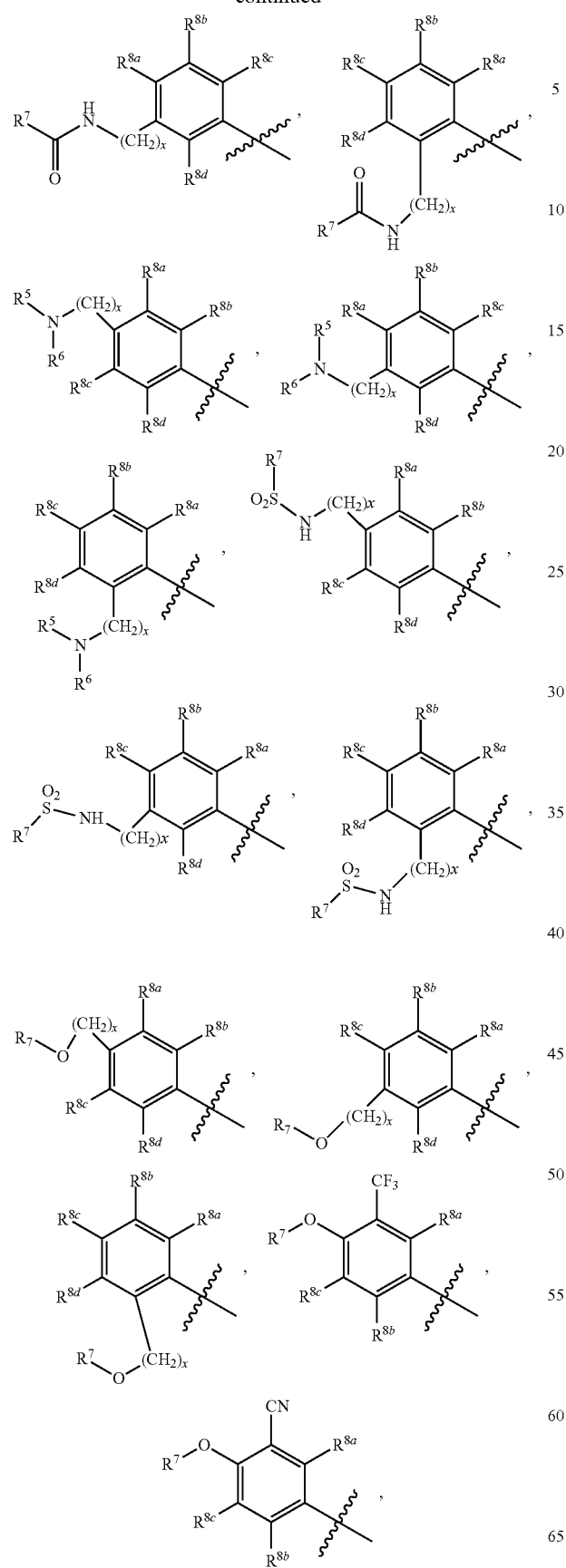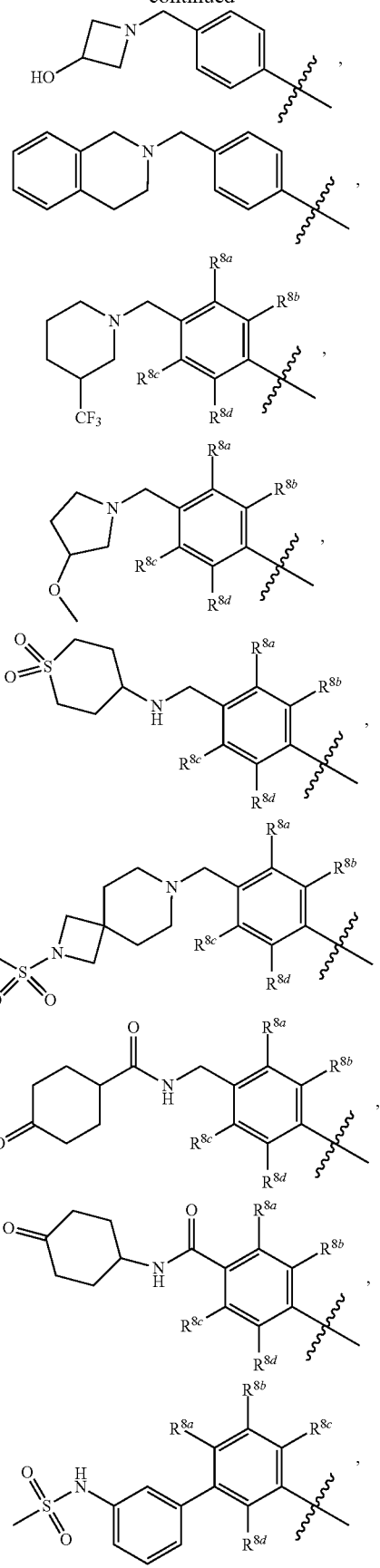

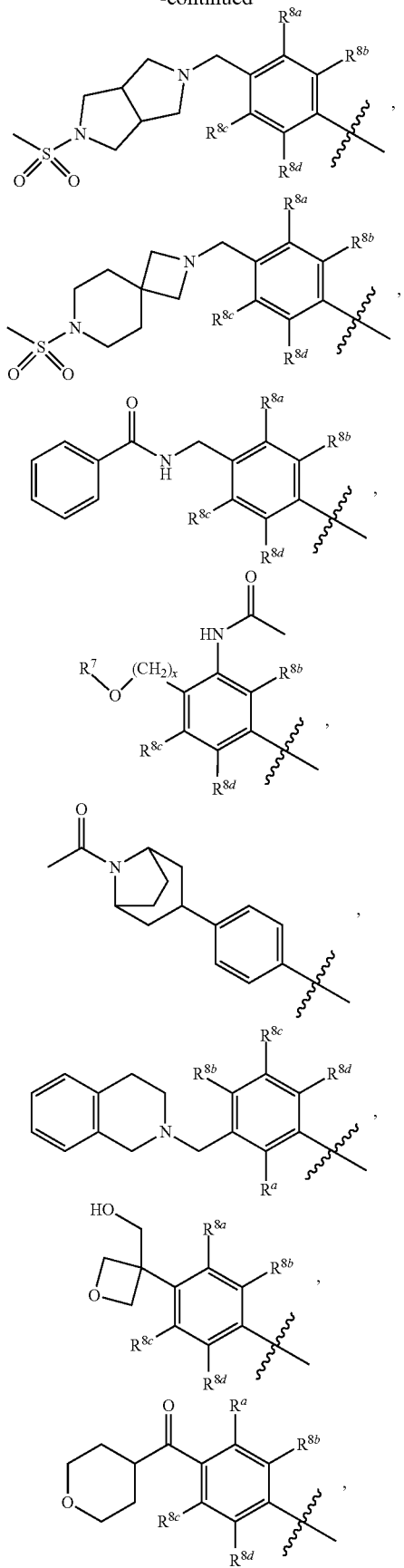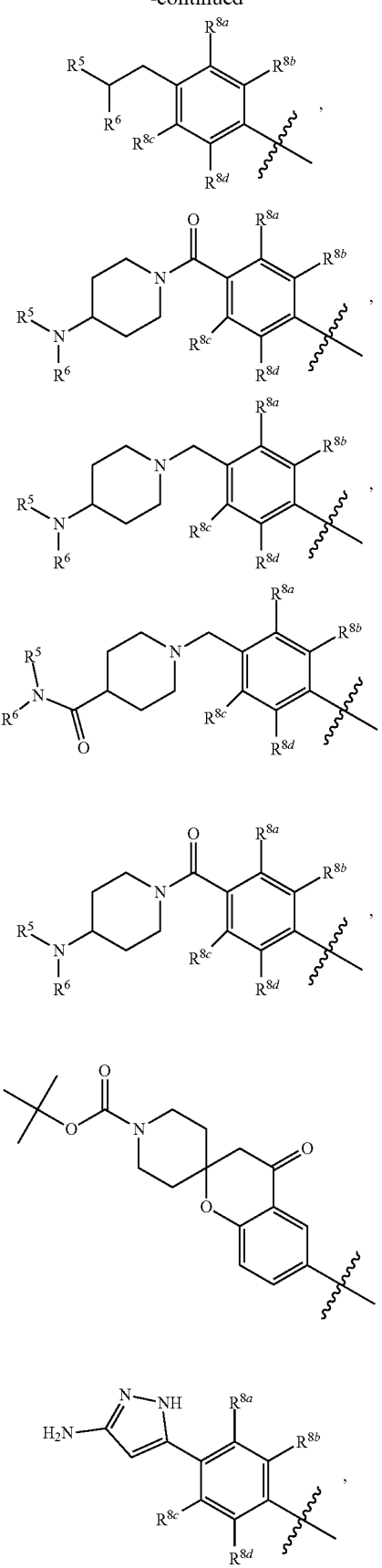

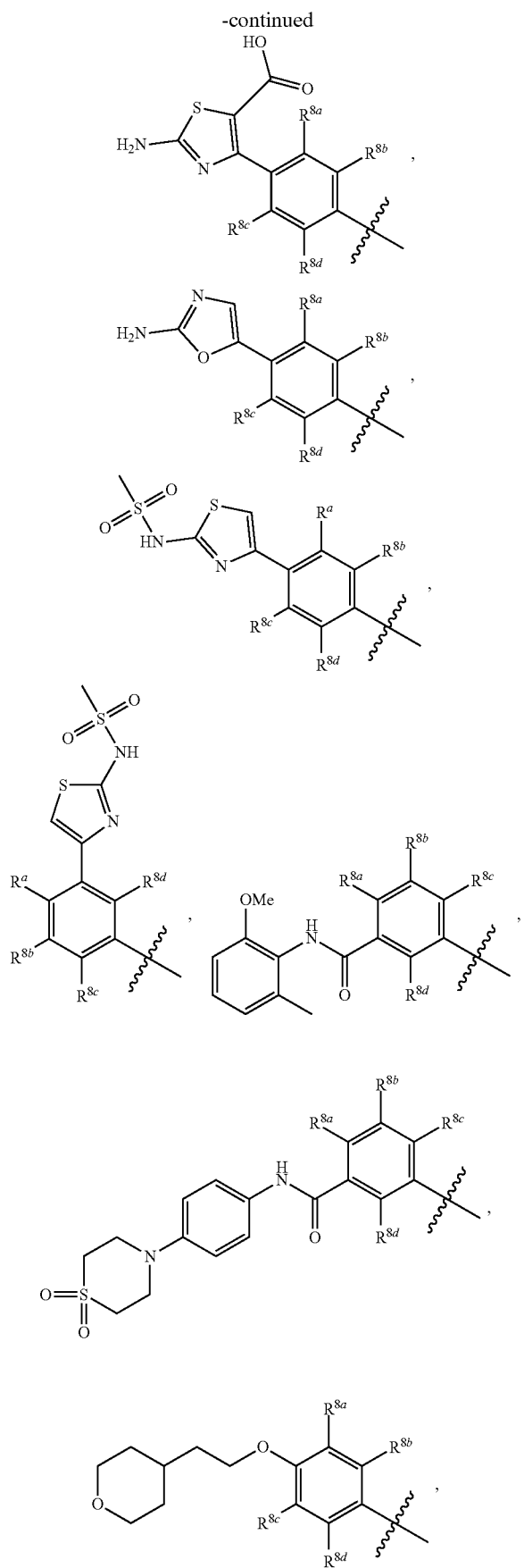
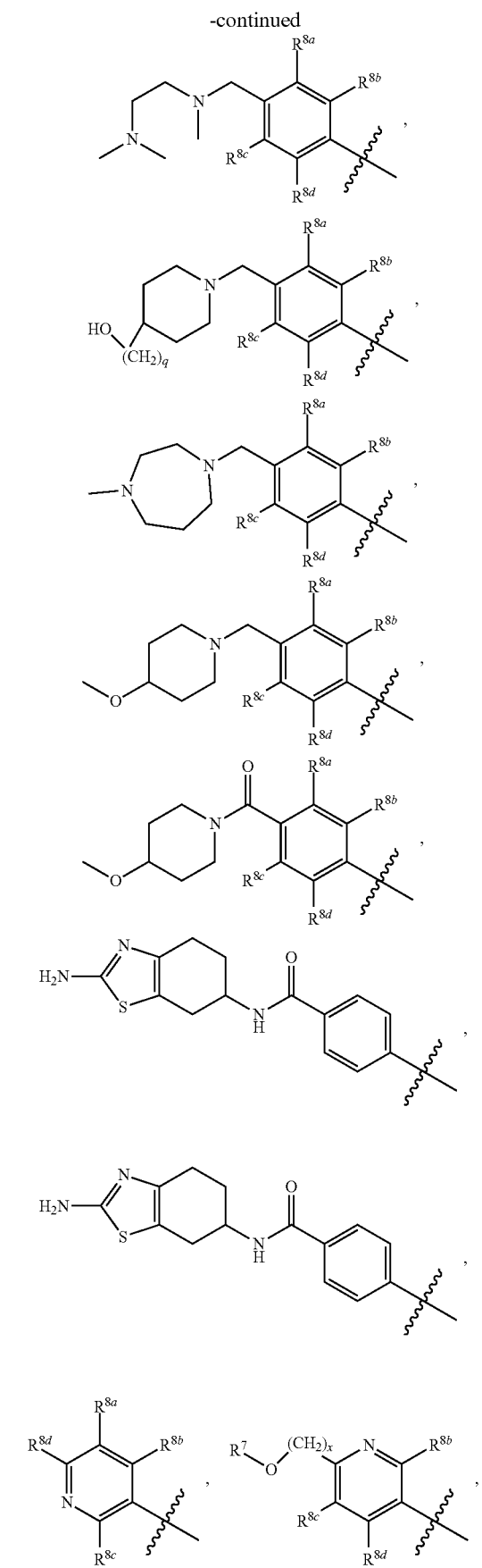

-continued
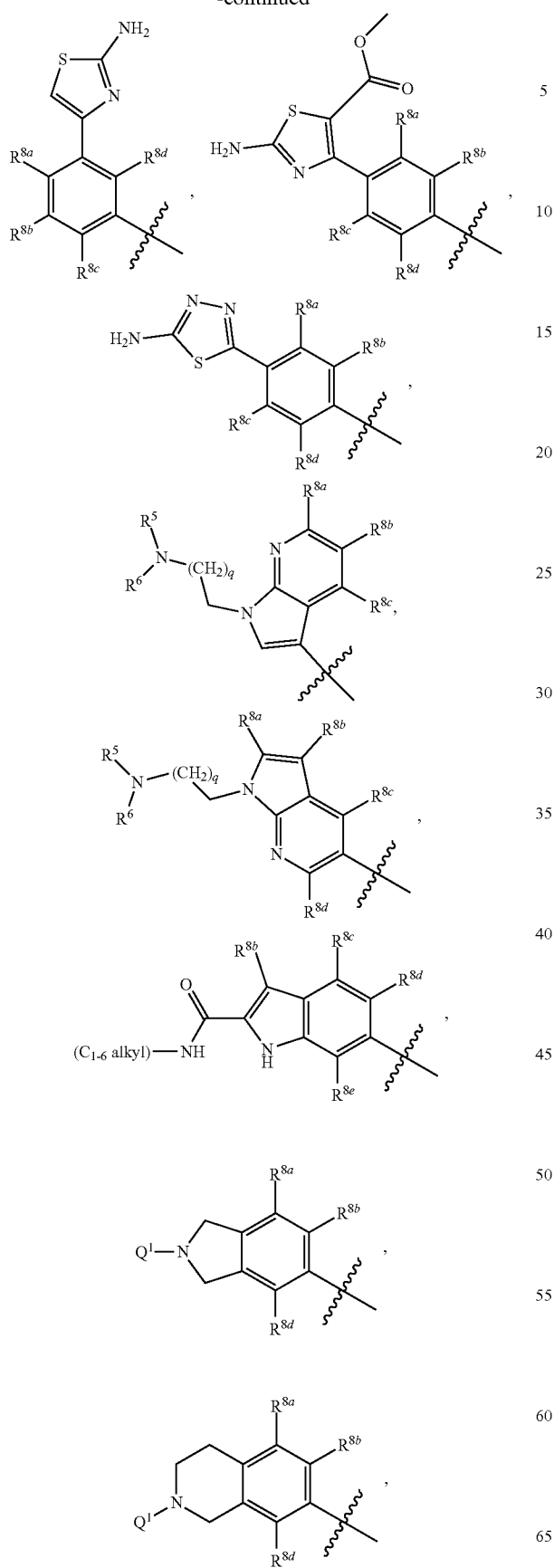
-continued
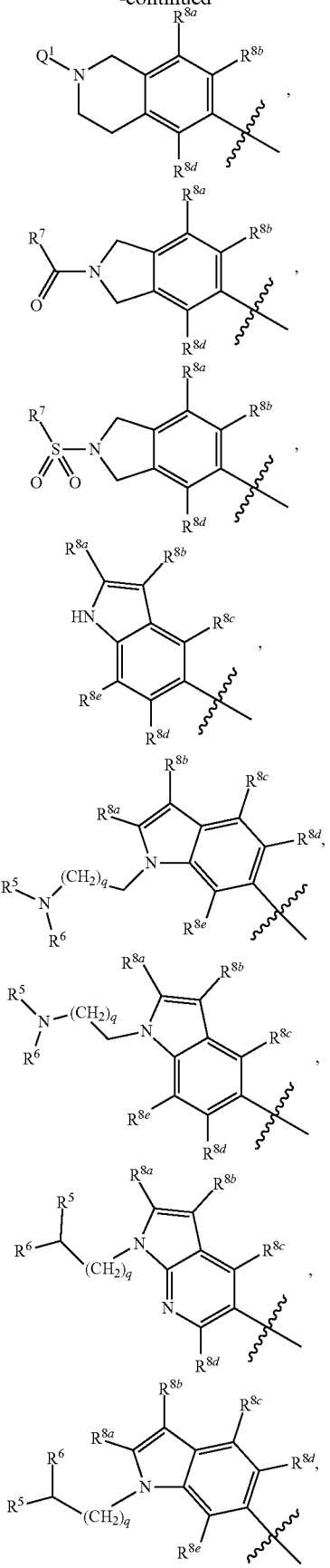

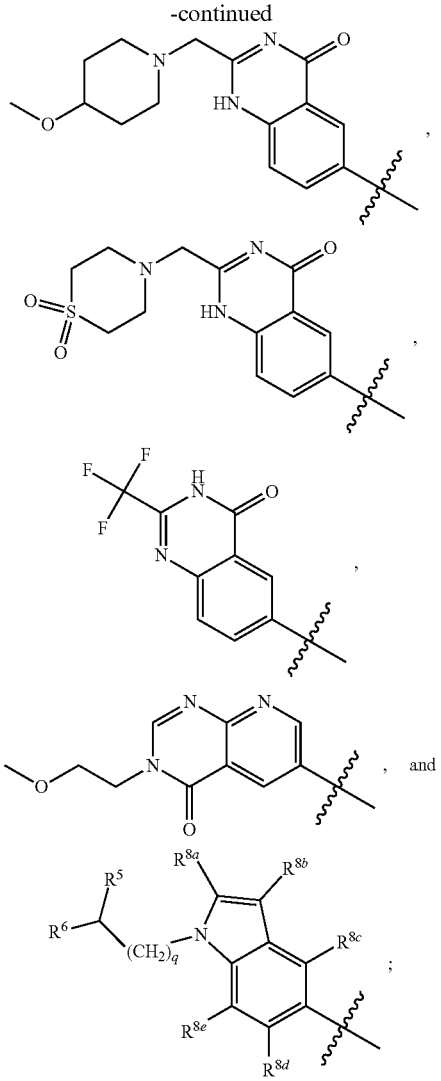

R² is selected from the group consisting of

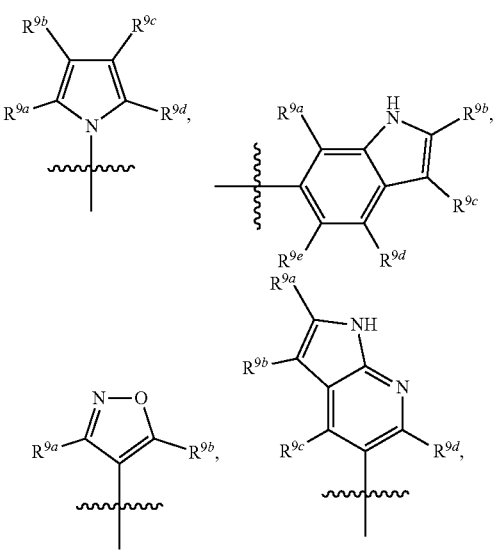

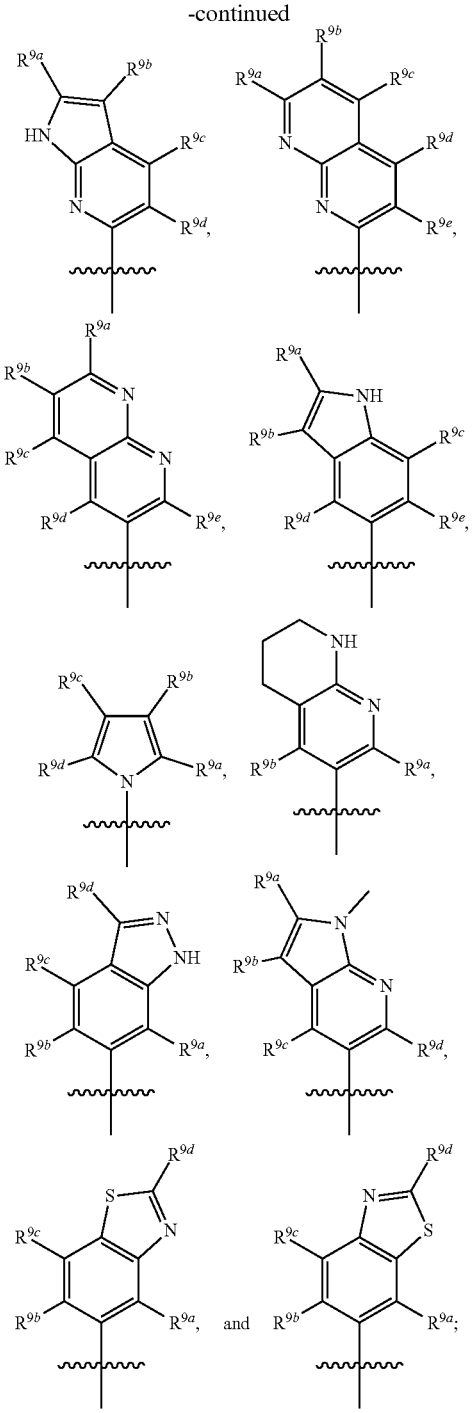

R³ is selected from the group consisting of —CO₂R⁴ᵈ, —C(=O)NH—S(=O)₂NR⁵R⁶, —S(=O)₂NHC(=O)R⁷, —NHS(=O)₂R⁷, and 1H-tetrazol-5-yl;

R⁴ᵃ, R⁴ᵇ, and R⁴ᶜ are each independently selected from the group consisting of fluorine, chlorine, bromine, iodine, and H;

R⁴ᵈ is selected from the group consisting of H, optionally substituted C₁₋₆ linear alkyl, and optionally substituted C₃₋₆ branched alkyl;

R⁵ is selected from the group consisting of H, optionally substituted C₁₋₆ linear alkyl, and optionally substituted C₃₋₆ branched alkyl;

$R^6$ is selected from the group consisting of H, optionally substituted $C_{1-6}$ linear alkyl, and optionally substituted $C_{3-6}$ branched alkyl; or $R^5$ and $R^6$ are taken together with the atoms to which they are connected to form a 3-, 4-, 5-, or 6-membered ring optionally containing a unit selected from the group consisting of oxygen, sulfur, SO, $SO_2$, $CF_2$, NH, $N(C_{1-6}$ alkyl), $N(C_{3-7}$ branched alkyl), $N(C_{3-6}$ cycloalkyl), N(heteroaryl), $NCO(C_{1-6}$alkyl), $NCO(C_{1-6}$ branched alkyl), $NCO(C_{3-6}$ cycloalkyl), $NCO_2(C_{1-6}$ alkyl), $NCO_2(C_{1-6}$ branched alkyl), $NCO_2(C_{3-6}$ cycloalkyl), $NCON(C_{1-6}$ alkyl)$_2$, $SO_2NH_2$, $NSO_2(C_{1-6}$ alkyl), $NSO_2(C_{3-6}$ branched alkyl), $NSO_2(C_{3-6}$ cycloalkyl), and $NSO_2Aryl$;

$R^7$ is selected from the group consisting of H, optionally substituted $C_{1-6}$ linear alkyl, optionally substituted $C_{3-6}$ branched alkyl, $C_{1-6}$ haloalkyl, optionally substituted phenyl, optionally substituted pyridyl, optionally substituted heteroaryl, and —$CH(R^5)(R^6)$;

$R^{8a}$, $R^{8b}$, $R^{8c}$, $R^{8d}$, and $R^{8e}$ are each independently selected from the group consisting of H, halogen, hydroxyl, CN, optionally substituted $C_{1-6}$ linear alkyl, optionally substituted $C_{3-6}$ branched alkyl, and $C_{1-6}$ alkoxy;

$R^{9a}$, $R^{9b}$, $R^{9c}$, $R^{9d}$ and $R^{9e}$ are each independently selected from the group consisting of H, halogen, optionally substituted $C_{1-6}$ linear alkyl, $C_{1-6}$ alkoxy, and optionally substituted $C_{3-6}$ branched alkyl;

$R^{10a}$ and $R^{10b}$ are each independently selected from the group consisting of H, optionally substituted $C_{1-6}$ linear alkyl, and optionally substituted $C_{1-6}$ branched alkyl;

$L^1$ is selected from the group consisting of —C≡C—, —CH=CH— and —$(CH_2)_n$—;

$L^2$ is selected from a group consisting of NH, $(CH_2)_m$, and

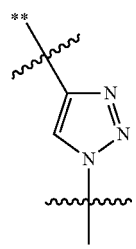

wherein "**" indicates the point of attachment for $R^2$:

$Q^1$ is selected from a group consisting of optionally substituted benzyl, $COR^7$, $SO_2R^7$

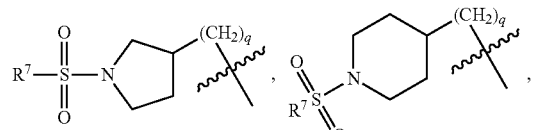

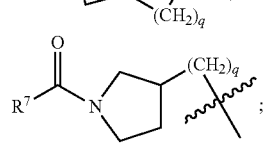

n is 0, 1, 2, or 3; m is 0, 1, 2, or 3; q is 1, 2, 3, or 4; and x is 0, 1, 2, or 3.

In certain embodiments, compound (I) is compound (II):

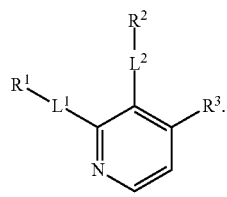

In certain embodiments, compound (I) is compound (III):

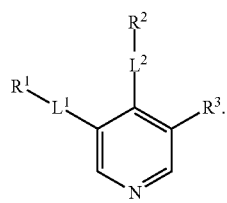

In certain embodiments, compound (I) is compound (IV):

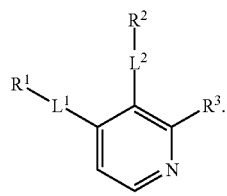

In certain embodiments, compound (I) is compound (V):

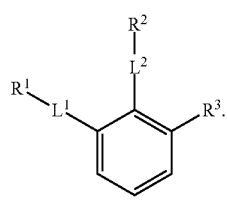

In certain embodiments, compound (I) is compound (VI):

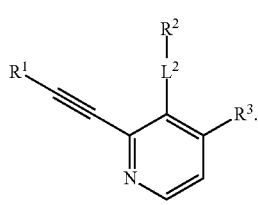

In certain embodiments, compound (I) is compound (VII):

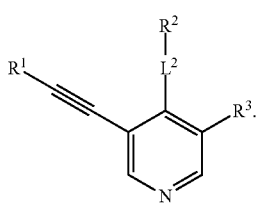

In certain embodiments, compound (I) is compound (VII)

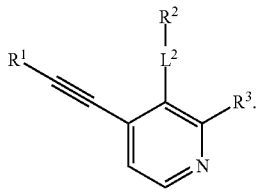

In certain embodiments, compound (I) is compound (IX):

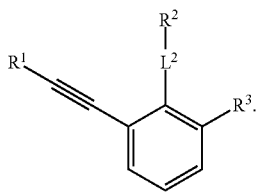

In certain embodiments, compound (I) is compound (XI):

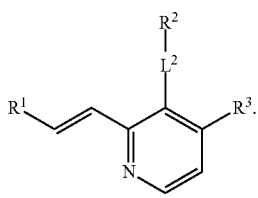

In certain embodiments, compound (I) is compound (XI):

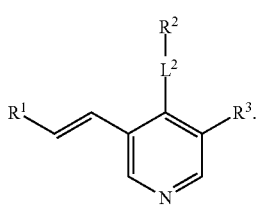

In certain embodiments, compound (I) is compound (XII):

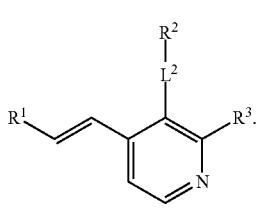

In certain embodiments, compound (I) is compound (XIII):

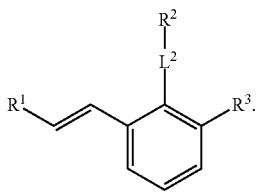

In certain embodiments, compound (I) is compound (XIV):

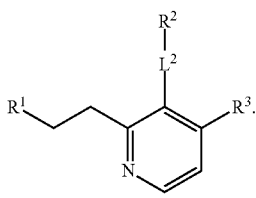

In certain embodiments, compound (I) is compound (XV):

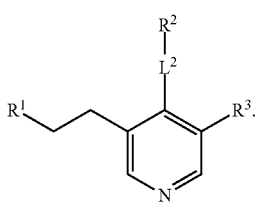

In certain embodiments, compound (I) is compound (XVI):

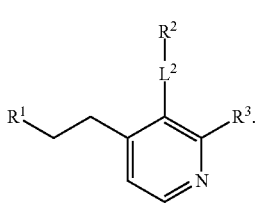

In certain embodiments, compound (I) is compound (XVII):

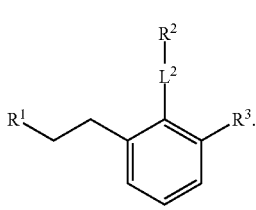

In certain embodiments, $X^1$ is $CR^4a$. In certain embodiments, $X^1$ is N. In certain embodiments, $X^1$ is $CR^{4a}$. In certain embodiments, $X^2$ is N. In certain embodiments, $X^3$ is $CR^{4a}$. In certain embodiments, $X^3$ is N. In certain embodiments, $R^1$ is further optionally substituted phenyl. In certain embodiments, R¹ is further optionally substituted heteroaryl. In certain embodiments, R¹ is further optionally substituted benzyl. In certain embodiments, R¹ is further optionally substituted heteroaryl methyl.

In certain embodiments, R¹ is

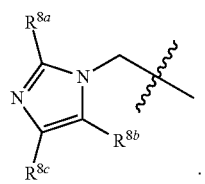

In certain embodiments, R¹ is

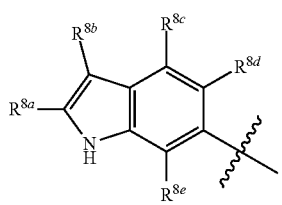

In certain embodiments, R¹ is

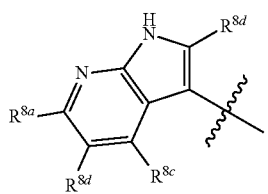

In certain embodiments, R¹ is

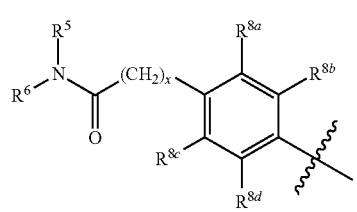

In certain embodiments, R¹ is

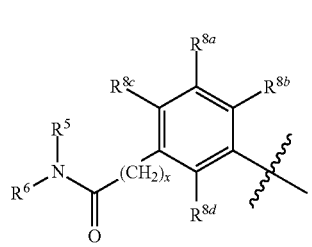

In certain embodiments, R¹ is

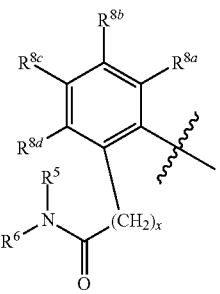

On certain embodiments, R¹ is

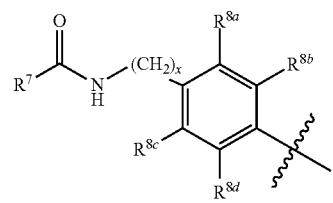

In certain embodiments, R¹ is

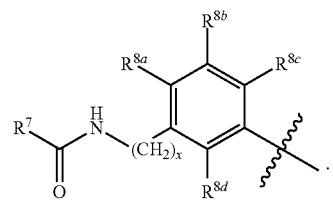

In certain embodiments, R¹ is

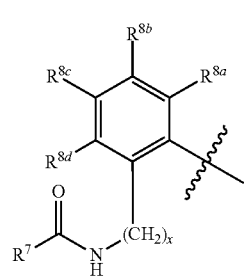

In certain embodiments, R¹ is

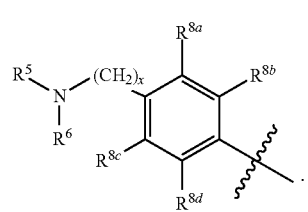

In certain embodiments, R¹ is
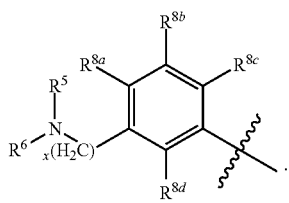
In certain embodiments, R¹ is
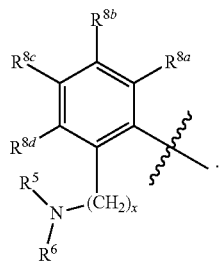
In certain embodiments, R¹ is
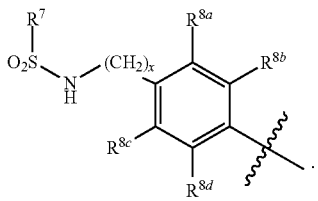
In certain embodiments, R¹ is
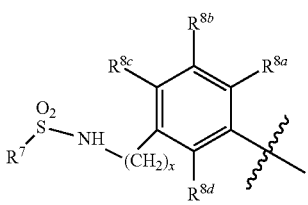
In certain embodiments, R¹ is
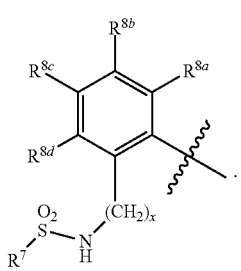
In certain embodiments, R¹ is
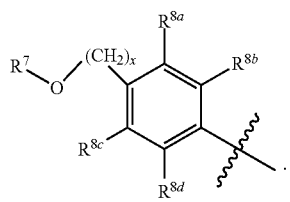
In certain embodiments, R¹ is
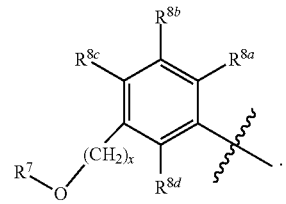
In certain embodiments, R¹ is
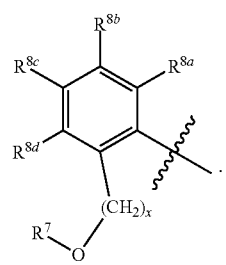
In certain embodiments, R¹ is
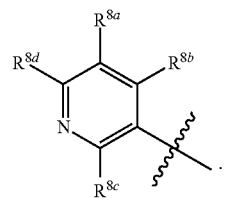
In certain embodiments, R¹ is
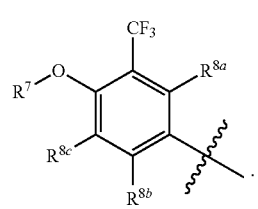

In certain embodiments, R¹ is
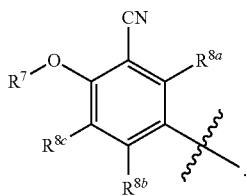
In certain embodiments, R¹ is
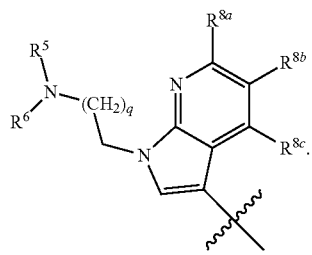
In certain embodiments, R¹ is
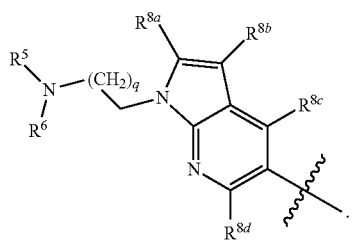
In certain embodiments, R¹ is
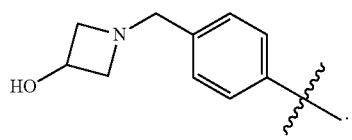 [SMILES: *c1ccc(CN2CC(O)C2)cc1]
In certain embodiments, R¹ is
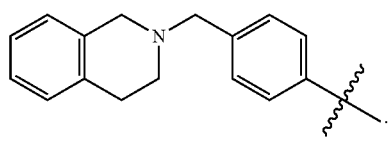 [SMILES: *c1ccc(CN2CCc3ccccc3C2)cc1]
In certain embodiments, R¹ is
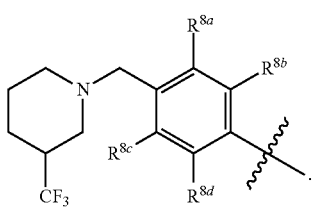
In certain embodiments, R¹ is
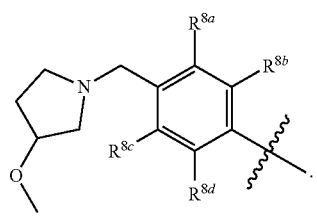
In certain embodiments, R¹ is
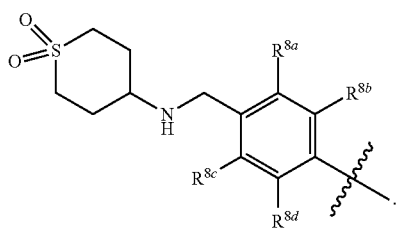
In certain embodiments, R¹ is
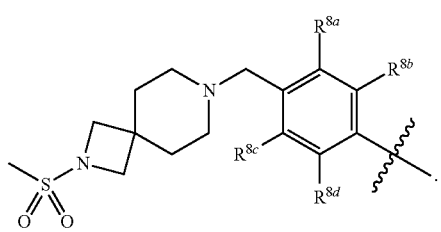
In certain embodiments, R¹ is
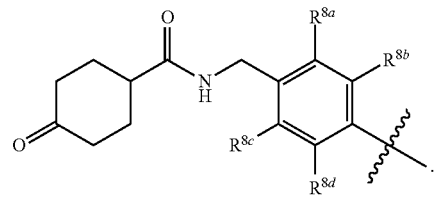
In certain embodiments, R¹ is
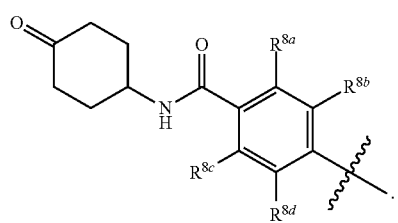

In certain embodiments, R¹ is
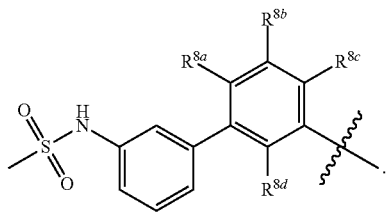
In certain embodiments, R¹ is
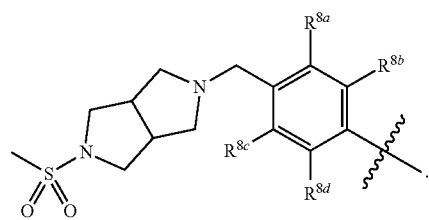
In certain embodiments, R¹ is
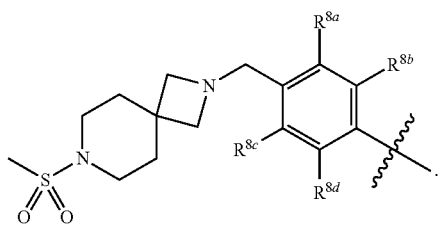
In certain embodiments, R¹ is
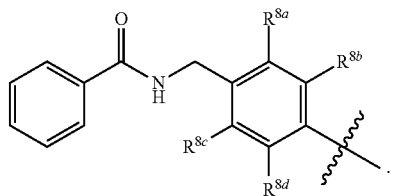
In certain embodiments, R¹ is
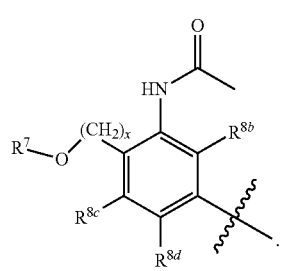
In certain embodiments, R¹ is
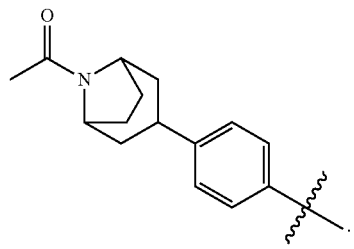 [SMILES: *c1ccc(C2CC3CCC(C2)N3C(C)=O)cc1]
In certain embodiments, R¹ is
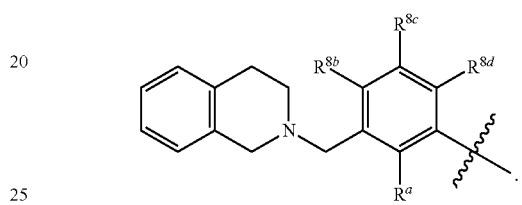
In certain embodiments, R¹ is
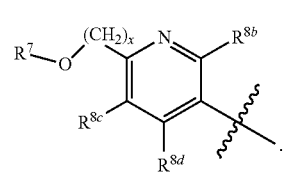
In certain embodiments, R¹ is
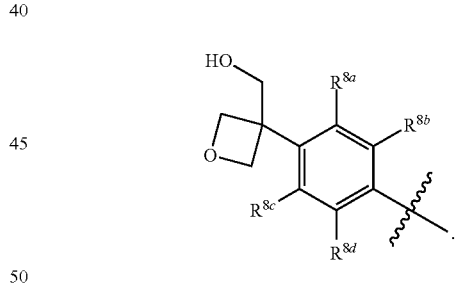
In certain embodiments, R¹ is
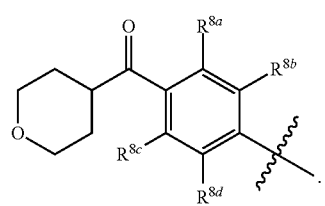

In certain embodiments, R¹ is
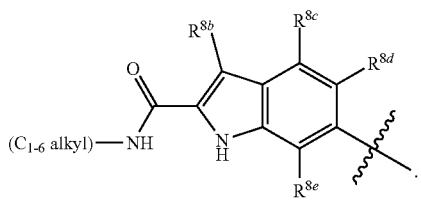
In certain embodiments, R¹ is
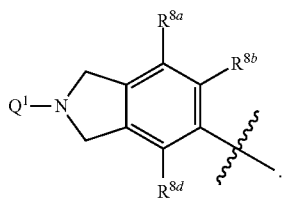
In certain embodiments, R¹ is
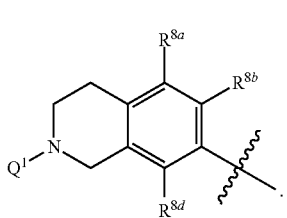
In certain embodiments, R¹ is
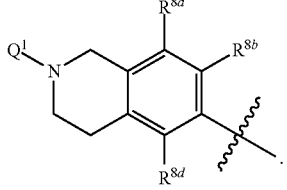
In certain embodiments, R¹ is
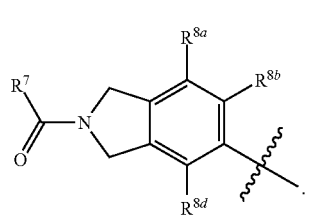
In certain embodiments, R¹ is
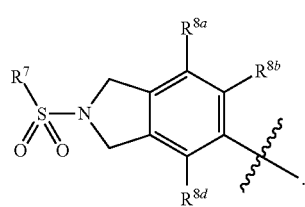
In certain embodiments, R¹ is
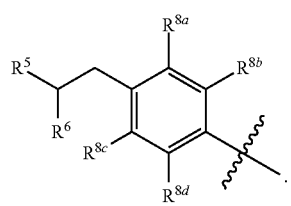
In certain embodiments, R¹ is
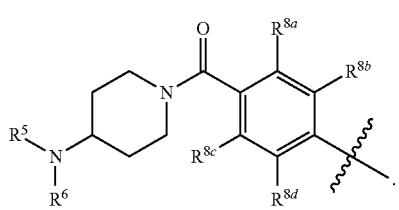
In certain embodiments, R¹ is
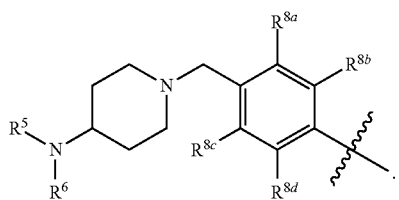
In certain embodiments, R¹ is
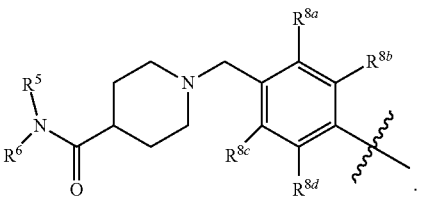
In certain embodiments, R¹ is
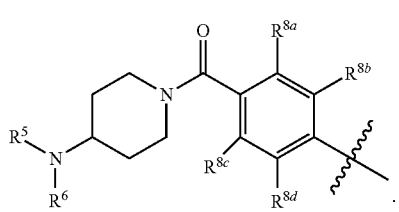

In certain embodiments, R¹ is
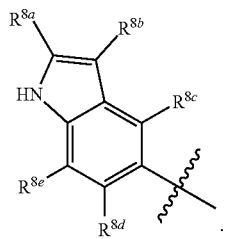
In certain embodiments, R¹ is
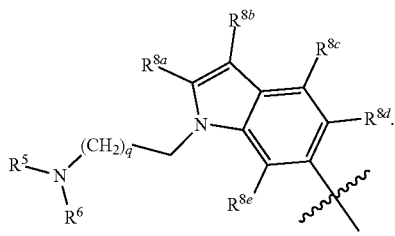
In certain embodiments, R¹ is
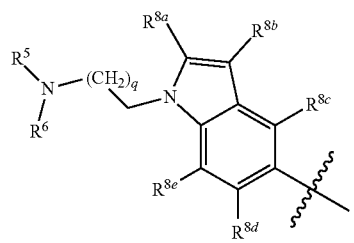
In certain embodiments, R¹ is
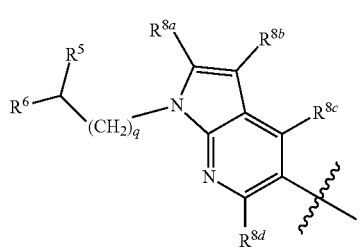
In certain embodiments, R¹ is
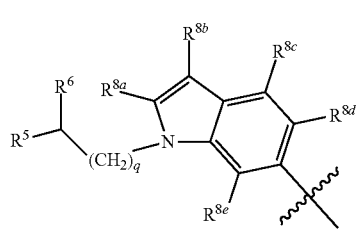
In certain embodiments, R¹ is
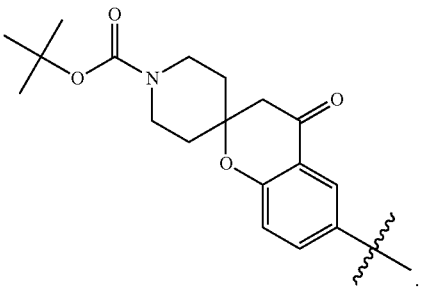 [SMILES: *c1ccc2c(c1)C(=O)CC1(CCN(C(=O)OC(C)(C)C)CC1)O2 ; "."]
In certain embodiments, R¹ is
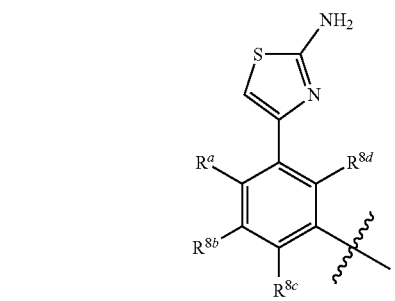
In certain embodiments, R¹ is
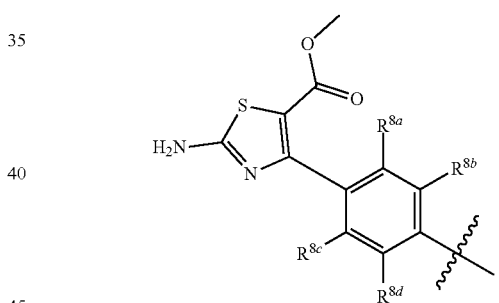
In certain embodiments, R¹ is
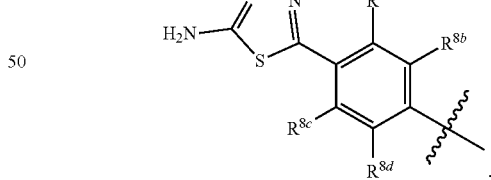
In certain embodiments, R¹ is
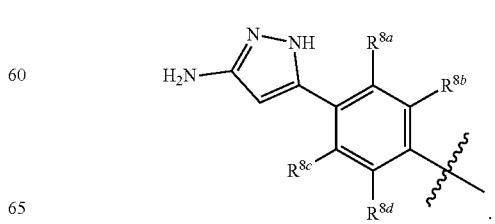

In certain embodiments, R¹ is
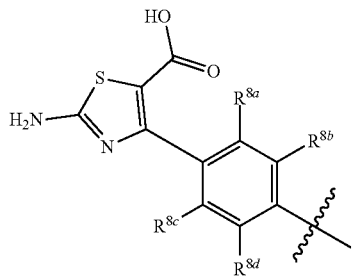
In certain embodiments, R¹ is
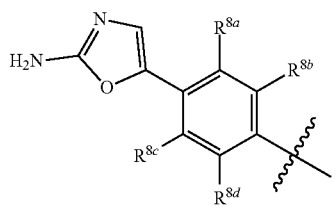
In certain embodiments, R¹ is
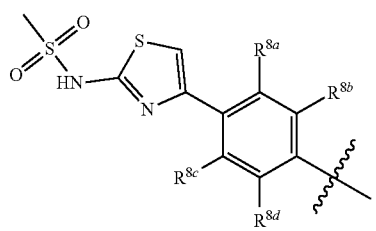
In certain embodiments, R¹ is
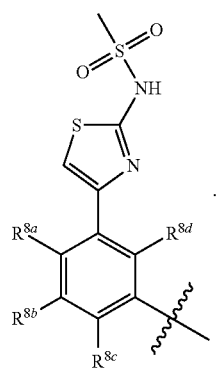
In certain embodiments, R¹ is
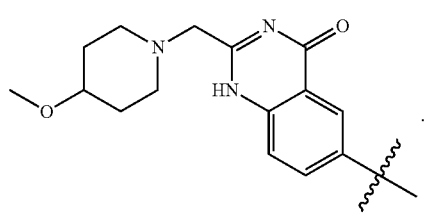 [SMILES: *c1ccc2[nH]c(CN3CCC(OC)CC3)nc(=O)c2c1]
In certain embodiments, R¹ is
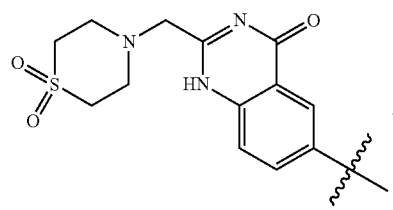
In certain embodiments, R¹ is
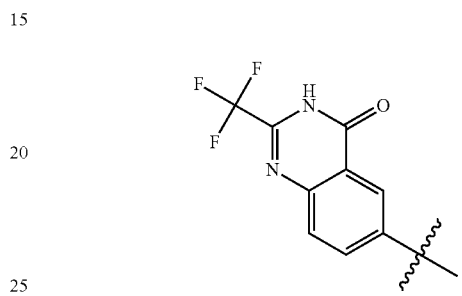
In certain embodiments, R¹ is
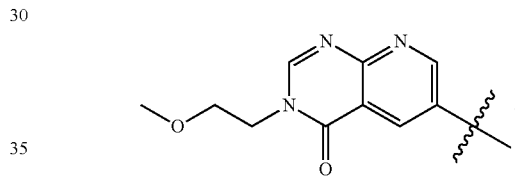
In certain embodiments, R¹ is
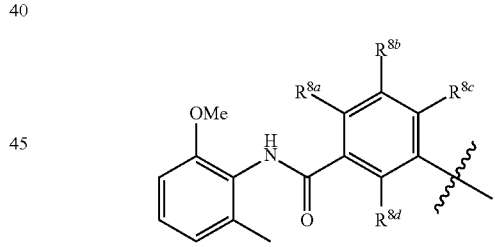
In certain embodiments, R¹ is
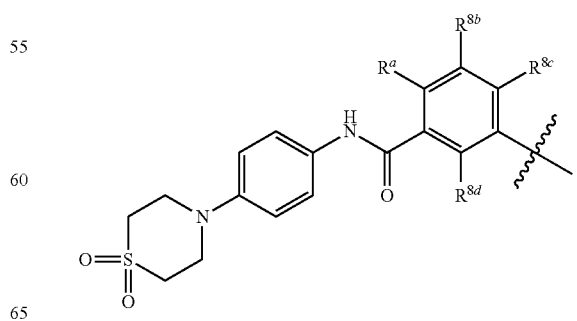

In certain embodiments, R¹ is

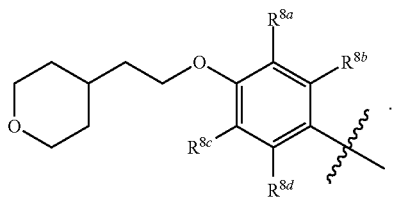

In certain embodiments, R¹ is

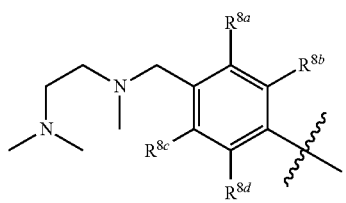

In certain embodiments, R¹ is

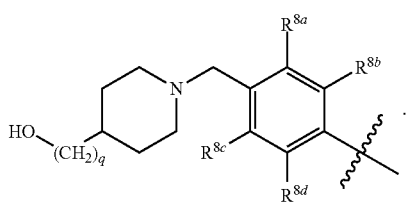

In certain embodiments, R¹ is

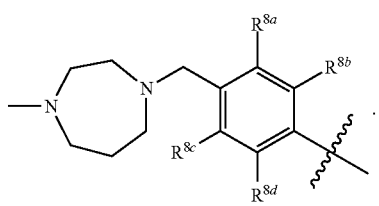

In certain embodiments, R¹ is

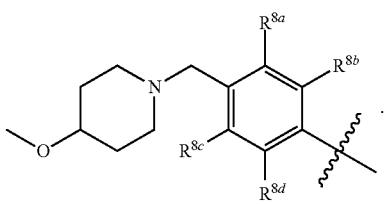

In certain embodiments, R¹ is

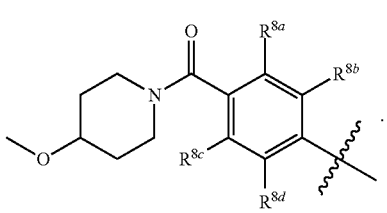

In certain embodiments, R¹ is

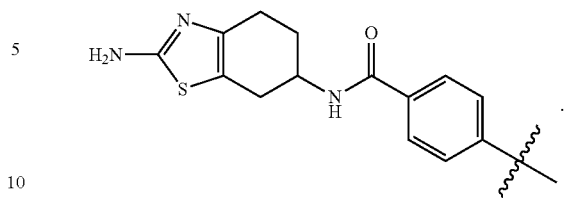

In certain embodiments, R¹ is

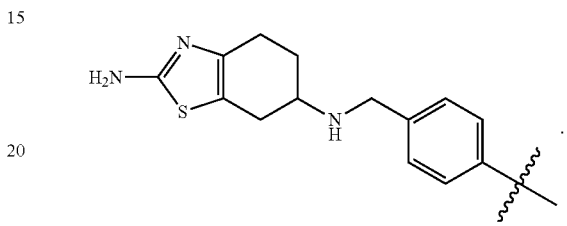

In certain embodiments, R¹ is

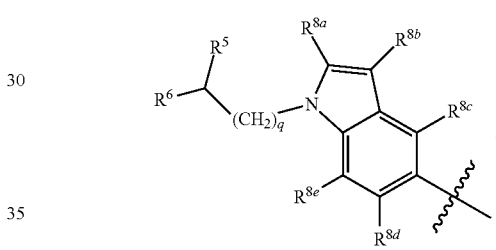

In certain embodiments, R² is further H. In certain embodiments, R² is further $NR^{10a}R^{10b}$. In certain embodiments, R² is further fluorine. In certain embodiments, R² is further optionally substituted phenyl. In certain embodiments, R² is further optionally substituted heteroaryl. In certain embodiments, R² is

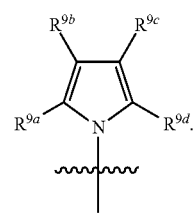

In certain embodiments, R² is

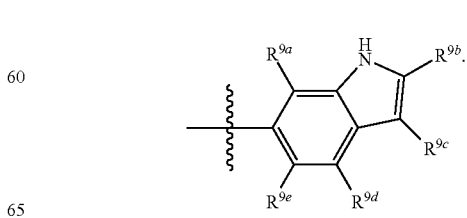

In certain embodiments, R² is
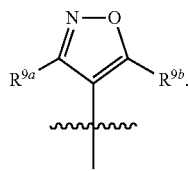
In certain embodiments, R² is
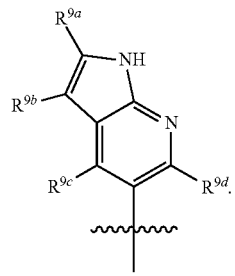
In certain embodiments, R² is
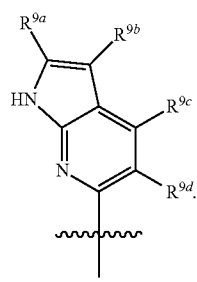
In certain embodiments, R² is
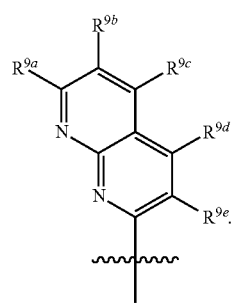
In certain embodiments, R² is
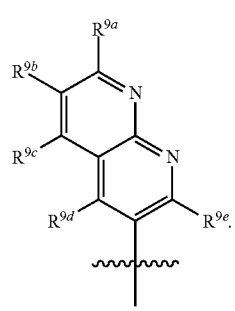
In certain embodiments, R² is
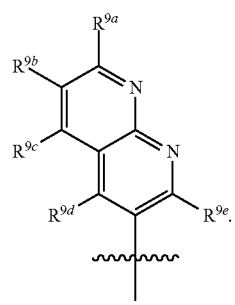
In certain embodiments, R² is
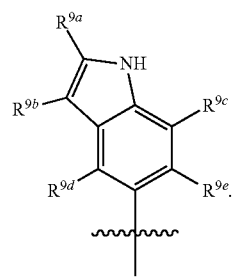
In certain embodiments, R² is
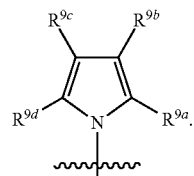
In certain embodiments, R² is
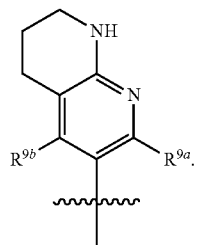
In certain embodiments, R² is
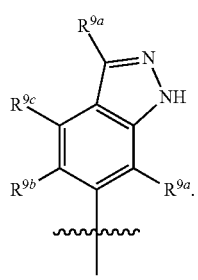

In certain embodiments, R² is

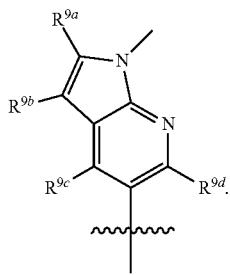

In certain embodiments, R² is

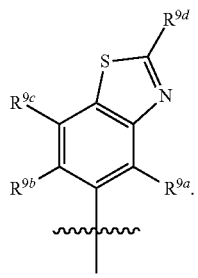

In certain embodiments, R² is

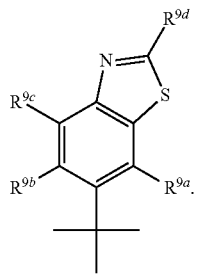

In certain embodiments, R³ is $CO_2R^{4d}$. In certain embodiments, R³ is $-C(=O)NHS(=O)_2NR^5R^6$. In certain embodiments, R³ is $-S(=O)_2NHC(=O)R^7$. In certain embodiments, R³ is $-NHS(=O)R^7$. In certain embodiments, R³ is 1H-tetrazol-5-yl.

In certain embodiments, $R^{4a}$ is H. In certain embodiments, $R^{4a}$ is fluorine. In certain embodiments, $R^{4a}$ is chlorine. In certain embodiments, $R^{4a}$ is bromine. In certain embodiments, $R^{4a}$ is iodine. In certain embodiments, $R^{4b}$ is H. In certain embodiments, $R^{4b}$ is fluorine. In certain embodiments, $R^{4b}$ is chlorine. In certain embodiments, $R^{4b}$ is bromine. In certain embodiments, $R^{4b}$ is iodine. In certain embodiments, $R^{4c}$ is H. In certain embodiments, $R^{4b}$ is fluorine. In certain embodiments, $R^{4c}$ is chlorine. In certain embodiments, $R^{4c}$ is bromine. In certain embodiments, $R^{4c}$ is iodine. In certain embodiments, $R^{4d}$ is H. In certain embodiments, $R^{4d}$ is optionally substituted $C_{1-6}$ linear alkyl. In certain embodiments, $R^{4d}$ is optionally substituted $C_3$ branched alkyl.

In certain embodiments, R⁵ is H, In certain embodiments, R⁵ is optionally substituted $C_{1-6}$ linear alkyl. In certain embodiments, R⁵ is optionally substituted $C_{3-6}$ branched alkyl.

In certain embodiments, R⁶ is H. In certain embodiments, R⁶ is optionally substituted $C_{1-6}$ linear alkyl. In certain embodiments, R⁶ is optionally substituted $C_{3-6}$ branched alkyl.

In certain embodiments, R⁵ and R⁶ are taken together with the atoms to which they are connected to form a 3, 4, 5, or 6 membered ring optionally containing a unit selected from the group consisting of oxygen, sulfur, SO, $SO_2$, $CF_2$, NH, $N(C_{1-6}$ alkyl), $N(C_{3-7}$ branched alkyl), $N(C_{3-6}$ cycloalkyl), N(heteroaryl), $NCO(C_{1-6}$ alkyl), $NCO(C_{3-6}$ branched alkyl), $NCO(C_{3-6}$ cycloalkyl), $NCO_2(C_{1-6}$ alkyl), $NCO_2(C_{1-6}$ branched alkyl), $NCO_2(C_{3-6}$ cycloalkyl), $NCON(C_{1-6}$ alkyl)$_2$, $SO_2NH_2$, $NSO_2(C_{1-6}$ alkyl), $NSO_2(C_{3-6}$ branched alkyl), $NSO_2(C_{3-6}$ cycloalkyl), and $NSO_2Aryl$.

In certain embodiments, R⁷ is H. In certain embodiments, R⁷ is optionally substituted $C_{1-6}$ linear alkyl. In certain embodiments, R⁷ is optionally substituted $C_{3-6}$ branched alkyl. In certain embodiments, R⁷ is $C_{1-6}$ haloalkyl. In certain embodiments, R⁷ is optionally substituted phenyl. In certain embodiments, R⁷ is optionally substituted pyridyl. In certain embodiments, R⁷ is optionally substituted heteroaryl. In certain embodiments, R⁷ is $-CH(R^5)(R^6)$.

In certain embodiments, $R^{8a}$ is H. In certain embodiments, $R^{8a}$ is optionally substituted $C_{1-6}$ linear alkyl. In certain embodiments, $R^{8a}$ is optionally substituted $C_{3-6}$ branched alkyl. In certain embodiments, $R^{8a}$ is halogen. In certain embodiments, $R^{8a}$ is hydroxyl. In certain embodiments, $R^{8a}$ is CN. In certain embodiments, $R^{8a}$ is $C_{1-6}$ alkoxy. In certain embodiments, $R^{8a}$ is $-(CH_2)_qNR^5R^6$. In certain embodiments. $R^{8b}$ is H. In certain embodiments, $R^{8b}$ is optionally substituted $C_{1-6}$ linear alkyl. In certain embodiments, $R^{8b}$ is optionally substituted $C_{3-6}$ branched alkyl. In certain embodiments, $R^{8b}$ is halogen. In certain embodiments, $R^{8b}$ is hydroxyl. In certain embodiments, $R^{8b}$ is CN. In certain embodiments, $R^{8b}$ is $C_{1-6}$ alkoxy. In certain embodiments, $R^{8b}$ is $-(CH_2)_qNR^5R^6$. In certain embodiments, $R^{8c}$ is H. In certain embodiments, $R^{8c}$ is optionally substituted $C_{1-6}$ linear alkyl. In certain embodiments, $R^{8c}$ is optionally substituted $C_{3-6}$ branched alkyl. In certain embodiments, $R^{8c}$ is halogen. In certain embodiments, $R^{8c}$ is hydroxyl. In certain embodiments, $R^{8c}$ is CN. In certain embodiments. $R^{8c}$ is $C_{1-6}$ alkoxy. In certain embodiments, $R^{8d}$ is H. In certain embodiments, $R^{8c}$ is optionally substituted $C_{1-6}$ linear alkyl. In certain embodiments, $R^{8d}$ is optionally substituted $C_{3-6}$ branched alkyl.

In certain embodiments, $R^{9a}$ is H. In certain embodiments, $R^{9a}$ is optionally substituted $C_{1-6}$ linear alkyl. In certain embodiments, $R^{9a}$ is optionally substituted $C_{3-6}$ branched alkyl. In certain embodiments, $R^{9a}$ is halogen. In certain embodiments, $R^{9a}$ is $C_{1-6}$ alkoxy. In certain embodiments, $R^{9b}$ is H. In certain embodiments, $R^{9b}$ is optionally substituted $C_{1-6}$ linear alkyl. In certain embodiments, $R^{9b}$ is optionally substituted $C_{3-6}$ branched alkyl. In certain embodiments, $R^{9b}$ is halogen. In certain embodiments, $R^{9b}$ is $C_{1-6}$ alkoxy. In certain embodiments, $R^{9c}$ is H. In certain embodiments, $R^{9c}$ is optionally substituted $C_{1-6}$ linear alkyl. In certain embodiments, $R^{9c}$ is optionally substituted $C_{3-6}$ branched alkyl. In certain embodiments, $R^{9c}$ is halogen. In certain embodiments, $R^{9c}$ is $C_{1-6}$ alkoxy. In certain embodiments, $R^{9d}$ is H. In certain embodiments, $R^{9d}$ is optionally substituted $C_{1-6}$ linear alkyl. In certain embodiments, $R^{9d}$ is optionally substituted $C_{3-6}$ branched alkyl. In certain embodiments, $R^{9d}$ is halogen. In certain embodiments. $R^{9d}$ is $C_{1-6}$ alkoxy. In certain embodiments, $R^{9e}$ is H. In certain embodiments, $R^{9e}$ is optionally substituted $C_{1-6}$ linear alkyl. In certain embodiments, $R^{9e}$ is optionally substituted $C_{3-6}$ branched alkyl. In certain embodiments, $R^{9e}$ is halogen. In certain embodiments, $R^{9e}$ is $C_{1-6}$alkoxy.

In certain embodiments, $R^{10a}$ is H. In certain embodiments, $R^{10a}$ is optionally substituted $C_{1-6}$ linear alkyl. In certain embodiments, $R^{10a}$ is optionally substituted $C_{1-6}$ branched alkyl. In certain embodiments, $R^{10b}$ is H. In certain embodiments, $R^{10b}$ is optionally substituted $C_{1-6}$ linear alkyl. In certain embodiments, $R^{10b}$ is optionally substituted $C_{1-6}$ branched alkyl.

In certain embodiments, $L^1$ is —C≡C—. In certain embodiments, $L^1$ is —CH=CH—. In certain embodiments, $L^1$ is $(CH_2)_n$. In certain embodiments, $L^2$ is NH. In certain embodiments, $L^2$ is $(CH_2)_m$. In certain embodiments. $L^2$ is

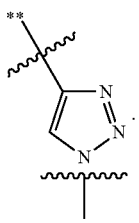

In certain embodiments, $Q^1$ is

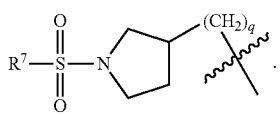

In certain embodiments, $Q^1$ is

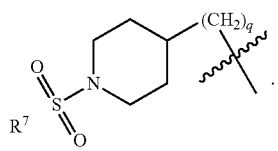

In certain embodiments, $Q^1$ is

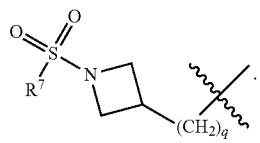

In certain embodiments, $Q^1$ is

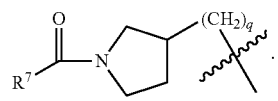

In certain embodiments, n is 0. In certain embodiments, n is 1. In certain embodiments, n is 2. In certain embodiments, n is 3. In certain embodiments, m is 0. In certain embodiments, m is 1. In certain embodiments, m is 2. In certain embodiments, m is 3. In certain embodiments, q is 1. In certain embodiments, q is 2. In certain embodiments, q is 3. In certain embodiments, q is 4. In certain embodiments, x is 0. In certain embodiments, x is 1. In certain embodiments, x is 2. In certain embodiments, x is 3.

In certain embodiments, compound (I) is compound (XVIII) or a pharmaceutically acceptable salt form thereof:

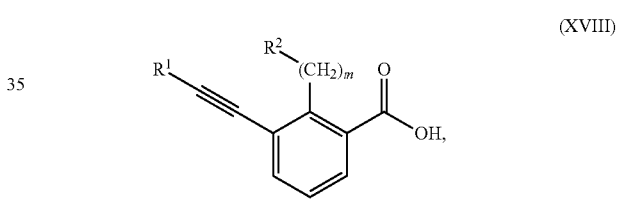

(XVIII)

wherein non-limiting examples of $R^1$, $R^2$, and m are defined in Table 1.

TABLE 1

| Entry | $R^1$ | $R^2$ | m |
|---|---|---|---|
| 1 | phenyl | 1H-pyrrolo[2,3-b]pyridine-5-yl | 0 |
| 2 | 4-fluorophenyl | 1H-pyrrolo[2,3-b]pyridine-5-yl | 0 |
| 3 | 4-(oxan-4-yloxy)phenyl | 1H-pyrrolo[2,3-b]pyridine-5-yl | 0 |
| 4 | 4-methoxyphenyl | 1H-pyrrolo[2,3-b]pyridine-5-yl | 0 |
| 5 | 3-carbamoyl-5-methoxyphenyl | 1H-pyrrolo[2,3-b]pyridine-5-yl | 0 |
| 6 | 2,4-difluorophenyl | 1H-pyrrolo[2,3-b]pyridine-5-yl | 0 |
| 7 | 4-acetamidophenyl | 1H-pyrrolo[2,3-b]pyridine-5-yl | 0 |
| 8 | 4-(4-methoxybenzene-sulfonamido)phenyl | 1H-pyrrolo[2,3-b]pyridine-5-yl | 0 |
| 9 | 4-(thiophene-2-sulfonamido)phenyl | 1H-pyrrolo[2,3-b]pyridine-5-yl | 0 |
| 10 | 4-(pyridine-3-amido)phenyl | 1H-pyrrolo[2,3-b]pyridine-5-yl | 0 |
| 11 | 4-methanesulfonamidophenyl | 1H-pyrrolo[2,3-b]pyridine-5-yl | 0 |
| 12 | 4-aminophenyl | 1H-pyrrolo[2,3-b]pyridine-5-yl | 0 |
| 13 | 4-(4-methoxybenzene-sulfonamido)phenyl | Indol-6-yl | 0 |
| 14 | 4-(thiophene-2-sulfonamido)phenyl | Indol-6-yl | 0 |
| 15 | 4-(pyridine-3-amido)phenyl | Indol-6-yl | 0 |
| 16 | 4-methanesulfonamidophenyl | Indol-6-yl | 0 |
| 17 | 4-(3-chloro-4-fluorobenzenesulfon amido)phenyl | Indol-6-yl | 0 |
| 18 | 3-carbamoyl-5-methoxyphenyl | Indol-6-yl | 0 |
| 19 | 4-[(2-methoxyethyl)(methyl)carbamoyl]phenyl | Indol-6-yl | 0 |
| 20 | 4-{[2-(dimethylamino)ethyl]carbamoyl}phenyl | Indol-6-yl | 0 |
| 21 | 4-(piperazine-1-carbonyl)phenyl | Indol-6-yl | 0 |

TABLE 1-continued

| Entry | R$^1$ | R$^2$ | m |
|---|---|---|---|
| 22 | 4-fluoro-3-(oxan-4-yloxy)phenyl | Indol-6-yl | 0 |
| 23 | 4-{[(4-carboxyphenyl)formamido]methyl}phenyl | Indol-6-yl | 0 |
| 23 | 4-[(3-hydroxyazetidin-1-yl)methyl]phenyl | Indol-6-yl | 0 |
| 24 | 3-(3-methanesulfonamidophenyl)phenyl | Indol-6-yl | 0 |
| 25 | 4-[(4-methoxypiperidin-1-yl)methyl]phenyl | Indol-6-yl | 0 |
| 26 | 4-[(4,4-difluoropiperidin-1-yl)methyl]phenyl | Indol-6-yl | 0 |
| 27 | 4-[(4-hydroxypiperidin-1-yl)methyl]phenyl | Indol-6-yl | 0 |
| 28 | 4-[(phenylformamido)methyl]phenyl | Indol-6-yl | 0 |
| 29 | 4-(oxan-4-ylmethoxy)phenyl | Indol-6-yl | 0 |
| 30 | 4-[2-(oxan-4-yl)ethoxy]phenyl | Indol-6-yl | 0 |
| 31 | 4-{[(2-fluorophenyl)formamido]methyl}phenyl | Indol-6-yl | 0 |
| 32 | 4-[(dimethylamino)methyl]phenyl | Indol-6-yl | 0 |
| 33 | 4-(aminomethyl)phenyl | Indol-6-yl | 0 |
| 34 | 4-{[(2-methoxyethyl)(methyl)amino]methyl}phenyl | Indol-6-yl | 0 |
| 35 | 4-{[(2-carboxyphenyl)formamido]methyl}phenyl | Indol-6-yl | 0 |
| 36 | 3-(morpholin-4-ylmethyl)phenyl | Indol-6-yl | 0 |
| 37 | 4-[(1,1-dioxo-1λ$^6$-thian-4-yl)oxy]phenyl | Indol-6-yl | 0 |
| 38 | 4-oxo-3,4-dihydroquinazolin-7-yl | Indol-6-yl | 0 |
| 39 | 2-methyl-4-oxo-3,4-dihydroquinazolin-7-yl | Indol-6-yl | 0 |
| 40 | 4-(morpholin-4-ylmethyl)phenyl | Indol-6-yl | 0 |
| 41 | 4-[(4-ethylpiperazin-1-yl)methyl]phenyl | Indol-6-yl | 0 |
| 42 | 4-[(4-methylpiperazin-1-yl)methyl]phenyl | Indol-6-yl | 0 |
| 43 | 4-[(1,1-dioxo-1λ$^6$-thiomorpholin-4-yl)methyl]phenyl | Indol-6-yl | 0 |
| 44 | 4-({[2-(dimethylamino)ethyl](meyhyl)amino}methyl)phenyl | Indol-6-yl | 0 |
| 45 | 4-{[4-(2-hydroxyethyl)piperidin-1-yl]methyl}phenyl | Indol-6-yl | 0 |
| 46 | 4-(oxan-4-yloxy)-3-(trifluoromethyl)phenyl | Indol-6-yl | 0 |
| 47 | 4-[(4-methyl-1,4-diazepan-1-yl)methyl]phenyl | Indol-6-yl | 0 |
| 48 | phenyl | 5-fluoro-indol-6-yl | 0 |
| 49 | phenyl | 7-fluoro-indol-6-yl | 0 |
| 50 | phenyl | 1,3-benzothiazol-5-yl | 0 |
| 51 | phenyl | 2-methyl-1,3-benzothiazol-5-yl | 0 |
| 52 | phenyl | 1-methyl-1H-pyrrolo[2,3-b]pyridin-6-yl | 0 |
| 53 | phenyl | 1,8-naphthyridin-3-yl | 0 |
| 54 | phenyl | 1,8-naphthyridin-2-yl | 0 |
| 55 | 1-[3-(morpholin-4-yl)propyl]-1H-pyrrolo[2,3-b]pyridin-3-yl | Indol-6-yl | 0 |
| 56 | 1-[2-(morpholin-4-yl)ethyl]-1H-pyrrolo[2,3-b]pyridin-3-yl | Indol-6-yl | 0 |
| 57 | 1-[2-(dimethylamino)ethyl]-1H-pyrrolo[2,3-b]pyridin-3-yl | Indol-6-yl | 0 |
| 58 | 1-[3-(dimethylamino)propyl]-1H-pyrrolo[2,3-b]pyridin-3-yl | Indol-6-yl | 0 |
| 59 | 1-[2-(dimethylamino)ethyl]-1H-pyrrolo[2,3-b]pyridin-3-yl | Indol-6-yl | 0 |
| 60 | 1-8-naphthyridin-2-yl | Indol-6-yl | 0 |
| 61 | 2-(5,6,7,8-tetrahydro-1,8-naphthyridin-3-yl) | Indol-6-yl | 0 |
| 62 | 1-[2-(morpholin-4-yl)ethyl]-1H-pyrrolo[2,3-b]pyridin-5-yl | Indol-6-yl | 0 |
| 63 | 1-[2-(dimethylamino)ethyl]-1H-pyrrolo[2,3-b]pyridin-5-yl | Indol-6-yl | 0 |
| 64 | 4-{8-azabicyclo[3.2.1]octan-3-yl}phenyl | Indol-6-yl | 0 |

In certain embodiments, R$^1$ is at least one selected form the group consisting of: 4-acetamidophenyl; 4-(aminoethyl)phenyl; 4-aminophenyl; 4-{8-azabicyclo[3.2.1]octan-3-yl}phenyl; 3-carbamoyl-5-methoxyphenyl; 4-{[(2-carboxyphenyl)formamido]methyl} phenyl; 4-{[(4-carboxyphenyl) formamido]methyl} phenyl; 4-(3-chloro-4-fluorobenzenesulfon amido) phenyl; 2,4-difluorophenyl; 4-[(4,4-difluoropiperidin-1-yl)methyl]phenyl; 4-{2-(dimethylamino)ethyl]carbamoyl} phenyl; 4-({[2-(dimethylamino)ethyl](methyl)amino}methyl)phenyl; 1-[2-(dimethylamino)ethyl]-1H-pyrrolo[2,3-b]pyridin-3-yl; 1-[3-(dimethylamino) propyl]-1H-pyrrolo[2,3-b]pyridin-3-yl; 4-[(dimethylamino)methyl]phenyl; 4-[(1,1-dioxo-1λ$^6$-thian-4-yl)oxy]phenyl; 4-[(1,1-dioxo-1λ$^6$-thiomorpholin-4-yl) methyl] phenyl; 4-[(4-ethylpiperazin-1-yl)methyl]phenyl; 4-fluoro-3-(oxan-4-yloxy)phenyl; 4-fluorophenyl; 4-{[(2-fluorophenyl) formamido]methyl}phenyl; 4-[(3-hydroxy azetidin-1-yl)methyl]phenyl; 4-{[4-(2-hydroxyethyl) piperidin-1-yl]methyl} phenyl; 4-[(4-hydroxypiperidin-1-yl)methyl]phenyl; 4-methanesulfonamidophenyl; 3-(3-methanesulfonamide phenyl)phenyl; 4-(4-methoxybenzenesulfonamido)phenyl; 4-{[(2-methoxyethyl)(methyl)amino] methyl}phenyl; 4-[(2-methoxyethyl)(methyl)carbamoyl] phenyl; 4-methoxyphenyl; 4-[(4-methoxypiperidin-1-yl) methyl]phenyl; 4-[(4-methyl-1,4-diazepan-1-yl)methyl] phenyl; 4-[(4-methylpiperazin-1-yl)methyl]phenyl;

2-methyl-4-oxo-3,4-dihydroquinazolin-7-yl; 3-(morpholin-4-ylmethyl)phenyl; 4-(morpholin-4-ylmethyl)phenyl; 1-[2-(morpholin-4-yl)ethyl]-1H-pyrrolo[2,3-b]pyridin-3-yl; 1-[3-(morpholin-4-yl)propyl]-1H-pyrrolo[2,3-b]pyridin-3-yl; 1-[2-(morpholin-4-yl)ethyl]-1H-pyrrolo[2,3-b]pyridin-5-yl; 1-[2-(dimethylamino)ethyl]-1H-pyrrolo[2,3-b]pyridin-5-yl, 1,8-naphthyridin-2-yl; 4-(oxan-4-ylmethoxy)phenyl; 4-[2-(oxan-4-yl)ethoxy]phenyl; 4-(oxan-4-yloxy)phenyl; 4-(oxan-4-yloxy)-3-(trifluoromethyl)phenyl; 4-oxo-3,4-dihydroquinazolin-7-yl; phenyl 4-[(phenylformamido)methyl]phenyl; 4-(piperazine-1-carbonyl)phenyl; 4-(pyridine-3-amido)phenyl; 2-(5,6,7,8-tetrahydro-1,8-naphthyridin-3-yl; and 4-(thiophene-2-sulfonamido)phenyl.

In certain embodiments, $R^2$ is at least one selected from the group consisting of: 1,3-benzothiazol-5-yl; 5-fluoro-indol-6-yl; 7-fluoro-indol-6-yl; Indol-6-yl; 2-methyl-1,3-benzothiazol-5-yl; 1-methyl-1H-pyrrolo[2,3-b]pyridin-6-yl; 1,8-naphthyridin-2-yl; 1,8-naphthyridin-3-yl; and 1H-pyrrolo[2,3-b]pyridine-5-yl.

As defined herein, a compound depicted by the racemic formula further stands for either of the two enantiomers or mixtures thereof, or in the case where a second chiral center is present, all possible diastereomers.

For the purposes of demonstrating the manner in which the compounds of the present invention are named and referred to herein, the compound of formula:

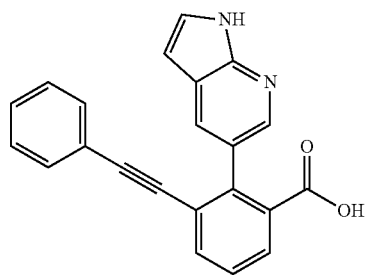 [SMILES: O=C(O)c1cccc(C#Cc2ccccc2)c1-c1cnc2[nH]ccc2c1]

has the chemical name 3-(2-phenylethynyl)-2-(H-pyrrolo[2,3-b]pyridin-5-yl)benzoic acid.

For the purposes of demonstrating the manner in which the compounds of the present invention are named and referred to herein, the compound of formula:

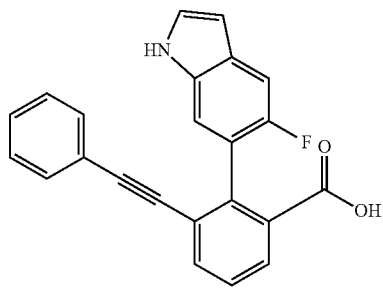 [SMILES: O=C(O)c1cccc(C#Cc2ccccc2)c1-c1cc2[nH]ccc2cc1F]

has the chemical name 2-(5-fluoro-1H-indol-6-yl)-3-(2-phenylethynyl) benzoic acid.

As defined herein, a compound depicted by a racemic formula further stands for either of the two enantiomers having the formula or mixtures thereof, or in the case where a second chiral center is present, all possible diastereomers.

The compounds described herein may form salts with acids and/or bases, and such salts are included in the present invention. In certain embodiments, the salts are pharmaceutically acceptable salts. The term "salts" embraces addition salts of free acids and/or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hemisulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate).

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, ammonium, N,N'-dibenzylethylene-diamine, chloroprocaine, choline, diethanolamine, ethylenediamine, meglumine (N-methylglucamine) and procaine.

All of these salts may be prepared from the corresponding compound by reacting, for example, the appropriate acid or base with the compound. Salts may be comprised of a fraction of less than one, one, or more than one molar equivalent of acid or base with respect to any compound of the invention.

In certain embodiments, the at least one compound of the invention is a component of a pharmaceutical composition further including at least one pharmaceutically acceptable carrier.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Methods of Making

The compounds described herein, and other related compounds having different substituents are synthesized using techniques and materials described herein and as described, for example, in Fieser & Fieser's Reagents for Organic Synthesis, Vol. 1-17 (John Wiley and Sons, 1991); Rodd's Chemistry of Carbon Compounds, Vol. 1-5 and Supplementals (Elsevier Science Publishers, 1989); Organic Reactions, Vol. 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry, $4^{th}$ Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Reagents used in the preparation of the compounds of this invention can be either commercially obtained or can be prepared by standard procedures described in the literature. In a non-limiting exemplification, compounds of the invention may be produced by one of the following reaction schemes.

Scheme 1.

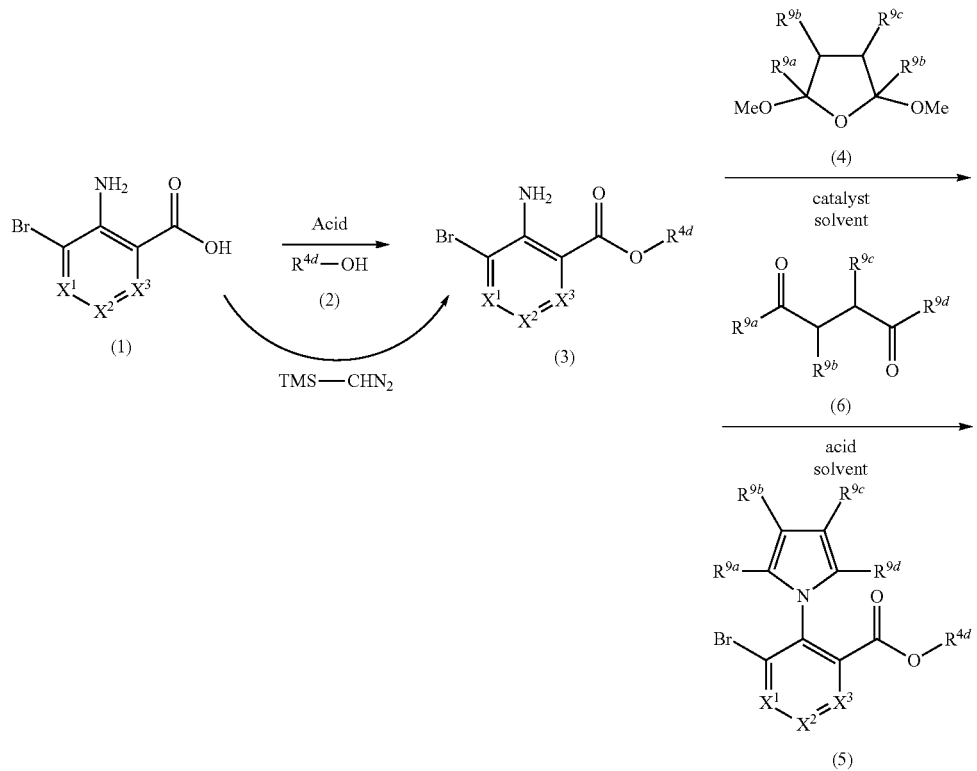

Suitably substituted compound (1) is reacted with suitably substituted compound (2) in the presence of an acid such as hydrochloric acid, sulfuric acid, trifluoroacetic acid, and the like, in an organic solvent such as methanol, ethanol, N,N-dimethylformamide, tetrahydrofuran, 1,4-dioxane, methylene chloride and the like, optionally heated, optionally heated with microwave irradiation, to provide compound (3). Alternatively, compound (1) may be reacted with trimethylsilyldiazomethane in an organic solvent such as methylene chloride, 1,2-dichloroethane, tetrahydrofuran, 1,4-dioxane, N,N-dimethylformamide, and the like to provide compound (3). Compound (3) is then reacted with compound (4) in the presence of a catalyst, such as 4-chloropyridine hydrochloride, in an organic solvent such as methylene chloride, 1,2-dichloroethane, tetrahydrofuran, 1,4-dioxane, N,N-dimethylformamide, and the like, optionally heated, optionally heated with microwave irradiation, to provide compound (5). Alternatively, compound (3) is reacted with compound (6), in the presence of an acid such as hydrochloric acid, sulfuric acid, trifluoroacetic acid, acetic acid, and the like, in an organic solvent such as methanol, ethanol, N,N-dimethylformamide, tetrahydrofuran, 1,4-dioxane, methylene chloride, 1,2-dichloroethane, and the like, optionally heated, optionally heated with microwave irradiation, to provide compound (5).

Scheme 2

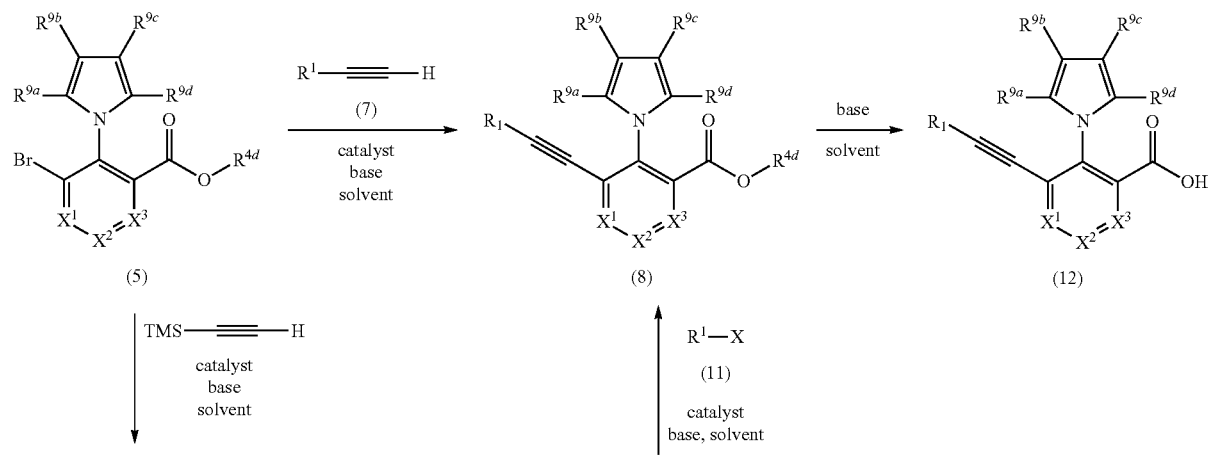

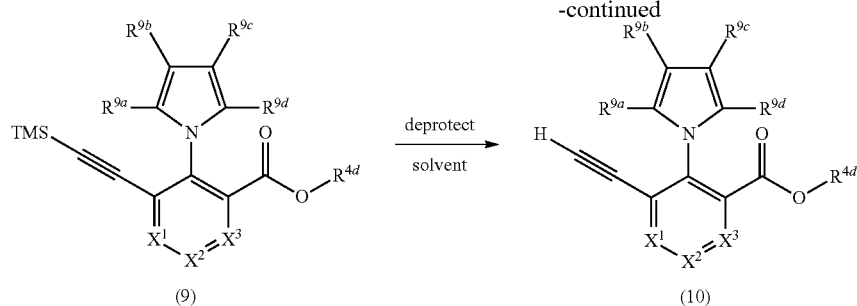

Compound (5) is reacted with compound (7), in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation, to provide compound (8). Alternatively, compound (5) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (9). Compound (9) is then deprotected by removal of the trimethylsilyl moiety by reacting compound (9) with a fluoride source such as tetrabutylammonium fluoride, and the like in an organic solvent such as tetrahydrofuran, 1,4-dioxane, methylene chloride, 1,2-dichloroethane, and the like to provide compound (10). Compound (10) is reacted with compound (11), wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine) palladium(0), dichlorobis (triphenylphosphine)palladium(II), palladium on carbon, bis (acetonitrile) dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (8). Compound (8) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (12).

Scheme 3.

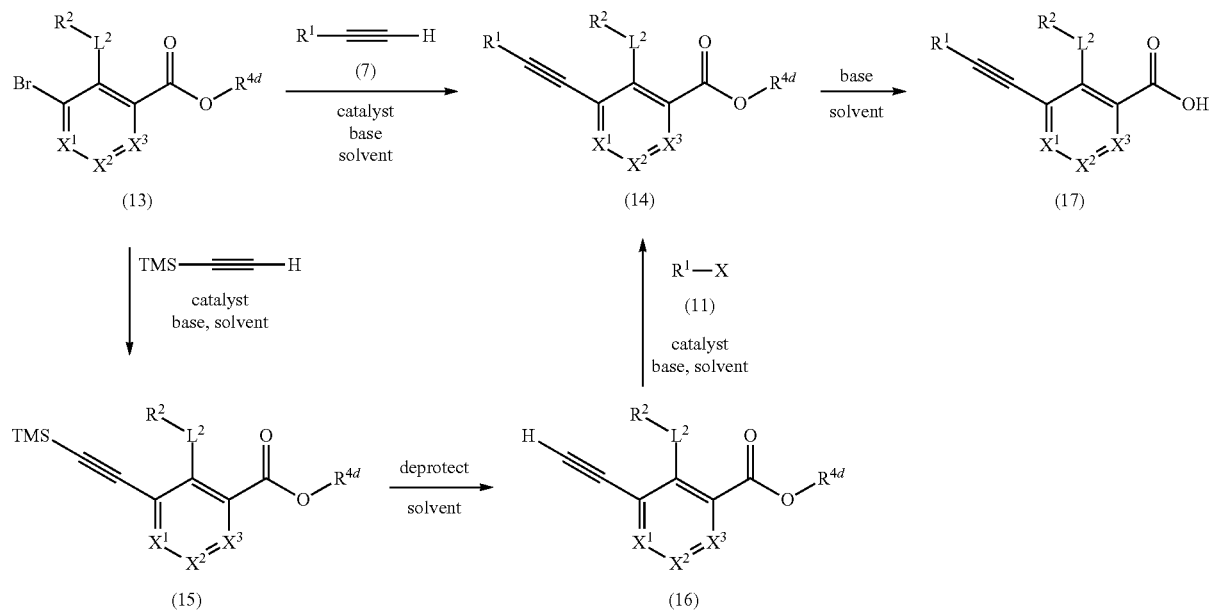

Compound (13) is reacted with compound (7) in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (14). Alternatively, compound (13) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine) palladium(0), dichlorobis (triphenylphosphine) palladium(II), palladium on carbon, bis(acetonitrile) dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (15). Compound (15) is then deprotected by removal of the trimethylsily moiety using a fluoride source such as tetrabutylammonium fluoride, the like in an organic solvent such as tetrahydrofuran, 1,4-dioxane, methylene chloride, 1,2-dichloroethane, and the like to provide compound (16). Compound (16) is reacted with compound (11), wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis (triphenylphosphine) palladium(0), dichlorobis (triphenylphosphine)palladium(II), palladium on carbon, bis(acetonitrile) dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (14). Compound (14) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (17).

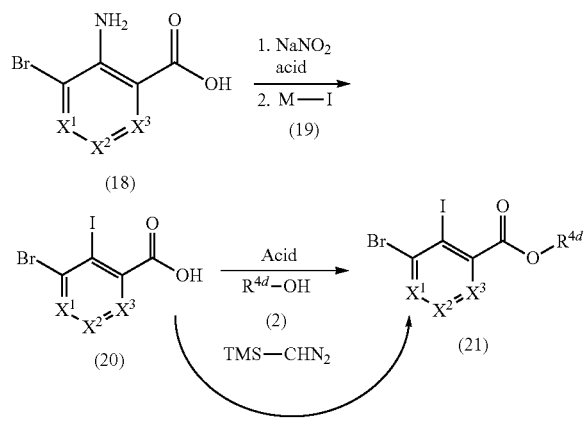

Scheme 4.

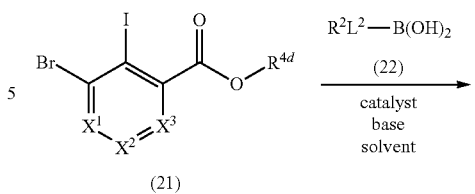

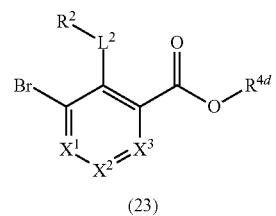

Compound (18) is reacted with sodium nitrite in the presence of an acid such as hydrochloric acid, sulfuric acid, acetic acid, trifluoroacetic acid, and the like, in an organic solvent such as methanol, ethanol, N,N-dimethylformamide, tetrahydrofuran, 1,4-dioxane, and the like, optionally heated, optionally heated with microwave irradiation. Further reaction with compound (19) wherein M is a metal such as sodium, potassium, and the like in an organic solvent such as methanol, ethanol, N,N-dimethylformamide, tetrahydrofuran, 1,4-dioxane, and the like, optionally heated, optionally heated with microwave irradiation to provide compound (20). Compound (20) is reacted with suitably substituted compound (2) in the presence of an acid such as hydrochloric acid, sulfuric acid, trifluoroacetic acid, and the like, in an organic solvent such as methanol, ethanol, N,N-dimethyl formamide, tetrahydrofuran, 1,4-dioxane, methylene chloride and the like, optionally heated, optionally heated with microwave irradiation to provide compound (21). Alternatively, compound (20) may be reacted with trimethylsilyl-diazomethane in an organic solvent such as methylene chloride, 1,2-dichloroethane, tetrahydrofuran, 1,4-dioxane, N,N-dimethylformamide, and the like to provide compound (21). Compound (21) is reacted with compound (22) in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in the presence of a base such as triethylamine, diisopropylethyl amine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N,N-dimethyl-formamide, tetrahydrofuran, 1,4-dioxane, 1,2-dimethoxyethane and the like, optionally heated, optionally heated with microwave irradiation to provide compound (23).

Scheme 5.

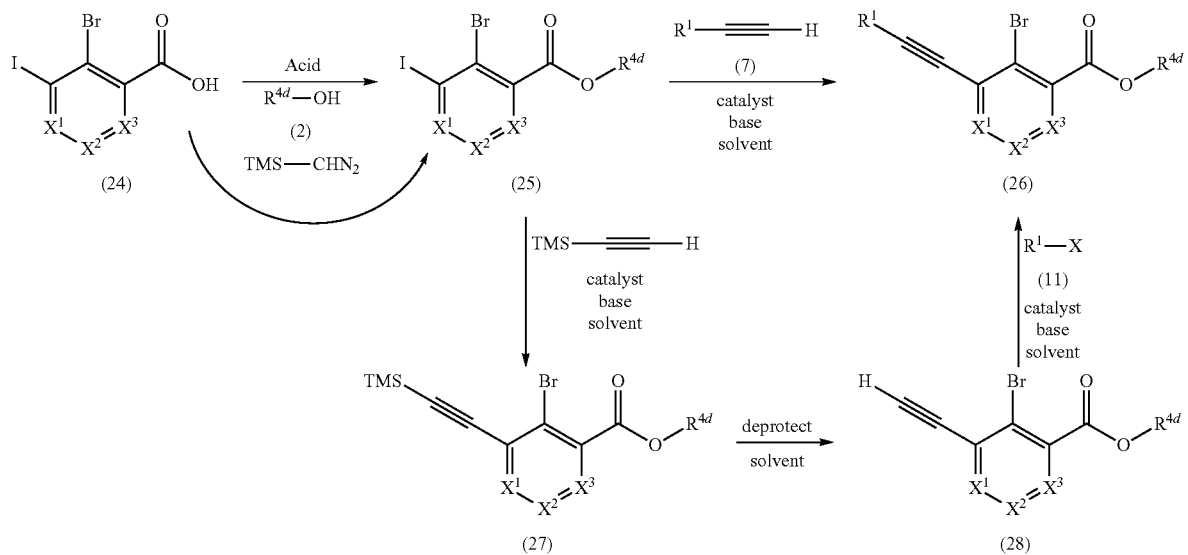

Compound (24) is reacted with suitably substituted compound (2) in the presence of an acid such as hydrochloric acid, sulfuric acid, trifluoroacetic acid, and the like, in an organic solvent such as methanol, ethanol, N,N-dimethylformamide, tetrahydrofuran, 1,4-dioxane, methylene chloride and the like, optionally heated, optionally heated with microwave irradiation to provide compound (25). Alternatively, compound (24) may be reacted with trimethylsilyldiazomethane in an organic solvent such as methylene chloride, 1,2-dichloroethane, tetrahydrofuran, 1,4-dioxane, N,N-dimethyl formamide, and the like to provide compound (25). Compound (25) is reacted with compound (7) in the presence of a base such as triethylamine, diisopropylethylamine, pyridine, 2,6-dimethylpyridine, and the like in the presence of a palladium catalyst such as palladium (II) acetate, tetrakis (triphenylphosphine)palladium(0), dichlorobis (triphenylphosphine) palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (26). Alternatively, compound (25) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium (II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (27). Compound (27) is then deprotected by removal of the trimethylsily moiety using a fluoride source such as tetrabutylammonium fluoride, and the like in an organic solvent such as tetrahydrofuran, 1,4-dioxane, methylene chloride, 1,2-dichloroethane, and the like to provide compound (28). Compound (28) is reacted with compound (11) wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (26).

Scheme 6.

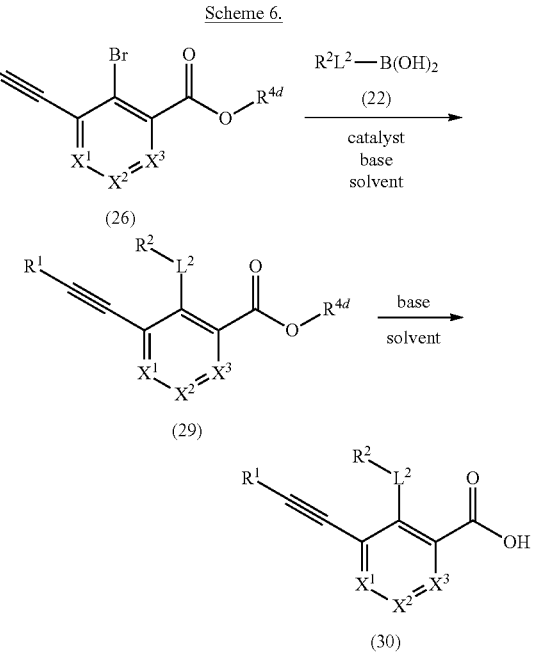

Compound (26) is reacted with compound (22) in the presence of a palladium catalyst such as palladium (II)

acetate, tetrakis(triphenylphosphine)palladium(0), dichlorobis(triphenylphosphine) palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, 1,2-dimethoxyethane and the like, optionally heated, optionally heated with microwave irradiation to provide compound (29). Compound (29) is reacted with a base such as sodium hydroxide, lithium hydroxide, potassium hydroxide, sodium carbonate, lithium carbonate, potassium carbonate, and the like, in an organic solvent such as methanol, ethanol. N,N-dimethylformamide, tetrahydrofuran, 1,4-dioxane, and the like, optionally heated, optionally heated with microwave irradiation to provide compound (30).

Scheme 7.

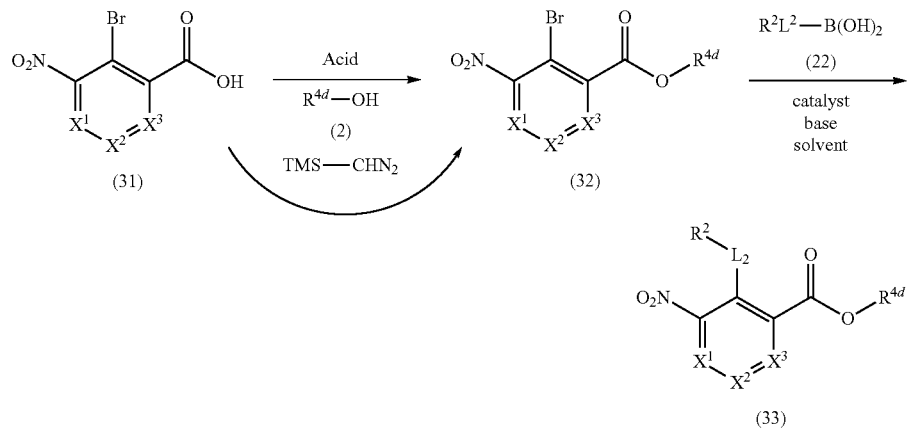

Compound (31) is reacted with suitably substituted compound (2) in the presence of an acid such as hydrochloric acid, sulfuric acid, trifluoroacetic acid, and the like, in an organic solvent such as methanol, ethanol, N,N-dimethylformamide, tetrahydrofuran, 1,4-dioxane, methylene chloride and the like, optionally heated, optionally heated with microwave irradiation to provide compound (32). Alternatively, compound (31) may be reacted with trimethylsilyldiazomethane in an organic solvent such as methylene chloride, 1,2-dichloroethane, tetrahydrofuran, 1,4-dioxane, N,N-dimethyl formamide, and the like to provide compound (32). Compound (32) is reacted with compound (22) in the presence of a palladium catalyst such as palladium (II) acetate, tetrakis(triphenylphosphine) palladium(0), dichlorobis (triphenylphosphine)palladium(II), palladium on carbon, bis(acetonitrile) dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, 1,2-dimethoxyethane and the like, optionally heated, optionally heated with microwave irradiation to provide compound (33).

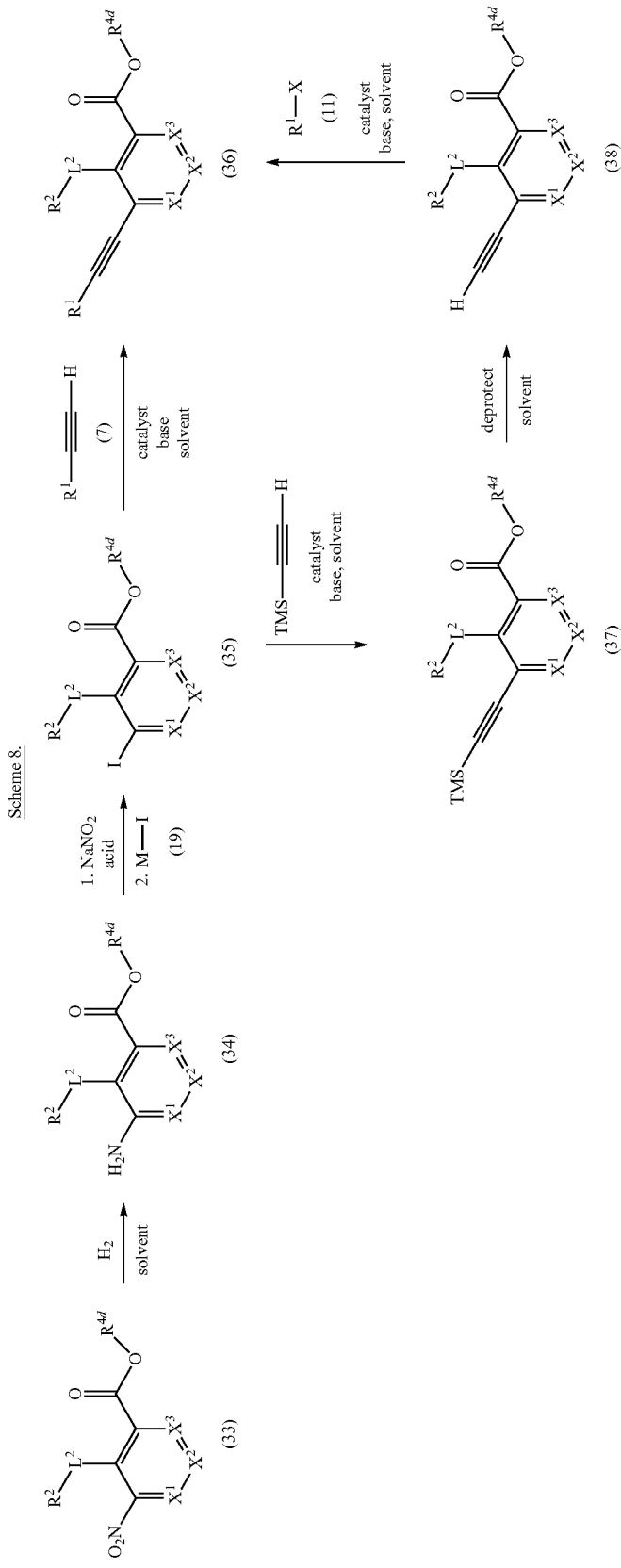

Compound (33) is reacted with hydrogen in the presence of a catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as methanol, ethanol, N,N-dimethylformamide, tetrahydrofuran, 1,4-dioxane, and the like to provide compound (34). Compound (34) is reacted with sodium nitrite in the presence of an acid such as hydrochloric acid, sulfuric acid, acetic acid, trifluoroacetic acid, and the like in an organic solvent such as methanol, ethanol, N,N-dimethylformamide, tetrahydrofuran, 1,4-dioxane, and the like, optionally heated, optionally heated with microwave irradiation. Further reaction with compound (19) wherein M is a metal such as sodium, potassium, and the like in an organic solvent such as methanol, ethanol, N,N-dimethylformamide, tetrahydrofuran, 1,4-dioxane, and the like, optionally heated, optionally heated with microwave irradiation to provide compound (35). Compound (35) is reacted with compound (7) in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (36). Alternatively, compound (35) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis(triphenylphosphine) palladium(0), dichlorobis (triphenylphosphine)palladium(II), palladium on carbon, bis(acetonitrile) dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (37). Compound (37) is then deprotected by removal of the trimethylsily moiety using a fluoride source such as tetrabutylammonium fluoride, and the like in an organic solvent such as tetrahydrofuran, 1,4-dioxane, methylene chloride, 1,2-dichloroethane, and the like to provide compound (38). Compound (38) is reacted with compound (11) wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (36).

Scheme 9.

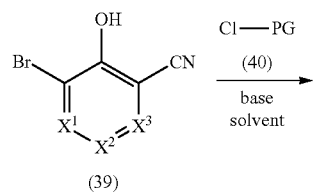

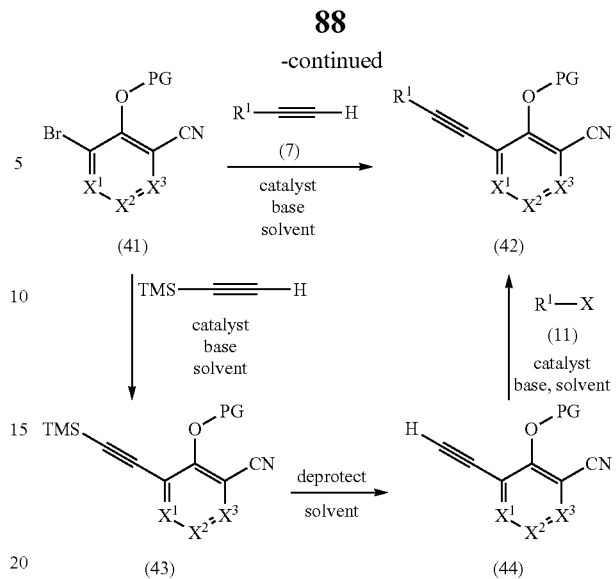

Compound (39) is reacted with compound (40) wherein PG is tert-butyldimethylsilyl, tert-butyldiphenylsilyl, acetyl, benzoyl and the like, in the presence of a base such as triethylamine, diisopropylethylamine, pyridine, 2,6-dimethylpyridine, and the like, in an organic solvent such as N,N-dimethylformamide, tetrahydrofuran, 1,4-dioxane, methylene chloride, 1,2-dichloroethane, and the like, to provide compound (41). Compound (41) is reacted with compound (7) in the presence of a base such as triethylamine, diisopropylethylamine, pyridine, 2,6-dimethylpyridine, and the like in the presence of a palladium catalyst such as palladium (II) acetate, tetrakis(triphenylphosphine) palladium(0), dichlorobis (triphenylphosphine)palladium(II), palladium on carbon, bis(acetonitrile) dichloropalladium (II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (42). Alternatively, compound (41) is reacted with trimethylsilyl acetylene in the presence of a base such as triethylamine, diisopropylethylamine, pyridine, 2,6-dimethylpyridine, and the like in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (43). Compound (43) is then deprotected by removal of the trimethylsily moiety using a fluoride source such as tetrabutylammonium fluoride, and the like in an organic solvent such as tetrahydrofuran, 1,4-dioxane, methylene chloride, 1,2-dichloroethane, and the like to provide compound (44). Compound (44) is reacted with compound (11), wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis (triphenylphosphine)palladium(0), dichlorobis (triphenylphosphine) palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (42).

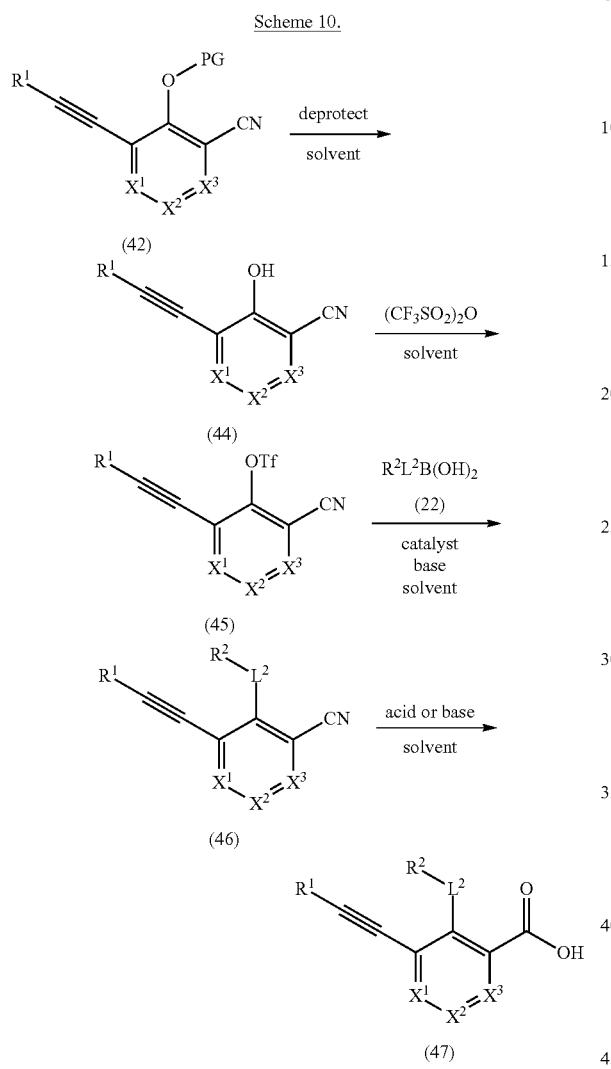

Scheme 10.

Compound (42) is deprotected by a fluoride source such as tetrabutylammonium fluoride and the like or a base such as aqueous sodium carbonate, potassium carbonate, cesium carbonate and the like, in an organic solvent such as methanol, ethanol, in an organic solvent such as tetrahydrofuran, 1,4-dioxane, and the like to provide compound (44). Compound (44) is reacted with trifluoromethanesulfonic anhydride, in an organic solvent such as tetrahydrofuran, 1,4-dioxane, methylene chloride, 1,2-dichloroethane, N,N-dimethylformamide, and the like, optionally in the presence of a base such as triethylamine, diisopropylethylamine, pyridine, 2,6-dimethylpyridine, and the like, to provide compound (45). Compound (45) is reacted with compound (22) in the presence of a palladium catalyst such as palladium (II) acetate, tetrakis(triphenylphosphine)palladium(0), dichlorobis (triphenylphosphine)palladium(II), palladium on carbon, bis(acetonitrile) dichloropalladium(II), and the like, in the presence of a base such as triethylamine, diisopropylethyl amine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, 1,2-dimethoxyethane and the like, optionally heated, optionally heated with microwave irradiation to provide compound (46). Compound (46) is then reacted with an acid such as hydrochloric acid, sulfuric acid, and the like, in a solvent such as water, N,N-dimethylformamide, tetrahydrofuran, 1,4-dioxane, and the like, optionally heated, optionally heated with microwave irradiation to provide compound (47). Alternatively, compound (46) is reacted with a base such as sodium hydroxide, lithium hydroxide, potassium hydroxide, and the like, in a solvent such as water, methanol, ethanol, N,N-dimethylformamide, tetrahydrofuran, 1,4-dioxane, and the like, optionally heated, optionally heated with microwave irradiation to provide compound (47).

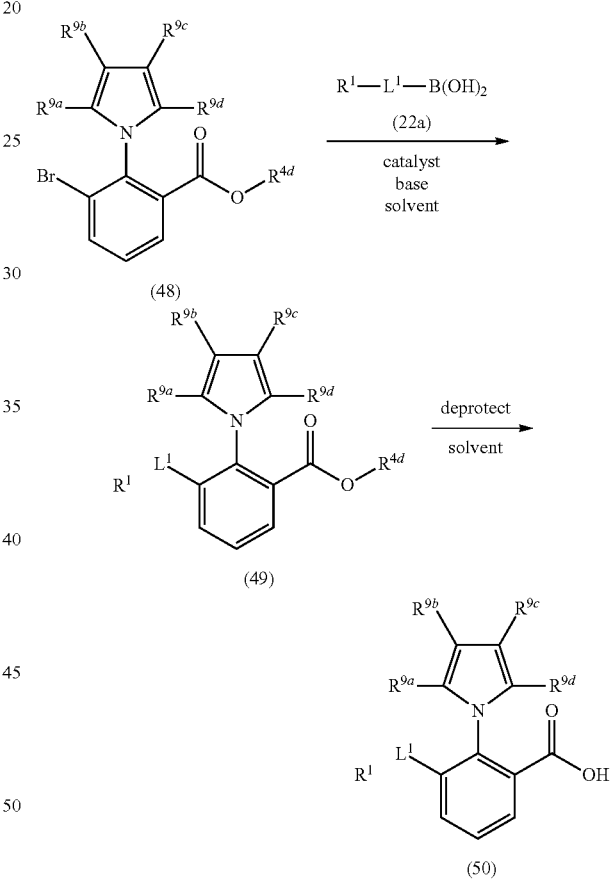

Scheme 11.

Compound (48) is reacted with compound (22a) in the presence of a palladium catalyst such as palladium (II) acetate, tetrakis(triphenylphosphine)palladium(0), dichlorobis(triphenylphosphine) palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol. N,N-dimethylformamide, tetrahydrofuran, 1,4-dioxane, and the like, optionally heated, optionally heated with microwave irradiation to provide compound (49). Compound (49) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (50).

ethanol, N,N-dimethylformamide, tetrahydrofuran, 1,4-dioxane, and the like to provide compound (54). Compound (54) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like,

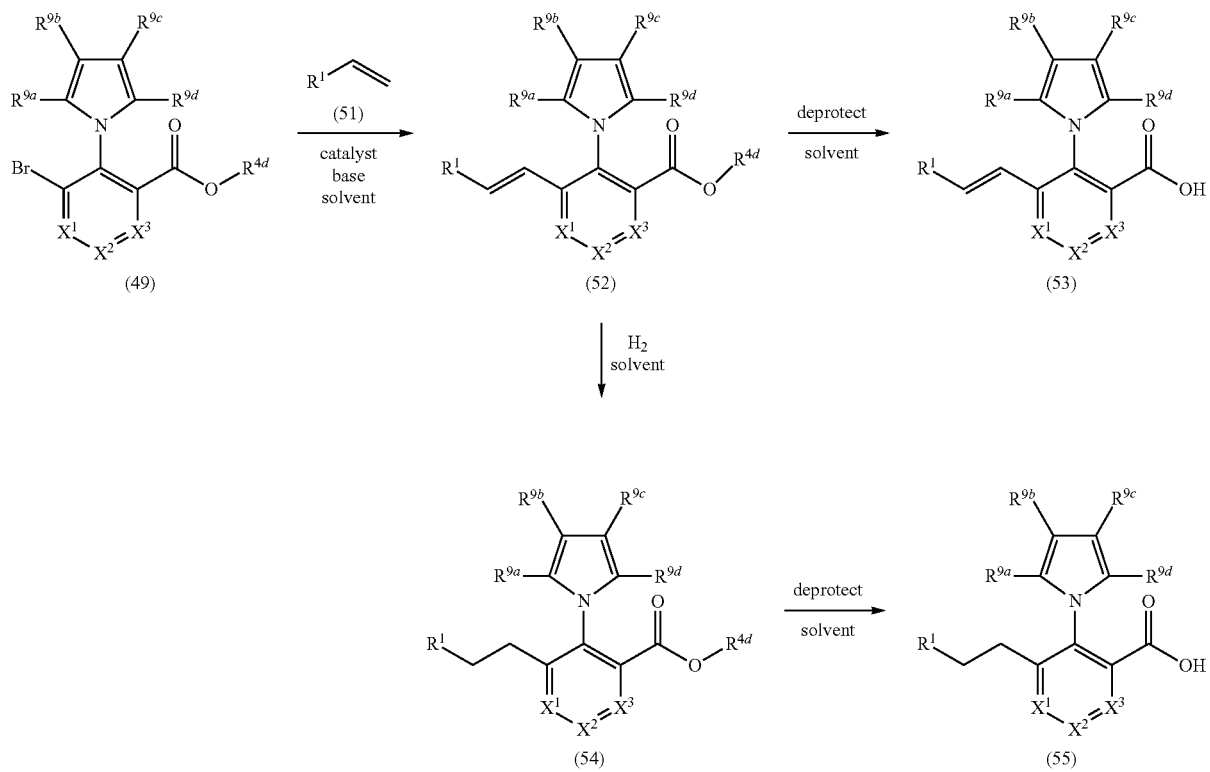

Scheme 12.

Compound (49) is reacted with compound (51) in the presence of a palladium catalyst such as palladium (II) acetate, tetrakis(triphenylphosphine)palladium(0), dichlorobis(triphenylphosphine) palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (52). Compound (52) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethyl formamide, tetrahydrofuran, 1,4-dioxane, and the like, optionally heated, optionally heated with microwave irradiation to provide compound (53). Alternatively, compound (52) is reacted with hydrogen in the presence of a catalyst such as palladium (II) acetate, tetrakis(triphenylphosphine) palladium(0), dichlorobis (triphenylphosphine)palladium(II), palladium on carbon, bis(acetonitrile) dichloropalladium (II), and the like, in an organic solvent such as methanol, optionally heated, optionally heated with microwave irradiation to provide compound (55).

Scheme 13.

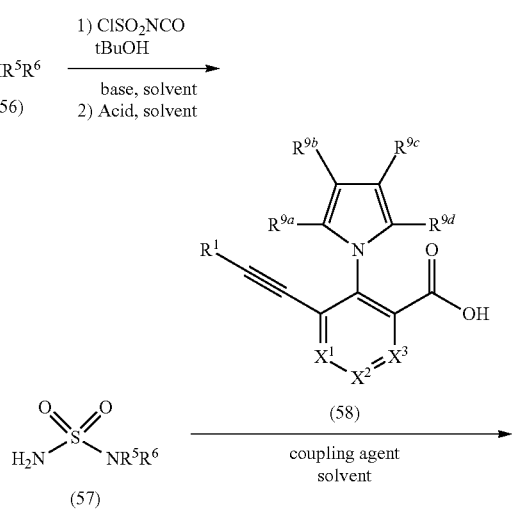

-continued

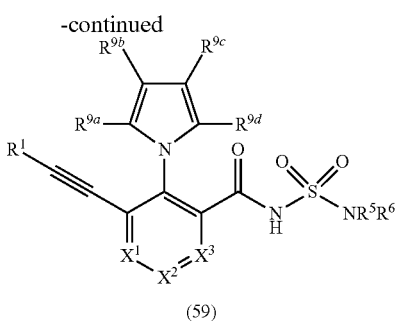

(59)

Compound (56) is reacted with chlorosulfonylisocyanate and tert-butanol in the presence of a base such as triethylamine, diisopropylethylamine, pyridine, 2,6-dimethylpyridine, and the like in a solvent such as methylene chloride, 1,2-dichloroethane, N,N-dimethylformamide, tetrahydrofuran, 1,4-dioxane, and the like, and then deprotected by treatment with an acid such as hydrogen chloride, trifluoroacetic acid, and the like in an organic solvent such as ethyl acetate, methylene chloride and the like to provide compound (57). Compound (57) is reacted with compound (58) in the presence of coupling agent such as 1-ethyl-3-(3-dimethylaminopropyl) carbodiimide, N,N'-Dicyclohexyl carbodiimide, O-Benzotriazole-N,N,N',N'-tetramethyl-uronium-hexafluoro-phosphate. O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidino phosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide compound (59).

Scheme 14.

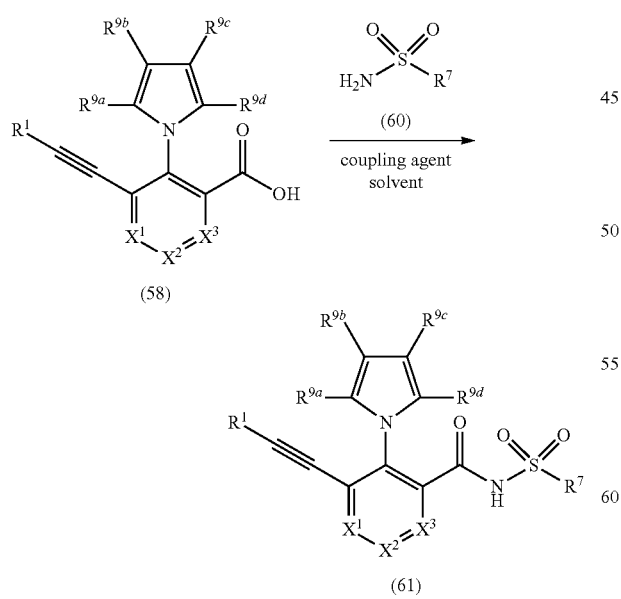

Alternatively, compound (58) is reacted with compound (60) in the presence of coupling agent such as 1-ethyl-3-(3- dimethylaminopropyl) carbodiimide, N,N'-Dicyclohexyl carbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidino-phosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide compound (61).

Scheme 15.

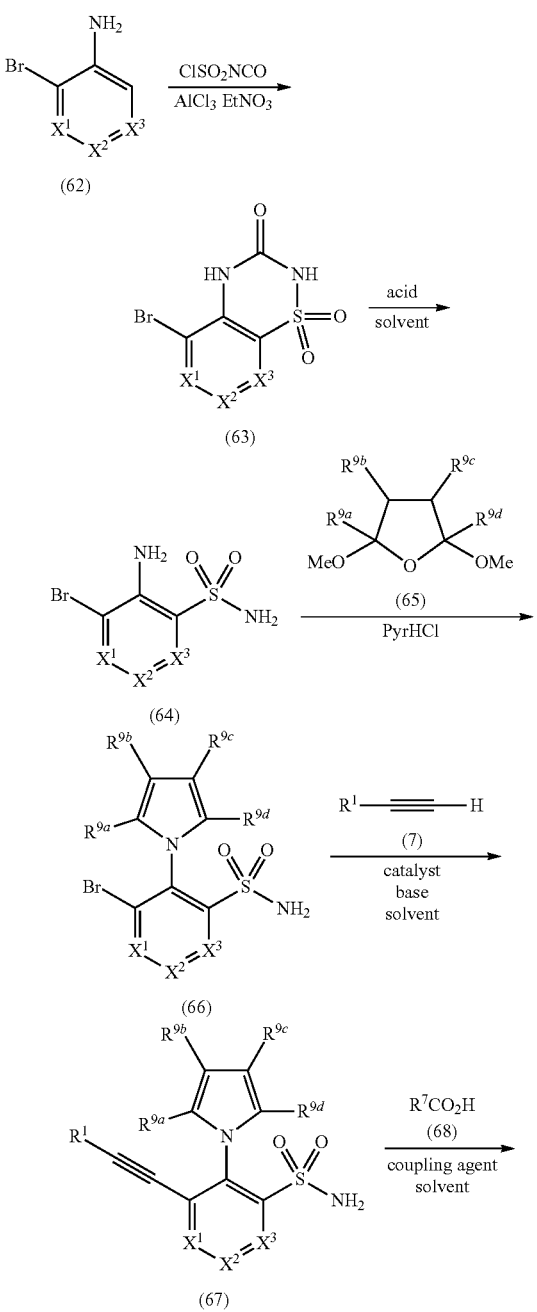

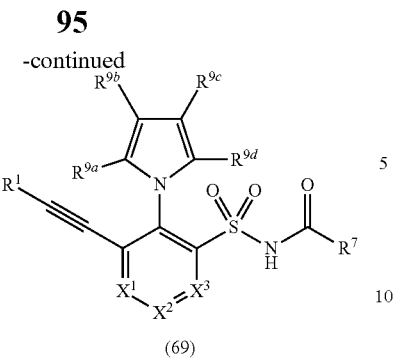

(69)

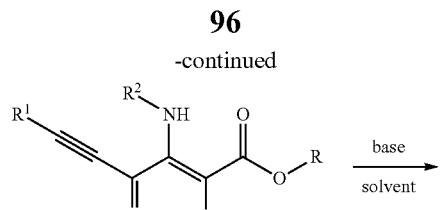

(72)

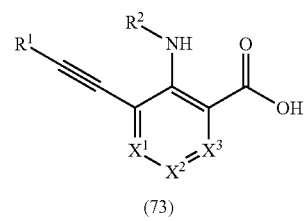

(73)

Compound (62) is reacted with chlorosulfonylisocyanate in the presence of aluminum trichloride in nitroethane to provide compound (63). Compound (63) is reacted with an acid such as hydrochloric acid, sulfuric acid, trifluoroacetic acid, acetic acid, and the like, optionally in an organic solvent such as tetrahydrofuran, 1,4-dioxane, dimethylformamide, methylene chloride, dichloroethane, methanol, ethanol, and the like, to provide compound (64). Compound (64) is reacted with compound (65) in the presence of pyridine hydrochloride, optionally in an organic solvent such as tetrahydrofuran, 1,4-dioxane, dimethylformamide, methylene chloride, 1,2-dichloroethane, methanol, ethanol, and the like, optionally heated, optionally heated with microwave irradiation to provide compound (66). Compound (66) is reacted with compound (7), in the presence of a base such as triethylamine, diisopropylethylamine, pyridine, 2,6-dimethylpyridine, and the like in the presence of a palladium catalyst such as palladium (II) acetate, tetrakis (triphenylphosphine)palladium(0), dichlorobis (triphenylphosphine)palladium(II), palladium on carbon, bis(acetonitrile) dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (67). Compound (67) is reacted with compound (68) in the presence of coupling agent such as 1-ethyl-3-(3-dimethylaminopropyl) carbodiimide, N,N'-Dicyclohexylcarbodiimide, O-Benzotriazole-N, N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide compound (69).

Compound (70) is reacted with compound (71), wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like, in an organic solvent such as tetrahydrofuran, 1,4-dioxane, dimethylformamide, methylene chloride, 1,2-dichloroethane, and the like, to provide compound (72). Compound (72) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (73).

Scheme 17.

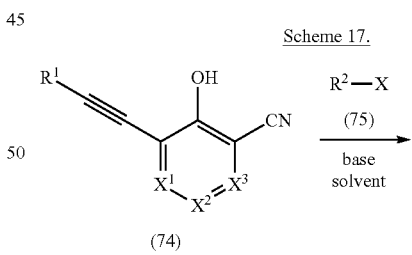

(74)

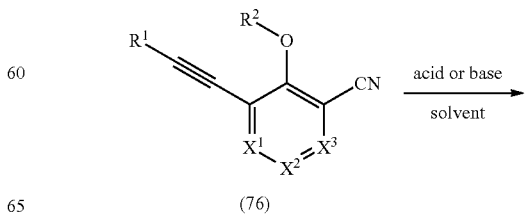

(76)

Scheme 16.

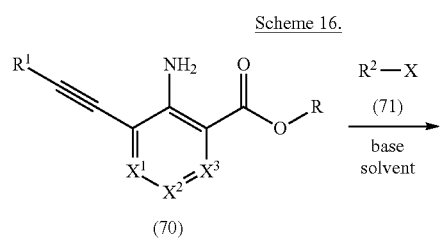

(70)

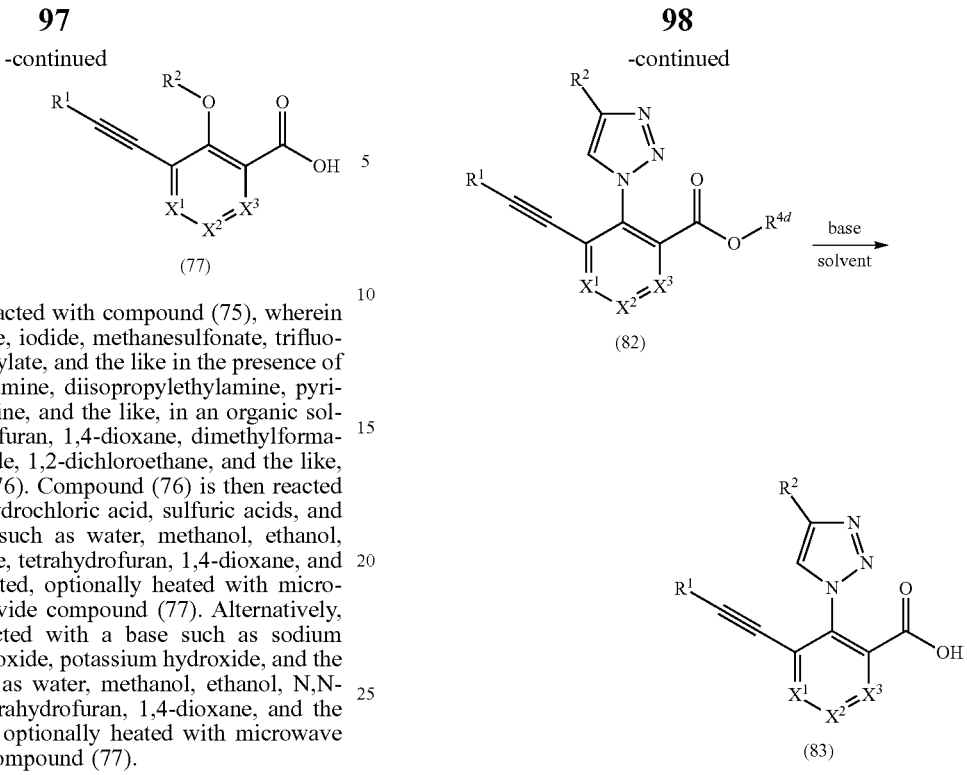

(77)

Compound (74) is reacted with compound (75), wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like, in an organic solvent such as tetrahydrofuran, 1,4-dioxane, dimethylformamide, methylene chloride, 1,2-dichloroethane, and the like, to provide compound (76). Compound (76) is then reacted with an acid such as hydrochloric acid, sulfuric acids, and the like, in a solvent such as water, methanol, ethanol, N,N-dimethylformamide, tetrahydrofuran, 1,4-dioxane, and the like, optionally heated, optionally heated with microwave irradiation to provide compound (77). Alternatively, compound (76) is reacted with a base such as sodium hydroxide, lithium hydroxide, potassium hydroxide, and the like, in a solvent such as water, methanol, ethanol, N,N-dimethylformamide, tetrahydrofuran, 1,4-dioxane, and the like, optionally heated, optionally heated with microwave irradiation to provide compound (77).

Scheme 18.

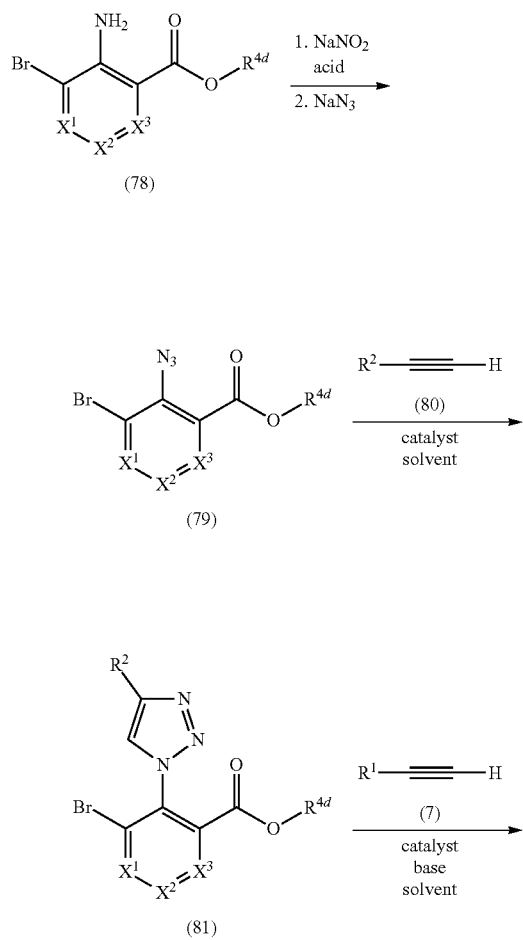

Compound (78) is reacted with sodium nitrite in the presence of an acid such as hydrochloric acid, sulfuric acid, tetrafluoroboric acid, and the like, optionally in a solvent such as water, methanol, ethanol, N,N-dimethylformamide, tetrahydrofuran, 1,4-dioxane, and the like, followed by reaction with sodium azide in a solvent such as water, methanol, ethanol, N,N-dimethylformamide, tetrahydrofuran, 1,4-dioxane, and the like to provide compound (79). Compound (79) is reacted with compound (80) in the presence of a catalyst such as sodium ascorbate and copper sulfate and the like, in an organic solvent such as methanol, ethanol, N,N-dimethylformamide, tetrahydrofuran, 1,4-dioxane, and the like, optionally heated, optionally heated with microwave irradiation to provide compound (81). Compound (81) is reacted with compound (7) in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloro palladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (82). Compound (82) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (83).

Scheme 19.

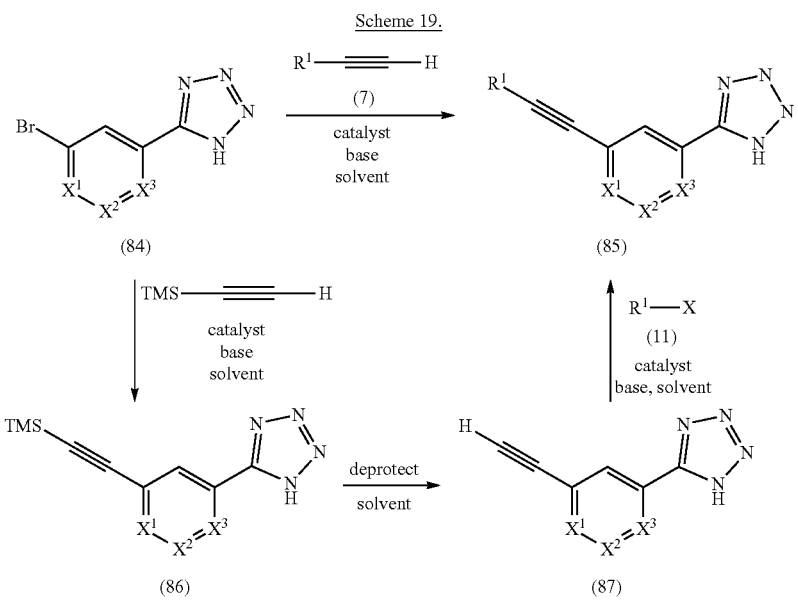

Compound (84) is reacted with compound (7), in the presence of a base such as pyridine, triethylamine, diisopropylethylamine, 2,6-dimethylpyridine, and the like, in the presence of a palladium catalyst such as palladium (II) acetate, tetrakis(triphenylphosphine)palladium(0), dichlorobis (triphenylphosphine)palladium(II), palladium on carbon, bis(acetonitrile)dichloro palladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (85). Alternatively, compound (84) is reacted with trimethylsilyl acetylene in the presence of a base such as triethylamine, diisopropylethyl amine, pyridine, 2,6-dimethylpyridine, and the like in the presence of a palladium catalyst such as palladium (II) acetate, tetrakis(triphenylphosphine)palladium(0), dichlorobis(triphenylphosphine) palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (86). Compound (86) is then deprotected by removal of the trimethylsily moiety using a fluoride source such as tetrabutylammonium fluoride, and the like in an organic solvent such as tetrahydrofuran, 1,4-dioxane, methylene chloride, 1,2-dichloroethane. N,N-dimethylformamide, and the like to provide compound (87). Alternatively, compound (86) is reacted with hydrogen fluoride in the presence of a base such as pyridine, 2,6-dimethylpyridine, triethyl amine, and the like, optionally in a solvent such as tetrahydrofuran, 1,4-dioxane, methylene chloride, 1,2-dichloroethane, N,N-dimethylformamide, and the like to provide compound (87). Alternatively, compound (86) is reacted with a base such as aqueous sodium hydroxide, potassium hydroxide, lithium hydroxide and the like, in a solvent such as tetrahydrofuran, 1,4-dioxane, methylene chloride, 1,2-dichloroethane, N,N-dimethylformamide, and the like, optionally heated, optionally heated with microwave irradiation to provide compound (87). Compound (87) is reacted with compound (11), wherein X is a leaving group such as chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (85).

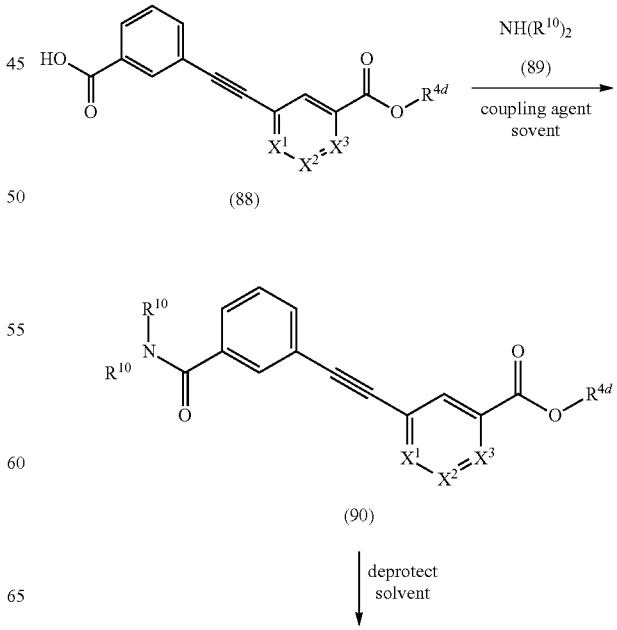

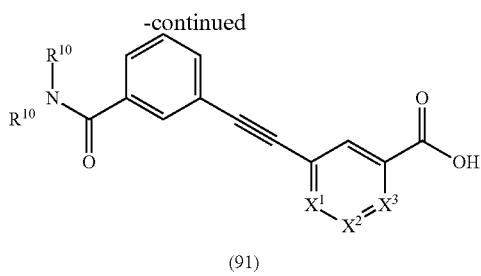

(91)

Compound (88) is reacted with compound (89), in the presence of coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N', N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide compound (90). Compound (90) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (91). Alternatively, compound (90) is reacted with an acid such as trifluoroacetic acid, hydrochloric acid, sulfuric acid, and the like, optionally in the presence of a solvent such as methanol, ethanol, N,N-dimethylformamide, tetrahydrofuran, 1,4-dioxane, methylene chloride and the like, optionally heated, optionally heated with microwave irradiation to provide compound (91).

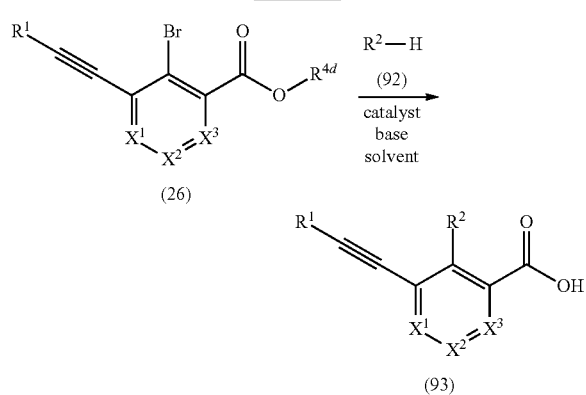

Compound (26) is reacted with compound (92), in the presence of a base such as potassium phosphate, cesium carbonate, potassium carbonate sodium carbonate, sodium tert-butoxide and the like in the presence of a copper (I) catalyst such as copper iodide and the like, or a palladium catalyst such as palladium (II) acetate, tetrakis(triphenylphosphine)palladium(0), dichlorobis (triphenylphosphine) palladium(II), palladium on carbon, bis(acetonitrile)dichloropalladium(II), and the like, in an organic solvent such as N,N-dimethylformamide, tetrahydrofuran, 1,4-dioxane, toluene, 1,2-dichloroethane, and the like, optionally heated, optionally heated with microwave irradiation to provide compound (93).

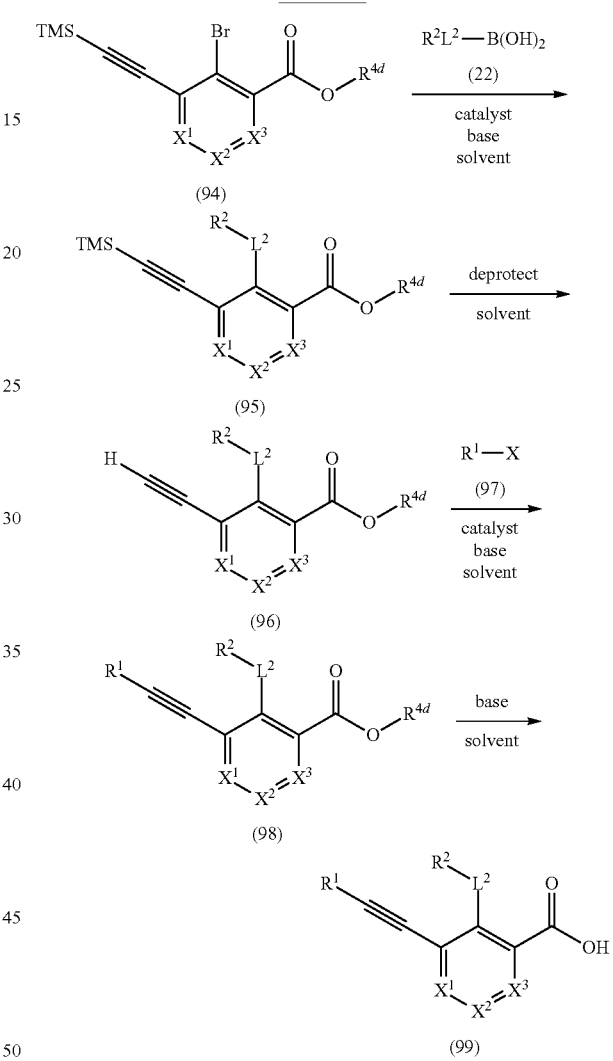

Compound (94) is reacted with compound (22) in the presence of a palladium catalyst such as palladium (II) acetate, tetrakis(triphenylphosphine)palladium(0), dichlorobis(triphenylphosphine) palladium(II), palladium on carbon, bis(acetonitrile)dichloropalladium(II), and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol. N,N-dimethylformamide, tetrahydrofuran, 1,4-dioxane, 1,2-dimethoxyethane and the like, optionally heated, optionally heated with microwave irradiation to provide compound (95). Compound (95) is then deprotected by removal of the trimethylsily moiety using a fluoride source such as tetrabutylammonium fluoride, and the like in an organic solvent such as tetrahydrofuran, 1,4-dioxane, methylene chloride, 1,2-dichloroethane, and the like to provide compound (96). Compound (96) is reacted with compound (97), wherein X is a chloride, bromide, iodide, methanesulfonate, trifluoromethanesulfonate, tosylate, and the like in the presence of a base such as triethylamine, diisopropylethylamine, pyridine, 2,6-dimethylpyridine, and the like in the presence of a palladium catalyst such as palladium (II) acetate, tetrakis(triphenylphosphine)palladium(0), dichlorobis (triphenylphosphine) palladium(II), palladium on carbon, bis(acetonitrile)dichloropalladium(II), and the like, in an organic solvent such as N,N-dimethylformamide, tetrahydrofuran, 1,4-dioxane, methylene chloride, 1,2-dichloroethane, and the like, optionally heated, optionally heated with microwave irradiation to provide compound (98). Compound (98) is reacted with a base such as sodium hydroxide, lithium hydroxide, potassium hydroxide, sodium carbonate, lithium carbonate, potassium carbonate, and the like, in an organic solvent such as methanol, ethanol. N,N-dimethylformamide, tetrahydrofuran, 1,4-dioxane, and the like, optionally heated, optionally heated with microwave irradiation to provide compound (99).

N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide compound (102). Alternatively, a compound of formula (100) is reacted with acyl chloride (103) in the presence of a base such as trimethylamine, diisopropylethylamine, N-methylmorpholine, pyridine and the like in a solvent such as dichloromethane, tetrahydrofuran and the like to provide compound (102). Compound (102) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (104). Alternatively, compound (102) is reacted with an acid such as trifluoroacetic acid, hydrochloric acid, sulfuric acid, and the like, optionally in the presence of a solvent such as methanol, ethanol, N,N-dimethylformamide, tetrahydrofuran, 1,4-dioxane, methylene chloride and the like, optionally heated, optionally heated with microwave irradiation to provide compound (104).

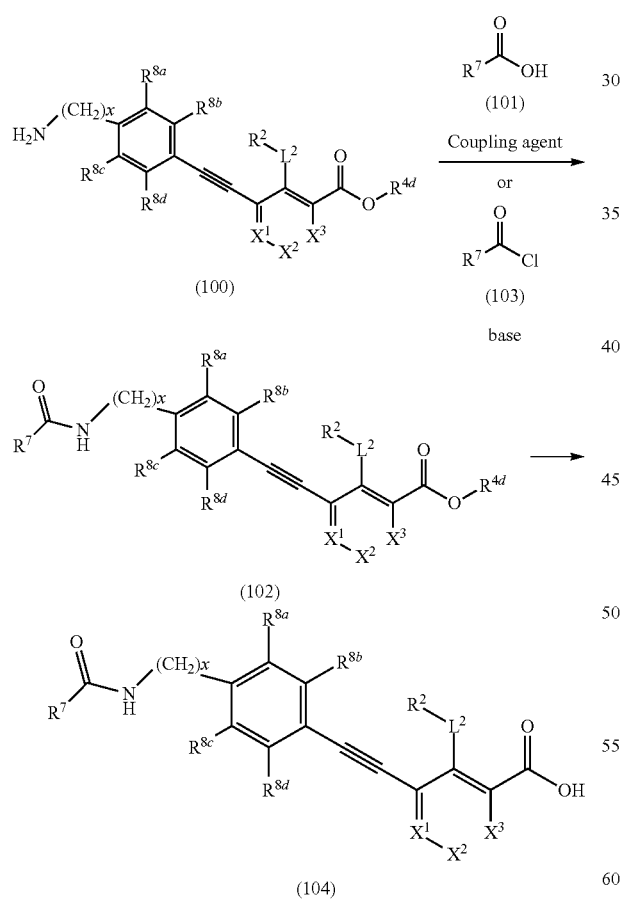

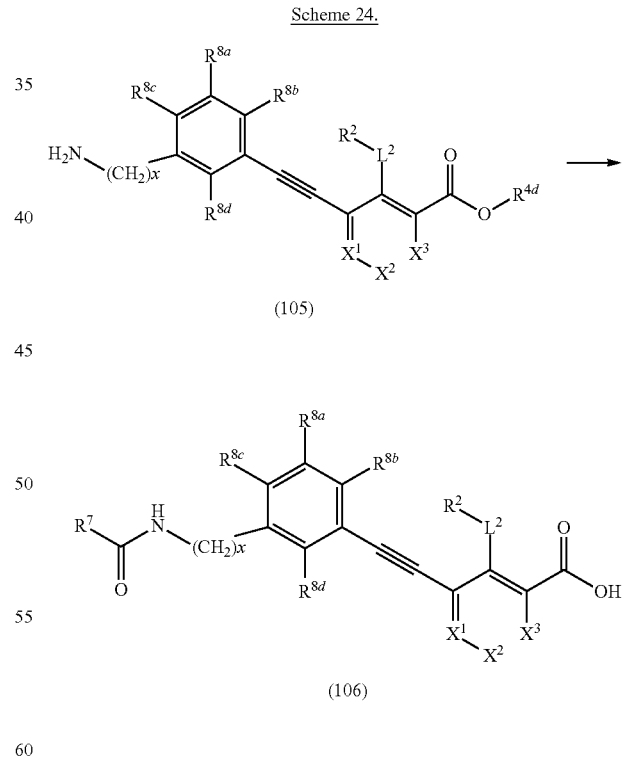

Compound (100) is reacted with compound (101), in the presence of coupling agent such as S-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N', Compound (105) is converted to compound (106) according to Scheme 24, using appropriate reagents, starting materials and purification methods known to those skilled in the art.

Scheme 25.

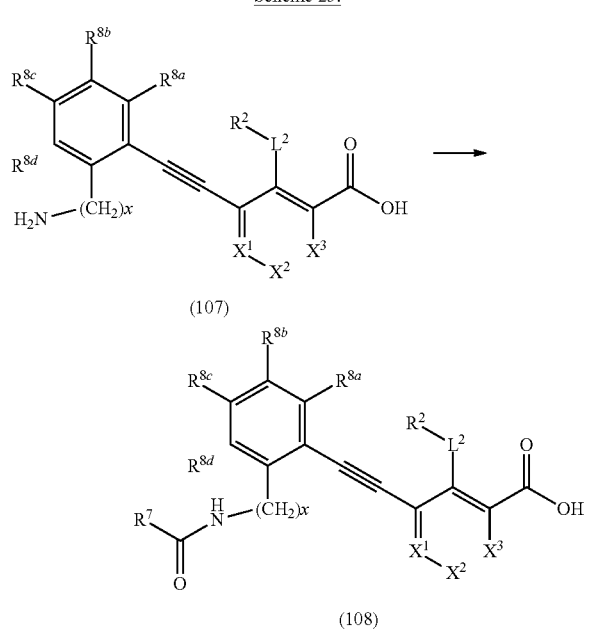

Compound (107) is converted to compound (108) according to Scheme 25, using appropriate reagents, starting materials and purification methods known to those skilled in the art.

Scheme 26.

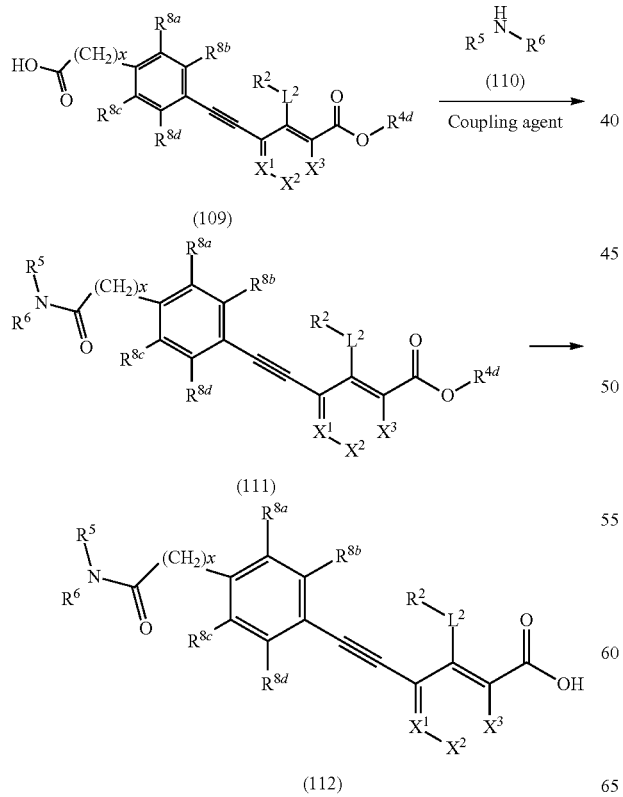

Compound (109) is reacted with compound (110), in the presence of coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidino-phosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, to provide compound (111). Compound (111) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (112). Alternatively, compound (111) is reacted with an acid such as trifluoroacetic acid, hydrochloric acid, sulfuric acid, and the like, optionally in the presence of a solvent such as methanol, ethanol, N,N-dimethylformamide, tetrahydrofuran, 1,4-dioxane, methylene chloride and the like, optionally heated, optionally heated with microwave irradiation to provide compound (112).

Scheme 27.

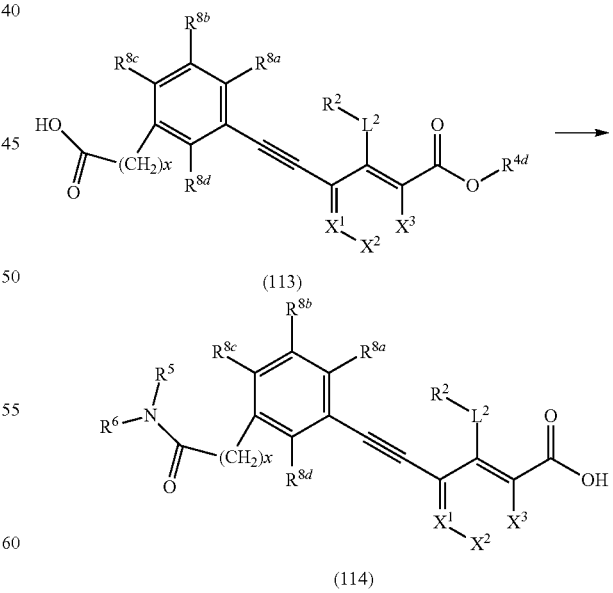

Compound (113) is converted to compound (114) according to Scheme 27, using appropriate reagents, starting materials and purification methods known to those skilled in the art.

Scheme 28.

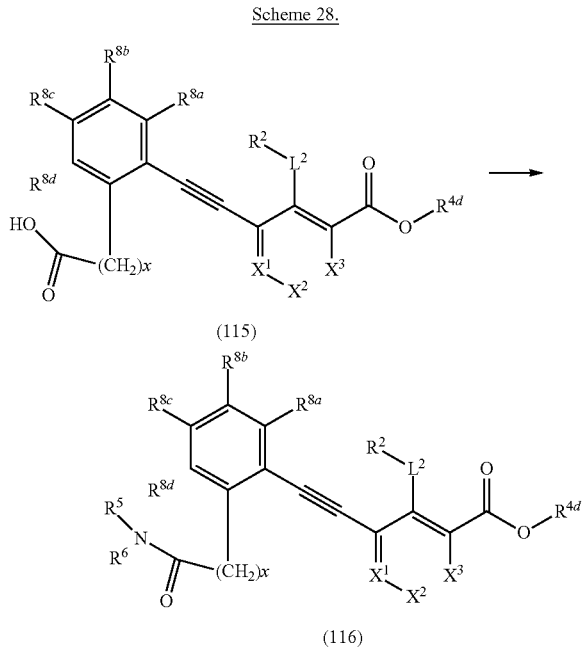

Compound (115) is converted to compound (116) according to Scheme 28, using appropriate reagents, starting materials and purification methods known to those skilled in the art.

Scheme 29.

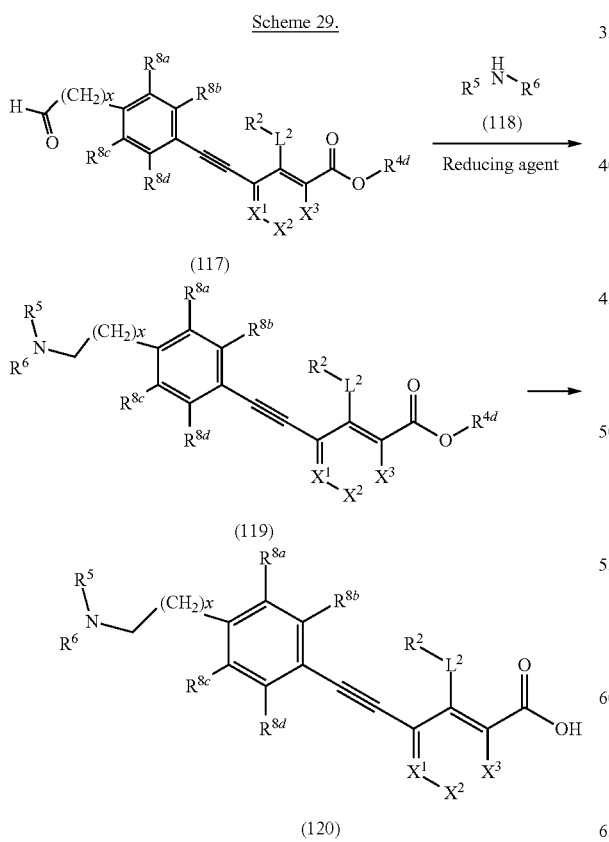

Compound (117) is reacted with compound (118), in the presence of a reducing agent such as sodium cyanoborohydride, sodium triacetoxyborohydride, and the like, in an organic solvent such as tetrahydrofuran, 1,4-dioxane, methanol, ethanol, and the like, to provide compound (119). Compound (119) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (120). Alternatively, compound (119) is reacted with an acid such as trifluoroacetic acid, hydrochloric acid, sulfuric acid, and the like, optionally in the presence of a solvent such as methanol, ethanol, N,N-dimethylformamide, tetrahydrofuran, 1,4-dioxane, methylene chloride and the like, optionally heated, optionally heated with microwave irradiation to provide compound (120).

Scheme 30.

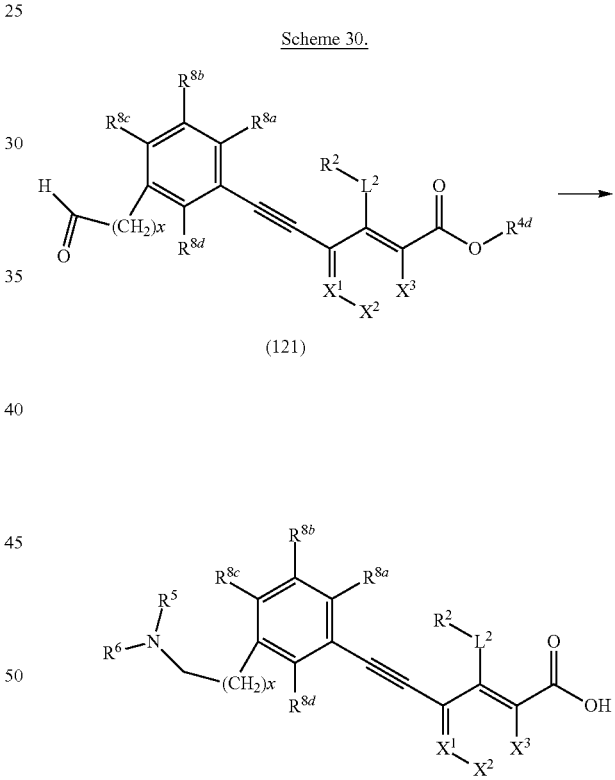

Compound (121) is converted to compound (122) according to Scheme 30, using appropriate reagents, starting materials and purification methods known to those skilled in the art.

Scheme 31.
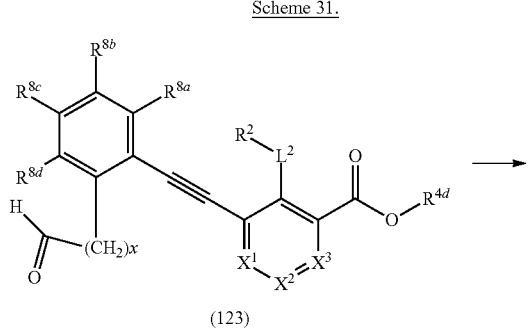
(123)
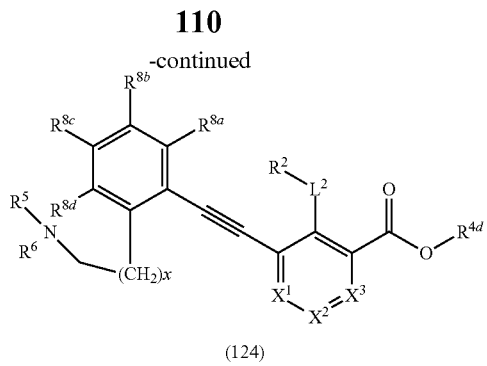
(124)
Compound (123) is converted to compound (124) according to Scheme 31, using appropriate reagents, starting materials and purification methods known to those skilled in the art.
Scheme 32.
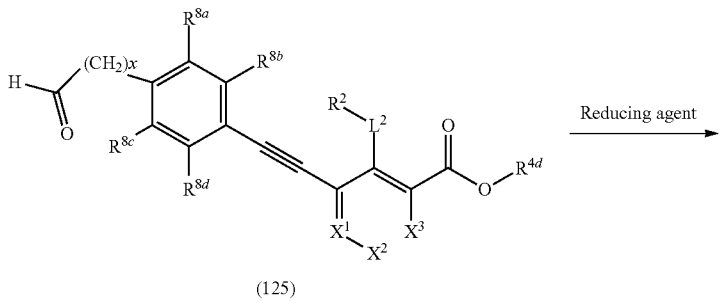
(125)
Reducing agent →
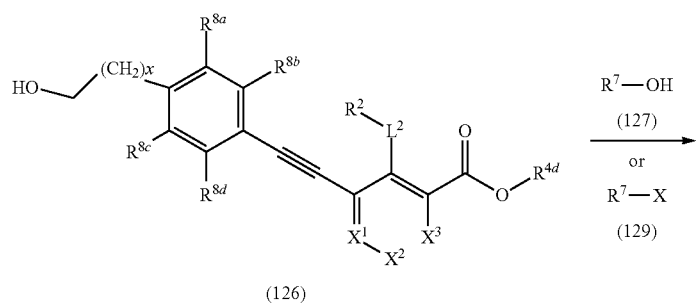
(126)
R$^7$—OH
(127)
or
R$^7$—X
(129)
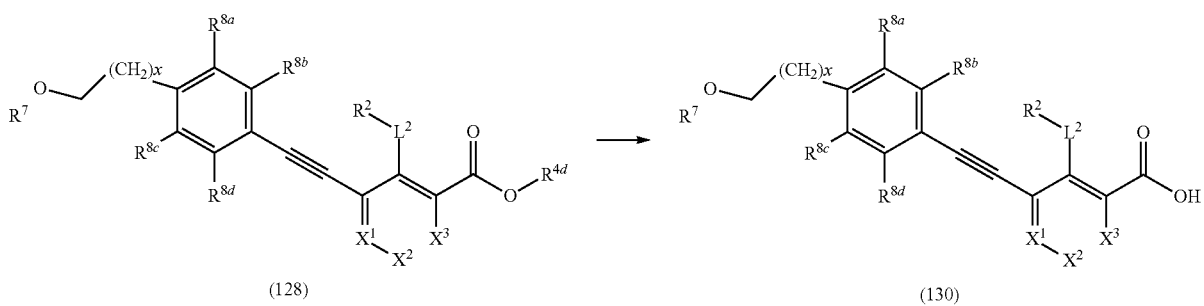
(128)　　(130)

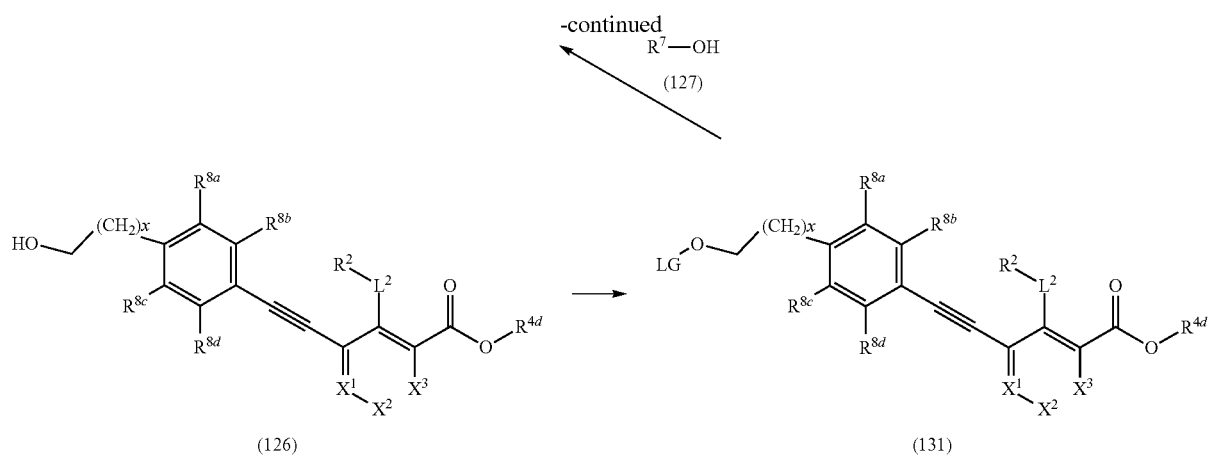

Compound (125) is reacted with a reducing agent such as sodium borohydride lithium aluminum hydride and the like, in an organic solvent such as tetrahydrofuran, 1,4-dioxane, methanol, ethanol, and the like, to provide compound (126). Compound (126) is reacted under Mitsunobu conditions with compound (127), in the presence of an agent such as diethylazodicarboxylate, diisopropylazodicarboxylate and the like, and a phosphine such as triphenylphosphine, and the like, in an organic solvent such as tetrahydrofuran, 1,4-dioxane, dichloromethane, and the like, to provide compound (128). Alternatively, compound (126) is reacted with compound (129), in which X is a leaving group such as a halogen, mesylate, tosylate and the like, in the presence of a base such as triethylamine, diisopropylethylamine, pyridine, sodium carbonate, potassium carbonate, sodium hydride, and the like, in a solvent such as tetrahydrofuran, dimethylformamide, and the like to provide compound (128). Alternatively, compound (126) is reacted with an activating group, which converts the hydroxy into a leaving group, such as methanesulfonyl chloride, tosyl chloride, and the like, in the presence of a base such as triethylamine, diisopropylethylamine, pyridine, sodium carbonate, potassium carbonate, sodium hydride, and the like, in a solvent such as tetrahydrofuran, dimethylformamide, and the like to provide compound (131), which is then treated with compound (127), in the presence of base such as triethylamine, diisopropylethylamine, pyridine, sodium carbonate, potassium carbonate, sodium hydride, and the like, in a solvent such as tetrahydrofuran, dimethylformamide, and the like to provide compound (128). A compound of formula (128) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (130). Alternatively, compound (128) is reacted with an acid such as trifluoroacetic acid, hydrochloric acid, sulfuric acid, and the like, optionally in the presence of a solvent such as methanol, ethanol, N,N-dimethylformamide, tetrahydrofuran, 1,4-dioxane, methylene chloride and the like, optionally heated, optionally heated with microwave irradiation to provide compound (130).

Scheme 33.

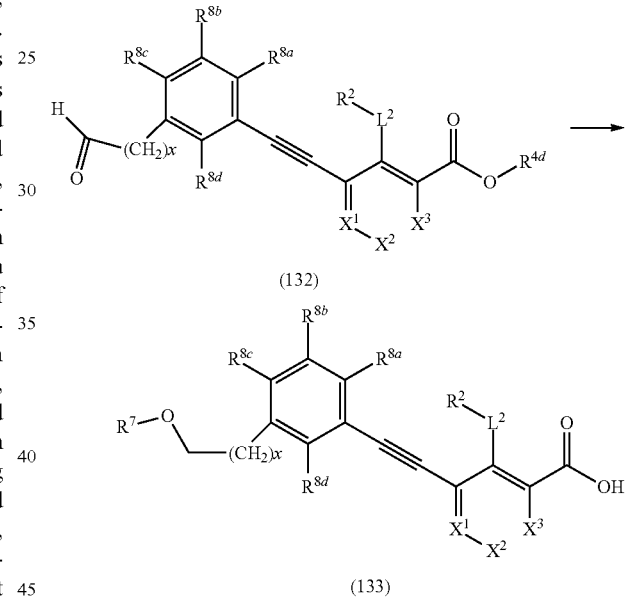

Compound (132) is converted to compound (133) according to Scheme 33, using appropriate reagents, starting materials and purification methods known to those skilled in the art.

Scheme 34.

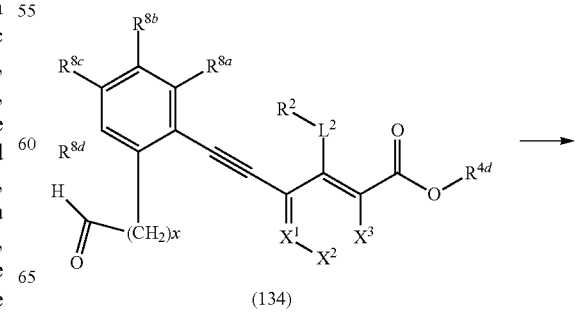

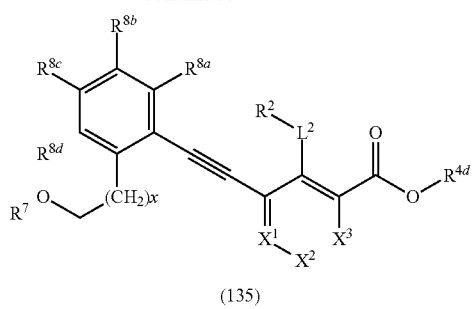

(135)

Compound (134) is converted to compound (135) according to Scheme 34, using appropriate reagents, starting materials and purification methods known to those skilled in the art.

Scheme 35.

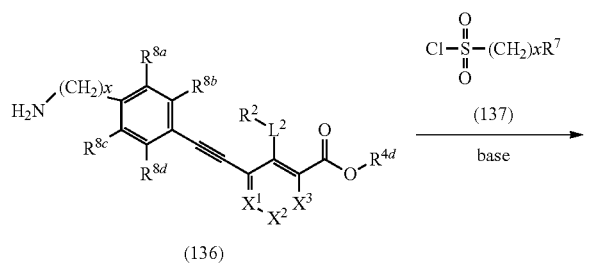

(136)

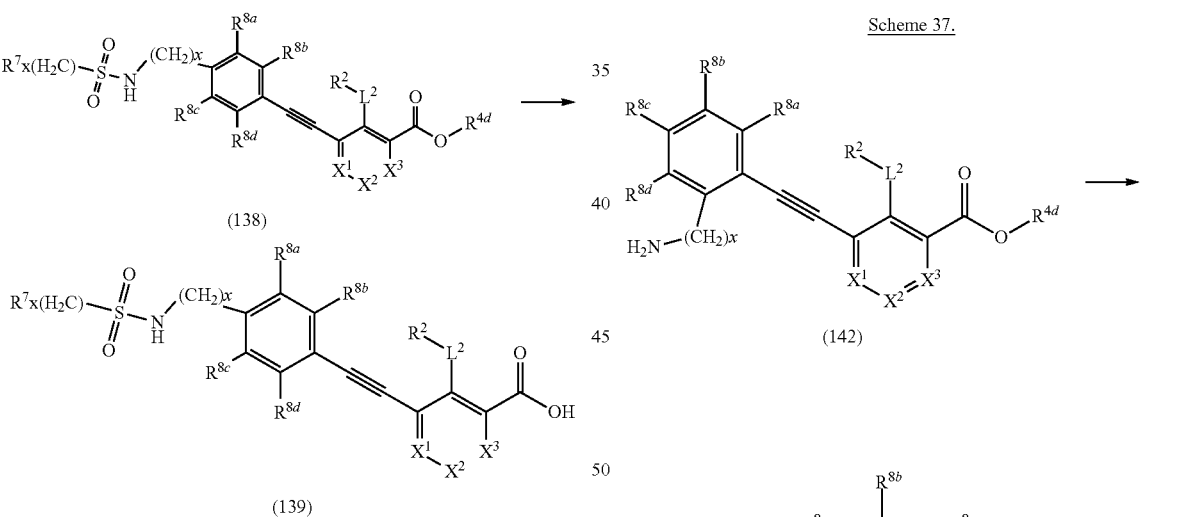

Compound (136) is reacted with a sulfonyl chloride of formula (137), in the presence of base such as triethylamine, diisopropylethylamine, pyridine, sodium carbonate, potassium carbonate, sodium hydride, and the like, in a solvent such as tetrahydrofuran, dimethylformamide, and the like to provide compound (128). A compound of formula (138) is reacted with a base such as sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, and the like, optionally heated, optionally heated with microwave irradiation to provide compound (139).

Scheme 36.

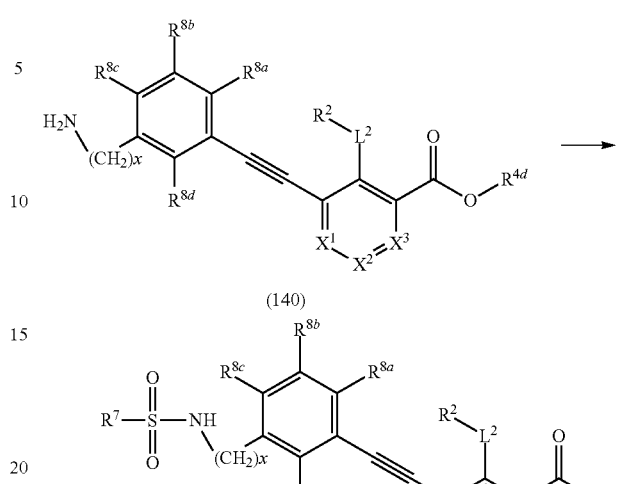

Compound (140) is converted to compound (141) according to Scheme 36, using appropriate reagents, starting materials and purification methods known to those skilled in the art.

Scheme 37.

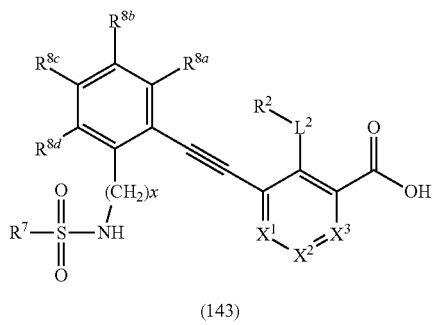

Compound (142) is converted to compound (143) according to Scheme 36, using appropriate reagents, starting materials and purification methods known to those skilled in the art.

Scheme 38

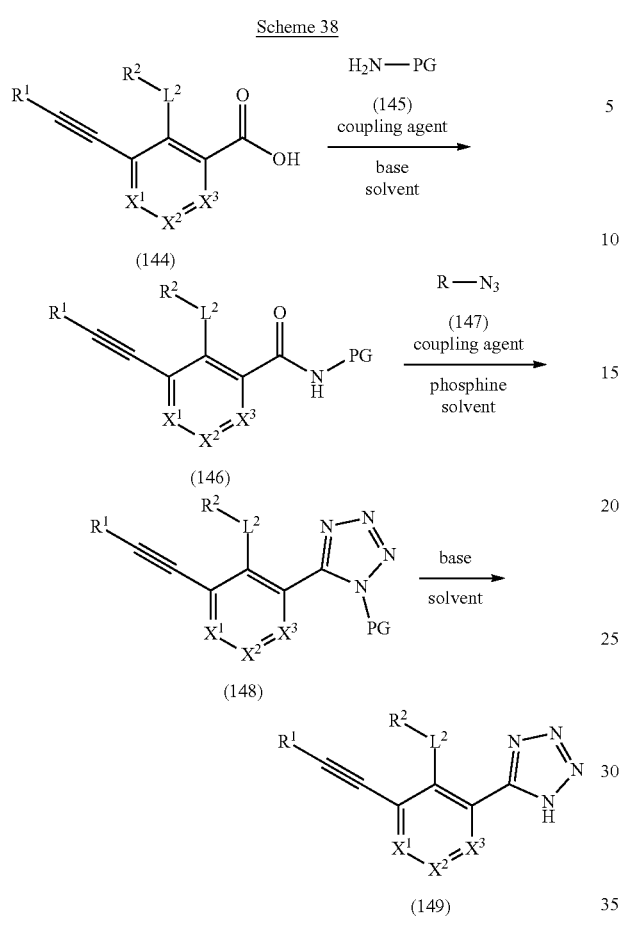

Compound (144) is reacted with compound (145), wherein PG is a protecting group such as a carboxylbenzy (Cbz), tert-butyloxycarbonyl (Boc), Fluorenylmethyloxycarbonyl (FMoc), and the like, in the presence of coupling agent such as 1-ethyl-3-(3-dimethylaminopropyl) carbodiimide, N,N'-Dicyclohexylcarbodiimide, O-Benzotriazole-N, N,N',N'-tetramethyl-uronium-hexafluoro-phosphate, O-(7-azabenzotriazol-1-yl)-N,N,N',N'-tetramethyl uronium hexafluorophosphate, Benzotriazole-1-yl-oxy-tris-(dimethylamino)-phosphonium hexafluoro phosphate, benzotriazol-1-yl-oxytripyrrolidinophosphonium hexafluorophosphate, and the like, in an organic solvent such as tetrahydrofuran, 1,4-dioxane, dimethylformamide, methylene chloride, dichloroethane, methanol, ethanol, and the like, optionally in the presence of a base such as triethylamine, diisopropylethyl amine, pyridine, 2,6-lutidine, and the like, optionally with heating, optionally with microwave irradiation, to provide compound (146). Compound (146) is reacted with a coupling agent such as diethylazodicarboxylate, diisopropylazodicarboxylate, di-tert-butyldicarboxylate and the like and a phoshine such as triphenylphosphine, tri-n-butylphosphine and the like, in the presence of compound (147), a suitably protected silyl azide, such as trimethylsilyl azide, in an organic solvent such as tetrahydrofuran, 1,4-dioxane, dimethylformamide, methylene chloride, dichloroethane, and the like, optionally with heating, optionally with microwave irradiation, to provide compound (148).

Compound (148) is reacted with a base such as sodium hydroxide, lithium hydroxide, potassium hydroxide, sodium carbonate, lithium carbonate, potassium carbonate, triethlamine, diisopropylethylamine, N-methylpyrrolidine (NMP), 2,6-lutidine, pyridine, and the like, in an organic solvent such as methanol, ethanol, N,N-dimethylformamide, tetrahydrofuran, 1,4-dioxane, and the like, optionally heated, optionally heated with microwave irradiation to provide compound (149). Alternatively, compound (148) is reacted with an acid such as trifluoroacetic acid, acetic acid, formic acid, hydrochloric acid, hydrobromic acid, and the like, in a solvent such as methanol, ethanol, N,N-dimethylformamide, tetrahydrofuran, 1,4-dioxane, methylene chloride, and the like, optionally heated, optionally heated with microwave irradiation to provide compound (149). Alternatively, compound (148) is reacted with hydrogen in the presence of a palladium catalyst such as palladium on carbon, palladium (II) acetate, tetrakis(triphenylphosphine) palladium(0), dichlorobis (triphenylphosphine)palladium(II), bis(acetonitrile)dichloropalladium(II), and the like, in a solvent such as methanol, ethanol, tetrahydrofuran, 1,4-dioxane, and the like to provide compound (149).

Scheme 39.

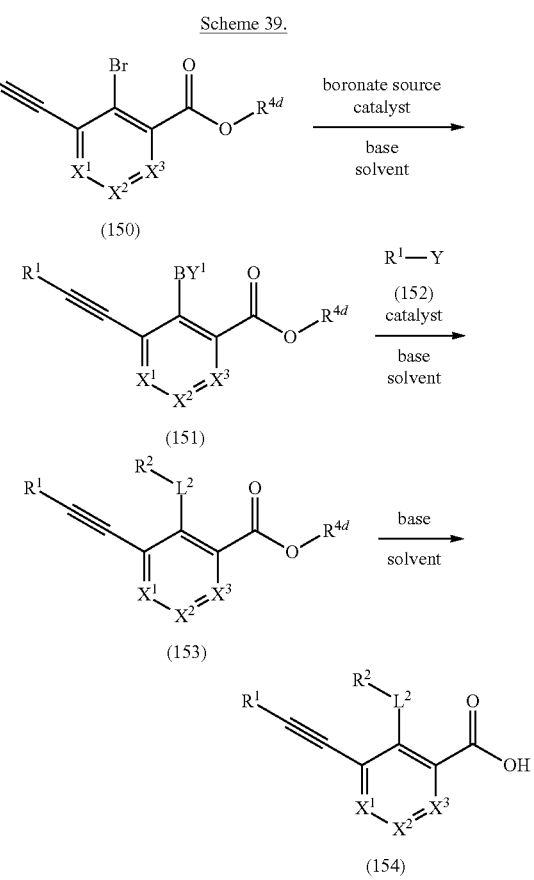

Compound (150) is reacted with a boronate source, such as bis(pinacolato)diboron 4,4,5,5-Tetramethyl-1,3,2-dioxaborolane, and the like, in the presence of a palladium catalyst such as palladium (II) acetate, tetrakis(triphenylphosphine) palladium(0), dichlorobis(triphenylphosphine) palladium (II), palladium on carbon, bis(acetonitrile)dichloropalladium(II), and the like, and a copper catalyst, such as copper (I) iodide and the like, in the presence of a base such as triethylamine, diisopropylethylamine, pyridine, 2,6-dimethylpyridine, sodium hydroxide, lithium hydroxide, potassium hydroxide, sodium carbonate, lithium carbonate, potassium carbonate, and the like, in an organic solvent such as methanol, ethanol, N,N-dimethylformamide, tetrahydrofuran, 1,4-dioxane, 1,2-dimethoxyethane and the like, optionally heated, optionally heated with microwave irradiation to provide compound (151) wherein Y1 is selected from the group consisting of pinacolato and (OH)$_2$. Compound (151) is reacted with compound (152), wherein Y is selected from the group consisting of chlorine, bromine, iodine, and trifluoromethanesulfonate, in the presence of a palladium catalyst such as [1,1'-bis (diphenylphosphino) ferrocene]palladium (II) dichloride dichloromethane adduct, palladium (II) acetate, tetrakis(triphenylphosphine)palladium(0), dichlorobis (triphenylphosphine)palladium(II), palladium on carbon, bis(acetonitrile)dichloro palladium (II), and the like, in the presence of a base such as triethylamine, diisopropylethylamine, pyridine, 2,6-dimethylpyridine, sodium hydroxide, lithium hydroxide, potassium hydroxide, sodium acetate, potassium acetate, sodium carbonate, lithium carbonate, potassium carbonate, and the like, in an organic solvent such as methanol, ethanol, N,N-dimethylformamide, tetrahydrofuran, 1,4-dioxane, 1,2-dimethoxyethane and the like, optionally heated, optionally heated with microwave irradiation to provide compound (153). Compound (153) is reacted with a base such as sodium hydroxide, lithium hydroxide, potassium hydroxide, sodium carbonate, lithium carbonate, potassium carbonate, and the like, in an organic solvent such as methanol, ethanol. N,N-dimethylformamide, tetrahydrofuran, 1,4-dioxane, and the like, optionally heated, optionally heated with microwave irradiation to provide compound (154).

Combination Therapies

The compounds identified using the methods described here are useful in the methods of the invention in combination with one or more additional agents useful for treating EBV infection and/or EBV-associated cancer. These additional agents may comprise compounds identified herein or agents, e.g., commercially available agents, known to treat, prevent, or reduce the symptoms of EBV infection and/or EBV-associated cancer.

One or more compounds of the invention described herein may be administered to a patient in need thereof with one or more of these agents. In certain embodiments, the compound of the invention is combined with one or more of agents, i.e., delivered to the patient concurrently. In other embodiment, the compound of the invention is delivered to the patient concurrently therewith one or more of these agents. In yet other embodiments, the compound of the invention is delivered prior to one or more of these agents. In yet other embodiments, the compound of the invention is delivered subsequent to one or more of these agents.

As used herein, combination of two or more compounds/agents may refer to a composition wherein the individual compounds/agents are physically mixed or wherein the individual compounds/agents are physically separated. A combination therapy encompasses administering the components/agents separately to produce the desired additive, complementary or synergistic effects. In certain embodiments, the compound and the agent are physically mixed in the composition. In other embodiments, the compound and the agent are physically separated in the composition.

In certain embodiments, an agent is administered prior to, concurrently with, or subsequent to the compound.

In certain embodiments, the agent is a chemotherapeutic. One of skill in the art would readily be able to select a chemotherapeutic for administration with one or more of the compound of the invention, based on the cancer being treated, patient physical condition, among others factors. In certain embodiment, the chemotherapeutic is selected from the group consisting of cisplatin, doxorubicin, 5-fluorouracil, cyclophosphamide, vincristine and prednisone.

In certain embodiments, the agent is an antiviral agent. In certain embodiments, the antiviral agent is selected from the group consisting of ganciclovir, acyclovir, valganciclovir, vidarabine, brivudine, cytarabine, idoxuridine, penciclovir, and famciclovir. In other embodiments, the antiviral agent is ganciclovir.

In certain embodiments, the agent is a histone deacetylase inhibitor. In certain embodiments, the histone deactylase inhibitor is selected from the group consisting of arginine butyrate, sodium butyrate, suberoylanilide hydroxamic acid (SAHA), and valproic acid.

In certain embodiments, the agent is a DNA methylation inhibitor. In certain embodiments, the DNA methylation inhibitor is 5'-azacytidine.

In certain embodiments, the agent is a proteasome inhibitor. In certain embodiments, the proteasome inhibitor is bortezamib.

In certain embodiments, the agent is an immunotherapy and/or vaccine. Desirably, the immunotherapy and/or vaccines are tailored to the patient and specific disease/conditions being treated. In certain embodiments, the immunotherapy and/or vaccine are tailored to the patient and specific cancer being treated. In certain embodiments, the immunotherapy is a patient derived (autologous) EBV specific T-cell or a non-patient derived EBV-specific T-cell (CART cells). In certain embodiments, the agent is an immunomodulator. In certain embodiments, the immunomodulator is at least one selected from Rituximab, PD1, PD-L1, CTLA4, antibodies to B-cells and modulators of regulatory T-cells and NK cells.

In certain embodiments, chemotherapy and/or radiation therapy bolster the effects of the EBV-activating therapy described herein. In other embodiments, immune-based therapies eradicate residual disease and activate endogenous immune responses. In yet other embodiments, such combination approaches (surgery plus chemotherapy/radiation plus immunotherapy) are anticipated to be successful in the treatment of many cancers along with the methods described herein.

The compounds identified using the methods described here are useful in the methods of the invention in combination with one or more additional treatment protocol useful for treating EBV infection and/or EBV-associated cancer. These additional treatment protocols may comprise treatment protocols known to treat, prevent, or reduce the symptoms of EBV infection and/or EBV-associated cancer.

In certain embodiments, adjunctive therapies for use with the methods and compositions described herein include acupuncture. In other embodiments, the non-chemical treatment protocol is surgery. In yet other embodiments, the non-chemical treatment protocol is chiropractic care. In yet other embodiments, the non-chemical treatment protocol is passive or active immunotherapy. In yet other embodiments, the non-chemical treatment protocol includes X-rays. In yet other embodiments, the non-chemical treatment protocol includes ultrasounds, among others. In other embodiments, adjunctive treatment protocols include diagnostic assessments, e.g., blood testing, to determine or monitor the progress of the infection, the course or status of the disease, relapse or any need for booster administrations of the compositions.

These additional treatment protocols may be administered prior to, concurrently with, or subsequent to administration of the compound of the invention. In certain embodiments, radiation is administered prior to, concurrently with, or subsequent to the compound.

Doses of the compound of the invention within the ranges described elsewhere herein may be used when the compound of the invention is administered in combination with an additional pharmacologically active reagent or in an additional treatment protocol. In other embodiments, lower doses of the compound of the invention are useful when administered in combination with an additional pharmacologically active reagent. In yet other embodiments, combination of the compound of the invention with another pharmacological agent or treatment protocol permits lower than usual dosages of the additional pharmacological agent or adjustment of the additional protocol regimen and/or lower doses of the compound of the invention to achieve the desired therapeutic effect.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Kits

Also provided are kits or packages of pharmaceutical formulations containing (i) at least one compound of the invention; and (ii) an antiviral and/or anticancer agent. In certain embodiments, the compound of the invention and the antiviral and/or anticancer agent are formulated for the desired delivery vehicle and route. In certain embodiments, the kit is also includes a chemotherapeutic agent described herein. In other embodiments, the compound and antiviral and/or anticancer agent are formulated for any suitable route, such as for oral or parenteral, for example, transdermal, transmucosal (e.g, sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In yet other embodiments, the kit is designed for delivery at home. The kit may thus include tubes or other containers, applicators, needles, syringes, and other appropriate packaging and instructions for use.

Methods

The invention provides a method of treating and/or preventing a disease or disorder caused by EBNA1 activity in a subject. The invention further provides a method of treating and/or preventing Epstein-Barr Virus (EBV) infection, and/or a disease or disorder associated with EBV infection, in a subject. The invention further provides a method of treating and/or preventing lytic and/or latent EBV Virus infection in a subject.

In certain embodiments, the disease or disorder is at least one selected from the group consisting of cancer, infectious mononucleosis, chronic fatigue syndrome, multiple sclerosis, systemic lupus erythematosus, and rheumatoid arthritis. In certain embodiments, the cancer is at least one selected from the group consisting of nasopharyngeal carcinoma, gastric carcinomas, non-hodgkin lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmactic lymphoma, nodal marginal zone B cell lymphoma, splenic marginal zone lymphoma, intravascular large B-cell lymphoma, primary effusion lymphoma, lyphomatoid granulomatosis, angioimmunoblastic lymphadenopathy, leiomyosarcomas, X-linked lymphoproliferative disease, post-transplant lymphoproliferative disorders, Hodgkin's lymphoma and breast cancer.

In certain embodiments, the methods of the invention comprise administering a therapeutically effective amount of a compound and/or composition of the invention to the subject in need thereof. In other embodiments, the compound of the invention is part of a pharmaceutical composition further comprising at least one pharmaceutically acceptable carrier. In yet other embodiments, the compound and/or composition is administered to the subject by at least one route selected from the group consisting of oral, nasal, inhalational, topical, buccal, rectal, pleural, peritoneal, vaginal, intramuscular, subcutaneous, transdermal, epidural, intratracheal, otic, intraocular, intrathecal, and intravenous routes. In yet other embodiments, the compound is administered as part of a pharmaceutical composition. In yet other embodiments, the subject is a mammal. In yet other embodiments, the mammal is human.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent in the composition. In yet other embodiments, the compound of the invention is the only biologically active agent in therapeutically effective amounts in the composition.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9.000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2.000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the dose of a compound of the invention is from about 1 mg and about 2,500 mg. In certain embodiments, a dose of a compound of the invention used in compositions described herein is less than about 10.000 mg, or less than about 8,000 mg, or less than about 6,000 mg, or less than about 5.000 mg, or less than about 3,000 mg, or less than about 2,000 mg, or less than about 1.000 mg, or less than about 500 mg, or less than about 200 mg, or less than about 50 mg. Similarly, in certain embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g, trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g, cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation". For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular)

form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85°%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier.

The unit dosage form may be for a single daily dose or one of multiple daily doses (e.g., about 1 to 5 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods $^1$H-NMR spectra were obtained on a Varian Mercury 300-MHz NMR or a Bruker 400 MHz NMR. Purity (%) and mass spectral data were determined with a Waters Alliance 2695 HPLC/MS (Waters Symmetry C18, 4.6×75 mm, 3.5 μm) with a 2996 diode array detector from 210-400 nm or with an Agilent Technologies-Ion-trap mass spectrometer-LC-MSD TRAPXCT PLUS.

Example 1

2-(1H-indol-6-yl)-3-[1-(2-morpholin-4-yl-ethyl)-1H-indol-6-ylethynyl]-benzoic acid

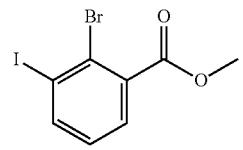

2-Bromo-3-iodo-benzoic acid methyl ester: To a stirring solution of 2-bromo-3-iodobenzoic acid (50.0 g, 0.15 mol) in methanol (125 mL) was added thionyl chloride (12.2 mL, 0.168 mol) over a period of 10 minutes at ice bath temperature. The reaction mixture was allowed to stir at 60° C. over a period of 12 hours. The resulting reaction mixture was allowed to reach room temperature, diluted with ethyl acetate (500 mL), washed with sodium bicarbonate (250 mL), water (2×250 mL), brine (250 mL), dried over sodium sulfate and filtered. Silica gel (100 g, 60-120 mesh) was added to the filtrate, stirred for 30 minutes at 25-30° C., filtered and concentrated under reduced pressure to give methyl 2-bromo-3-iodobenzoate as a pale yellow liquid (50.0 g, 96%). $^1$H NMR (400 MHz, DMSO-$d_6$) δ 8.11 (dd, J=7.8, 1.5 Hz, 1H), 7.62 (dd, J=7.6, 1.5 Hz, 1H), 7.23 (t, J=7.7 Hz, 1H), 3.85 (s, 3H). MS m/z (M+) 340.9, (M+2) 342.9.

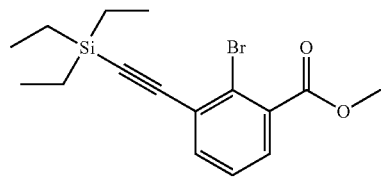 [SMILES: CC[Si](C#Cc1cccc(C(=O)OC)c1Br)(CC)CC]

2-bromo-3-triethylsilanylethynyl-benzoic acid methyl ester: A solution of methyl 2-bromo-3-iodobenzoate (400 g, 1.176 mol) in tetrahydrofuran and triethylamine (1.0 L:1.0 L) was deaerated using a argon gas over a period of 15 minutes. To this solution were added bis(triphenylphosphine) palladium(II) dichloride (8.24 g, 0.0117 mol), copper (I) iodide (11.23 g, 0.058 mol) and triethyl-ethynyl-silane (253.6 mL, 1.412 mol) at ambient temperature over a period of 30 minutes. The reaction mixture was allowed to stir at ambient temperature over a period of 4 hours. The reaction mixture was concentrated under reduced pressure, diethyl ether (1.5 L) was added to the crude product, stirred for 30 minutes and filtered through celite pad. The filtrate was then concentrated under reduced pressure to give 2-bromo-3-triethylsilanylethynyl-benzoic acid methyl ester as a light brown liquid (372 g, 90%). $^1$H NMR (400 MHz, DMSO-$d_6$) δ 7.70 (ddd, J=16.6, 7.7, 1.7 Hz, 2H), 7.49 (t, J=7.7 Hz, 1H), 3.86 (s, 3H), 1.01-1.05 (t, J=7.9 Hz, 9H), 0.65-0.71 (q, J=7.7 Hz, 6H). MS m/z (M+353.3, (M+2) 355.2.

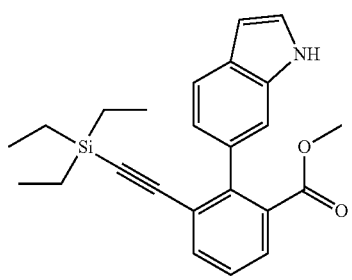 [SMILES: CC[Si](C#Cc1cccc(C(=O)OC)c1-c1ccc2cc[nH]c2c1)(CC)CC]

2-(1H-Indol-6-yl)-3-triethylsilanyl ethynyl-benzoic acid methyl ester: A solution of 2-bromo-3-triethylsilanylethynyl-benzoic acid methyl ester (300 g, 0.85 mol) in 1,4-dioxane:water (750 mL:750 mL) was deaerated using a argon gas over a period of 15 minutes. To this solution were added 6-(4,4,5,5-tetramethyl-[1,3,2]dioxaborolan-2-yl)-1H-indole (227.1 g, 0.93 mol), [1,1'-Bis(diphenyl phosphino) ferrocene]dichloropalladium(II), complex with dichloromethane (6.94 g, 0.0085 mol) and potassium carbonate (235 g, 1.7 mol) at ambient temperature. The reaction mixture was heated to 90° C. over a period of 3 hours. The resultant reaction mixture was then allowed to reach ambient temperature, diluted with ethyl acetate (2 L) and filtered through celite. The aqueous layer was separated and organic layer was washed with water (500 mL), brine (500 mL), dried (sodium sulfate), filtered and concentrated under reduced pressure. The resultant crude product was suspended with 10% ethyl acetate in hexane, stirred for 30 minutes, filtered, and dried to give 2-(1H-indol-6-yl)-3-triethylsilanylethynyl-benzoic acid methyl ester as a brown solid (248 g, 75%). $^1$H NMR (400 MHz, DMSO-$d_6$) δ 11.08 (s, 1H), 7.68 (ddd, J=10.9, 7.7, 1.4 Hz, 2H), 7.55-7.39 (m, 2H), 7.36 (t, J=2.7 Hz, 1H), 7.32-7.25 (m, 1H), 6.84 (dd, J=8.1, 1.5 Hz, 1H), 6.43 (ddd, J=3.1, 1.9, 0.9 Hz, 1H), 3.45 (s, 3H), 0.69 (t, J=7.9 Hz, 9H), 0.36 (q, J=7.7 Hz, 6H). MS m/z (M+H) 390.2.

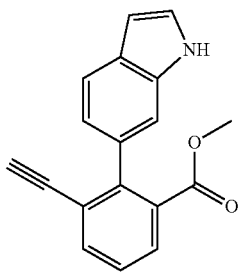 [SMILES: C#Cc1cccc(C(=O)OC)c1-c1ccc2cc[nH]c2c1]

3-ethynyl-2-(1H-indol-6-yl)-benzoic acid methyl ester: To a stirring solution of 2-(1H-indol-6-yl)-3-triethylsilanylethynyl-benzoic acid methyl ester (250 g, 0.645 mol) in tetrahydrofuran (1.25 L) was added 1.0 M tetrabutylammonium fluoride (838 mL, 0.838 mol) at 0-5° C. over a period of 30 minutes. The reaction mixture was allowed to stir at ambient temperature over a period 60 minutes. Completion of the reaction was monitored by TLC and LC-MS. The reaction mixture was concentrated under reduced pressure. The resultant crude product was then diluted with ethyl acetate (2000 mL) and washed with water (2×500 mL). Organic layer was washed with brine (600 mL), dried over sodium sulfate, filtered and concentrated under reduced pressure. The resultant crude product was purified through silica gel cartridge eluting with ethyl acetate/hexanes to give 3-ethynyl-2-(1H-indol-6-yl)-benzoic acid methyl ester as pale yellow solid (124 g, 70%). $^1$H NMR (400 MHz, DMSO-$d_6$) δ 11.16 (s, 1H), 7.74 (dd, J=7.7, 1.4 Hz, 1H), 7.68 (dd, J=7.7, 1.4 Hz, 1H), 7.57-7.35 (m, 3H), 7.31 (dt, J=1.7, 0.9 Hz, 1H), 6.85 (dd, J=8.2, 1.6 Hz, 1H), 6.45 (ddd, J=3.0, 1.9, 0.9 Hz, 1H), 4.03 (s, 3H), 3.44 (s, 1H). MS m/z (M+H) 276.3.

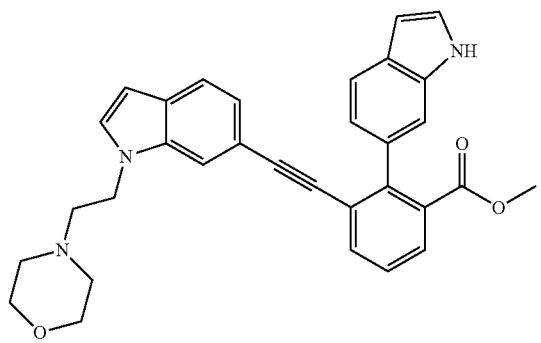 [SMILES: COC(=O)c1cccc(C#Cc2ccc3ccn(CCN4CCOCC4)c3c2)c1-c1ccc2cc[nH]c2c1]

2-(1H-indol-6-yl)-3-[1-(2-morpholin-4-yl-ethyl)-1H-indol-6-ylethynyl]-benzoic acid methyl ester: To a stirring solution of 6-bromo-1-(2-morpholin-4-yl-ethyl)-1H-indole (560 mg, 1.82 mmol) in toluene:triethylamine (5:5 mL) was added cesium carbonate (1.54 g, 4.73 mmol) and the reaction mixture was deaerated using an argon gas balloon for 15 minutes. To this suspension was added palladium (II) acetonitrile dichloride complex (5.0 mg, 0.0182 mmol) and 2-dicyclohexylphosphino-2',4',6'-triisopropylbiphenyl (26 mg, 0.055 mmol) at ambient temperature. The resulting reaction mixture was stirred under inert atmosphere for 30 minutes. To the above reaction mixture, 3-ethynyl-2-(1H-indol-6-yl)-benzoic acid methyl ester (500 mg, 1.82 mmol) was added and the reaction mass was heated to 90° C. for a period of 4 hours. The resultant reaction mixture was then allowed to cool to ambient temperature and diluted with ethyl acetate (50 mL) and filtered through celite. The organic layer was washed with water (2×20 mL), brine (20 mL), dried (sodium sulfate), filtered and concentrated under reduced pressure. The resultant crude product was purified through silica gel cartridge eluting with dichloromethane/methanol to give the product 2-(1H-indol-6-yl)-3-[1-(2-morpholin-4-yl-ethyl)-1H-indol-6-ylethynyl]-benzoic acid methyl ester as pale yellow solid in 49% yield. $^1$H NMR (400 MHz, DMSO-$d_6$) δ 11.22 (s, 1H), 7.79 (dd. J=7.6, 1.2 Hz, 1H), 7.67 (dd, J=8.0, 1.2 Hz, 1H), 7.62 (d, J=8.0 Hz, 1H), 7.51-7.41 (m, 5H), 7.15 (s, 1H), 6.99 (dd, J=8.0, 1.6 Hz, 1H), 6.82 (dd, J=8.0, 1.2 Hz, 1H), 6.50 (s, 1H), 6.40 (d, J=3.2 Hz, 1H), 4.14 (t, J=6.4 Hz, 2H), 3.49-3.47 (m, 7H), 2.55 (t, J=6.0 Hz, 2H), 2.35 (bs, 4H). MS m/z (M+H) 504.2.

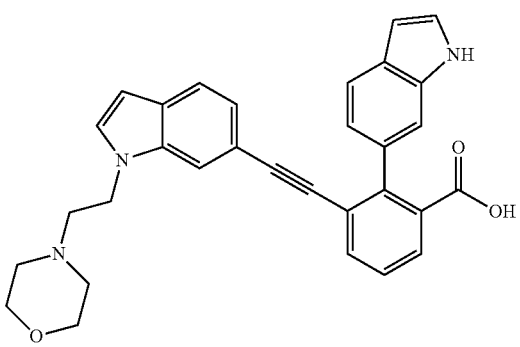 [SMILES: O=C(O)c1cccc(C#Cc2ccc3ccn(CCN4CCOCC4)c3c2)c1-c1ccc2cc[nH]c2c1]

2-(1H-indol-6-yl)-3-[1-(2-morpholin-4-yl-ethyl)-1H-indol-6-ylethynyl]-benzoic acid: To a solution of 2-(1H-indol-6-yl)-3-[1-(2-morpholin-4-yl-ethyl)-1H-indol-6-ylethynyl]-benzoic acid methyl ester (120 mg, 0.24 mmol) in tetrahydrofuran:methanol (1:1 mL) was added 2N sodium hydroxide (aq) (48 mg, 1.2 mmol) and the resulting solution was stirred for about 24 hours at ambient temperature. The reaction mixture was then concentrated and the pH adjusted to 4 using 1 N hydrochloric acid solution. The aqueous layer was then extracted using ethyl acetate (2×25 mL), washed with water (20 mL) and brine (10 mL). The organic layers were combined, dried (sodium sulfate), filtered and concentrated under reduced pressure. The resulting crude product was then purified using reversed phase HPLC to give the 2-(1H-indol-6-yl)-3-[1-(2-morpholin-4-yl-ethyl)-1H-indol-6-ylethynyl]-benzoic acid as pale yellow solid in 70% yield. $^1$H NMR (400 MHz, DMSO-$d_6$) δ 12.70 (brs, 1H), 11.22 (s, 1H), 7.74 (dd, J=7.6, 1.2 Hz, 1H), 7.65 (dd, J=7.6, 1.2 Hz, 1H), 7.61 (d, J=8.4 Hz, 1H), 7.48-7.44 (m, 3H), 7.42-7.40 (m, 2H), 7.14 (s, 1H), 7.06 (dd, J=8.0, 1.6 Hz, 1H), 6.80 (dd, J=8.0, 0.8 Hz, 1H), 6.49 (s, 1H), 6.39 (d, J=2.8 Hz, 1H), 4.14 (t, J=6.4 Hz, 2H), 3.49 (t, J=4.0 Hz, 4H), 2.55 (bs, 2H), 2.35 (bs, 4H). MS m/z (M+H) 490.3.

Example 2

3-[3-Acetylamino-4-(tetrahydro-pyran-4-yloxy)-phenylethynyl]-2-(1H-indol-6-yl)-benzoic acid

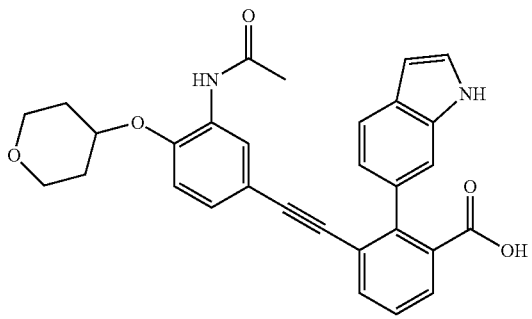 [SMILES: CC(=O)Nc1cc(C#Cc2cccc(C(=O)O)c2-c2ccc3cc[nH]c3c2)ccc1OC1CCOCC1]

3-[3-Acetylamino-4-(tetrahydro-pyran-4-yloxy)-phenylethynyl]-2-(1H-indol-6-yl)-benzoic acid was prepared by the same procedure as Example 1. $^1$H NMR (400 MHz, DMSO-$d_6$) δ 12.70 (s, 1H), 11.15 (d, J=2.6 Hz, 1H), 8.95 (s, 1H), 7.82 (s, 1H), 7.73 (dd, J=7.8, 1.4 Hz, 1H), 7.66-7.54 (m, 2H), 7.48-7.34 (m, 3H), 7.08-6.98 (m, 2H), 6.74 (dd, J=8.5, 2.2 Hz, 1H), 4.59 (tt, J=8.6, 4.2 Hz, 1H), 3.85 (dt, J=11.6, 4.4 Hz, 2H), 3.49-3.33 (m, 3H), 2.09 (s, 3H), 1.90 (dt, J=13.5, 3.9 Hz, 2H). 1.64 (dtd, J=13.0, 9.0, 4.0 Hz, 2H). MS m/z (M+H) 495.4.

Example 3

3-[4-(8-Acetyl-8-aza-bicyclo[3.2.1]oct-3-yl)-phenylethynyl]-2-(1H-indol-6-yl)-benzoic acid

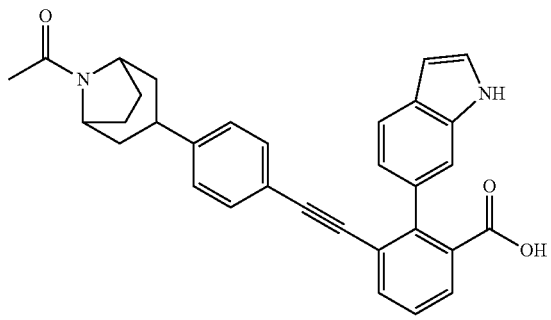 [SMILES: CC(=O)N1C2CCC1CC(c1ccc(C#Cc3cccc(C(=O)O)c3-c3ccc4cc[nH]c4c3)cc1)C2]

3-[4-(8-Acetyl-8-aza-bicyclo[3.2.1]oct-3-yl)-phenylethynyl]-2-(1H-indol-6-yl)-benzoic acid was prepared by the same procedure as Example 1. $^1$H NMR (400 MHz, DMSO-$d_6$) δ 11.16 (s, 1H), 7.61-7.54 (m, 1H), 7.49 (dd, J=16.2, 7.7 Hz, 3H), 7.38-7.29 (m, 2H), 7.25-7.11 (m, 2H), 7.10-7.00 (m, 3H), 6.44 (s, 1H), 4.48 (d, J=5.5 Hz, 1H), 4.25-4.18 (m, 1H), 3.14 (tt, J=11.4, 6.1 Hz, 1H), 1.99 (s, 4H), 2.00-1.80 (m, 2H), 1.80 (s, 2H), 1.81-1.66 (m, 2H), 1.70-1.50 (m, 2H). MS m/z (M+H) 489.4.

Example 4

3-[1-(2-Dimethylamino-ethyl)-1H-pyrrolo[2,3-b]pyridin-5-ylethynyl]-2-(1H-indol-6-yl)-benzoic acid

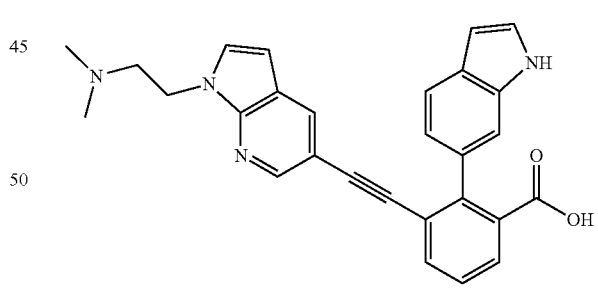

3-[1-(2-Dimethylamino-ethyl)-1H-pyrrolo[2,3-b]pyridin-5-ylethynyl]-2-(1H-indol-6-yl)-benzoic acid was prepared by the same procedure as Example 1. $^1$H NMR (400 MHz DMSO-$d_6$) δ 11.21 (s, 1H), 7.97 (d, J=1.9 Hz, 1H), 7.71 (dd. J=7.5, 1.7 Hz, 2H), 7.63-7.55 (m, 3H), 7.50-7.37 (m, 3H), 7.06 (dd, J=8.1, 1.6 Hz, 1H), 6.48 (s, 1H), 6.39 (d, J=3.5 Hz, 1H), 4.29 (t, J=6.5 Hz, 2H), 2.60 (t, J=6.5 Hz, 2H), 2.14 (s, 6H). MS m/z (M+H) 449.2

Example 5

3-[1-(3-Dimethylamino-propyl)-1H-pyrrolo[2,3-b]pyridin-5-ylethynyl]-2-(1H-indol-6-yl)-benzoic acid

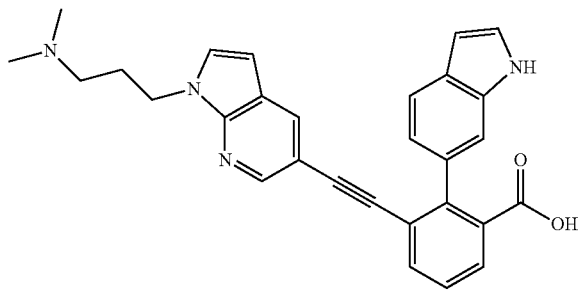 [SMILES: CN(C)CCCn1ccc2cc(C#Cc3cccc(C(=O)O)c3-c3ccc4cc[nH]c4c3)cnc21]

3-[1-(3-Dimethylamino-propyl)-1H-pyrrolo[2,3-b]pyridin-5-ylethynyl]-2-(1H-indol-6-yl)-benzoic acid was prepared by the same procedure as Example 1. $^1$H NMR (400 MHz, DMF-$d_7$) δ 11.62 (d, J=2.3 Hz, 1H), 8.38 (s, 1H), 8.14 (q, J=2.9 Hz, 2H), 8.07-7.96 (m, 3H), 7.90-7.78 (m, 3H), 7.47 (dd, J=8.1, 1.6 Hz, 1H), 6.89 (s, 1H), 6.82 (d, J=3.5 Hz, 1H), 4.63 (t, J=7.1 Hz, 2H), 2.59 (t, J=7.0 Hz, 2H), 2.54 (s, 6H), 2.28 (p, J=7.1 Hz, 2H). MS m/z (M+H) 463.2.

Example 6

2-(1H-indol-6-yl)-3-[1-(3-morpholin-4-yl-propyl)-1H-pyrrolo[2,3-b]pyridin-5-ylethynyl]-benzoic acid

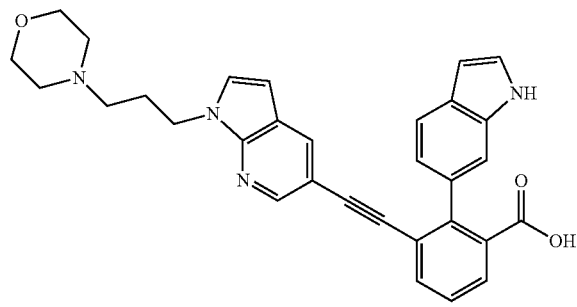

2-(1H-indol-6-yl)-3-[1-(3-morpholin-4-yl-propyl)-1H-pyrrolo[2,3-b]pyridin-5-ylethynyl]-benzoic acid was prepared by the same procedure as Example 1. $^1$H NMR (400 MHz, DMSO-$d_6$) δ 12.72 (s, 1H), 11.22 (d, J=2.5 Hz, 1H), 7.96 (d, J=1.9 Hz, 1H), 7.79-7.56 (m, 4H), 7.51-7.38 (m, 3H), 7.05 (dd, J=8.1, 1.6 Hz, 1H), 6.49 (s, 1H), 6.40 (d, J=3.5 Hz, 1H), 4.24 (t, J=7.0 Hz, 2H), 3.52 (t, J=4.6 Hz, 4H), 2.27 (s, 4H), 2.18 (t, J=7.0 Hz, 2H), 1.90 (p, J=7.0 Hz, 2H). MS m/z (M+H) 505.2.

Example 7

2-(1H-indol-6-yl)-3-[1-(3-morpholin-4-yl-propyl)-1H-pyrrolo[2,3-b]pyridin-3-ylethynyl]-benzoic acid

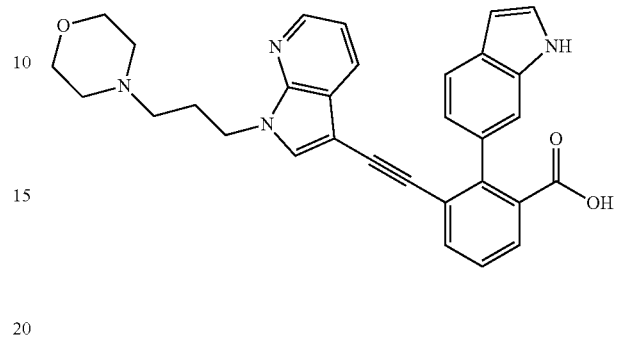

2-(1H-indol-6-yl)-3-[1-(3-morpholin-4-yl-propyl)-1H-pyrrolo[2,3-b]pyridin-5-ylethynyl]-benzoic acid was prepared by the same procedure as Example 1. $^1$H NMR (400 MHz, DMSO-$d_6$) δ 12.72 (s, 1H), 11.16 (s, 1H), 8.20 (dd, J=4.6, 1.7 Hz, 1H), 7.78-7.66 (m, 2H), 7.65-7.54 (m, 2H), 7.49-7.39 (m, 3H), 6.99 (dd, J=8.1, 1.5 Hz, 1H), 6.90-6.77 (m, 2H), 6.51 (s, 1H), 4.22 (t, J=7.0 Hz, 2H), 3.50 (t, J=4.6 Hz, 4H), 2.25 (s, 4H), 2.19 (t, J=6.9 Hz, 2H), 1.90 (p, J=7.0 Hz, 2H). MS m/z (M+H) 505.2.

Example 8

2-(1H-indol-6-yl)-3-[1-(2-morpholin-4-yl-ethyl)-1H-pyrrolo[2,3-b]pyridin-5-ylethynyl]-benzoic acid

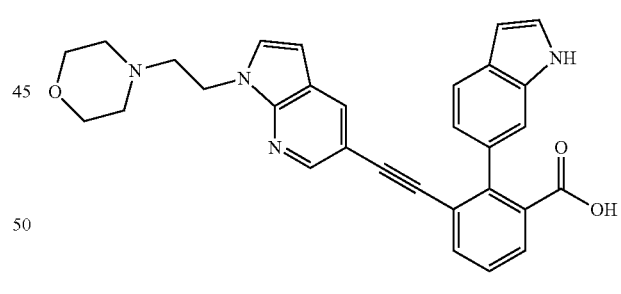

2-(1H-indol-6-yl)-3-[1-(2-morpholin-4-yl-ethyl)-1H-pyrrolo[2,3-b]pyridin-5-ylethynyl]-benzoic acid was prepared by the same procedure as Example 1. $^1$H NMR (400 MHz, DMSO-$d_6$) δ 12.72 (s, 1H), 11.21 (d, J=2.4 Hz, 1H), 7.96 (d, J=2.0 Hz, 1H), 7.80-7.69 (m, 2H), 7.70-7.56 (m, 3H), 7.52-7.38 (m, 3H), 7.05 (dd, J=8.1, 1.6 Hz, 1H), 6.49 (s, 1H), 6.40 (d, J=3.5 Hz, 1H), 4.33 (t, J=6.4 Hz, 2H), 3.49 (t, J=4.6 Hz, 4H), 2.65 (t, J=6.5 Hz, 2H), 2.40 (d, J=4.7 Hz, 4H). MS m/z (M+H) 491.3.

Example 9

3-[1-(2-Dimethylamino-ethyl)-1H-pyrrolo[2,3-b]pyridin-3-ylethynyl]-2-(1H-indol-6-yl)-benzoic acid

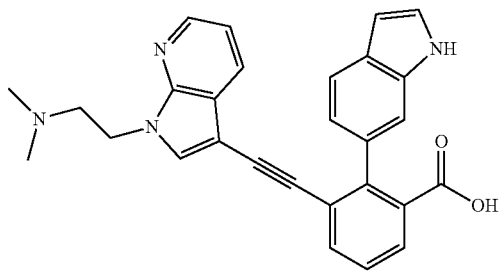 [SMILES: CN(C)CCn1cc(C#Cc2cccc(C(=O)O)c2-c2ccc3cc[nH]c3c2)c2cccnc21]

3-[1-(2-Dimethylamino-ethyl)-1H-pyrrolo[2,3-b]pyridin-3-ylethynyl]-2-(1H-indol-6-yl)-benzoic acid was prepared by the same procedure as Example 1. $^1$H NMR (400 MHz, DMSO-$d_6$) δ 12.68 (bs, 1H), 11.18 (d, J=2.5 Hz, 1H), 8.20 (dd. J=4.3, 2.0 Hz, 1H), 7.76 (s, 1H), 7.72 (dd, J=7.7, 1.4 Hz, 1H), 7.66-7.55 (m, 2H), 7.50-7.39 (m, 3H), 6.99 (dd, J=8.1, 1.5 Hz, 1H), 6.87-6.76 (m, 2H), 6.52 (ddd, J=3.0, 2.0, 0.9 Hz, 1H), 4.29 (t, J=6.3 Hz, 2H), 2.63 (t, J=6.3 Hz, 2H), 2.15 (s, 6H). MS m/z (M+H) 449.4.

Example 10

2-(1H-indol-6-yl)-3-[1-(2-morpholin-4-yl-ethyl)-1H-pyrrolo[2,3-b]pyridin-3-ylethynyl]-benzoic acid

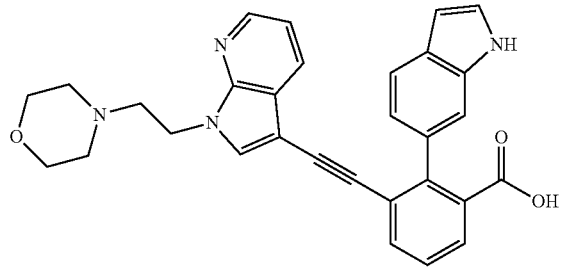 [SMILES: O=C(O)c1cccc(C#Cc2cn(CCN3CCOCC3)c3ncccc23)c1-c1ccc2cc[nH]c2c1]

2-(1H-indol-6-yl)-3-[1-(2-morpholin-4-yl-ethyl)-1H-pyrrolo[2,3-b]pyridin-3-ylethynyl]-benzoic acid was prepared by the same procedure as Example 1. $^1$H NMR (400 MHz, DMSO-$d_6$) δ 11.08 (s, 1H), 8.18 (d, J=4.8 Hz, 1H), 7.72 (s, 1H), 7.53-7.42 (m, 2H), 7.38-7.29 (m, 2H), 7.20 (s, 2H), 7.10 (d, J=8.1 Hz, 1H), 6.97 (d, J=7.8 Hz, 1H), 6.86-6.79 (m, 1H), 6.45 (s, 1H), 4.30 (t, J=6.3 Hz, 2H), 3.48 (t, =4.6 Hz, 4H), 2.64 (d, J=6.1 Hz, 2H), 2.39 (s, 4H). MS m/z (M+H) 491.4.

Example 11

3-[1-(3-Dimethylamino-propyl)-1H-pyrrolo[2,3-b]pyridin-3-ylethynyl]-2-(1H-indol-6-yl)-benzoic acid

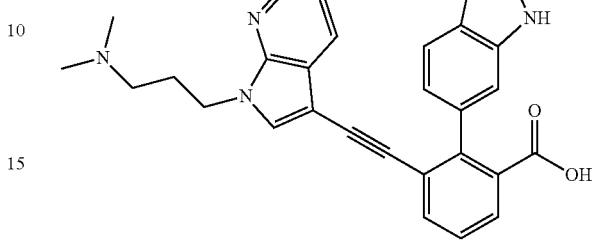

3-[1-(3-Dimethylamino-propyl)-1H-pyrrolo[2,3-b]pyridin-3-ylethynyl]-2-(1H-indol-6-yl)-benzoic acid was prepared by the same procedure as Example 1. $^1$H NMR (400 MHz, DMSO-$d_6$) δ 11.17 (1, J==2.3 Hz, 1H), 8.21 (dd, J=4.5, 1.7 Hz, 1H), 7.75 (s, 1H), 7.78-7.66 (m, 1H), 7.66-7.54 (m, 2H), 7.50-7.39 (m, 3H), 6.99 (dd, J=8.1, 1.5 Hz, 1H), 6.90-6.78 (m, 2H), 6.52 (s, 1H), 4.20 (t, J=7.1 Hz, 2H), 2.19 (t, J=7.1 Hz, 2H), 2.13 (s, 6H), 1.87 (p, J=7.1 Hz, 2H). MS m/z (M+H) 463.5.

Example 12

3-(1-[2-(1,1-Dioxo-1$\lambda^6$-thiomorpholin-4-yl-ethyl]-1H-pyrrolo[2,3-b]pyridin-5-ylethynyl)-2-(H-indol-6-yl)-benzoic acid

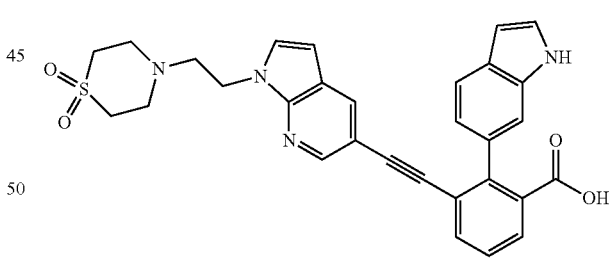

3-{1-[2-(1,1-Dioxo-1$\lambda^6$-thiomorpholin-4-yl)-ethyl]-1H-pyrrolo[2,3-b]pyridin-5-ylethynyl}-2-(1H-indol-6-yl)-benzoic acid was prepared by the same procedure as Example 1. $^1$H NMR (400 MHz, DMSO-$d_6$) δ 12.72 (s, 1H), 11.21 (s, 1H), 7.96 (d, J=1.9 Hz, 1H), 7.80-7.69 (m, 2H), 7.70-7.61 (m 2H), 7.60 (d, J=8.1 Hz, 1H), 7.52-7.38 (m, 3H), 7.05 (dd, J=8.2, 1.6 Hz, 1H), 6.49 (s, 1H), 6.41 (d, J=3.5 Hz, 1H), 4.32 (t, =6.3 Hz, 2H), 2.98 (q, J=3.9 Hz 4H), 2.95-2.82 (m, 6H). MS nm/z (M+H) 539.3.

Example 13

2-(1H-indol-6-yl)-3-[1-(2-morpholin-4-yl-ethyl)-1H-indol-5-ylethynyl]-benzoic acid

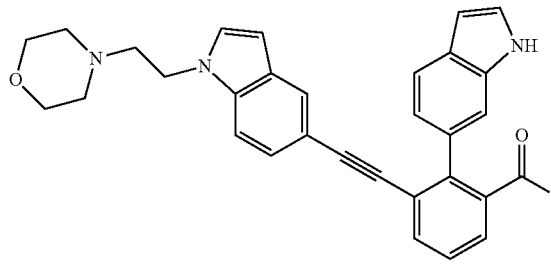

2-(1H-indol-6-yl)-3-[1-(2-morpholin-4-yl-ethyl)-1H-indol-5-ylethynyl]-benzoic acid was prepared by the same procedure as Example 1. $^1$H NMR (400 MHz, DMSO-d$_6$) δ 12.68 (s, 1H), 11.21 (d, J=2.3 Hz, 1H), 7.73 (dd, J=7.7, 1.5 Hz, 1H), 7.66-7.55 (m, 2H), 7.49-7.36 (m, 4H), 7.33 (d, J=1.4 Hz, 1H), 7.04 (dd, J=8.1, 1.6 Hz, 1H), 6.87 (dd, J=8.5, 1.6 Hz, 1H), 6.49 (s, 1H), 6.34 (d, J=3.1 Hz, 1H), 4.24 (t, J=6.5 Hz, 2H), 3.50 (t, J=4.6 Hz, 4H), 2.60 (t, J=6.5 Hz, 2H), 2.38 (s, 2H), 2.38 (d, J=9.3 Hz, 2H). MS m/z (M+H) 490.3.

Example 14

2-(1H-indol-6-yl)-3-[1-(3-morpholin-4-yl-propyl)-1H-indol-5-ylethynyl]-benzoic acid

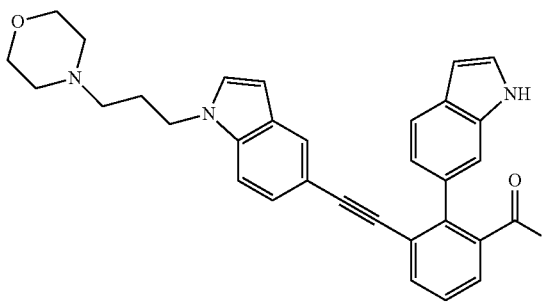

2-(1H-indol-6-yl)-3-[1-(3-morpholin-4-yl-propyl)-1H-indol-5-ylethynyl]-benzoic acid was prepared by the same procedure as Example 1. $^1$H NMR (400 MHz, DMSO-d$_6$) δ 11.21 (t, J=2.3 Hz, 1H), 7.72 (dd, J=7.7, 1.4 Hz, 1H), 7.66-7.55 (m, 2H), 7.49-7.36 (m, 6H), 7.33 (d, J=1.4 Hz, 1H), 7.04 (dd, J=8.1, 1.6 Hz, 1H), 6.86 (dd, J=8.5, 1.6 Hz, 1H), 6.49 (s, 1H), 6.35 (d, J=3.1 Hz, 1H), 4.16 (t, J=6.7 Hz, 2H), 3.55 (t, J=4.6 Hz, 4H), 2.26 (d, J=5.7 Hz, 4H), 2.11 (t, J=6.8 Hz, 2H), 1.86 (q, J=6.8 Hz, 2H). MS m/z (M+H) 504.3.

Example 15

2-(1H-indol-6-yl)-3-[1-(3-morpholin-4-yl-propyl)-1H-indol-6-ylethynyl]-benzoic acid

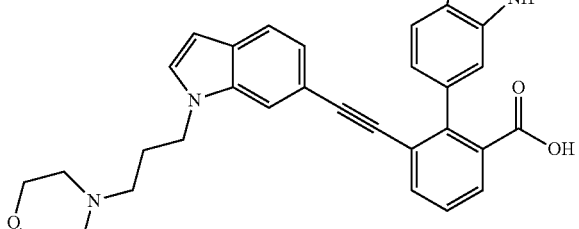

2-(1H-indol-6-yl)-3-[1-(3-morpholin-4-yl-propyl)-1H-indol-6-ylethynyl]-benzoic acid was prepared by the same procedure as Example 1. $^1$H NMR (400 MHz, DMSO-d$_4$) δ 11.22 (s, 1H), 7.73 (dd, J=7.7, 1.4 Hz, 1H), 7.68-7.57 (m, 2H), 7.51-7.38 (m, 5H), 7.20 (s, 1H), 7.05 (dd, J=8.1, 1.5 Hz, 1H), 6.77 (dd, J=8.2, 1.3 Hz, 1H), 6.49 (s, 1H), 6.41 (d, J=3.0 Hz, 1H), 4.10 (t, J=6.2 Hz, 2H), 3.58 (s, 4H), 2.28 (s, 4H), 2.09 (s, 2H), 1.84 (s, 2H). MS m/z (M+H) 504.3.

Example 16

2-(1H-Indol-6-yl)-3-(5,6,7,8-tetrahydro-[1,8]naphthyridin-3-ylethynyl)-benzoic acid

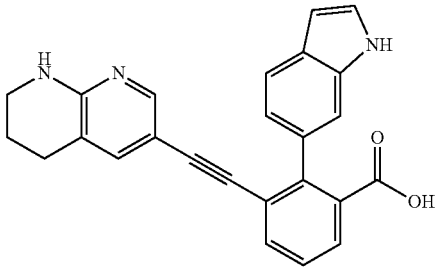 [SMILES: O=C(O)c1cccc(C#Cc2cnc3c(c2)CCCN3)c1-c1ccc2cc[nH]c2c1]

2-(1H-Indol-6-yl)-3-(5,6,7,8-tetrahydro-[1,8]naphthyridin-3-ylethynyl)-benzoic acid was prepared by the same procedure as Example 1. $^1$H NMR (400 MHz, DMSO-d$_6$) δ 12.69 (s, 1H), 11.20 (s, 1H), 7.62 (dd, J=13.5, 7.7 Hz, 2H), 7.58-7.48 (m, 2H), 7.42 (t, J=7.3 Hz, 2H), 6.96 (d, J=8.2 Hz, 1H), 6.91-6.90 (m, 2H), 6.75 (s, 1H), 6.47 (t, J=2.4 Hz, 1H), 3.30-3.29 (m, 2H), 3.22 (t, J=4.3 Hz, 2H), 1.69-1.67 (m, 2H). MS m/z (M+H) 394.0.

Example 17

2-(1H-indol-6-yl)-3-[1-(tetrahydro-pyran-4-ylmethyl)-1H-pyrrolo[2,3-b]pyridin-5-ylethynyl]-benzoic acid

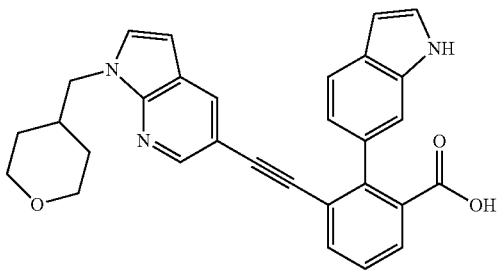 [SMILES: O=C(O)c1cccc(C#Cc2cnc3c(ccn3CC3CCOCC3)c2)c1-c1ccc2cc[nH]c2c1]

2-(1H-Indol-6-yl)-3-[1-(tetrahydro-pyran-4-ylmethyl)-1H-pyrrolo[2,3-b]pyridin-5-ylethynyl]-benzoic acid was prepared by the same procedure as Example 1. $^1$H NMR (400 MHz, DMSO-d$_6$) δ 12.74 (s, 1H), 11.21 (s, 1H), 7.98 (d, J=1.9 Hz, 1H), 7.80-7.71 (m, 2H), 7.64 (d, J=7.6 Hz, 1H), 7.60 (s, 1H), 7.59-7.56 (m, 2H), 7.50-7.42 (m, 1H), 7.41 (t, J=2.7 Hz, 1H), 7.05 (dd, J=8.1, 1.6 Hz, 1H), 6.49 (t, J=2.6 Hz, 1H), 6.41 (d, J=3.5 Hz, 1H), 4.11 (d, J=7.3 Hz, 2H), 3.85-3.71 (m, 2H), 3.17 (td, J=11.5, 2.5 Hz, 2H), 2.06 (ddd, J=11.4, 7.2, 4.0 Hz, 1H), 1.36-1.18 (m, 4H). MS m/z (M+H) 476.2.

Example 18

2-(1H-Indol-6-yl)-3-[1-(tetrahydro-pyran-4-ylmethyl)-1H-indol-5-ylethynyl]-benzoic acid

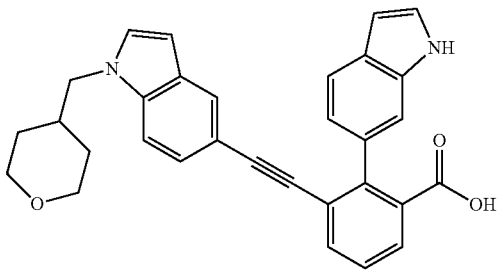 [SMILES: O=C(O)c1cccc(C#Cc2ccc3c(ccn3CC3CCOCC3)c2)c1-c1ccc2cc[nH]c2c1]

2-(1H-Indol-6-yl)-3-[1-(tetrahydro-pyran-4-ylmethyl)-1H-indol-5-ylethynyl]-benzoic acid was prepared by the same procedure as Example 1. $^1$H NMR (400 MHz, DMSO-d$_6$) δ 12.68 (s, 1H), 11.21 (t, J=2.2 Hz, 1H), 7.72 (dd, J=7.7, 1.4 Hz, 1H), 7.63 (dd, J=7.7, 1.4 Hz, 1H), 7.59 (d, J=8.1 Hz, 1H), 7.48-7.43 (m, 2H), 7.43-7.39 (m, 2H), 7.38 (d, J=3.1 Hz, 1H), 7.34 (d, J=1.5 Hz, 1H), 7.04 (dd, J=8.2, 1.6 Hz, 1H), 6.86 (dd, J=8.5, 1.6 Hz, 1H), 6.49 (ddd, J=3.0, 1.9, 0.9 Hz, 1H), 6.35 (dd, J=3.1, 0.8 Hz, 1H), 4.03 (d, J=7.2 Hz, 2H), 3.85-3.73 (m, 2H), 3.16 (td, J=11.4, 2.7 Hz, 2H), 2.06-1.89 (m, 1H), 1.38-1.18 (m, 4H). MS m/z (M+H) 475.2.

Example 19

2-(1H-Indol-6-yl)-3-[1-(1-methanesulfonyl-piperidin-4-ylmethyl)-1H-indol-5-ylethynyl]-benzoic acid

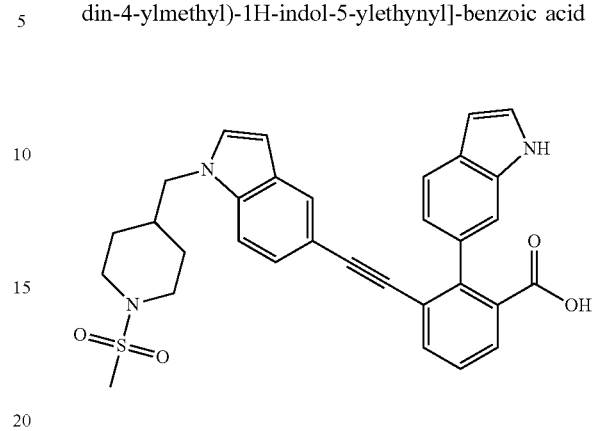

2-(1H-Indol-6-yl)-3-[1-(1-methanesulfonyl-piperidin-4-ylmethyl)-1H-indol-5-ylethynyl]-benzoic acid was prepared by the same procedure as Example 1. $^1$H NMR (400 MHz, DMSO-d$_6$) δ 12.68 (s, 1H), 11.21 (s, 1H), 7.76-7.69 (m, 1H), 7.65-7.56 (m, 2H), 7.50-7.33 (m, 6H), 7.04 (dd, =8.2, 1.6 Hz, 1H), 6.86 (dd, J=8.6, 1.6 Hz, 1H), 6.52-6.47 (m, 1H), 6.36 (d, J=3.1 Hz, 1H), 4.07 (d, J=7.2 Hz, 2H), 3.50 (d, J=11.7 Hz, 2H), 2.79 (s, 3H), 2.57 (td, J=12.0, 2.5 Hz, 2H), 1.86 (d, J=3.8 Hz, 1H), 1.56-1.43 (m, 2H), 1.26 (dd, J=13.4, 9.5 Hz, 2H). MS m/z (M+H) 552.3.

Example 20

2-(1H-Indol-6-yl)-3-[1-(1-methanesulfonyl-piperidin-4-ylmethyl)-1-pyrrolo[2,3-b]pyridin-5-ylethynyl]-benzoic acid

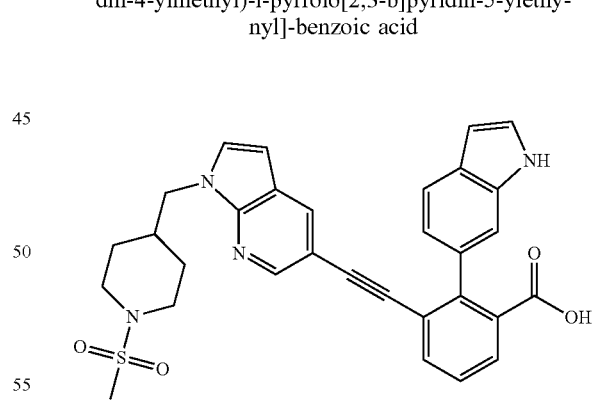

2-(1H-Indol-6-yl)-3-[1-(1-methanesulfonyl-piperidin-4-ylmethyl)-1H-pyrrolo[2,3-b]pyridin-5-ylethynyl]-benzoic acid was prepared by the same procedure as Example 1. $^1$H NMR (400 MHz, DMSO-d$_6$) δ 12.71 (s, 1H), 11.21 (t, J=2.2 Hz, 1H), 7.97 (d, J=2.0 Hz, 1H), 7.85-7.73 (m, 2H), 7.66 (dd, J=7.7, 1.4 Hz, 1H), 7.63-7.57 (m, 2H), 7.55-7.24 (m, 3H), 7.05 (dd, J=8.2, 1.6 Hz, 1H), 6.49 (t, J=2.5 Hz, 1H), 6.42 (d, J=3.4 Hz, 1H), 4.15 (d, J=7.3 Hz, 2H), 3.49 (d, J=11.8 Hz, 2H), 2.73-2.52 (m, 5H), 1.97 (m, 1H), 1.49 (d, J=12.6 Hz, 2H), 1.24 (m, 2H). MS m/z (M+H) 553.2.

Example 21

3-[1-(1,1-Dioxo-hexahydro-1λ⁶-thiopyran-4-ylmethyl)-1H-pyrrolo[2,3-b]pyridin-5-ylethynyl]-2-(1H-indol-6-yl)-benzoic acid

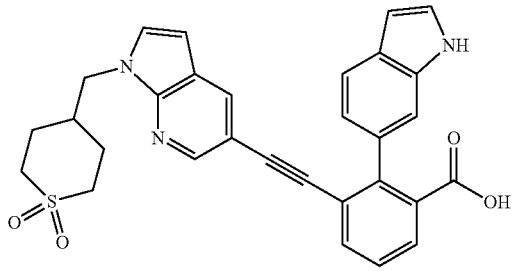 [SMILES: O=C(O)c1cccc(C#Cc2cnc3c(ccn3CC3CCS(=O)(=O)CC3)c2)c1-c1ccc2cc[nH]c2c1]

3-[1-(1,1-Dioxo-hexahydro-1λ⁶-thiopyran-4-ylmethyl)-1H-pyrrolo[2,3-b]pyridin-5-ylethynyl]-2-(1H-indol-6-yl)-benzoic acid was prepared by the same procedure as Example 1. ¹H NMR (400 MHz, DMSO-d₆) δ 12.75 (s, 1H), 11.21 (d, J=2.4 Hz, 1H), 7.97 (d, J=2.0 Hz, 1H), 7.75 (dt, J=3.9, 2.2 Hz, 2H), 7.65 (dd, J=7.8, 1.4 Hz, 1H), 7.63-7.55 (m, 2H), 7.53-7.37 (m, 3H), 7.05 (dd, J=8.1, 1.6 Hz, 1H), 6.49 (t, J=2.4 Hz, 1H), 6.43 (d, J=3.5 Hz, 1H), 4.18 (d, J=7.3 Hz, 2H), 3.02 (qd, J=12.7, 9.4 Hz, 4H), 2.17 (ddt, J=12.1, 8.2, 4.1 Hz, 1H), 1.76 (d, J=13.7 Hz, 2H), 1.72-1.51 (m, 2H). MS m/z (M+H) 524.5.

Example 22

3-{1-[2-(1,1-Dioxo-1λ⁶-thiomorpholin-4-yl)-ethyl]-1H-indol-5-yl-ethynyl}-2-(1H-indol-6-yl)-benzoic acid

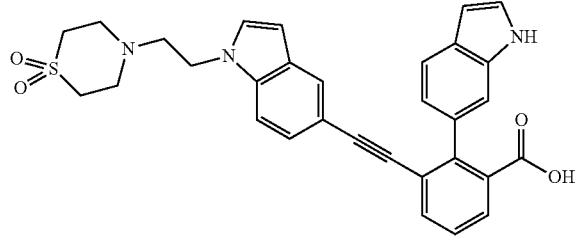 [SMILES: O=C(O)c1cccc(C#Cc2ccc3c(ccn3CCN3CCS(=O)(=O)CC3)c2)c1-c1ccc2cc[nH]c2c1]

3-{1-[2-(1,1-Dioxo-λ⁶-thiomorpholin-4-yl)-ethyl]-1H-indol-5-yl-ethynyl}-2-(1H-indol-6-yl)-benzoic acid was prepared the same procedure as Example 1. ¹H NMR (400 MHz, DMSO-d₆) δ 11.20 (s, 1H), 7.73 (dd, J=7.6, 1.2 Hz, 1H), 7.64-7.57 (m, 2H), 7.46-7.40 (m, 5H), 7.33 (d, J=0.8 Hz, 1H), 7.05 (dd, J=8.4, 1.6 Hz, 1H), 6.87 (dd, J=8.4, 1.2 Hz, 1H), 6.48 (d, J=2 Hz, 1H), 6.35 (d, J=3.2 Hz, 1H), 4.23 (t, J=6.4 Hz, 2H), 2.99 (d, J=5.2 Hz, 4H), 2.91 (d, J=5.6 Hz, 4H), 2.81 (t, J=6.4 Hz, 2H). MS m/z (M–H) 536.3.

Example 23

3-{1-[2-(1,1-Dioxo-1λ⁶-thiomorpholin-4-yl)-ethyl]-1H-indol-6-ylethynyl}-2-(1H-indol-6-yl)-benzoic acid

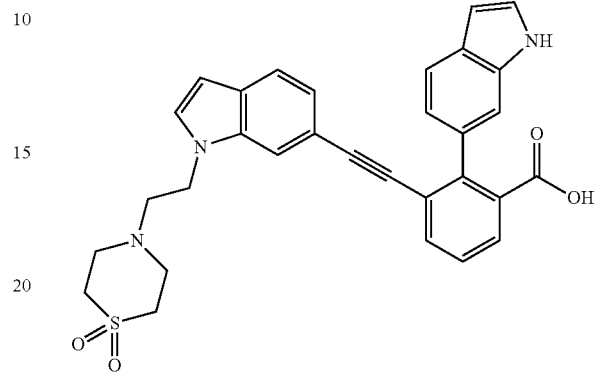

3-{1-[2-(1,1-Dioxo-1λ⁶-thiomorpholin-4-yl)-ethyl]-1H-indol-6-ylethynyl}-2-(1H-indol-6-yl)-benzoic acid was prepared the same procedure as Example 1. ¹H NMR (400 MHz, DMSO-d₆) δ 12.68 (s, 1H), 11.21 (s, 1H), 7.74 (dd, J=8.0, 1.2 Hz, 1H), 7.65 (dd, J=7.6, 1.2 Hz, 1H), 7.61 (d, J=8.0 Hz, 1H), 7.48-7.43 (m, 3H), 7.43-7.40 (m, 2H), 7.16 (s, 1H), 7.05 (dd, J=8.0, 1.6 Hz, 1H), 6.79 (dd, J=8.0, 1.2 Hz, 1H), 6.50 (s, 1H), 6.40 (d, J=3.2 Hz, 1H), 4.13 (t, J=6.4 Hz, 2H), 2.96 (d, J=4.0 Hz, 4H), 2.87 (d, J=5.6 Hz, 4H), 2.76 (t, J=6.4 Hz, 2H). MS m/z (M+H) 538.2.

Example 24

3-{1-[3-(1,1-Dioxo-1λ⁶-thiomorpholin-4-yl)-propyl]-1H-indol-5-yl-ethynyl}-2-(1H-indol-6-yl)-benzoic acid

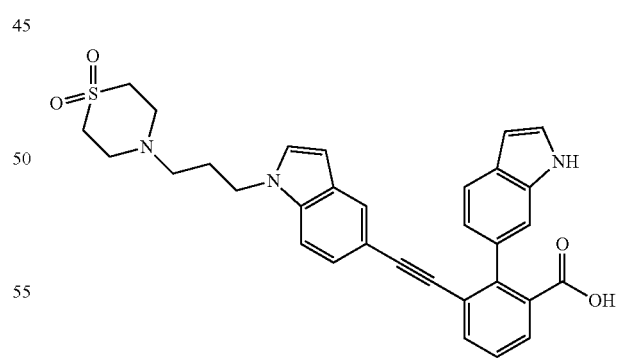

3-{1-[3-(1,1-Dioxo-1λ⁶-thiomorpholin-4-yl)-propyl]-1H-indol-5-ylethynyl}-2-(1H-indol-6-yl)-benzoic acid was prepared by the same procedure as Example 1. ¹H NMR (400 MHz, DMSO-d₆) δ 12.64 (brs, 1H), 1.19 (s, 1H), 7.68-7.56 (m, 3H), 7.45-7.33 (m, 6H), 7.05 (d, J=8.0 Hz, 1H), 6.87 (d, =7.2 Hz, 1H), 6.48 (s, 1H), 6.35 (s, 1H), 4.17 (t, 2H), 3.05 (m, 4H), 2.74 (m, 4H), 2.25 (t, 2H), 1.84 (t, 2H), MS m/z (M–H) 550.3.

Example 25

3-{1-[3-(1,1-Dioxo-1λ⁶-thiomorpholin-4-yl)-propyl]-1H-indol-6-yl-ethynyl}-2-(1H-indol-6-yl)-benzoic acid

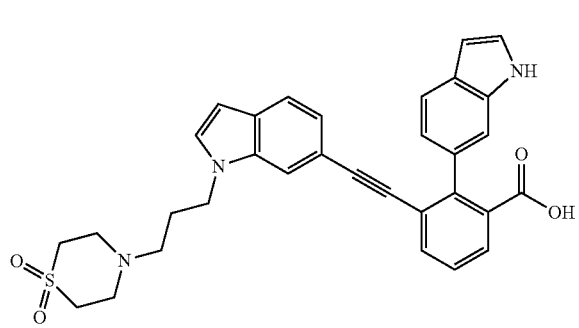 [SMILES: O=C(O)c1cccc(C#Cc2ccc3ccn(CCCN4CCS(=O)(=O)CC4)c3c2)c1-c1ccc2cc[nH]c2c1]

3-{1-[3-(1,1-Dioxo-1λ⁶-thiomorpholin-4-yl)-propyl]-1H-indol-6-ylethynyl}-2-(1H-indol-6-yl)-benzoic acid was prepared the same procedure as Example 1. ¹H NMR (400 MHz, DMSO-d₆) δ 12.71 (brs, 1H), 11.21 (s, 1H), 7.74 (d, J=7.2 Hz, 1H), 7.64-5.59 (m, 2H), 7.46-7.40 (m, 5H), 7.19 (s, 1H), 7.06 (d, J=8.0 Hz, 1H), 6.77 (d, J=8.0 Hz, 1H), 6.50 (s, 1H), 6.40 (d, J=2.8 Hz, 1H), 4.12 (t, J=6.4 Hz, 2H), 3.03 3.01 (m 4H), 2.73-2.71 (m 4H), 2.21 (t, J=6.4 Hz, 2H), 1.80 (t, J=6.4 Hz, 2H). MS m/z (M−H) 550.2.

Example 26

3-[4-(1,1-Dioxo-hexahydro-1λ⁶-thiopyran-4-yloxymethyl)-phenyethynyl]-2-(1H-indol-6-yl)-benzoic acid

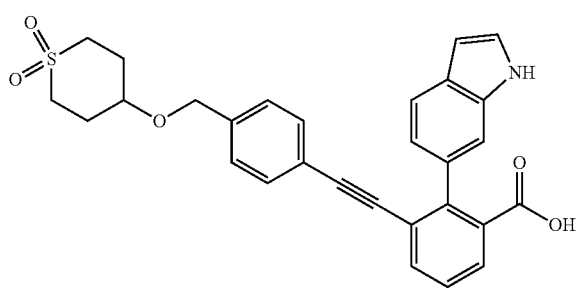 [SMILES: O=C(O)c1cccc(C#Cc2ccc(COC3CCS(=O)(=O)CC3)cc2)c1-c1ccc2cc[nH]c2c1]

3-[4-(1,1-Dioxo-hexahydro-1λ⁶-thiopyran-4-yloxymethyl)-phenylethynyl]-2-(1H-indol-6-yl)-benzoic acid was prepared the same procedure as Example 1. ¹H NMR (400 MHz, DMSO-d₆) δ12.70 (brs, 1H), 11.20 (s, 1H, NH), 7.74 (dd, J=6.8, 0.8 Hz, 1H), 7.68 (dd, J=7.6, 1.2 Hz, 1H), 7.58 (d, J=8.4 Hz, 1H), 7.46 (t, J=8 Hz, 1H), 7.41-7.38 (m, 2H), 7.27 (d, J=8 Hz, 2H), 7.12 (d, J=8.4 Hz, 2H), 7.03 (dd, J=8.4, 1.6 Hz, 1H), 6.47 (s, 1H), 4.48 (s, 2H), 3.68-3.64 (m, 1H), 3.13-2.99 (m, 4H), 2.13-2.04 (m, 4H). MS m/z (M+H) 500.1.

Example 27

2-(1H-Indol-6-yl)-3-[4-(tetrahydro-pyran-4-yloxymethyl)-phenylethynyl]-benzoic acid

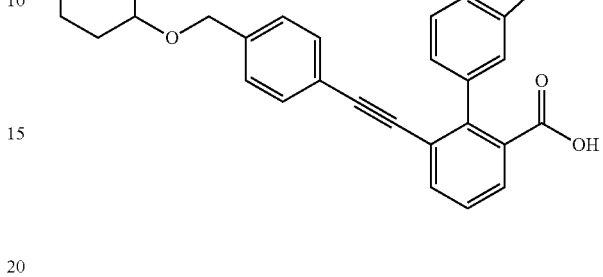

2-(1H-Indol-6-yl)-3-[4-(tetrahydro-pyran-4-yloxymethyl)-phenylethynyl]-benzoic acid was prepared the same procedure as Example 1. ¹H NMR (400 MHz, DMSO-d₆) δ12.76 (brs, 1H), 11.18 (s, 11-, NH), 7.73 (dd, J=7.6, 1.2 Hz, 1H), 7.65 (dd, J=7.6, 1.2 Hz, 1H), 7.57 (d, J=8.0 Hz, 1H), 7.46-7.42 (m, 2H), 7.39 (t, J=2.4 Hz, 2H), 7.24 (d, J=8 Hz, 2H), 7.11 (d, J=8.0 Hz, 2H), 7.03 (dd, J=8.4, 1.6 Hz, 1H), 6.46 (s, 1H), 4.47 (s, 1H), 3.81-3.76 (m, 2H), 3.51 (q, J=4.4 Hz, 1H), 3.32-3.28 (m, 2H), 1.78-1.73 (m, 2H), 1.46-1.42 (m, 2H). MS m/z (M−H) 450.2.

Example 28

2-(1H-Indol-6-yl)-3-(4-isopropoxymethyl-phenylethynyl)-benzoic acid

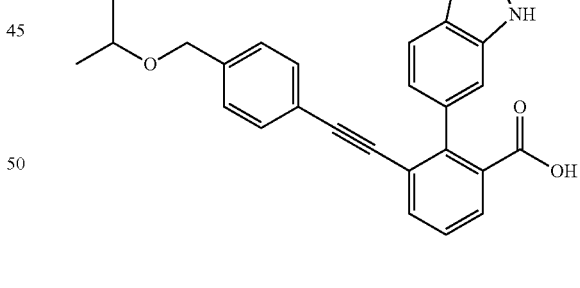

2-(1H-indol-6-yl)-3-(4-isopropoxymethyl-phenylethynyl)-benzoic acid was prepared by the same procedure as Example 1. 2-(1H-indol-6-yl)-3-(4-isopropoxymethyl-phenylethynyl)-benzoic acid methyl ester. ¹H NMR (400 MHz, DMSO-d₆) δ 12.75 (s, 1H), 11.19 (s, 1H), 7.73 (d, J=7.7 Hz, 1H), 7.65 (d, J=7.7 Hz, 1H), 7.57 (d, J=8.2 Hz, 1H), 7.49-7.36 (m, 3H), 7.22 (d, J=8.2 Hz, 2H), 7.09 (d, J=8.2 Hz, 2H), 7.02 (dd, J=8.2, 1.6 Hz, 1H), 6.47 (s, 1H), 4.41 (s, 2H), 3.59 (p, J=6.1 Hz, 1H), 1.11 (d, J=6.1 Hz, 6H). MS m/z (M−H) 408.3.

Example 29

2-(1H-Indol-6-yl)-3-[4-(1-oxo-hexahydro-1λ⁴-thio-pyran-4-yloxy)-phenylethynyl]-benzoic acid

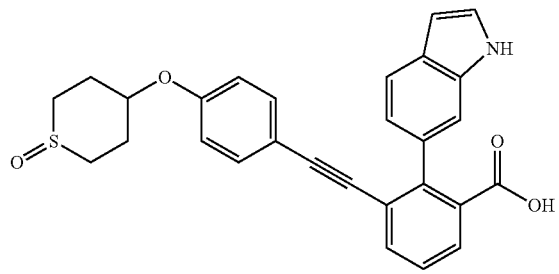 [SMILES: O=C(O)c1cccc(C#Cc2ccc(OC3CCS(=O)CC3)cc2)c1-c1ccc2cc[nH]c2c1]

2-(1H-Indol-6-yl)-3-[4-(1-oxo-hexahydro-1λ⁴-thiopyran-4-yloxy)-phenylethynyl]-benzoic acid was prepared by the same procedure as Example 1. ¹H NMR (400 MHz, DMSO-d₆) δ 12.70 (s, 1H), 11.19 (s, 1H), 7.71 (dd, J=7.7, 1.4 Hz, 1H), 7.64 (dd, J=7.7, 1.4 Hz, 1H), 7.57 (d, J=8.1 Hz, 1H), 7.45 (t J=7.7 Hz, 1H), 7.42-7.34 (m, 2H), 7.12-7.04 (m, 2H), 7.02 (dd, J=8.2, 1.6 Hz, 1H), 6.97-6.89 (m, 2H), 6.47 (t, J=2.7 Hz, 1H), 4.69 (dt, J=5.6, 2.8 Hz, 1H), 2.90 (td, J=12.9, 11.9, 3.1 Hz, 2H), 2.68 (ddd, J=12.9, 5.1, 2.5 Hz, 2H), 2.31 (ddt, J=14.7, 12.0, 2.9 Hz, 2H), 1.88-1.74 (m, 2H). MS m/z (M+H) 470.1.

Example 30

2-(1H-indol-6-yl)-3-(3-morpholin-4-ylmethyl-1H-indol-6-ylethynyl)-benzoic acid

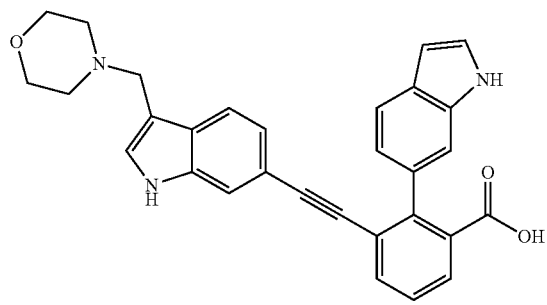 [SMILES: O=C(O)c1cccc(C#Cc2ccc3c(CN4CCOCC4)c[nH]c3c2)c1-c1ccc2cc[nH]c2c1]

2-(1H-indol-6-yl)-3-(3-morpholin-4-ylmethyl-1H-indol-6-ylethynyl)-benzoic acid was prepared by the same procedure as Example 1. ¹H NMR (400 MHz, DMSO-d₆) δ 12.64 (s, 1H), 11.20 (s, 1H), 11.08 (d, J=2.4 Hz, 1H), 7.75 (dd, J=7.8, 1.4 Hz, 1H), 7.66-7.56 (m, 2H), 7.52 (d, J=8.2 Hz, 1H), 7.50-7.37 (m, 3H), 7.31 (d, J=2.4 Hz, 1H), 7.21 (s, 1H), 7.07 (dd, J=8.2, 1.6 Hz, 1H), 6.75 (dd, J=8.2, 1.4 Hz, 1H), 6.48 (s, 1H), 3.60-3.48 (m, 6H), 2.34 (s, 4H). MS m/z (M+H) 476.2.

Example 31

2-(1H-indol-6-yl)-3-[3-(4-methanesulfonyl-piperazin-1-ylmethyl)-1H-indol-6-ylethynyl]-benzoic acid

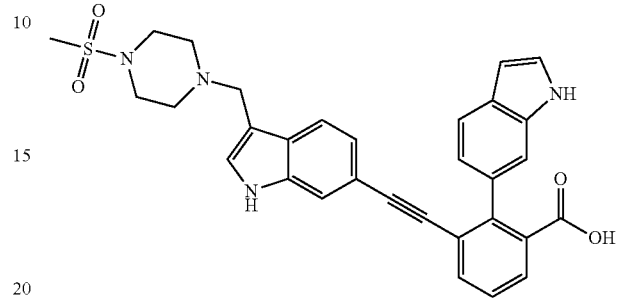

2-(1H-indol-6-yl)-3-[3-(4-methanesulfonyl-piperazin-1-ylmethyl)-1H-indol-6-ylethynyl]-benzoic acid was prepared by the same procedure as Example 1. ¹H NMR (400 MHz, DMSO-d₆) δ 12.69 (bs, 1H), 11.20 (s, 1H), 11.10 (s, 1H), 7.75 (d, J=7.5 Hz, 1H), 7.61 (dd, J=13.6, 7.9 Hz, 1H), 7.55-7.41 (m, 2H), 7.45-7.37 (m, 3H), 7.32 (s, 1H), 7.22 (s, 1H), 7.07 (dd, J=8.1, 1.6 Hz, 1H), 6.75 (d, J=8.3 Hz, 1H), 6.49 (s, 1H), 3.63 (s, 2H), 3.05 (s, 4H), 2.84 (s, 3H), 2.44 (s, 4H). MS m/z (M−H) 552.0.

Example 32

3-[3-(1,1-Dioxo-1λ⁶-thiomorpholin-4-ylmethyl)-1H-indol-6-ylethynyl]-2-(1H-indol-6-yl)-benzoic acid

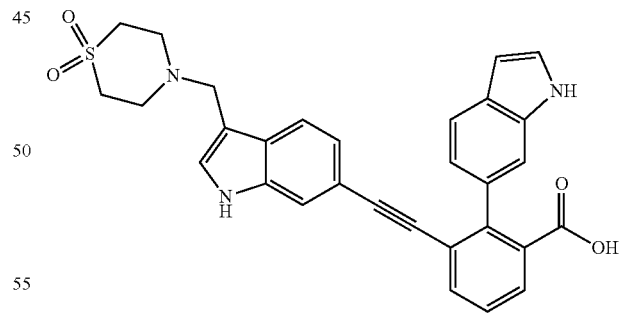

3-[3-(1,1-Dioxo-1λ⁶-thiomorpholin-4-ylmethyl)-1H-indol-6-ylethynyl]-2-(1H-indol-6-yl)-benzoic acid was prepared by the same procedure as Example 1. ¹H NMR (400 MHz, DMSO-d₆) δ 12.61 (s, 1H), 11.19 (t, J=2.1 Hz, 1H), 11.12 (s, 1H), 7.75 (dd, J=7.7, 1.4 Hz, 1H), 7.67-7.52 (m, 3H), 7.50-7.33 (m, 4H), 7.22 (s, 1H), 7.07 (dd. J=8.2, 1.6 Hz, 1H), 6.74 (dd, J=8.2, 1.4 Hz, 1H), 6.48 (s, 1H), 3.77 (s, 2H), 3.05 (s, 2H), 3.05 (d, J=10.7 Hz, 2H), 2.85 (d, J=4.6 Hz, 4H). MS m/z (M−H) 522.6.

Example 33

2-(1H-indol-6-yl)-3-(2-morpholin-4-ylmethyl-1H-indol-6-ylethynyl)-benzoic acid

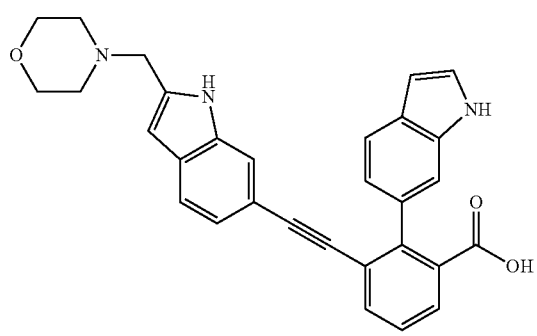 [SMILES: O=C(O)c1cccc(C#Cc2ccc3cc(CN4CCOCC4)[nH]c3c2)c1-c1ccc2cc[nH]c2c1]

2-(1H-indol-6-yl)-3-(2-morpholin-4-ylmethyl-1H-indol-6-ylethynyl)-benzoic acid was prepared by the same procedure as Example 1. $^1$H NMR (400 MHz, CD3OD) δ 7.70 (ddd, J=17.5, 7.7, 1.4 Hz, 2H), 7.60 (d, J=8.2 Hz, 1H), 7.49-7.34 (m, 3H), 7.28 (d J=3.2 Hz, 1H), 7.17-7.07 (m, 2H), 6.77 (dd, J=8.2, 1.4 Hz, 1H), 6.57 (s, 1H), 6.51 (dd. J=3.2, 1.0 Hz, 1H), 4.24 (s, 2H), 3.81 (s, 4H), 3.06 (s, 4H). MS m/z (M−H) 474.8.

Example 34

3-[2-(1,1-Dioxo-1λ$^6$-thiomorpholin-4-ylmethyl)-1H-indol-6-ylethynyl]-2-(1H-indol-6-yl)-benzoic acid

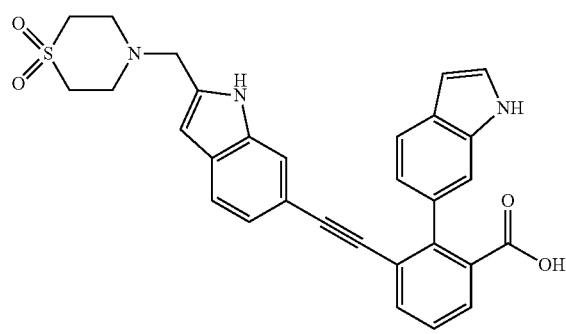 [SMILES: O=C(O)c1cccc(C#Cc2ccc3cc(CN4CCS(=O)(=O)CC4)[nH]c3c2)c1-c1ccc2cc[nH]c2c1]

3-[2-(1,1-Dioxo-1λ$^6$-thiomorpholin-4-ylmethyl)-1H-indol-6-ylethynyl]-2-(1H-indol-6-yl)-benzoic acid was prepared by the same procedure as Example 1. $^1$H NMR (400 MHz, DMSO-d$_6$) δ 12.69 (s, 1H), 11.22-11.13 (m, 2H), 7.74 (dd, J=7.7, 1.4 Hz, 1H), 7.65-7.56 (m, 2H), 7.48-7.40 (m, 2H), 7.42-7.31 (m, 2H), 7.20 (s, 1H), 7.08 (dd, J=8.1, 1.6 Hz, 1H), 6.73 (dd, J=8.1, 1.4 Hz, 1H), 6.47 (s, 1H), 6.31 (d, J=1.8 Hz, 1H), 3.81 (s, 2H), 3.11 (t, J=5.1 Hz, 4H), 2.90 (dd, J=7.0, 3.6 Hz, 4H). MS m/z (M−H) 522.4.

Example 35

3-[1-(4-ethoxy-2-methyl-butyl)-6-fluoro-1H-indol-5-ylethynyl]-2-(1H-indol-6-yl)-benzoic acid

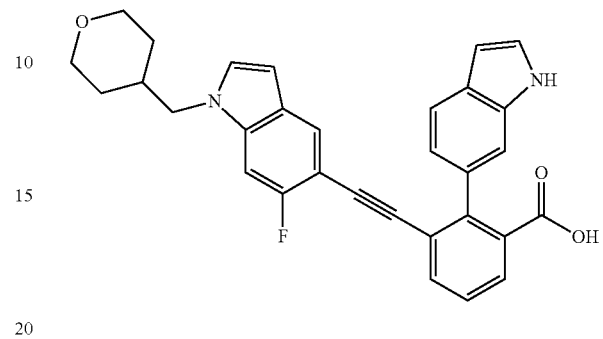

3-[6-Fluoro-1-(tetrahydro-pyran-4-ylmethyl)-1H-indol-5-ylethynyl]-2-(1H-indol-6-yl)-benzoic acid was prepared by the same procedure as Example 1. $^1$H NMR (400 MHz, DMSO-d$_6$) δ 11.17 (s, 1H), 7.66 (d, J=7.6 Hz, 1H), 7.59 (d, J=7.7 Hz, 1H), 7.54 (d, J=8.2 Hz, 1H), 7.50-7.34 (m, 5H), 7.20 (d, J=6.9 Hz, 1H), 7.05 (dd, J=8.1, 1.5 Hz, 1H), 6.46 (s, 1H), 6.33 (d, J=3.1 Hz, 1H), 4.00 (d, J=7.2 Hz, 2H), 3.83-3.73 (m, 2H), 3.17 (td, J=11.4, 2.7 Hz, 2H), 1.98 (s, 1H), 1.33-1.16 (m, 4H). MS m/z (M−H) 491.4.

Example 36

3-[7-fluoro-1-(tetrahydro-pyran-4-ylmethyl)-1H-indol-6-ylethynyl]-2-(1H-indol-6-yl)-benzoic acid

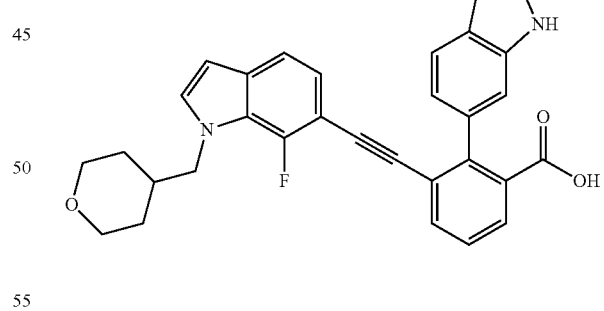

3-[7-fluoro-1-(tetrahydro-pyran-4-ylmethyl)-1H-indol-6-ylethynyl]-2-(1H-indol-6-yl)-benzoic acid was prepared by the same procedure as Example 1. $^1$H NMR (400 MHz, DMSO-d$_6$) δ 11.11 (s, 1H), δ 7.53 (s, 1H), 7.51-7.39 (m, 3H), 7.41-7.24 (m, 3H), 7.22 (d, J=8.2 Hz, 1H), 7.13 (dd, J=8.1, 1.6 Hz, 1H), 6.67 (dd, J=8.2, 5.9 Hz, 1H), 6.43 (dt, J=18.8, 2.5 Hz, 1H), 4.11 (d, J=7.1 Hz, 2H), 3.81 (dd, J=10.9, 3.6 Hz, 2H), 3.20 (m, 2H), 1.93 (bs, 1H), 1.26 (dt, J=13.7, 6.5 Hz, 4H). MS m/z (M+H) 493.3.

Example 37

3-[1-(1,1-dioxo-hexahydro-1λ⁶-thiopyran-4-ylmethyl)-7-fluoro-1H-indol-6-ylethynyl]-2-(1H-indol-yl)-benzoic acid

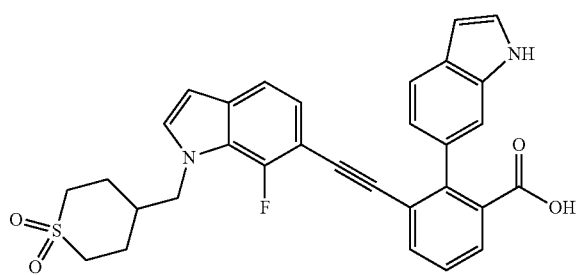 [SMILES: O=C(O)c1cccc(C#Cc2ccc3ccn(CC4CCS(=O)(=O)CC4)c3c2F)c1-c1ccc2cc[nH]c2c1]

3-[1-(1,1-dioxo-hexahydro-1λ⁶-thiopyran-4-ylmethyl)-7-fluoro-1H-indol-6-ylethynyl]-2-(1H-indol-1)-benzoic acid was prepared by the same procedure as Example 1. ¹H NMR (400 MHz, DMSO-d₆) δ 11.12 (s, 1H), 7.55 (s, 1H), 7.52-7.37 (m, 3H), 7.30 (dd, J=5.4, 2.5 Hz, 2H), 7.27-7.12 (m, 3H), 6.68 (dd, J=8.2, 5.8 Hz, 1H), 6.46 (t, J=2.7 Hz, 1H), 6.41 (t, J=2.4 Hz, 1H), 4.17 (d, J=7.2 Hz, 2H), 3.28-2.87 (m, 4H), 2.05 (s, 1H), 1.71 (q, J=13.9, 11.9 Hz, 4H). MS m/z (M+H) 541.3.

Example 38

3-[1-(1,1-dioxo-hexahydro-1λ⁶-thiopyran-4-ylmethyl)-6-fluoro-1H-indol-5-ylethynyl]-2-(1H-indol-6-yl)-benzoic acid

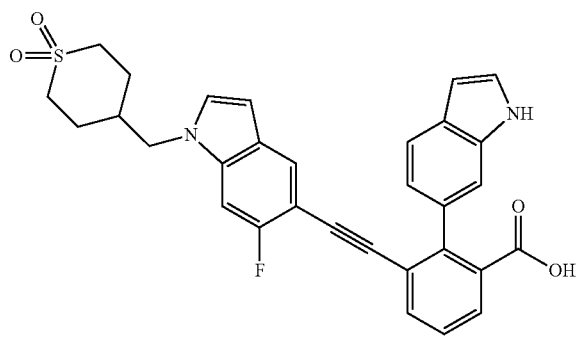 [SMILES: O=C(O)c1cccc(C#Cc2cc3ccn(CC4CCS(=O)(=O)CC4)c3cc2F)c1-c1ccc2cc[nH]c2c1]

3-[1-(1,1-dioxo-hexahydro-1λ⁶-thiopyran-4-ylmethyl)-6-fluoro-1H-indol-5-ylethynyl]-2-(1H-indol-6-yl)-benzoic acid was prepared by the same procedure as Example 1. ¹H NMR (400 MHz, DMSO-d₆) δ 12.70 (s, 1H), 11.18 (s, 1H), 7.73 (d, J=7.7 Hz, 1H), 7.65 (d, J=7.7 Hz, 1H), 7.60-7.34 (m, 6H), 7.22 (d, J=6.9 Hz, 1H), 7.03 (dd, J=8.1, 1.6 Hz, 1H), 6.47 (t, J=2.3 Hz, 1H), 6.35 (d, J=3.2 Hz, 1H), 4.08 (d, J=7.3 Hz, 2H), 3.05-2.99 (m, 4H), 2.11-2.05 (m, 1H), 1.75 (d, J=14.0 Hz, 2H), 1.65 (d, J=11.9 Hz, 2H). MS m/z (M+H) 541.3.

Example 39

3-(7-fluoro-3-morpholin-4-ylmethyl-1H-indol-6-ylethynyl)-2-(1H-indol-6-yl)-benzoic acid

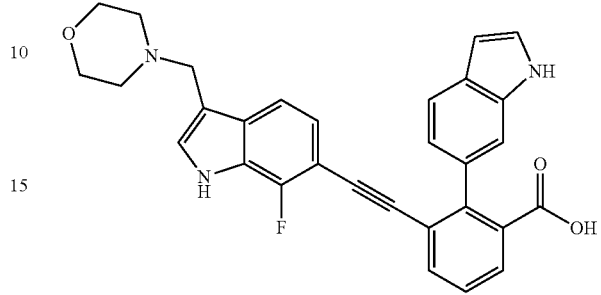

3-(7-fluoro-3-morpholin-4-ylmethyl-1H-indol-6-ylethynyl)-2-(1H-indol-6-yl)-benzoic acid was prepared by the same procedure as Example 1. ¹H NMR (400 MHz, DMSO-d₆) δ 11.65 (d, J=2.5 Hz, 1H), 11.17 (s, 1H), 7.74 (dd, J=7.7, 1.4 Hz, 1H), 7.64 (dd, J=7.7, 1.4 Hz, 1H), 7.56 (d, J=8.1 Hz, 1H), 7.50-7.41 (m, 2H), 7.41-7.31 (m, 3H), 7.07 (dd, J=8.2, 1.6 Hz, 1H), 6.65 (dd, J=8.2, 6.1 Hz, 1H), 6.46 (t, J=2.4 Hz, 1H), 3.56 (s, 2H), 3.52 (d, J=4.5 Hz, 4H), 2.40-2.23 (m, 4H). MS m/z (M+H) 494.2.

Example 40

3-(6-fluoro-3-morpholin-1-ylmethyl-1H-indol-5-ylethynyl)-2-(1H-indol-6-yl)-benzoic acid

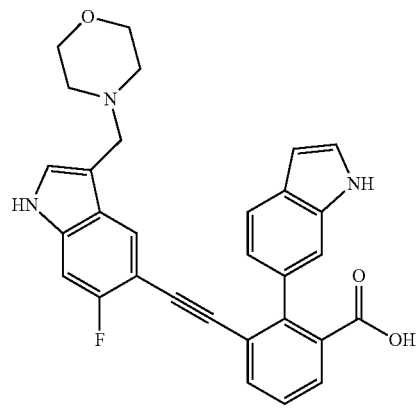 [SMILES: O=C(O)c1cccc(C#Cc2cc3c(CN4CCOCC4)c[nH]c3cc2F)c1-c1ccc2cc[nH]c2c1]

3-(6-fluoro-3-morpholin-4-ylmethyl-1H-indol-5-ylethynyl)-2-(1H-indol-6-yl)-benzoic acid was prepared by the same procedure as Example 1. ¹H NMR (400 MHz, DMSO-d₆) δ 12.67 (s, 1H), 11.18 (d, J=2.6 Hz, 2H), δ 7.73 (dd, J=7.7, 1.4 Hz, 1H), 7.67-7.57 (m 2H), 7.50-7.34 (m, 3H), 7.32-7.22 (m, 2H), 7.18-7.03 (m, 2H), 6.46 (t, J=2.4 Hz, 1H), 3.56-3.46 (m, 4H), 3.39 (bs, 2H), 2.30 (s, 4H). MS m/z (M+H) 494.3.

Example 41

3-((4-(2H-tetrazol-5-yl)phenyl)ethynyl)-2-(1H-indol-6-yl)benzoic acid

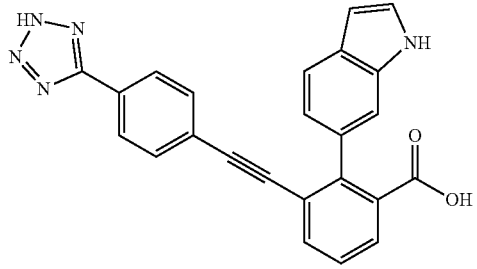 [SMILES: O=C(O)c1cccc(C#Cc2ccc(-c3nn[nH]n3)cc2)c1-c1ccc2cc[nH]c2c1]

3-((4-(2H-tetrazol-5-yl)phenyl)ethynyl)-2-(1H-indol-6-yl)benzoic acid was prepared by the same procedure as Example 1. $^1$H NMR (300 MHz, CD3OD) δ ppm 7.84 (d, J=8.21 Hz, 2 H) 7.76 (d, J=7.62 Hz, 2 H) 7.59-7.64 (m, 1 H) 7.42-7.50 (m, 2 H) 7.30 (d, J=2.93 Hz, 1 H) 7.19 (d, J=8.21 Hz, 2 H) 7.06 (dd, J=8.06, 1.32 Hz, 1 H) 6.52 (d, J=3.22 Hz, 1 H). MS m/z (M+H) 406.2.

Example 42

3-((3-(2H-tetrazol-5-yl)phenyl)ethynyl)-2-(1H-indol-6-yl)benzoic acid

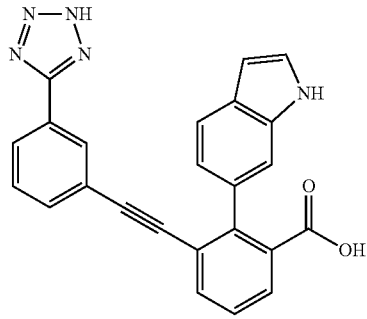 [SMILES: O=C(O)c1cccc(C#Cc2cccc(-c3nn[nH]n3)c2)c1-c1ccc2cc[nH]c2c1]

3-((3-(2H-tetrazol-5-yl)phenyl)ethynyl)-2-(1H-indol-6-yl)benzoic acid was prepared by the same procedure as Example 1. $^1$H NMR (300 MHz, CD3OD) δ ppm 7.87 (d, J=7.04 Hz, 1 H) 7.73-7.82 (m, 3 H) 7.56-7.67 (m, 2 H) 7.36-7.49 (m, 3 H) 7.25 (br, s., 1 H) 7.16 (d, J=7.92 Hz 1 H) 7.07 (d, J=7.92 Hz, 1 H) 6.47 (br, s., 1 H). MS m/z (M+H) 406.1.

Example 43

2-(1H-indol-6-yl)-3-((4-(oxazol-5-yl)phenyl)ethynyl)benzoic acid

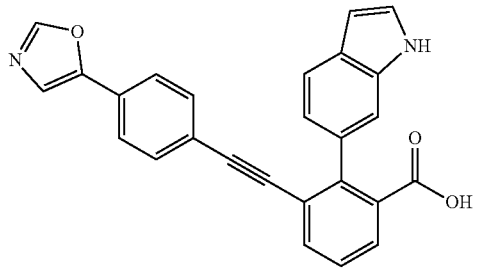 [SMILES: O=C(O)c1cccc(C#Cc2ccc(-c3cnco3)cc2)c1-c1ccc2cc[nH]c2c1]

2-(1H-indol-6-yl)-3-((4-(oxazol-5-yl)phenyl)ethynyl)benzoic acid was prepared by the same procedure as Example 1. $^1$H NMR (300 MHz, CD3OD) δ ppm 8.21 (s, 1 H) 7.73 (d, J=7.92 Hz, 2 H) 7.60 (d, J=8.21 Hz, 1 H) 7.53 (d, J=8.21 Hz, 2 H) 7.38-7.50 (m, 3 H) 7.29 (s, 1 H) 7.00-7.15 (m, 3 H) 6.51 (d, J=2.64 Hz, 1 H). MS m/z (M+H) 405.1.

Example 44

2-(1H-indol-6-yl)-3-((4-(6-oxo-1,6-dihydropyridazin-3-yl)phenyl)ethynyl)benzoic acid

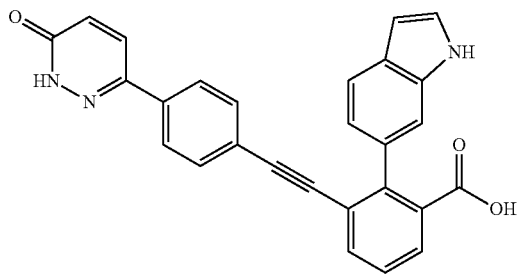 [SMILES: O=C(O)c1cccc(C#Cc2ccc(-c3ccc(=O)[nH]n3)cc2)c1-c1ccc2cc[nH]c2c1]

2-(1H-indol-6-yl)-3-((4-(6-oxo-1,6-dihydropyridazin-3-yl)phenyl)ethynyl)benzoic acid was prepared by the same procedure as Example 1. $^1$H NMR (300 MHz, CD3OD) δ ppm 7.95 (d, J=9.97 Hz, 1 H) 7.72 (dd, J=11.87, 8.06 Hz, 4 H) 7.60 (d, J=8.21 Hz, 1 H) 7.40-7.49 (m, 2 H) 7.29 (d, J=2.93 Hz, 1H) 6.97-7.16 (m, 4 H) 6.51 (d, J=2.93 Hz, 1 H). MS m/z (M+H) 432.1.

Example 45

2-(1H-indol-6-yl)-3-((3-methoxy-4-(morpholinomethyl)phenyl)ethynyl)benzoic acid

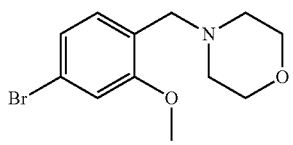

4-(4-bromo-2-methoxybenzyl)morpholine: 4-bromo-2-methoxybenzaldehyde (214 mg, 1 mmol) and morpholine (87 mg, 1 mmol) were dissolved in tetrahydrofuran at room temperature. Sodium triacetoxyborohydride (254 mg, 1.2 mmol) was added to the mixture. The reaction was heated to 50° C. for 18 hours. Then, saturated sodium bicarbonate solution was added to quench the reaction. Ethyl acetate was added to reaction mixture and layers were separated. The organic layer was combined and concentrated to give crude product 4-(4-bromo-2-methoxybenzyl)morpholine as oil which was used for next step without further purification.

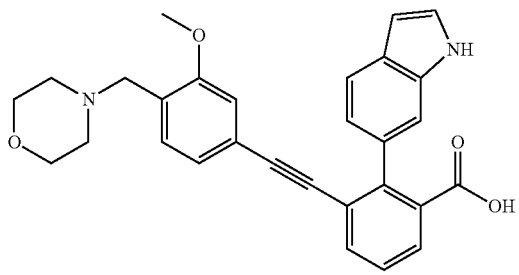 [SMILES: COc1cc(C#Cc2cccc(C(=O)O)c2-c2ccc3cc[nH]c3c2)ccc1CN1CCOCC1]

2-(1H-indol-6-yl)-3-((3-methoxy-4-(morpholinomethyl) phenyl)ethynyl)benzoic acid: 4-(4-Bromo-2-methoxybenzyl)morpholine and 3-ethynyl-2-(1H-indol-6-yl)-benzoic acid methyl ester were reacted following the same procedure as Example 1. $^1$H NMR (300 MHz, CD3OD) δ ppm 10.61 (br, s., 1 H) 7.74 (dd, J=11.73, 7.62 Hz, 2 H) 7.60 (d, J=8.21 Hz, 1 H) 7.38-7.52 (m, 2 H) 7.19-7.31 (m, 2 H) 7.03 (dd, J=8.21, 1.17 Hz, 1 H) 6.81 (d, J=7.92 Hz, 1 H) 6.36-6.57 (m, 2 H) 4.25 (s, 2 H) 3.83 (br, s., 1 H) 3.63 (s, 3 H) 3.20 (br, s., 4 H). MS m/z (M+H) 467.2.

Example 46

3-((3-hydroxy-4-(morpholine-4-carbonyl)phenyl) ethynyl)-2-(1H-indol-6-yl)benzoic acid

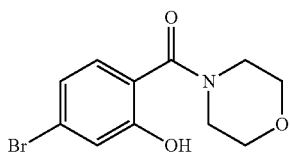 [SMILES: O=C(c1ccc(Br)cc1O)N1CCOCC1]

(4-Bromo-2-hydroxyphenyl)(morpholino)methanone: 4-Bromo-2-hydroxybenzoic acid (215.9 mg, 1 mmol) morpholine (87 mg, 1 mmol) and diisopropyl ethyl amine (260 mg, 2 mmol) were dissolved in N,N-dimethylformamide, 1-[Bis(dimethylamino)methylene]-1H-1,2,3-triazolo[4,5-b] pyridinium 3-oxid hexafluorophosphate (HATU) (456 mg, 1.2 mmol) was added and the reactions were stirred at ambient temperature for 18 hours. Then the solvent was removed under vacuum. The resulting oil was purified with column chromatography (methylene chloride/methanol) to give the product (4-bromo-2-hydroxyphenyl)(morpholino) methanone as pale yellow solid.

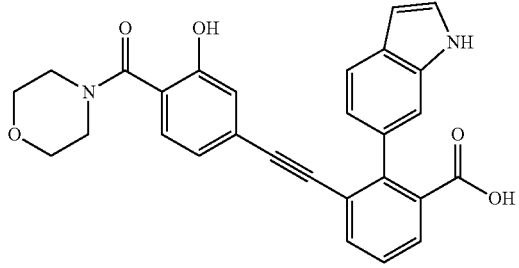 [SMILES: O=C(O)c1cccc(C#Cc2ccc(C(=O)N3CCOCC3)c(O)c2)c1-c1ccc2cc[nH]c2c1]

3-((3-hydroxy-4-(morpholine-4-carbonyl)phenyl)ethynyl)-2-(1H-indol-6-yl)benzoic acid: (4-Bromo-2-hydroxyphenyl)morpholino)methanone and 3-ethynyl-2-(1H-indol-6-yl)-benzoic acid methyl ester were reacted following the same procedure as Example 1. $^1$H NMR (300 MHz, CD3OD) δ ppm 7.65-7.74 (m, 3 H) 7.58 (d, J=8.21 Hz, 1 H) 7.42 (d, J=5.57 Hz, 3 H) 7.25 (d, J=2.93 Hz, 1 H) 7.08 (d, J=9.38 Hz, 1 H) 7.01 (d, J=7.92 Hz, 1 H) 6.64 (s, 1 H) 6.57 (d, J=9.09 Hz, 1 H) 6.47 (s., 1 H) 3.64 (br, s., 3 H). MS m/z (M+H) 467.2.

Example 47

2-(1H-Indol-6-yl)-3-[3-methoxy-4-(4-morpholin-4-yl-piperidin-1-ylmethyl)-phenylethynyl]-benzoic acid

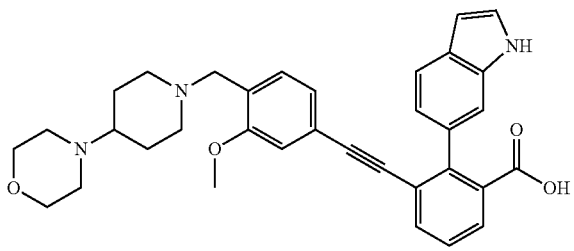 [SMILES: COc1cc(C#Cc2cccc(C(=O)O)c2-c2ccc3cc[nH]c3c2)ccc1CN1CCC(N2CCOCC2)CC1]

2-(1H-Indol-6-yl)-3-[3-methoxy-4-(4-morpholin-4-yl-piperidin-1-ylmethyl)-phenylethynyl]-benzoic acid was prepared by the same procedure as Example 45. $^1$H NMR (300 MHz, CD$_3$OD) δ ppm 7.75 (dd, J=13.49, 7.62 Hz, 2 H) 7.58 (d, J=8.21 Hz, 1 H) 7.36-7.49 (m, 2 H) 7.27 (d, J=2.93 Hz, 1 H) 7.22 (d, J=7.62 Hz, 1 H) 6.97 (d, J=8.21 Hz, 1 H) 6.76 (d, J=7.62 Hz, 1 H) 6.48 (d, J=3.22 Hz, 1 H) 6.41 (s, 1 H) 4.21 (s, 2 H) 3.88 (br, s., 4 H) 3.44-3.65 (m, 1 H) 3.59 (s, 3 H) 3.48-3.52 (m, 2 H) 3.22 (br, s., 3 H) 3.01 (t, J=12.31 Hz, 2 H) 2.26 (d, J=12.61 Hz, 2 H) 1.95 (d, J=11.43 Hz, 2 H). MS m/z (M+H) 550.4.

Example 48

3-((4-((4,4-difluoropiperidin-1-yl)methyl)-3-methoxyphenyl) ethynyl)-2-(1H-indol-6-yl)benzoic acid

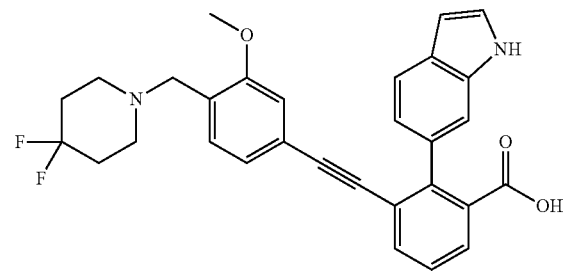 [SMILES: COc1cc(C#Cc2cccc(C(=O)O)c2-c2ccc3cc[nH]c3c2)ccc1CN1CCC(F)(F)CC1]

3-((4-((4,4-difluoropiperidin-1-yl)methyl)-3-methoxyphenyl)ethynyl)-2-(1H-indol-6-yl) benzoic acid was prepared by the same procedure as Example 45. $^1$H NMR (300 MHz CD$_3$OD) δ ppm 7.74 (dd, J=12.31, 7.62 Hz, 2 H) 7.60 (d, J=7.92 Hz, 1 H) 7.38-7.50 (m, 2 H) 7.25 (d, J=7.62 Hz, 2 H) 7.04-7.11 (m, 1 H) 7.02 (dd, J=8.21, 1.17 Hz, 1 H) 6.81 (d, J=7.04 Hz, 1 H) 6.48 (d, J=2.64 Hz, 1 H) 6.43 (s, 1 H) 4.29 (s, 2 H) 3.61 (s, 3 H) 3.36 (br, s., 4 H) 2.28 (br, s., 4 H). MS m/z (M+H) 501.3.

Example 49

3-((4-((4-(dimethylcarbamoyl)piperidin-1-yl)methyl)-3-methoxy phenyl) ethynyl)-2-(1H-indol-6-yl)benzoic acid

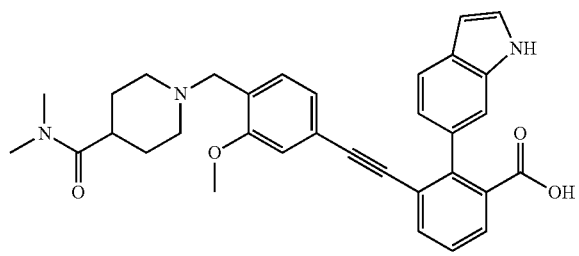 [SMILES: COc1cc(C#Cc2cccc(C(=O)O)c2-c2ccc3cc[nH]c3c2)ccc1CN1CCC(C(=O)N(C)C)CC1]

3-((4-((4-(dimethylcarbamoyl)piperidin-1-yl)methyl)-3-methoxyphenyl)ethynyl)-2-(1H-indol-6-yl)benzoic acid was prepared by the same procedure as Example 45. $^1$H NMR (300 MHz, CD$_3$OD) δ ppm 7.75 (dd, J=13.05, 7.77 Hz, 2 H) 7.60 (d, J=8.21 Hz, 1 H) 7.38-7.51 (m, 2 H) 7.20-7.33 (m, 2 H) 7.03 (d, J=8.21 Hz, 1 H) 6.82 (d, J=7.62 Hz, 1 H) 6.48 (d, J=2.93 Hz, 1 H) 6.44 (s, 1 H) 4.20 (s, 2 H) 3.62 (s, 3 H) 3.45 (d, J=12.90 Hz, 1 H) 3.09 (s, 4 H) 2.99 (d, J=14.07 Hz, 2 H) 2.91 (s, 4 H) 1.79-1.96 (m, 3 H). MS m/z (M+H) 536.3.

Example 50

3-((3-hydroxy-4-(4-morpholinopiperidine-1-carbonyl)phenyl)ethynyl)-2-(1H-indol-6-yl)benzoic acid

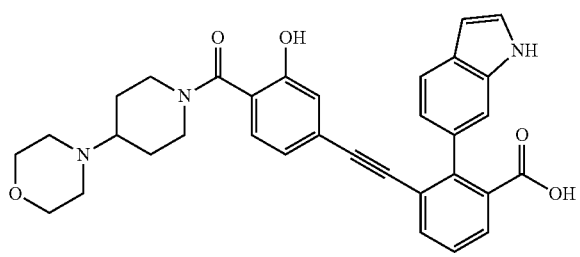 [SMILES: O=C(O)c1cccc(C#Cc2ccc(C(=O)N3CCC(N4CCOCC4)CC3)c(O)c2)c1-c1ccc2cc[nH]c2c1]

3-((3-hydroxy-4-(4-morpholinopiperidine-1-carbonyl)phenyl)ethynyl)-2-(1H-indol-6-yl) benzoic acid was prepared by the same procedure as Example 46. $^1$H NMR (300 MHz, CD$_3$OD) δ ppm 7.71 (d, J=7.62 Hz, 3 H) 7.57 (d, J=8.21 Hz, 1 H) 7.32-7.46 (m, 2 H) 7.25 (br, s., 1 H) 7.06 (d, J=8.21 Hz, 1 H) 7.00 (d, J=7.92 Hz, 1 H) 6.66 (s, 1 H) 6.57 (d, J=7.62 Hz, 1 H) 6.47 (br, s., 1 H) 3.41 (d, J=11.43 Hz, 4 H) 1.64 (d, J=8.80 Hz, 4 H). MS mm/z (M+H) 550.2.

Example 51

3-((4-(4,4-difluoropiperidine-1-carbonyl)-3-hydroxyphenyl) ethynyl)-2-(1H-indol-6-yl)benzoic acid

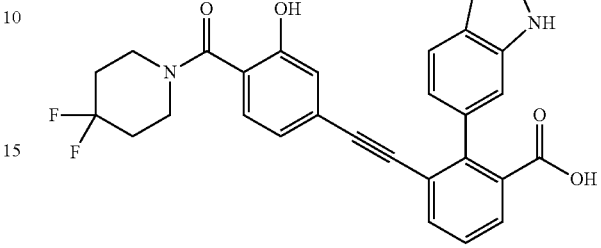

3-((4-(4,4-difluoropiperidine-1-carbonyl)-3-hydroxyphenyl)ethynyl)-2-(1H-indol-6-yl)benzoic acid was prepared by the same procedure as Example 46. $^1$H NMR (300 MHz, CD$_3$OD) δ ppm 7.72 (d, J=7.62 Hz, 2 H) 7.58 (d, J=8.21 Hz, 1 H) 7.37-7.49 (m, 2 H) 7.26 (d, J=2.64 Hz, 1 H) 7.04 (dd, J=11.87, 8.06 Hz, 2 H) 6.65 (s, 1 H) 6.57 (d, J=7.92 Hz, 1 H) 6.48 (d, J=3.22 Hz, 1 H) 2.00 (br, s., 4 H). MS m/z (M+H) 501.2.

Example 52

2-(1H-indol-1-yl)-3-((4-((1-(methylsulfonyl)piperidin-4-yl)methyl)phenyl) ethynyl) benzoic acid

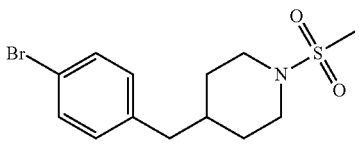 [SMILES: CS(=O)(=O)N1CCC(Cc2ccc(Br)cc2)CC1]

4-(4-Bromo-benzyl)-1-methanesulfonyl-piperidine: To a dichloromethane (2 mL) solution of 4-(4-bromobenzyl)piperidine (253 mg, 1 mmol) and triethylamine (80 mg, 1.2 mmol) at 0° C., methanesulfonyl chloride (171 mg, 1.5 mmol) was added slowly. The reaction was warmed up to room temperature and stirred for 16 hours. Water (2 mL) was added and the layers were separated. The water layer was extracted 2×3 mL dichloromethane. The combined solvent was dried with sodium sulfate, filtered and removed under vacuum. The crude material used in next step without further purification.

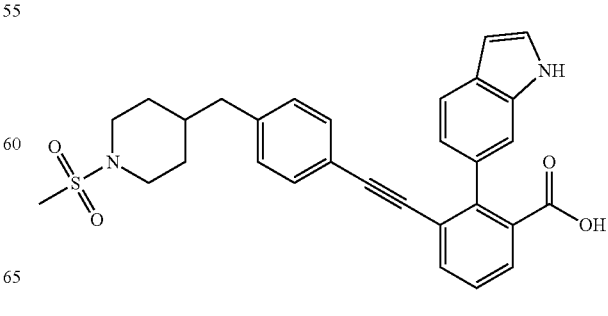

2-(1H-indol-6-yl)-3-((4-((1-(methylsulfonyl) piperidin-4-yl)methyl)phenyl)ethynyl) benzoic acid: 4-(4-Bromo-benzyl)-1-methanesulfonyl-piperidine and 3-ethynyl-2-(1H-indol-6-yl)-benzoic acid methyl ester were reacted following the same procedure as Example 1. ¹H NMR (300 MHz, CDCl₃) δ ppm 8.27 (br, s., 1 H) 7.68-7.85 (m, 3 H) 7.64 (d, J=8.21 Hz, 1 H) 7.31-7.43 (m, 2 H) 7.09-7.20 (m, 2 H) 6.55 (br, s., 1 H) 6.11 (br, s., 2 H) 3.71 (d, =12.02 Hz, 2 H) 2.71 (s, 3 H) 2.37-2.61 (m, 5 H) 1.64 (d, J=12.90 Hz, 2 H) 1.44-1.57 (m, 1 H) 1.17-1.39 (m, 2 H). MS m/z (M+H) 513.1.

Example 53

2-(1H-indol-6-yl)-3-((4-((1-((trifluoromethyl)sulfonyl)piperidin-4-yl)methyl) phenyl)ethynyl)benzoic acid

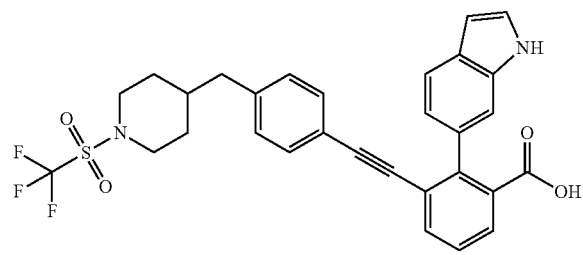 [SMILES: O=C(O)c1cccc(C#Cc2ccc(CC3CCN(S(=O)(=O)C(F)(F)F)CC3)cc2)c1-c1ccc2cc[nH]c2c1]

2-(1H-indol-6-yl)-3-((4-((1-((trifluoromethyl)sulfonyl) piperidin-4-yl)methyl) phenyl)ethynyl)benzoic acid was prepared by the same procedure as Example 52. ¹H NMR (300 MHz, CDCl₃) δ ppm 8.21 (br, s., 1 H) 7.83 (d, J=7.62 Hz, 1 H) 7.74 (d, J=7.62 Hz, 1 H) 7.65 (d, J=8.21 Hz, 1 H) 7.31-7.45 (m, 2 H) 7.10-7.21 (m, 2 H) 6.56 (br, s., 1 H) 6.27 (br, s., 3 H) 3.89 (d, J=12.90 Hz, 2 H) 2.92 (t, J=12.31 Hz, 2 H) 2.49 (d, =-6.74 Hz, 2 H) 1.53-1.72 (m, 3 H) 1.12-1.34 (m, 2 H). MS m/z (M+H) 557.1.

Example 54

2-(1H-indol-6-yl)-3-((4-((1-(isopropylsulfonyl)piperidin-4-yl)methyl) phenyl) ethynyl) benzoic acid

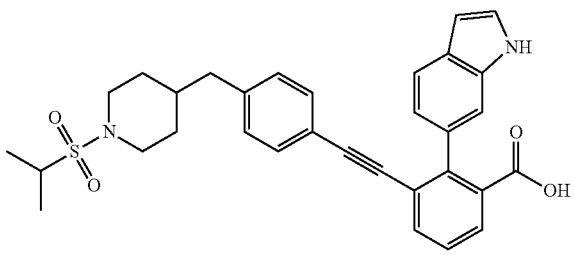 [SMILES: CC(C)S(=O)(=O)N1CCC(Cc2ccc(C#Cc3cccc(C(=O)O)c3-c3ccc4cc[nH]c4c3)cc2)CC1]

2-(1H-indol-6-yl)-3-((4-((1-(isopropylsulfonyl)piperidin-4-yl)methyl)phenyl) ethynyl) benzoic acid was prepared by the same procedure as Example 52. ¹H NMR (300 MHz, CDCl₃) δ ppm 8.25 (br, s., 1 H) 7.83 (d, J=7.62 Hz, 1 H) 7.74 (d, J=7.62 Hz, 1 H) 7.65 (d, J=7.92 Hz, 1 H) 7.33-7.42 (m, 2 H) 7.09-7.22 (m, 2 H) 6.56 (br, s., 1 H) 5.90 (br, s., 2 H) 3.74 (d, J=12.61 Hz, 2 H) 3.13 (quin, J=6.82 Hz, 1 H) 2.74 (t, J=11.87 Hz, 2 H) 2.46 (d, J=6.74 Hz, 2 H) 1.49-1.63 (m, 3 H) 1.12-1.36 (m, 8 H). MS m/z (M+H) 541.

Example 55

3-((4-((1-acetylpiperidin-4-yl)methyl)phenyl)ethynyl)-2-(1H-indol-6-yl)benzoic acid

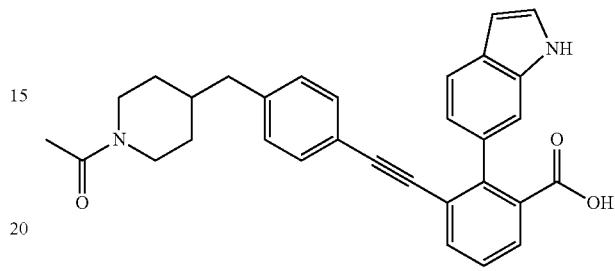

3-((4-((1-acetylpiperidin-4-yl)methyl)phenyl)ethynyl)-2-(1H-indol-6-yl)benzoic acid was prepared by the same procedure as Example 52. ¹H NMR (300 MHz, CDCl₃) δ ppm 8.24 (br, s., 1 H) 7.83 (d, J=7.62 Hz, 1 H) 7.74 (d, J=7.62 Hz, 1 H) 7.65 (d, J=7.92 Hz, 1 H) 7.33-7.41 (m, 2 H) 7.16-7.19 (m, 2 H) 6.96-6.93 (m, 4 H) 6.55 (s, 1 H) 4.49-4.52 (m, 1H) 3.71-3.75 (m, 1 H) 2.90-2.98 (m, 2 H) 2.44-2.46 (m, 3H) 2.07 (s, 3 H) 1.61-1.64 (m, 3 H) 1.08-1.12 (m, 2 H). MS m/z (M+H) 477.2.

Example 56

3-((2-acetylisoindolin-5-yl)ethynyl)-2-(1H-indol-6-yl)benzoic acid

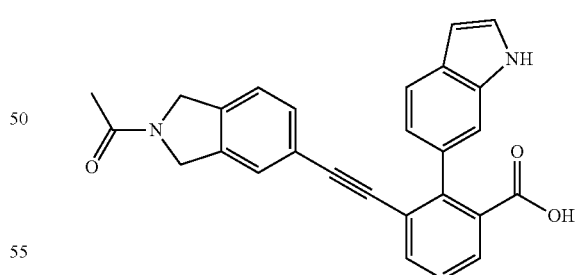

3-((2-acetylisoindolin-5-yl)ethynyl)-2-(1H-indol-6-yl) benzoic acid was prepared by the same procedure as Example 52. ¹H NMR (300 MHz, CD₃OD) δ ppm 7.77 (d, J=7.92 Hz, 2 H) 7.64 (d, J=7.92 Hz, 1 H) 7.44-7.54 (m, 2 H) 7.37 (br, s., 1 H) 7.22 (d, J=4.69 Hz, 1 H) 7.02-7.12 (m, 2 H) 6.98 (br, s., 1 H) 6.55 (br, s., 1 H) 2.63 (d, J=1.47 Hz, 4 H) 2.15 (s, 3 H). MS m/z (M+H) 421.1.

Example 57

2-(1H-indol-6-yl)-3-((2-(isopropylsulfonyl)isoindolin-5-yl)ethynyl)benzoic acid

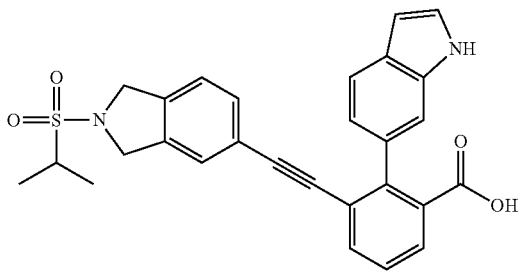 [SMILES: CC(C)S(=O)(=O)N1Cc2ccc(C#Cc3cccc(C(=O)O)c3-c3ccc4cc[nH]c4c3)cc2C1]

2-(1H-indol-6-yl)-3-((2-(isopropylsulfonyl)isoindolin-5-yl)ethynyl)benzoic acid was prepared by the same procedure as Example 52. $^1$H NMR (300 MHz, CDCl$_3$) δ ppm 8.21 (br, s., 1 H) 7.89 (d, J=7.92 Hz, 1 H) 7.75 (d, =7.62 Hz, 1 H) 7.68 (d, J=8.21 Hz, 1 H) 7.37-7.48 (m, 3 H) 7.15 (d, J=8.21 Hz, 1 H) 6.99-7.07 (m, 1 H) 6.89-6.98 (m, 1 H) 6.71 (s, 1 H) 6.61 (br, s., 1 H) 4.68 (s, 2 H) 4.59 (s, 2 H) 3.31 (dt, J=13.71, 6.78 Hz, 1 H) 1.38 (d, J=7.04 Hz, 6 H). MS m/z (M+H) 485.2.

Example 58

2-(1H-indol-6-yl)-3-((2-(1-(methylsulfonyl)pyrrolidin-3-yl)-1,2,3,4-tetrahydroisoquinolin-7-yl)ethynyl)benzoic acid

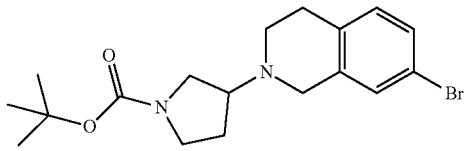 [SMILES: CC(C)(C)OC(=O)N1CCC(N2CCc3ccc(Br)cc3C2)C1]

7-Bromo-2-(pyrrolidin-3-yl)-1,2,3,4-tetrahydroisoquinoline: 7-Bromo-1,2,3,4-tetrahydro-isoquinoline (211 mg, 1 mmol) and tert-butyl 3-oxopyrrolidine-1-carboxylate (185 mg, 1 mmol) were dissolved in 1,2-dichloroethane at room temperature. NaBH(OAc)$_3$ (254 mg, 1.2 mmol) and 1 drop of acetic acid was added to the mixture. The reaction was stirred at room temperature for 18 hours. Then, saturated sodium bicarbonate solution was added to quench the reaction. Ethyl acetate was added to reaction mixture and layers were separated. The organic layer was combined and concentrated to give crude material. The crude material was stirred with 4N HCl in dioxane (2 mL) for 18 hours. The reaction was basified with 2N sodium hydroxide solution until pH=10. Then the reaction was extracted with 3×10 ml methylene chloride. The combined methylene chloride was dried with sodium sulfate and removed under vacuum. The crude product was used in next step without further purification.

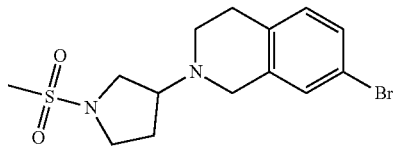 [SMILES: CS(=O)(=O)N1CCC(N2CCc3ccc(Br)cc3C2)C1]

7-Bromo-2-(1-methanesulfonyl-pyrrolidin-3-yl)-1,2,3,4-tetrahydroisoquinoline: To the dichloromethane (2 mL) solution of 7-bromo-2-(pyrrolidin-3-yl)-1,2,3,4-tetrahydroisoquinoline (280 mg, 1 mmol) and triethylamine (80 mg, 1.2 mmol) at 0° C., methanesulfonyl chloride (171 mg, 1.5 mmol) was added slowly. The reaction was warmed to room temperature and stirred for 16 hours. Water (2 mL) was added and the layers were separated. The water layer was extracted 2×3 mL dichloromethane. The combined solvent was dried with sodium sulfate and removed under vacuum, the crude material used in next step without further purifications.

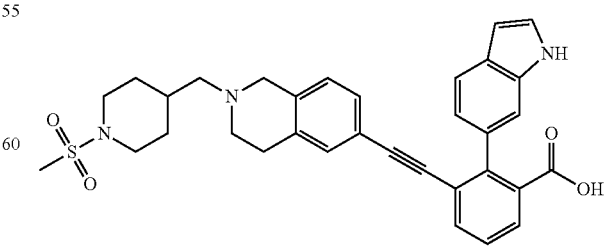

2-(1H-indol-6-yl)-3-((2-(1-(methylsulfonyl) pyrrolidin-3-yl)-1,2,3,4-tetrahydroisoquinolin-7-yl)ethynyl)benzoic acid: 7-Bromo-2-(1-methanesulfonyl-pyrrolidin-3-yl)-1,2,3,4-tetrahydroisoquinoline and 3-ethynyl-2-(1H-indol-6-yl)-benzoic acid methyl ester were reacted following the same procedure as Example 1. $^1$H NMR (300 MHz, CD$_3$OD) δ ppm 7.72 (dd, J=15.83, 7.62 Hz, 2 H) 7.59 (d, J=7.92 Hz, 1 H) 7.27-7.49 (m, 3 H) 6.96-7.19 (m, 3 H) 6.63 (s, 1 H) 6.53 (d, J=3.22 Hz, 1 H) 4.26 (d, J=2.35 Hz, 2 H) 4.01-4.15 (m, 1 H) 3.85 (dd, J=10.85, 7.62 Hz, 1 H) 3.49-3.68 (m, 4 H) 3.33-3.47 (m, 1 H) 3.13 (t, J=6.16 Hz, 2 H) 2.98 (s, 3 H) 2.47-2.63 (m, 1 H) 2.17-2.36 (m, 1 H). MS m/z (M+H) 540.2.

Example 59

2-(1H-indol-6-yl)-3-((2-((1-(methylsulfonyl)piperidin-4-yl)methyl)-1,2,3,4-tetrahydroisoquinolin-6-yl)ethynyl)benzoic acid 2-(1H-indol-6-yl)-3-((2-((1-(methylsulfonyl)piperidin-4-yl)methyl)-1,2,3,4-tetrahydroisoquinolin-6-yl)ethynyl)benzoic acid was prepared by the same procedure as Example 58. $^1$H NMR (300 MHz, CD$_3$OD) δ ppm 7.72 (dd, J=9.97, 7.92 Hz, 2 H) 7.58 (d, J=8.21 Hz, 1 H) 7.36-7.49 (m, 2 H) 7.29 (d, J=3.23 Hz, 1 H) 6.90-7.11 (m, 3 H) 6.76 (s, 1 H) 6.51 (d, J=2.93 Hz, 1 H) 4.35 (br, s., 1 H) 3.72 (d, J=12.02 Hz, 2 H) 3.49 (br, s., 1 H) 3.12 (d, J=6.74 Hz, 2 H) 2.97 (br, s., 2 H) 2.59-2.88 (m, 5 H) 2.05 (dd, J=10.85, 7.33 Hz, 1 H) 1.86 (d, J=12.61 Hz, 2 H) 1.34 (qd, J=12.22, 3.81 Hz, 2 H). MS m/z (M+H) 568.2.

Example 60

2-(1H-indol-6-yl)-3-((2-(1 methylsulfonyl)azetidin-3-yl)-1,3,4-tetrahydro isoquinolin-6-yl) ethynyl) benzoic acid

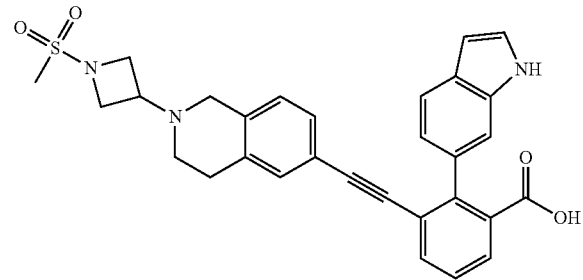 [SMILES: CS(=O)(=O)N1CC(N2CCc3cc(C#Cc4cccc(C(=O)O)c4-c4ccc5cc[nH]c5c4)ccc3C2)C1]

2-(1H-indol-6-yl)-3-((2-(1-(methylsulfonyl)azetidin-3-yl)-1,2,3,4-tetrahydroisoquinolin-6-yl) ethynyl)benzoic acid was prepared by the same procedure as Example 58. $^1$H NMR (300 MHz, CD3OD) δ ppm 7.73 (dd, J=12.17, 7.77 Hz, 2 H) 7.58 (d, J=8.21 Hz, 1 H) 7.38-7.50 (m, 2 H) 7.28 (d, J=2.93 Hz, 1 H) 6.92-7.07 (m, 3 H) 6.77 (s, 1 H) 6.50 (d, J=3.22 Hz, 1 H) 4.29 (s, 2 H) 4.11-4.26 (m, 5 H) 3.41 (t, J=6.16 Hz, 2 H) 2.92-3.03 (m, 5 H). MS m/z (M+H) 526.1.

Example 61

2-(1H-indol-1-yl)-3-((2-((1-(methylsulfonyl)pyrrolidin-3-yl)methyl)-1,2,3,4-tetrahydroisoquinolin-6-yl) ethynyl)benzoic acid

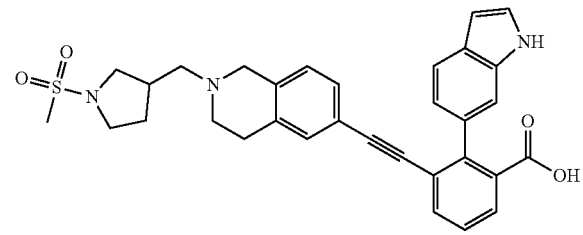 [SMILES: CS(=O)(=O)N1CCC(CN2CCc3cc(C#Cc4cccc(C(=O)O)c4-c4ccc5cc[nH]c5c4)ccc3C2)C1]

2-(1H-indol-6-yl)-3-((2-((1-(methylsulfonyl)pyrrolidin-3-yl)methyl)-1,2,3,4-tetrahydro-isoquinolin-6-yl)ethynyl) benzoic acid was prepared by the same procedure as Example 58. $^1$H NMR (300 MHz, CD$_3$OD) δ ppm 7.72 (dd. J=10.85, 7.92 Hz, 2 H) 7.58 (d, J=8.21 Hz, 1 H) 7.39-7.48 (m, 2 H) 7.29 (d, J=2.93 Hz, 1 H) 6.90-7.10 (m, 3 H) 6.76 (s, 1 H) 6.50 (d, J=2.64 Hz, 1 H) 4.38 (br, s., 2 H) 3.40-3.69 (m, 5 H) 2.95-3.14 (m, 4 H) 2.89 (s, 3 H) 2.71-2.84 (m, 1 H) 2.14-2.35 (m, 1 H) 1.67-1.83 (m, 1 H). MS m/z (M+H) 554.2.

Example 62

2-(1H-indol-6-yl)-3-((2-((1-(methylsulfonyl)pyrrolidin-3-yl)methyl)-1,2,3,4-tetrahydroisoquinolin-7-yl) ethynyl)benzoic acid

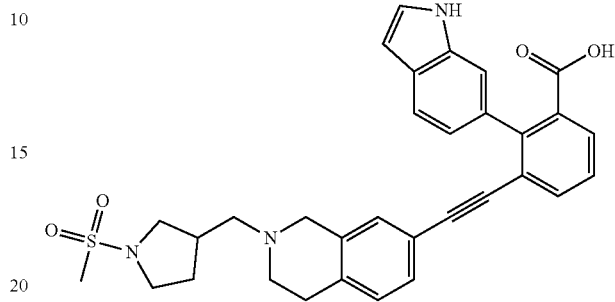

2-(1H-indol-6-yl)-3-((2-((1-(methylsulfonyl)pyrrolidin-3-yl)methyl)-1,2,3,4-tetrahydro-isoquinolin-7-yl)ethynyl) benzoic acid was prepared by the same procedure as Example 58. $^1$H NMR (300 MHz, CD$_3$OD) δ ppm 7.71 (dd, J=12.31, 7.62 Hz, 2 H) 7.58 (d, J=7.92 Hz, 1 H) 7.37-7.49 (m, 2 H) 7.25-7.36 (m, 1 H) 6.95-7.12 (m, 3 H) 6.69 (s, 1 H) 6.52 (d, J=3.22 Hz, 1 H) 4.22 (br, s., 2 H) 3.62 (dd, J=9.97, 7.33 Hz, 1 H) 3.47 (td, J=9.16, 3.37 Hz, 3 H) 2.98-3.14 (m, 3 H) 2.90 (s, 3 H) 2.71-2.87 (m, 1 H) 2.15-2.28 (m, 1 H) 1.64-1.85 (m, 1 H). MS m/z (M+H) 554.2.

Example 63

3-((2-((1-acetylpyrrolidin-3-yl)methyl)-1,2,3,4-tetrahydro isoquinolin-7-yl)ethynyl)-2-(H-indol-6-yl) benzoic acid

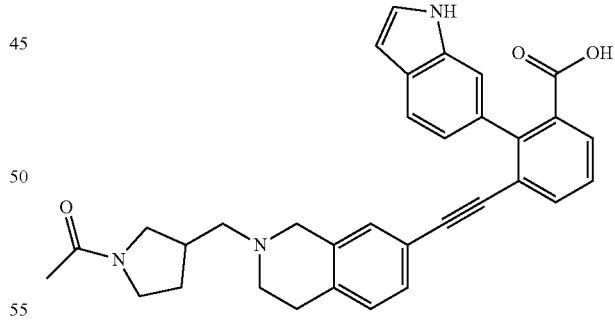

3-((2-((1-acetylpyrrolidin-3-yl)methyl)-1,2,3,4-tetrahydroisoquinolin-7-yl)ethynyl)-2-(1H-indol-6-yl)benzoic acid was prepared by the same procedure as Example 58. $^1$H NMR (300 MHz, CD3OD) δ ppm 7.71 (dd, J=11.58, 7.77 Hz, 2 H) 7.58 (d, J=8.21 Hz, 1 H) 7.34-7.47 (m, 2 H) 7.24-7.33 (m, 1 H) 6.94-7.15 (m, 3 H) 6.72 (d, J=15.83 Hz, 1 H) 6.39-6.55 (m, 1 H) 4.23 (br, s., 2 H) 3.73-3.87 (m, 1 H) 3.43-3.69 (m, 4 H) 3.15-3.25 (m, 1 H) 2.95-3.15 (m, 3 H) 2.57-2.88 (m, 1 H) 2.11-2.32 (m, 1 H) 2.04 (m, 3 H) 1.60-1.90 (m 1 H). MS m/z (M+H) 518.2.

Example 64

2-(1H-indol-6-yl)-3-((2-((1-(methylsulfonyl)azetidin-3-yl)methyl)-1,2,3,4-tetrahydroisoquinolin-6-yl)ethynyl)benzoic acid

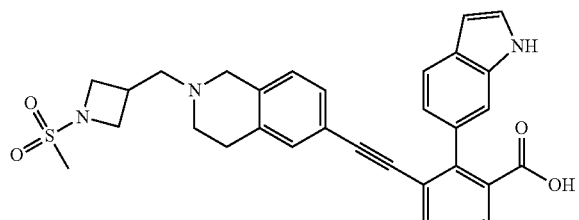

2-(1H-indol-6-yl)-3-((2-((1-(methylsulfonyl)azetidin-3-yl)methyl)-1,2,3,4-tetrahydroiso quinolin-6-yl)ethynyl)benzoic acid was prepared by the same procedure as Example 58. $^1$H NMR (300 MHz, CD$_3$OD) δ ppm 7.68-7.79 (m, 2 H) 7.58 (d, J=-8.21 Hz, 1 H) 7.35-7.49 (m, 2 H) 7.28 (d, J=2.93 Hz, 1H) 6.99-7.08 (m, 2 H) 6.88-6.99 (m, 1 H) 6.76 (s, 1 H) 6.50 (d, J=2.93 Hz, 1 H) 4.34 (s, 2 H) 4.10 (t, J=8.21 Hz, 2 H) 3.78 (dd, J=7.92, 6.45 Hz, 2 H) 3.38-3.61 (m, 4 H) 3.09-3.25 (m, 1 H) 2.99 (t, J=6.16 Hz, 2 H) 2.94 (s, 3 H). MS m/z (M+H) 540.2.

Example 65

2-(1H-indol-6-yl)-3-((2-((1-(methylsulfonyl)azetidin-3-yl)methyl)-1,2,3,4-tetrahydroisoquinolin-7-yl)ethynyl)benzoic acid

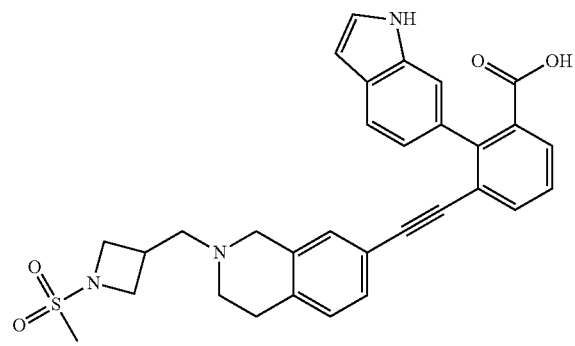 [SMILES: CS(=O)(=O)N1CC(CN2CCc3ccc(C#Cc4cccc(C(=O)O)c4-c4ccc5cc[nH]c5c4)cc3C2)C1]

2-(1H-indol-6-yl)-3-((2-((1-(methylsulfonyl)azetidin-3-yl)methyl)-1,2,3,4-tetrahydroiso quinolin-7-yl)ethynyl)benzoic acid was prepared by the same procedure as Example 58. $^1$H NMR (300 MHz, CD$_3$OD) δ ppm 7.67-7.78 (m, 2 H) 7.59 (d, J=7.92 Hz, 1 H) 7.36-7.47 (m, 2 H) 7.31 (d, J=2.93 Hz, 1 H) 6.89-7.13 (m, 3 H) 6.71 (s, 1 H) 6.52 (d, J=2.93 Hz, 1 H) 4.05-4.24 (m, 4 H) 3.79 (dd, J=8.06, 6.60 Hz, 2 H) 3.43-3.59 (m, 4 H) 3.05-3.24 (m, 3 H) 2.96 (s, 3 H). MS m/z (M+H) 540.2.

Example 66

2-(1H-indol-6-yl)-3-((2-(3-(methylsulfonamido)benzyl)-1,2,3,4-tetrahydroisoquinolin-6-yl)ethynyl)benzoic acid

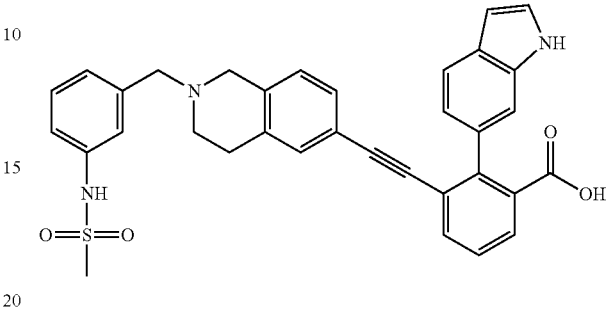

2-(1H-indol-6-yl)-3-((2-(3-(methylsulfonamido)benzyl)-1,2,3,4-tetrahydroisoquinolin-6-yl)ethynyl)benzoic acid was prepared by the same procedure as Example 58. $^1$H NMR (300 MHz, CD$_3$OD) δ ppm 7.768-7.75 (m, 2 H) 7.57 (d, J=8.21 Hz, 1 H) 7.38-7.50 (m, 4 H) 7.23-7.35 (m, 3 H) 6.90-7.03 (m, 3 H) 6.75 (s, 1 H) 6.49 (d, =-2.64 Hz, 1 H) 4.39 (s, 2 H) 4.29 (s, 2 H) 3.50 (br, s., 2 H) 2.91-3.06 (m, 5 H). MS m/z (M+H) 576.2.

Example 67

2-(1H-indol-6-yl)-3-((2-(3-(methylsulfonamido)benzyl)-1,2,3,4-tetrahydroisoquinolin-7-yl)ethynyl)benzoic

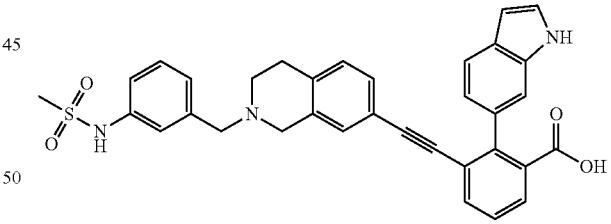

2-(1H-indol-6-yl)-3-((2-(3-(methylsulfonamido)benzyl)-1,2,3,4-tetrahydroisoquinolin-7-yl) ethynyl)benzoic acid was prepared by the same procedure as Example 58. $^1$H NMR (300 MHz, CD$_3$OD) δ ppm 7.74 (dd, J=7.77, 1.03 Hz, 1 H) 7.67 (dd, J=7.77, 1.03 Hz, 1 H) 7.50-7.57 (m, 2 H) 7.48 (s, 1 H) 7.34-7.46 (m, 3 H) 7.30 (d, J=7.62 Hz, 1 H) 7.17 (d, J=2.93 Hz, 1 H) 7.04-7.12 (m, 1 H) 6.91-7.04 (m, 2 H) 6.33-6.45 (m, 2 H) 4.40 (s, 2 H) 4.08 (s, 2 H) 3.53 (br, s., 2 H) 3.09 (1, J=6.16 Hz, 2 H) 2.99-3.05 (m, 3 H). MS m/z (M+H) 576.2.

Example 68

2-(1H-indol-6-yl)-3-((2-(1-(methylsulfonyl)pyrrolidin-3-yl)isoindolin-5-yl)ethynyl)benzoic acid

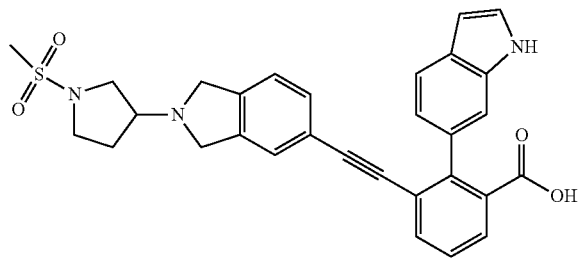 [SMILES: CS(=O)(=O)N1CCC(N2Cc3ccc(C#Cc4cccc(C(=O)O)c4-c4ccc5cc[nH]c5c4)cc3C2)C1]

2-(1H-indol-6-yl)-3-((2-(1-(methylsulfonyl)pyrrolidin-3-yl)isoindolin-5-yl)ethynyl)benzoic acid was prepared by the same procedure as Example 58. $^1$H NMR (30×) MHz, CD$_3$OD) δ ppm 7.73 (t, J=7.92 Hz, 2 H) 7.58 (d, J=8.21 Hz, 1 H) 7.37-7.50 (m, 2 H) 7.27-7.31 (m, 1 H) 7.23 (d, J=7.92 Hz, 1 H) 7.00-7.12 (m, 2 H) 6.97 (s, 1 H) 6.50 (d, J=2.93 Hz, 1 H) 4.54-4.72 (m, 4 H) 4.12-4.31 (m, 1 H) 3.76 (dd, J=11.29, 6.89 Hz, 1 H) 3.51-3.67 (m, 2 H) 3.34-3.47 (m, 1 H) 2.96 (s, 3 H) 2.43-2.65 (m, 1 H) 2.14-2.36 (m, 1 H). MS m/z (M+H) 556.3.

Example 69

2-(1H-indol-6-yl)-3-((2-(1-(methylsulfonyl)azetidin-3-yl)isoindolin-5-yl)ethynyl)benzoic acid

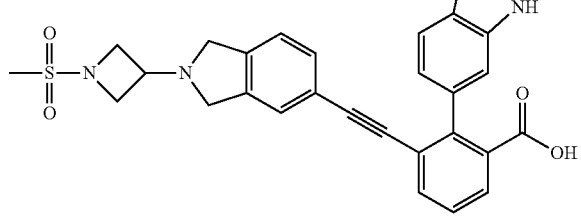

2-(1H-indol-6-yl)-3-((2-(1-(methylsulfonyl)azetidin-3-yl)isoindolin-5-yl)ethynyl)benzoic acid was prepared by the same procedure as Example 58. $^1$H NMR (300 MHz, CD$_3$OD) δ ppm 7.73 (t, J=7.77 Hz, 2 H) 7.57 (d, J=8.21 Hz, 1 H) 7.35-7.48 (m, 2 H) 7.17-7.31 (m, 1 H) 6.90-7.12 (m, 3 H) 6.49 (d, J=3.22 Hz, 1 H) 4.62 (s, 2 H) 4.55 (s, 2 H) 4.19-4.33 (m, 3 H) 4.05-4.19 (m, 2 H) 2.91-3.05 (m, 3 H). MS m/z (M+H) 512.

Example 70

2-(1H-indol-6-yl)-3-((2-((1-(methylsulfonyl)pyrrolidin-3-yl) methyl)isoindolin-5-yl)ethynyl)benzoic acid

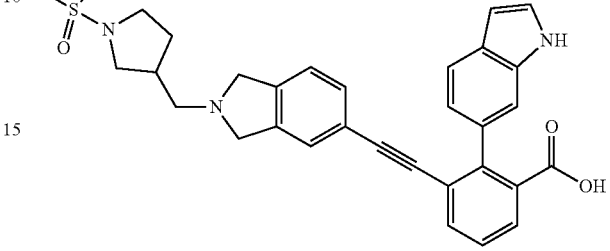

2-(1H-indol-6-yl)-3-((2-((1-(methylsulfonyl)pyrrolidin-3-yl)methyl)isoindolin-5-yl)ethynyl) benzoic acid was prepared by the same procedure as Example 58. $^1$H NMR (300 MHz, CD$_3$OD) δ ppm 7.73 (t, J=7.92 Hz, 2 H) 7.58 (d, J=7.92 Hz, 1 H) 7.39-7.49 (m, 2 H) 7.21-7.34 (m, 2 H) 6.86-7.15 (m, 3 H) 6.50 (d, J=2.93 Hz, 1 H) 4.51-4.73 (m, 3 H) 3.63 (dd, J=9.82, 7.48 Hz, 1 H) 3.44-3.57 (m, 3 H) 3.34-3.42 (m, 1 H) 3.05-3.16 (m, 1 H) 2.91 (s, 3 H) 2.64-2.83 (m, 1 H) 2.15-2.36 (m, 1 H) 1.70-1.94 (m, 1 H). MS m/z (M+H) 540.2.

Example 71

2-(1H-indol-6-yl)-3-((2-((1-(methylsulfonyl)azetidin-3-yl)methyl) isoindolin-5-yl)ethynyl)benzoic acid

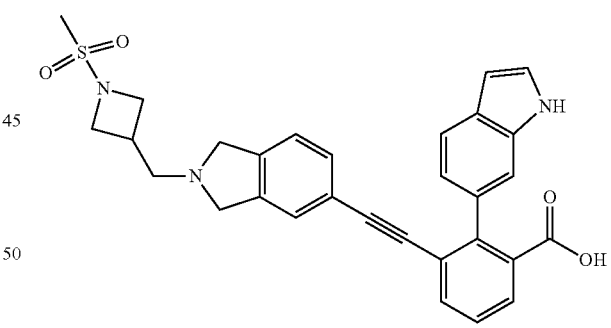

2-(1H-indol-6-yl)-3-((2-((1-(methylsulfonyl)azetidin-3-yl)methyl)isoindolin-5-yl)ethynyl) benzoic acid was prepared by the same procedure as Example 58. $^1$H NMR (300 MHz, CD$_3$OD) δ ppm 7.73 (t, J=8.21 Hz, 2 H) 7.58 (d, J=8.21 Hz, 1 H) 7.37-7.48 (m, 2 H) 7.18-7.32 (m, 2 H) 7.01-7.12 (m, 2 H) 6.95 (s, 1 H) 6.50 (d, J=2.93 Hz, 0 H) 4.64 (br, s., 2 H) 4.57 (br, s., 2 H) 4.09 (t, J=8.21 Hz, 2 H) 3.79 (dd, J=8.06, 6.30 Hz, 2 H) 3.70 (d, J=7.04 Hz, 2 H) 3.03-3.16 (m, 1 H) 2.95 (s, 3 H). MS m/z (M+H) 526.2.

Example 72

2-(1H-indol-6-yl)-3-((2-((1-(methylsulfonyl)piperidin-4-yl) methyl)isoindolin-5-yl)ethynyl)benzoic acid

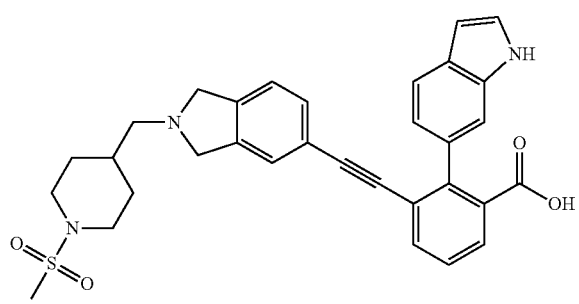 [SMILES: CS(=O)(=O)N1CCC(CN2Cc3ccc(C#Cc4cccc(C(=O)O)c4-c4ccc5cc[nH]c5c4)cc3C2)CC1]

2-(1H-indol-6-yl)-3-((2-((1-(methylsulfonyl)piperidin-4-yl)methyl)isoindolin-5-yl)ethynyl) benzoic acid was prepared by the same procedure as Example 58. $^1$H NMR (300 MHz, CD$_3$OD) δ ppm 7.74 (t, J=7.92 Hz, 2 H) 7.58 (d, J=8.21 Hz, 1 H) 7.37-7.50 (m, 2 H) 7.18-7.33 (m, 2 H) 7.01-7.15 (m, 2 H) 6.98 (s, 1 H) 6.50 (d, J=2.93 Hz, 1 H) 4.65 (d, J=19.06 Hz, 2 H) 3.78 (d, J=11.73 Hz, 2 H) 3.36 (d, J=7.04 Hz, 2 H) 2.72-2.89 (m, 5 H) 1.86-2.08 (m, 3 H) 1.30-1.49 (m, 2 H). MS m/z (M+H) 554.2.

Example 73

2-(1H-indol-6-yl)-3-((2-(methylsulfonyl)-1,2,3,4-tetrahydroiso quinolin-7-yl)ethynyl)benzoic acid

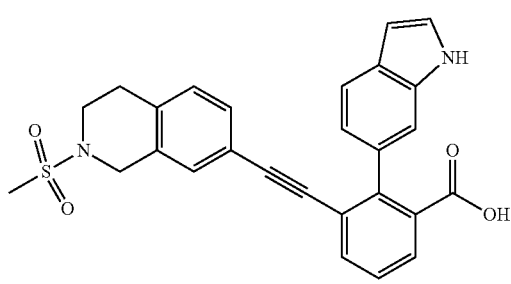 [SMILES: CS(=O)(=O)N1CCc2ccc(C#Cc3cccc(C(=O)O)c3-c3ccc4cc[nH]c4c3)cc2C1]

2-(1H-indol-6-yl)-3-((2-(methylsulfonyl)-1,2,3,4-tetrahydroisoquinolin-7-yl)ethynyl)benzoic acid was prepared by the same procedure as Example 52. $^1$H NMR (300 MHz, CD$_3$OD) δ ppm 7.71 (dd, J=10.11, 7.77 Hz, 2 H) 7.59 (d, J=8.21 Hz, 1 H) 7.37-7.47 (m, 2 H) 7.30 (s, 1 H) 7.00 (d, J=9.67 Hz, 1 H) 6.83-6.93 (m, 1 H) 6.56 (s, 1 H) 4.18 (s, 2 H) 3.45 (t, J=5.86 Hz, 2 H) 2.82-2.91 (m, 5 H). MS m/z (M+H) 471.2.

Example 74

2-(1H-indol-6-yl)-3-((2-(isopropylsulfonyl)-1,2,3,4-tetrahydro isoquinolin-7-yl)ethynyl)benzoic acid

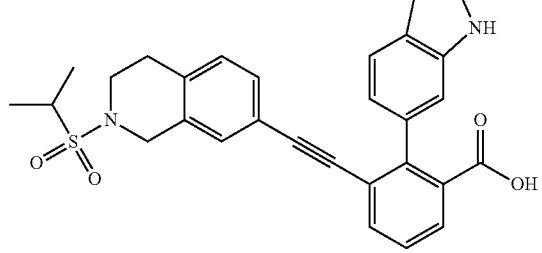

2-(1H-indol-6-yl)-3-((2-(isopropylsulfonyl)-1,2,3,4-tetrahydroisoquinolin-7-yl)ethynyl) benzoic acid was prepared by the same procedure as Example 52. $^1$H NMR (30×) MHz, CD$_3$OD) δ ppm 7.63-7.75 (m, 2 H) 7.58 (d, J=8.21 Hz, 1 H) 7.24-7.47 (m, 3 H) 7.01 (dd, J=8.21, 1.17 Hz, 1 H) 6.79-6.96 (m, 2 H) 6.48 (s, 1 H) 4.22 (s, 2 H) 3.49 (t, J=5.86 Hz, 2 H) 2.77 (t, J=5.86 Hz, 2 H) 1.17-1.36 (m, 6 H). MS m/z (M+H) 499.1.

Example 75

2-(1H-indol-1-yl)-3-((2-propionyl-1,2,3,4-tetrahydroisoquinolin-7-yl)ethynyl) benzoic acid

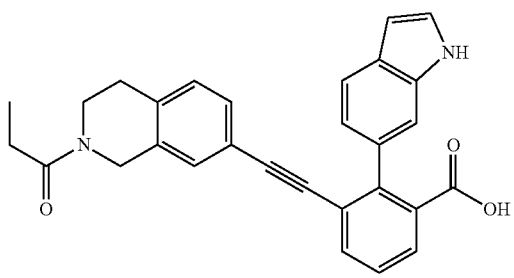 [SMILES: CCC(=O)N1CCc2ccc(C#Cc3cccc(C(=O)O)c3-c3ccc4cc[nH]c4c3)cc2C1]

2-(1H-indol-6-yl)-3-((2-propionyl-1,2,3,4-tetrahydroisoquinolin-7-yl)ethynyl)benzoic acid was prepared by the same procedure as Example 52. $^1$H NMR (30×) MHz, CD$_3$OD) δ ppm 7.63-7.75 (m, 2 H) 7.58 (dd, J=8.06, 2.78 Hz, 1 H) 7.35-7.49 (m, 2 H) 7.30 (s, 1 H) 7.01 (d, J=8.21 Hz, 1 H) 6.89-6.98 (m, 1 H) 6.75-6.89 (m, 1 H) 6.49-6.66 (m, 1 H) 4.39 (d, J=18.47 Hz, 2 H) 3.66 (t, J=5.86 Hz, 1 H) 3.58 (t, J=5.86 Hz, 1 H) 2.64-2.80 (m, 2 H) 2.41 (qd, J=7.43, 2.93 Hz, 2 H) 1.11 (t, J=7.48 Hz, 3 H). MS m/z (M+H) 449.3.

Example 76

2-(1H-indol-6-yl)-3-((2-(methylsulfonyl)-1,2,3,4-tetrahydro-isoquinolin-6-yl)ethynyl)benzoic acid

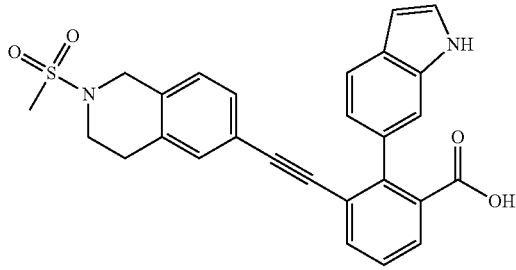 [SMILES: CS(=O)(=O)N1CCc2cc(C#Cc3cccc(C(=O)O)c3-c3ccc4cc[nH]c4c3)ccc2C1]

2-(1H-indol-6-yl)-3-((2-(methylsulfonyl)-1,2,3,4-tetrahydroisoquinolin-6-yl)ethynyl)benzoic acid was prepared by the same procedure as Example 52. ¹H NMR (300 MHz, CD3OD) δ ppm 7.63-7.74 (m, 2 H) 7.58 (d, J=8.21 Hz, 1 H) 7.34-7.48 (m, 2 H) 7.28 (s, 1 H) 7.02 (dd, J=8.21, 1.17 Hz, 1 H) 6.87 (q, J=8.60 Hz, 2 H) 6.66 (s, 1 H) 4.28 (s, 2 H) 3.38 (t, J=5.86 Hz, 2 H) 2.81 (s, 3 H) 2.70 (t, J=5.86 Hz, 2 H). MS m/z (M+H) 471.1.

Example 77

2-(1H-indol-6-yl)-3-((2-(isopropylsulfonyl)-1,2,3,4-tetrahydroiso quinolin-6-yl)ethynyl)benzoic acid

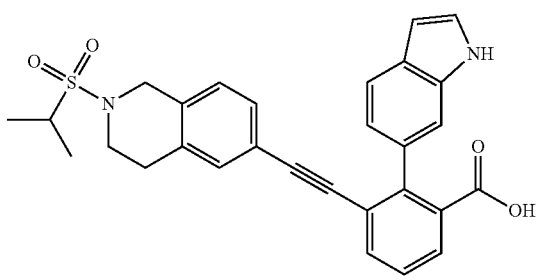 [SMILES: CC(C)S(=O)(=O)N1CCc2cc(C#Cc3cccc(C(=O)O)c3-c3ccc4cc[nH]c4c3)ccc2C1]

2-(1H-indol-6-yl)-3-((2-(isopropylsulfonyl)-1,2,3,4-tetrahydroisoquinolin-6-yl)ethynyl) benzoic acid was prepared by the same procedure as Example 52. ¹H NMR (300 MHz, CD3OD) δ ppm 7.35-7.77 (m, 5 H) 7.28 (s, 1 H) 7.02 (dd, J=8.06, 1.32 Hz, 1 H) 6.82-6.96 (m, 2 H) 6.66 (s, 1 H) 4.40 (s, 2 H) 3.51 (t, J=6.01 Hz, 2 H) 2.68 (t, J=5.86 Hz, 2 H) 1.27 (d, J=6.74 Hz, 6 H). MS m/z (M+H) 499.2.

Example 78

3-((2-acetyl-1,2,3,4-tetrahydroisoquinolin-6-yl)ethynyl)-2-(1H-indol-6-yl)benzoic acid

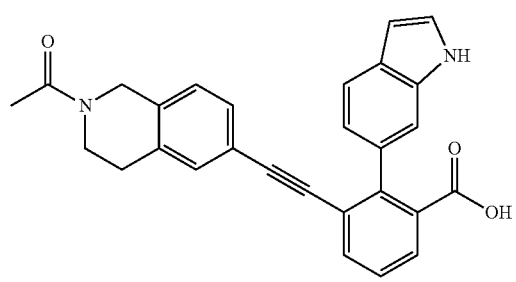 [SMILES: CC(=O)N1CCc2cc(C#Cc3cccc(C(=O)O)c3-c3ccc4cc[nH]c4c3)ccc2C1]

3-((2-acetyl-1,2,3,4-tetrahydroisoquinolin-6-yl)ethynyl)-2-(1H-indol-6-yl)benzoic acid was prepared by the same procedure as Example 52. ¹H NMR (300 MHz, CD3OD) δ ppm 7.70 (t, J=8.06 Hz, 2 H) 7.58 (d, J=7.92 Hz, 1 H) 7.35-7.51 (m, 2 H) 7.28 (s, 1 H) 6.83-7.08 (m, 3 H) 6.68 (s, 1 H) 4.57 (br, s., 2 H) 3.48-3.77 (m, 2 H) 2.69 (t, J=5.57 Hz, 1 H) 2.61 (t, J=5.72 Hz, 1 H) 2.12 (s, 3 H). MS nm/z (M+H) 435.2.

Example 79

2-(1H-indol-6-yl)-3-((2-propionyl-1,2,3,4-tetrahydroisoquinolin-6-yl)ethynyl) benzoic acid

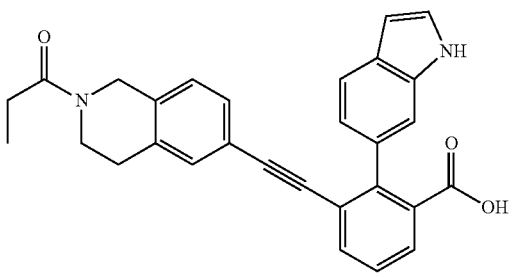 [SMILES: CCC(=O)N1CCc2cc(C#Cc3cccc(C(=O)O)c3-c3ccc4cc[nH]c4c3)ccc2C1]

2-(1H-indol-6-yl)-3-((2-propionyl-1,2,3,4-tetrahydroisoquinolin-6-yl)ethynyl)benzoic acid was prepared by the same procedure as Example 52. ¹H NMR (300 MHz, CD3OD) δ ppm 7.63-7.75 (m, 2 H) 7.58 (d, J=8.21 Hz, 1 H) 7.34-7.48 (m, 2 H) 7.28 (s, 1 H) 7.02 (d, J=8.21 Hz, 1 H) 6.80-6.98 (m, 2 H) 6.66 (s, 1 H) 4.53 (d, J=4.98 Hz, 2 H) 3.64 (t, J=6.01 Hz, 1 H) 3.57 (t, J=5.86 Hz, 1 H) 2.60 (dt, J=16.93, 5.75 Hz, 2 H) 2.40 (q, J=7.33 Hz, 2 H) 1.08 (q, J=7.52 Hz, 3 H). MS m/z (M+H) 449.2.

Example 80

3-[4-(4-cyano-phenoxymethyl)-phenylethynyl]-2-(1H-indol-6-yl)-benzoic acid

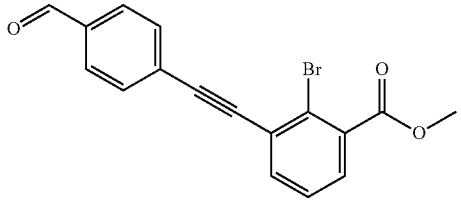 [SMILES: COC(=O)c1cccc(C#Cc2ccc(C=O)cc2)c1Br]

2-Bromo-3-(4-formyl-phenylethynyl)-benzoic acid methyl ester: A solution of methyl 2-bromo-3-iodobenzoate (1.5 g, 4 mmol) and 4-ethynyl-benzaldehyde (0.51 g, 4 mmol) in tetrahydrofuran:triethylamine (8:8 mL) was deaerated using a N2 gas balloon for 15 minutes. To this solution were added bis(triphenylphosphine) palladium(II) dichloride (310 mg, 0.04 mmol) and copper (I) iodide (50 mg, 0.3 mmol) and stirred for 16 hours at ambient temperature. The reaction mixture was then filtered through celite using ethyl acetate (50 mL). The resultant solution was the concentrated under reduced pressure and purified through silica gel cartridge eluting with ethyl acetate/hexanes to give a pale yellow solid in 67% yield.

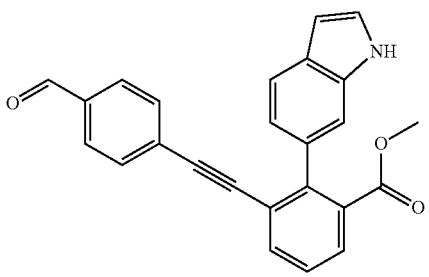 [SMILES: COC(=O)c1cccc(C#Cc2ccc(C=O)cc2)c1-c1ccc2cc[nH]c2c1]

3-(4-Formyl-phenylethynyl)-2-(1H-indol-6-yl)-benzoic acid methyl ester: To a stirring solution of 2-bromo-3-(4-formyl-phenylethynyl)-benzoic acid methyl ester (250 mg, 0.95 mmol) in 1,4-dioxane:water (2.5:2.5 mL) were added 6-indole boronic acid (277 mg, 1.13 mmol), [1,1'-Bis(diphenylphosphino)ferrocene]dichloropalladium(II), complex with dichloromethane (78 mg, 0.095 mmol), potassium carbonate (321 mg, 2.4 mmol) and resulting mixture was heated to 90° C. for 3 h. The resultant mixture was then allowed to cool to ambient temperature and was diluted with ethyl acetate (50 mL) and filtered through celite. The aqueous layer was separated and extracted with ethyl acetate (2×25 mL) and then the combined organic layer was washed with water (20 mL), brine (20 mL), dried (sodium sulfate), filtered and concentrated under reduced pressure. The resultant crude product was purified through silica gel cartridge eluting with ethyl acetate/hexanes to give a yellow solid in 70% yield. $^1$H NMR (400 MHz, DMSO-$d_6$) δ 11.22 (s, 1H), 9.95 (s, 1H), 7.87 (dd, J=8.0, 1.6 Hz, 1H), 7.81 (d, J=8.4 Hz, 2H), 7.75 (dd, J=7.6, 1.2 Hz, 1H), 7.61 (d, J=8.4 Hz, 1H), 7.53 (t, J=8.0 Hz, 1H), 7.44-7.41 (m, 2H), 7.33 (d, J=8.0 Hz, 2H), 6.98 (dd, J=8.0, 1.6 Hz, 1H), 6.49 (dd, J=2.0, 0.8 Hz, 1H), 3.49 (s, 3H). MS m/z (M−H) 378.2.

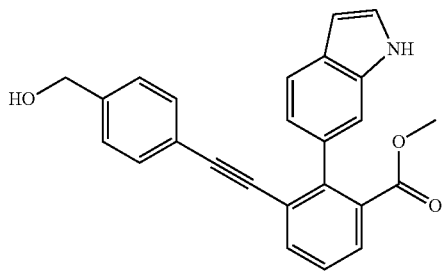 [SMILES: COC(=O)c1cccc(C#Cc2ccc(CO)cc2)c1-c1ccc2cc[nH]c2c1]

3-(4-Hydroxymethyl-phenylethynyl)-2-(1H-indol-6-yl)-benzoic acid methyl ester: To a stirring solution of 3-(4-formyl-phenylethynyl)-2-(1H-indol-6-yl)-benzoic acid methyl ester (2 g, 5.26 mmol) in methanol (40 mL) was added sodium borohydride (0.234 mg, 6.32 mmol) at 0-5° C., and stirred for 1 h at ambient temperature. The reaction mixture was then diluted with ethyl acetate (300 mL) and washed with water (2×50 mL). The organic layer was washed with brine (50 mL), dried (sodium sulfate), filtered and concentrated under reduced pressure. The resultant crude product was purified through silica gel cartridge eluting with ethyl acetate/hexanes to give a pale yellow solid in 90% yield. $^1$H NMR (400 MHz, DMSO-$d_6$) δ 11.20 (s, 1H), 7.79 (d, J=8.0 Hz, 1H), 7.68 (d, J=7.6 Hz, 1H), 7.58 (d, J=8.4 Hz, 1H), 7.49 (t, J=7.6 Hz, 1H), 7.42-7.40 (m, 2H), 7.21 (d, J=7.6 Hz, 2H), 7.09 (d, J=8.0 Hz, 2H), 6.95 (d, J=8.0 Hz, 1H), 6.47 (bs, 1H), 5.23 (t, J=5.6 Hz, 1H), 4.44 (d, J=5.2 Hz, 2H), 3.49 (s, 3H). MS m/z (M−H) 380.0.

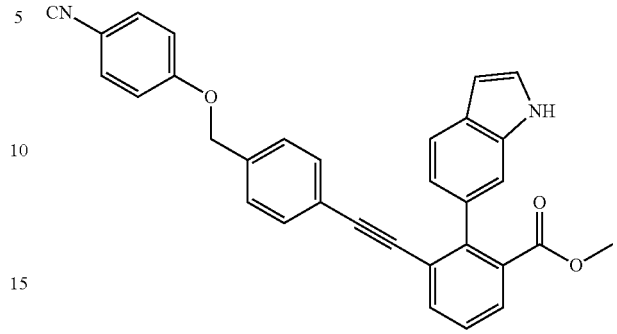

3-[4-(4-Cyano-phenoxymethyl)-phenylethynyl]-2-(1H-indol-6-yl)-benzoic acid methyl ester: To a stirring solution of 3-(4-hydroxymethyl-phenylethynyl)-2-(1H-indol-6-yl)-benzoic acid methyl ester (400 mg, 1.06 mmol) in tetrahydrofuran (6 mL) were added 1,1'-(azodicarbonyl)-dipiperidine (400 mg, 1.60 mmol), tributylphosphine (0.8 mL, 1.6 mmol), 4-cyanophenol (116 mg, 1.06 mmol) and stirred for 12 hours at ambient temperature. The reaction mixture was then diluted with ethyl acetate (100 mL) and washed with water (2×20 mL). The organic layer was washed with brine (10 mL), dried (sodium sulfate), filtered and concentrated under reduced pressure. The resultant crude product was purified through silica gel cartridge eluting with ethyl acetate/hexanes to give an off-white solid in 50% yield. $^1$H NMR (400 MHz, DMSO-$d_6$) δ 11.21 (s, 1H), 7.79-7.75 (m, 3H), 7.71 (dd, J=7.6, 1.2 Hz, 1H), 7.59 (d, J=8.4 Hz, 1H), 7.42 (s, 1H), 7.40 (t, J=2.8 Hz, 2H), 7.37 (d, J=8.0 Hz, 2H), 7.18-7.13 (m, 4H), 6.96 (dd, J=8.0, 1.6 Hz, 1H), 6.48 (bs, 1H), 5.17 (s, 2H), 3.48 (s, 3H). MS m/z (M−H) 483.1.

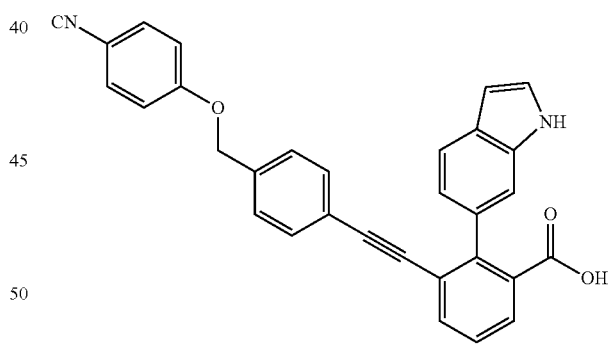

3-[4-(4-Cyano-phenoxymethyl)-phenylethenyl]-2-(1H-indol-6-yl)-benzoic acid: To a solution of 3-[4-(4-cyano-phenoxymethyl)-phenylethynyl]-2-(1H-indol-6-yl)-benzoic acid methyl ester (200 mg, 0.42 mmol) in tetrahydrofuran:methanol (1:1 mL) was added 2N sodium hydroxide (aq) (84 mg, 2.1 mmol) and the resulting solution was stirred for about 24 hours at ambient temperature. The reaction mixture was then concentrated and the pH adjusted to 4 using 1 N hydrochloric acid solution. The aqueous layer was then extracted using ethyl acetate (2×25 mL) and washed with water (20 mL) and brine (10 mL). The organic layers were combined, dried (sodium sulfate), filtered and concentrated under reduced pressure. The resulting crude product was then purified using reversed phase HPLC to give an off-white solid in 70% yield. $^1$H NMR (400 MHz, DMSO-$d_6$) δ 12.80 (bs, 1H), 11.19 (s, 1H), 7.77-7.74 (m, 3H), 7.68 (dd, J=7.6, 1.2 Hz, 1H), 7.58 (d, J=8.0 Hz, 1H), 7.46 (t, J=8.0 Hz, 1H), 7.42 (s, 1H), 7.39 (t, J=2.8 Hz, 1H), 7.37 (d, J=7.6 Hz, 2H), 7.17-7.13 (m, 4H), 7.03 (dd, J=8.4, 1.6 Hz, 1H), 6.47 (t, J=2 Hz, 1H), 5.17 (s, 2H). MS m/z (M−H) 469.0.

Example 81

3-[4-(3-cyano-phenoxymethyl)-phenyl ethynyl]-2-(1H-indol-6-yl)-benzoic acid

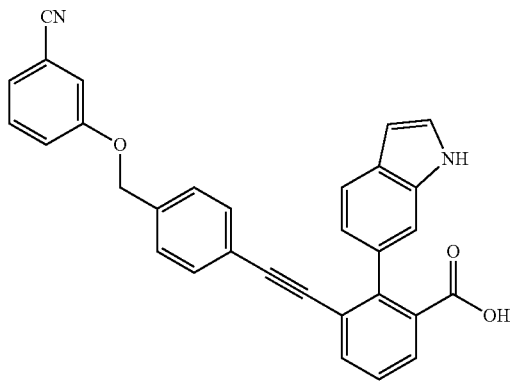 [SMILES: N#Cc1cccc(OCc2ccc(C#Cc3cccc(C(=O)O)c3-c3ccc4cc[nH]c4c3)cc2)c1]

3-[4-(3-cyano-phenoxymethyl)-phenyl ethynyl]-2-(1H-indol-6-yl)-benzoic acid was prepared by the same procedure as Example 80. $^1$H NMR (400 MHz, DMSO-$d_6$) δ 12.77 (s, 1H), 11.20 (s, 1H), 7.75 (dd, J=7.7, 1.4 Hz, 1H), 7.66 (dd, J=7.8, 1.4 Hz, 1H), 7.58 (d, J=8.1 Hz, 1H), 7.53-7.29 (m, 9H), 7.19-7.12 (m, 2H), 7.03 (dd, J=8.1, 1.6 Hz, 1H), 6.47 (s, 1H), 5.14 (s, 2H). MS m/z (M+H) 469.1.

Example 82

3-[4-carbamoyl-phenoxymethyl)-phenylethynyl]-2-(1H-indol-6-yl)-benzoic acid

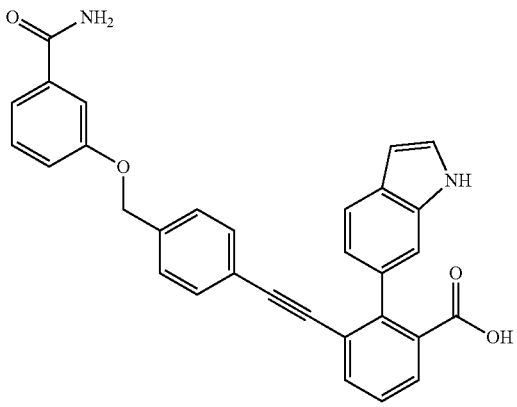 [SMILES: NC(=O)c1cccc(OCc2ccc(C#Cc3cccc(C(=O)O)c3-c3ccc4cc[nH]c4c3)cc2)c1]

3-[4-(3-carbamoyl-phenoxymethyl)-phenylethynyl]-2-(1H-indol-6-yl)-benzoic acid was prepared by the same procedure as Example 80. $^1$H NMR (400 MHz, DMSO-$d_6$) δ 11.19 (t, J=2.2 Hz, 1H), 7.95 (s, 1H), 7.72 (dd, J=7.7, 1.4 Hz, 1H), 7.63 (dd, J=7.7, 1.4 Hz, 1H), 7.57 (d, J=8.1 Hz, 1H), 7.48 (t, J=2.0 Hz, 1H), 7.49-7.39 (m, 3H), 7.43-7.30 (m, 5H), 7.19-7.08 (m, 3H), 7.04 (dd, J=8.2, 1.6 Hz, 1H), 6.47 (s, 1H), 5.11 (s, 2H). MS m/z (M+H) 487.1.

Example 83

2-(1H-indol-6-yl)-3-[4-(4-trifluoromethyl-phenoxymethyl)-phenyl ethynyl]-benzoic acid

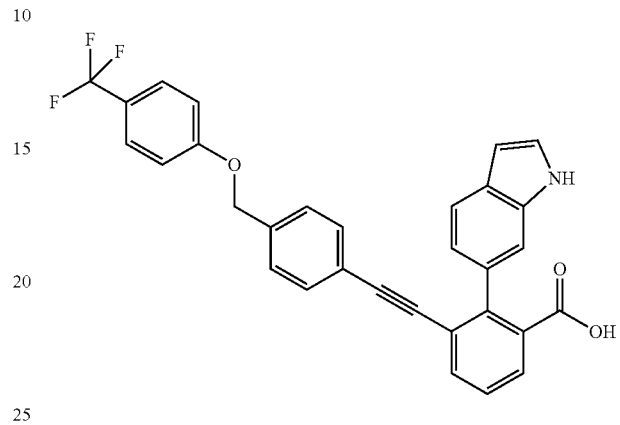

2-(1H-indol-6-yl)-3-[4-(4-trifluoromethyl-phenoxymethyl)-phenylethynyl]-benzoic acid was prepared by the same procedure as Example 80. $^1$H NMR (400 MHz, DMSO-$d_6$) δ 12.75 (s, 1H), 11.19 (s, 1H), 7.74 (d, J=7.8 Hz, 1H), 7.65 (dd, J=8.5, 6.7 Hz, 3H), 7.57 (d, J=8.1 Hz, 1H), 7.50-7.33 (m, 5H), 7.16 (d, J=8.1 Hz, 4H), 7.03 (dd, J=8.1, 1.6 Hz, 1H), 6.47 (t, J=2.3 Hz, 1H), 5.17 (s, 2H). MS m/z (M−H) 510.1.

Example 84

2-(1H-indol-6-yl)-3-[4-(3-trifluoromethyl-phenoxymethyl)-phenyl ethynyl]-benzoic acid

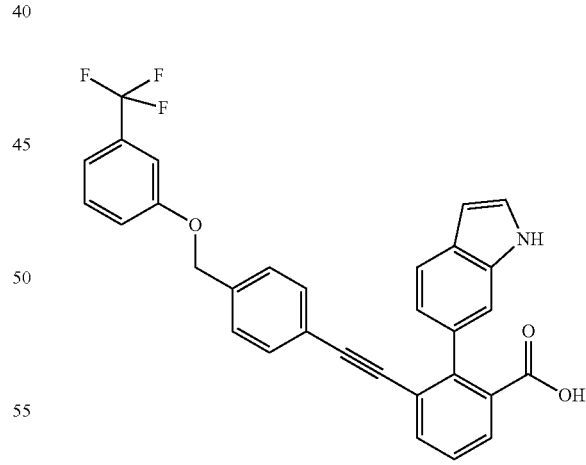

2-(1H-indol-6-yl)-3-[4-(3-trifluoromethyl-phenoxymethyl)-phenylethynyl]-benzoic acid was prepared by the same procedure as Example 80. $^1$H NMR (400 MHz, DMSO-$d_6$) δ 12.75 (s, 1H), 11.20 (d, J=2.6 Hz, 1H), 7.75 (dd, J=7.7, 1.4 Hz, 1H), 7.67 (dd, J=7.7, 1.4 Hz, 1H), 7.58 (d, J=8.2 Hz, 1H), 7.56-7.44 (m, 1H), 7.47-7.36 (m, 3H), 7.37 (s, 2H), 7.29 (d, J=8.1 Hz, 3H), 7.16 (d, J=8.2 Hz, 2H), 7.03 (dd, J=8.2, 1.6 Hz, 1H), 6.47 (s, 1H), 5.16 (s, 2H). MS m/z (M−H) 510.9.

Example 85

2-(1H-indol-1-yl)-3-[4-(4-methoxy-phenoxymethyl)-phenyl ethynyl]-benzoic acid

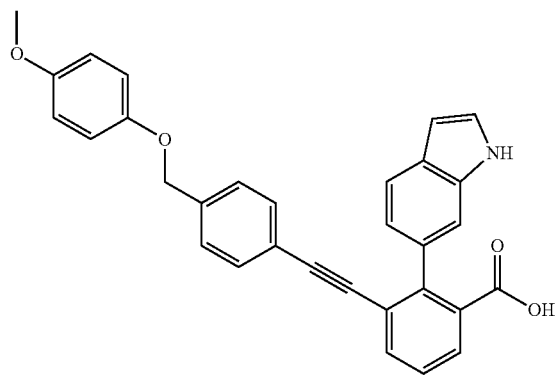 [SMILES: COc1ccc(OCc2ccc(C#Cc3cccc(C(=O)O)c3-c3ccc4cc[nH]c4c3)cc2)cc1]

2-(1H-indol-6-yl)-3-[4-(4-methoxy-phenoxymethyl)-phenylethynyl]-benzoic acid was prepared by the same procedure as Example 80. $^1$H NMR (400 MHz, DMSO-$d_6$) δ 12.73 (s, 1H), 11.20 (t, J=2.2 Hz, 1H), 7.75 (dd, J=7.7, 1.4 Hz, 1H), 7.67 (dd, J=7.8, 1.4 Hz, 1H), 7.58 (d, J=8.2 Hz, 1H), 7.51-7.36 (m, 3H), 7.36-7.29 (m, 2H), 7.17-7.10 (m, 2H), 7.02 (dd, J=8.2, 1.6 Hz, 1H), 6.94-6.85 (m, 2H), 6.88-6.79 (m, 2H), 6.50-6.44 (m, 1H), 5.00 (s, 2H), 3.68 (s, 3H). MS m/z (M−H) 472.1.

Example 86

3-[4-(4-carbamoyl-phenoxymethyl)-phenylethynyl]-2-(1H-indol-6-yl)-benzoic acid

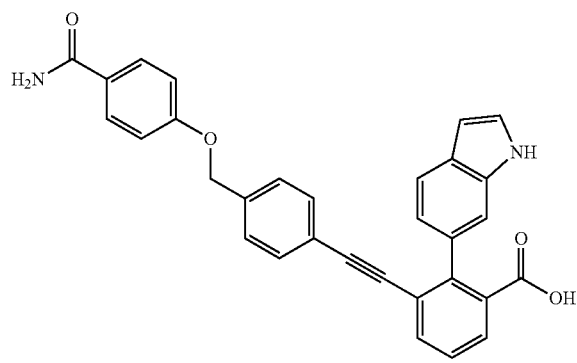 [SMILES: NC(=O)c1ccc(OCc2ccc(C#Cc3cccc(C(=O)O)c3-c3ccc4cc[nH]c4c3)cc2)cc1]

3-[4-(4-carbamoyl-phenoxymethyl)-phenylethynyl]-2-(1H-indol-6-yl)-benzoic acid was prepared by the same procedure as Example 80. $^1$H NMR (400 MHz, DMSO-$d_6$) δ 12.81 (s, 1H), 11.17 (s, 1H), 7.86-7.77 (m, 3H), 7.69 (d, J=7.5 Hz, 1H), 7.58 (dd, J=18.2, 7.7 Hz, 1H), 7.44 (s, 1H), 7.44-7.32 (m, 5H), 7.16 (dd, J=10.4, 8.5 Hz, 3H), 7.10-6.97 (m, 3H), 6.46 (s, 1H), 5.13 (s, 2H). MS m/z (M+H) 487.0.

Example 87

2-(1H-indol-6-yl)-3-[4-(3-methoxy-phenoxymethyl)-phenyl ethynyl]-benzoic acid

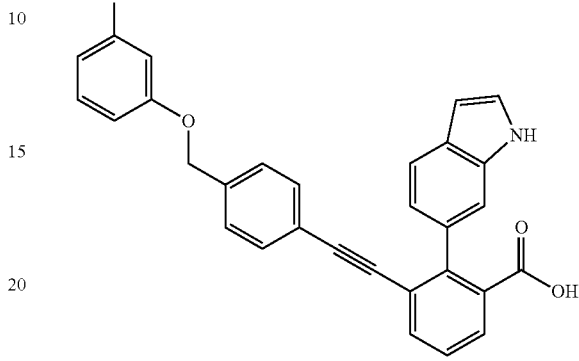

2-(1H-indol-6-yl)-3-[4-(3-methoxy-phenoxymethyl)-phenylethynyl]-benzoic acid was by the same procedure as Example 80. $^1$H NMR (400 MHz, DMSO-$d_6$) δ 12.76 (s, 1H), 11.21 (t, J=2.3 Hz, 1H), 7.75 (dd, J=7.7, 1.4 Hz, 1H), 7.67 (dd, J=7.8, 1.4 Hz, 1H), 7.58 (d, J=8.1 Hz, 1H), 7.51-7.36 (m, 3H), 7.35 (d, J=8.1 Hz, 2H), 7.21-7.11 (m, 3H), 7.02 (dd, J=8.1, 1.6 Hz, 1H), 6.59-6.47 (m, 3H), 6.47 (s, 1H), 5.05 (s, 2H), 3.71 (s, 3H). MS m/z (M+H) 474.1.

Example 88

2-(1H-indol-6-yl)-3-(4-phenoxymethyl-phenylethynyl)-benzoic acid

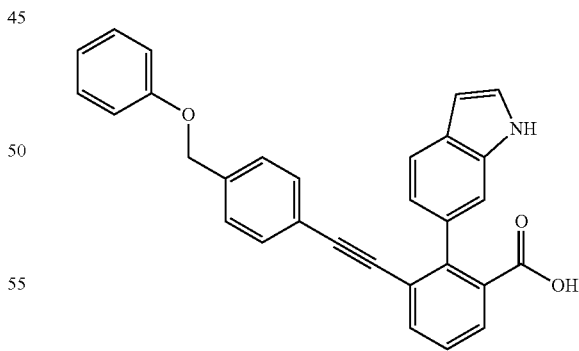

2-(1H-indol-6-yl)-3-(4-phenoxymethyl-phenylethynyl)-benzoic acid was prepared by the same procedure as Example 80. $^1$H NMR (400 MHz, DMSO-$d_6$) δ 12.74 (s, 1H), 11.20 (s, 1H), 7.75 (d, J=7.7 Hz, 1H), 7.67 (d, J=7.5 Hz, 1H), 7.58 (d, J=8.1 Hz, 1H), 7.46 (t, J=7.7 Hz, 1H), 7.45-7.32 (m, 4H), 7.27 (t, J=8.0 Hz, 2H), 7.15 (d, J=8.0 Hz, 2H), 7.02 (dd, J=8.1, 1.6 Hz, 1H), 6.94 (dd, J=19.2, 7.8 Hz, 3H), 6.47 (s, 1H), 5.06 (s, 2H). MS m/z (M+H) 444.0.

Example 89

3-[4-(2-fluoro-phenoxymethyl)-phenylethynyl]-2-(1H-indol-6-yl)-benzoic acid

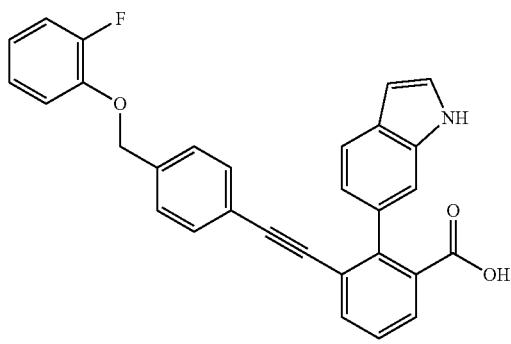 [SMILES: O=C(O)c1cccc(C#Cc2ccc(COc3ccccc3F)cc2)c1-c1ccc2cc[nH]c2c1]

3-[4-(2-fluoro-phenoxymethyl)-phenylethynyl]-2-(1H-indol-6-yl)-benzoic acid was prepared by the same procedure as Example 80. $^1$H NMR (400 MHz, DMSO-$d_6$) δ 12.74 (s, 1H), 11.21 (d, J=2.3 Hz, 1H), 7.76 (dd, J=7.7, 1.4 Hz, 1H), 7.68 (dd, J=7.8, 1.4 Hz, 1H), 7.58 (d, J=8.2 Hz, 1H), 7.46 (dd, J=15.9, 8.1 Hz, 2H), 7.43-7.32 (m, 3H), 7.26-7.12 (m, 4H), 7.14-7.05 (m, 1H), 7.02 (dd, J=8.1, 1.6 Hz, 1H), 6.93 (tdd, J=7.7, 4.6, 1.6 Hz, 1H), 6.47 (s, 1H), 5.14 (s, 2H). MS m/z (M+H) 462.0.

Example 90

2-(1H-indol-6-yl)-3-[4-(pyridin-3-yloxymethyl)phenylethynyl]-benzoic acid

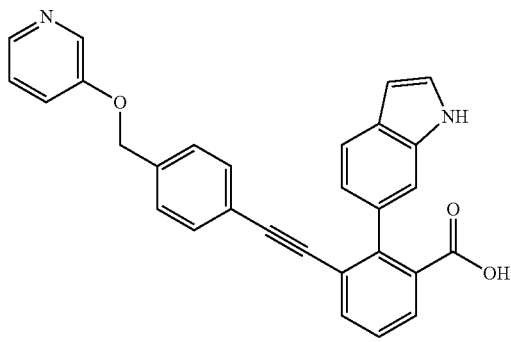 [SMILES: O=C(O)c1cccc(C#Cc2ccc(COc3cccnc3)cc2)c1-c1ccc2cc[nH]c2c1]

2-(1H-indol-6-yl)-3-[4-(pyridin-3-yloxymethyl)-phenylethynyl]-benzoic acid was prepared by the same procedure as Example 80. $^1$H NMR (400 MHz, DMSO-$d_6$) 12.72 (s, 1H), 11.19 (s, 1H), 8.33 (d, J=2.9 Hz, 1H), 8.16 (dd. J=4.6, 1.3 Hz, 1H), 7.76 (dd, J=7.8, 1.4 Hz, 1H), 7.68 (dd, J=7.8, 1.4 Hz, 1H), 7.58 (d, J=8.1 Hz, 1H), 7.51-7.24 (m, 7H), 7.19-7.12 (m, 2H), 7.02 (dd, J=8.1, 1.6 Hz, 1H), 6.47 (s, 1H), 5.15 (s, 2H). MS m/z (M+H) 445.0.

Example 91

3-[4-(3-chloro-phenoxymethyl)-phenylethynyl]-2-(1H-indol-6-yl)-benzoic acid

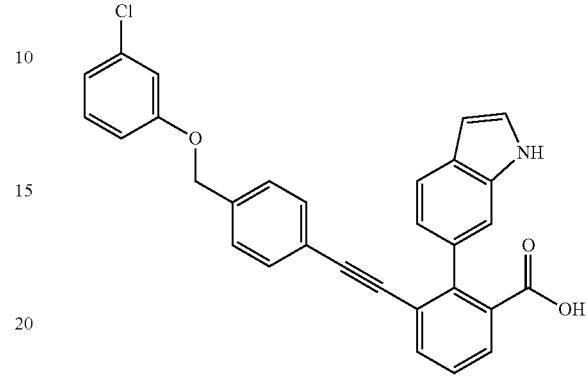

-[4-(3-chloro-phenoxymethyl)-phenylethynyl]-2-(1H-indol-6-yl)-benzoic acid was prepared by the same procedure as Example 80. $^1$H NMR (400 MHz, DMSO-$d_6$) δ 12.75 (s, 1H), 11.20 (s, 1H), 7.75 (dd, J=7.6, 1.4 Hz, 1H), 7.70-7.63 (m, 1H), 7.58 (d, J=8.2 Hz, 1H), 7.51-7.25 (m, 6H), 7.15 (d, J=7.9 Hz, 2H), 7.11-6.91 (m, 4H), 6.47 (t, J=2.5 Hz, 1H), 5.10 (s, 2H). MS m/z (M+H) 478.0.

Example 92

3-[4-(3,4-dichloro-phenoxymethyl)-phenylethynyl]-2-(H-indol-6-yl)-benzoic acid

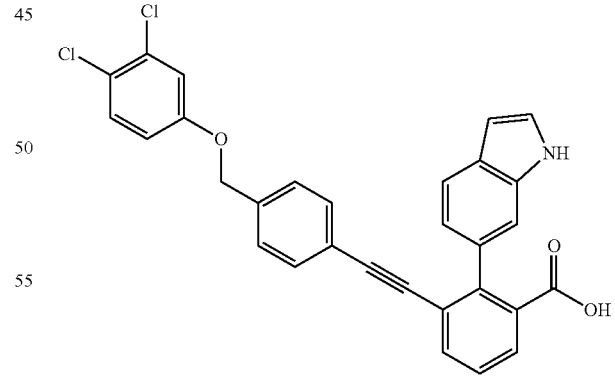

3-[4-(3,4-dichloro-phenoxymethyl)-phenylethynyl]-2-(1H-indol-6-yl)-benzoic acid was prepared by the same procedure as Example 80. $^1$H NMR (400 MHz, DMSO-$d_6$) δ 12.76 (s, 1H), 11.20 (s, 1H), 7.75 (d, J=7.6 Hz, 1H), 7.67 (d, J=7.6 Hz, 1H), 7.58 (d, J=8.2 Hz, 2H), 7.55-7.27 (m, 6H), 7.15 (d, J=7.8 Hz, 2H), 7.06-6.96 (m, 2H), 6.47 (t, J=2.3 Hz, 1H), 5.11 (s, 2H). MS m/z (M, 512.0 and (M+2) 514.0.

Example 93

2-(1H-indol-6-yl)-3-[4-(2-trifluoromethyl-phenoxymethyl)-phenylethynyl]-benzoic acid

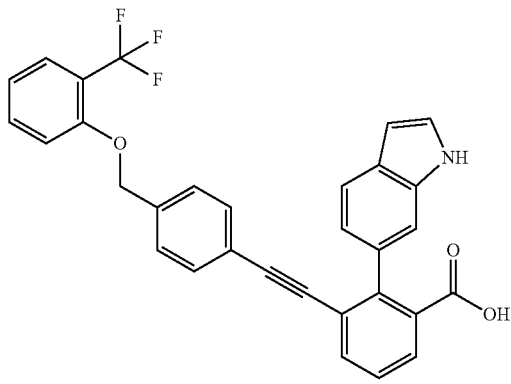 [SMILES: O=C(O)c1cccc(C#Cc2ccc(COc3ccccc3C(F)(F)F)cc2)c1-c1ccc2cc[nH]c2c1]

2-(1H-indol-6-yl)-3-[4-(2-trifluoromethyl-phenoxymethyl)-phenylethynyl]-benzoic acid was prepared by the same procedure as Example 80. $^1$H NMR (400 MHz, DMSO-d$_6$) δ 12.74 (s, 1H), 11.20 (d, J=2.3 Hz, 1H), 7.75 (dd, J=7.7, 1.4 Hz, 1H), 7.71-7.55 (m, 4H), 7.51-7.36 (m, 3H), 7.34 (d, J=8.0 Hz, 2H), 7.28 (d, J=8.4 Hz, 1H), 7.16 (d, J=8.1 Hz, 2H), 7.10 (t, J=7.6 Hz, 1H), 7.02 (dd, J=8.2, 1.6 Hz, 1H), 6.47 (s, 1H), 5.24 (s, 2H). MS m/z (M+H) 512.0.

Example 94

3-[4-(2-cyano-phenoxymethyl)-phenylethynyl]-2-(1H-indol-6-yl)-benzoic acid

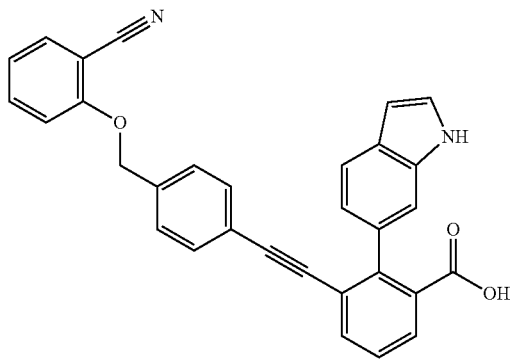 [SMILES: N#Cc1ccccc1OCc1ccc(C#Cc2cccc(C(=O)O)c2-c2ccc3cc[nH]c3c2)cc1]

3-[4-(2-cyano-phenoxymethyl)-phenylethynyl]-2-(1H-indol-6-yl)-benzoic acid was prepared by the same procedure as Example 80. $^1$H NMR (400 MHz, DMSO-d$_6$) δ 12.74 (s, 1H), 11.20 (t, J=2.2 Hz, 1H), 7.75 (ddd, J=7.6, 3.9, 1.5 Hz, 2H), 7.65 (ddd, J=16.4, 7.7, 1.6 Hz, 2H), 7.58 (d, J=8.2 Hz, 1H), 7.55-7.35 (m, 5H), 7.27 (d, J=8.4 Hz, 1H), 7.21-7.14 (m, 2H), 7.10 (td, J=7.6, 0.9 Hz, 1H), 7.02 (dd, J=8.1, 1.6 Hz, 1H), 6.47 (s, 1H), 5.26 (s, 2H). MS m/z (M+H) 469.2.

Example 95

2-(1H-indol-6-yl)-3-[4-(4-methanesulfonyl-phenoxymethyl)-phenylethynyl]-benzoic acid 2-(1H-indol-6-yl)-3-[4-(4-methanesulfonyl-phenoxymethyl)-phenylethynyl]-benzoic acid was prepared by the same procedure as Example 80. $^1$H NMR (400 MHz, DMSO-d$_6$) 11.18 (d, J=2.6 Hz, 1H), 7.87-7.78 (m, 2H), 7.69 (d, J=7.7 Hz, 1H), 7.58 (dd, J=16.6, 7.9 Hz, 2H), 7.47-7.33 (m, 5H), 7.24-7.13 (m, 4H), 7.04 (dd, J=8.2, 1.6 Hz, 1H), 6.46 (s, 1H), 5.19 (s, 2H), 3.14 (s, 3H). MS m/z (M+H) 522.0.

Example 96

2-(1H-indol-6-yl)-3-[4-(pyrimidin-5-yloxymethyl)-phenylethynyl]-benzoic acid 2-(1H-indol-6-yl)-3-[4-(pyrimidin-5-yloxymethyl)-phenylethynyl]-benzoic acid was prepared by the same procedure as Example 80. $^1$H NMR (400 MHz, DMSO-d$_6$) δ 12.74 (s, 1H), 11.20 (s, 1H), 8.81 (s, 1H), 8.59 (s, 2H), 7.76 (dd, J=7.7, 1.4 Hz, 1H), 7.68 (dd. J=7.8, 1.4 Hz, 1H), 7.58 (d, J=8.2 Hz, 1H), 7.47 (t, J=7.7 Hz, 1H), 7.45-7.35 (m, 4H), 7.16 (d, J=8.2 Hz, 2H), 7.02 (dd, J=8.1, 1.6 Hz, 1H), 6.51-6.44 (m, 1H), 5.24 (s, 2H). MS m/z (M+H) 446.1.

Example 97

2-(1H-indol-6-yl)-3-[4-(2-methanesulfonyl-phenoxymethyl)-phenylethynyl]-benzoic acid

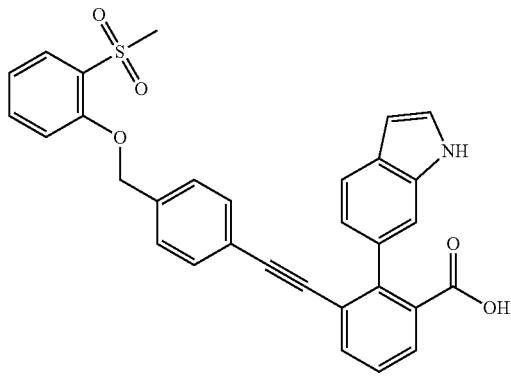 [SMILES: CS(=O)(=O)c1ccccc1OCc1ccc(C#Cc2cccc(C(=O)O)c2-c2ccc3cc[nH]c3c2)cc1]

2-(1H-indol-6-yl)-3-[4-(2-methanesulfonyl-phenoxymethyl)-phenylethynyl]-benzoic acid was prepared by the same procedure as Example 80. $^1$H NMR (400 MHz, DMSO-$d_6$) δ 12.74 (s, 1H), 11.20 (t, J=2.3 Hz, 1H), 7.79 (ddd, J=24.5, 7.7, 1.6 Hz, 2H), 7.67 (ddd, J=8.2, 6.4, 1.6 Hz, 2H), 7.58 (d, J=8.1 Hz, 1H), 7.51-7.36 (m, 5H), 7.31 (d, J=8.4 Hz, 1H), 7.18 (d, J=7.8 Hz, 3H), 7.03 (dd, J=8.1, 1.6 Hz, 1H), 6.47 (s, 1H), 5.31 (s, 2H), 3.20 (s, 3H). MS m/z (M+H) 522.0.

Example 98

2-(1H-indol-6-yl)-3-[4-(3-methanesulfonyl-phenoxymethyl)-phenylethynyl]-benzoic acid

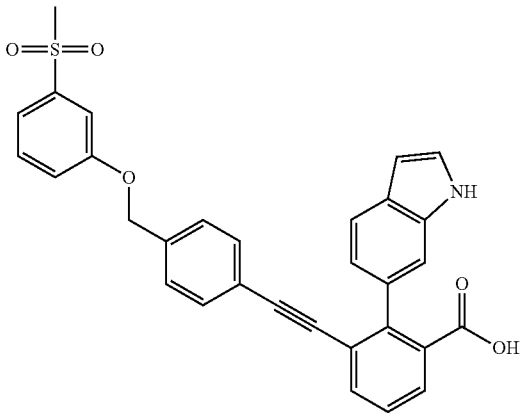 [SMILES: CS(=O)(=O)c1cccc(OCc2ccc(C#Cc3cccc(C(=O)O)c3-c3ccc4cc[nH]c4c3)cc2)c1]

2-(1H-Indol-6-yl)-3-[4-(3-methanesulfonyl-phenoxymethyl)-phenylethynyl]-benzoic acid was prepared by the same procedure as Example 80. $^1$H NMR (400 MHz, DMSO-$d_6$) δ 12.75 (s, 1H), 11.21 (t, J=2.2 Hz, 1H), 7.76 (dd, J=7.7, 1.4 Hz, 1H), 7.68 (dd, J=7.8, 1.4 Hz, 1H), 7.62-7.52 (m, 2H), 7.53-7.29 (m, 8H), 7.20-7.13 (m, 2H), 7.03 (dd, J=8.1, 1.6 Hz, 1H), 6.47 (s, 1H), 5.18 (s, 2H), 3.21 (s, 3H). MS mm/z (M+H) 522.1.

Example 99

2-(1H-Indol-6-yl)-3-{2-[3-(3-methanesulfonamidophenyl)phenyl]ethynyl}benzoic acid

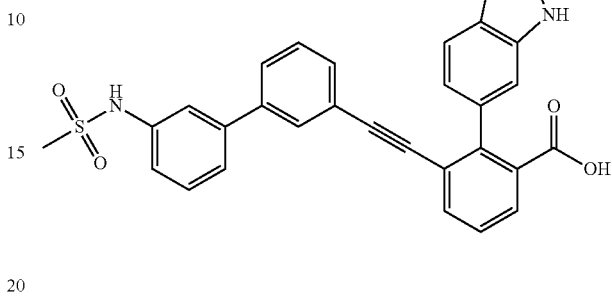

2-(1H-Indol-6-yl)-3-{2-[3-(3-methanesulfonamidophenyl)phenyl]ethynyl} benzoic acid was prepared by the same procedure as Example 1. $^1$H NMR (300 MHz, DMSO-d6) δ 11.16 (s, 1 H), 9.81 (s, 1 H), 7.64-7.80 (m, 2 H), 7.32-7.62 (m, 7 H), 7.10-7.29 (m, 4 H), 7.02 (dd, J=8.21, 1.47 Hz, 2 H), 6.46 (br s, 1 H), 3.01 (s, 3 H), 2.50-2.78 (m, 1 H). MS m/z (M+H) 507.4.

Example 100

2-(1H-Indol-6-yl)-3-{2-[6-(oxan-4-yloxy)pyridin-3-yl]ethynyl}benzoic acid

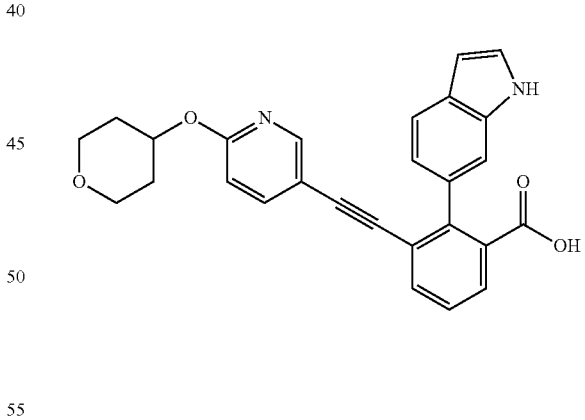

2-(1H-Indol-6-yl)-3-{2-[6-(oxan-4-yloxy)pyridin-3-yl]ethynyl}benzoic acid was prepared by the same procedure as Example 1. $^1$H NMR (300 MHz, DMSO-d6) δ 11.16 (br s, 1 H), 7.90 (d, J=2.35 Hz, 1 H), 7.59-7.80 (m, 2 H), 7.55 (d, J=8.21 Hz, 1 H), 7.22-7.50 (m, 4 H), 6.99 (dd, J=8.06, 1.32 Hz, 1 H), 6.71 (d, J=8.50 Hz, 1 H), 6.44 (br s, 1 H), 5.10 (td, J=8.87, 4.25 Hz, 1 H), 3.70-3.83 (m 2 H), 3.64 (br s, 1 H) 3.19-3.47 (m, 2 H), 1.91 (br d, J=10.55 Hz, 2 H), 1.37-1.75 (m, 2 H). MS m/z (M+H) 439.5.

Example 101

2-(1H-Indol-6-yl)-3-{2-[2-(propylcarbamoyl)-1H-indol-6-yl]ethynyl}benzoic acid

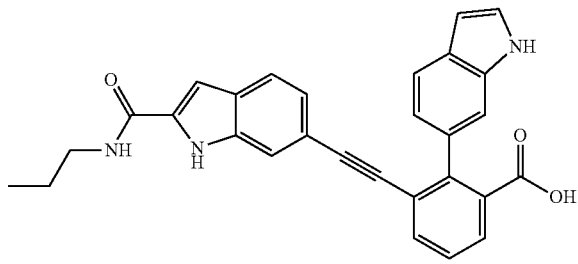 [SMILES: CCCNC(=O)c1cc2ccc(C#Cc3cccc(C(=O)O)c3-c3ccc4cc[nH]c4c3)cc2[nH]1]

2-(1H-Indol-6-yl)-3-{2-[2-(propylcarbamoyl)-1H-indol-6-yl]ethynyl}benzoic acid was prepared by the same procedure as Example 1. $^1$H NMR (300 MHz, DMSO-d6) δ 11.60-11.65 (m, 1 H), 11.13-11.16 (m, 1 H), 8.44-8.50 (m, 1 H), 7.80-7.83 (m, 1 H), 7.67-7.76 (m, 1 H), 7.51-7.62 (m, 1 H), 7.26-7.48 (m, 3 H), 6.91-7.08 (m, 2 H), 6.80-6.90 (m, 1 H), 6.67-6.78 (m, 1 H), 6.45 (br d, J=2.05 Hz, 1 H) 2.89-3.23 (m, 2 H), 1.44-1.59 (m, 2 H), 1.11-1.27 (bs, 1 H), 0.77-0.94 (m, 3 H). MS m/z (M+H) 462.6.

Example 102

2-(1H-Indol-6-yl)-3-{2-[3-(1,2,3,4-tetrahydroisoquinolin-2-ylmethyl)phenyl]ethynyl}benzoic acid

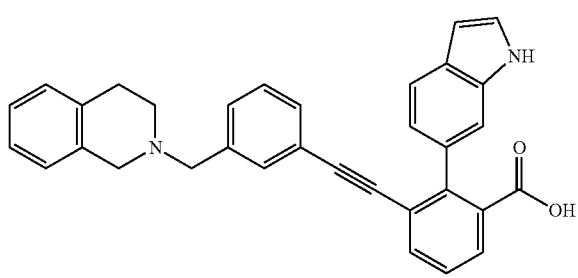 [SMILES: O=C(O)c1cccc(C#Cc2cccc(CN3CCc4ccccc4C3)c2)c1-c1ccc2cc[nH]c2c1]

2-(1H-Indol-6-yl)-3-{2-[3-(1,2,3,4-tetrahydroisoquinolin-2-ylmethyl)phenyl]ethynyl}benzoic acid was prepared by the same procedure as Example 1. $^1$H NMR (30×) MHz, DMSO-d6) δ 11.15 (br s, 1 H), 7.58-7.92 (m, 4 H), 7.19-7.55 (m, 7 H), 6.86-7.14 (m, 4 H), 6.39 (br s, 1 H), 3.41-3.72 (m, 4 H), 2.65-2.98 (m, 2 H), 2.51-2.64 (m, 2 H). MS m/z (M+H) 483.2.

Example 103

3-{2-[3-Cyano-4-(oxan-4-yloxy)phenyl]ethynyl}-2-(1H-indol-6-yl)benzoic acid

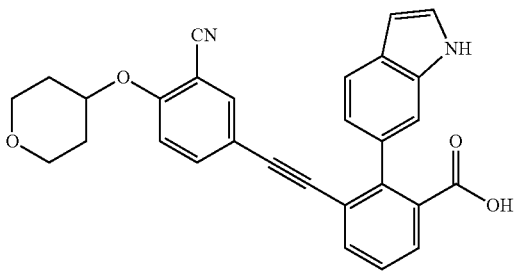 [SMILES: N#Cc1cc(C#Cc2cccc(C(=O)O)c2-c2ccc3cc[nH]c3c2)ccc1OC1CCOCC1]

3-{2-[3-Cyano-4-(oxan-4-yloxy)phenyl]ethynyl}-2-(1H-indol-6-yl)benzoic acid was prepared by the same procedure as Example 1. $^1$H NMR (300 MHz, DMSO-d6) δ 12.74 (br s, 1 H), 11.17 (br s, 1 H), 7.50-7.80 (m, 3 H), 7.20-7.50 (m, 5 H), 6.86-7.16 (m, 2 H), 6.45 (br s, 1 H), 4.56-4.84 (m, 1 H), 3.64-3.91 (m, 2 H), 3.36-3.60 (m, 2 H), 1.86-2.08 (m, 2 H), 1.57 (ddt, J=12.94, 8.61, 4.18, 4.18 Hz, 2 H). MS m/z (M+H) 463.5.

Example 104

3-[2-(3-{[4-(Ethoxycarbonyl)piperazin-1-yl]methyl}phenyl) ethynyl]-2-(1H-indol-6-yl)benzoic acid

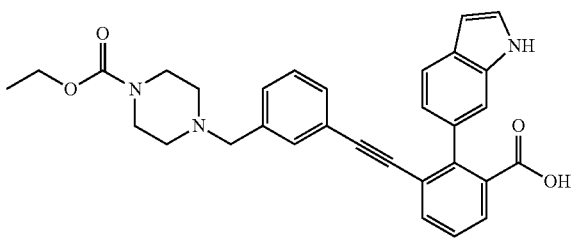 [SMILES: CCOC(=O)N1CCN(Cc2cccc(C#Cc3cccc(C(=O)O)c3-c3ccc4cc[nH]c4c3)c2)CC1]

3-[2-(3-{[4-(Ethoxycarbonyl)piperazin-1-yl]methyl}phenyl)ethynyl]-2-(1H-indol-6-yl) benzoic acid was prepared by the same procedure as Example 1. $^1$H NMR (300 MHz, DMSO-d6) δ 11.16 (br s, 1 H), 7.60-7.75 (m, 2 H), 7.55 (d, J=7.92 Hz, 1 H), 7.28-7.48 (m, 2 H), 7.21 (br d, J=4.40 Hz, 3 H), 6.77-7.11 (m, 3 H), 6.43 (br s, 1 H), 4.00 (q, J=7.04 Hz, 2 H), 3.39 (s, 2 H) 2.07-2.44 (m, 8 H), 1.15 (t, J=7.04 Hz, 3 H). MS m/z (M+H) 508.3.

Example 105

3-(2-{4-[3-(Hydroxymethyl)oxetan-3-yl]phenyl}ethynyl)-2-(1H-indol-6-yl)benzoic acid

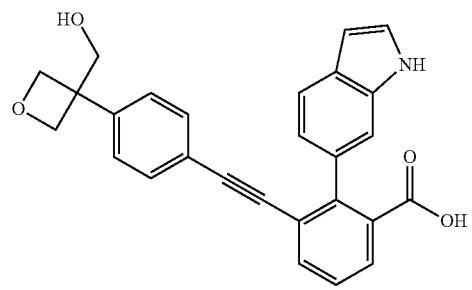 [SMILES: O=C(O)c1cccc(C#Cc2ccc(C3(CO)COC3)cc2)c1-c1ccc2cc[nH]c2c1]

3-(2-{4-[3-(Hydroxymethyl)oxetan-3-yl]phenyl}ethynyl)-2-(1H-indol-6-yl)benzoic acid was prepared by the same procedure as Example 1. $^1$H NMR (300 MHz, DMSO-d6) δ 11.15 (br s., 1 H), 7.59-7.93 (m, 2 H), 7.29-7.49 (m, 2 H), 7.20 (br d, J=7.92 Hz, 1 H), 6.92-7.14 (m, 4 H), 6.84 (br s, 2 H), 6.44 (br s, 1 H), 5.06 (br s, 1 H), 4.37-4.73 (m, 4 H), 3.36-3.74 (m, 2 H). MS m/z (M+H) 424.0.

Example 106

3-{2-[3-(5-Amino-1H-pyrazol-3-yl)phenyl]ethynyl}-2-(1H-indol-6-yl)benzoic acid

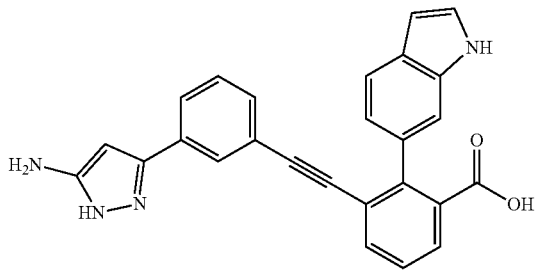 [SMILES: Nc1cc(-c2cccc(C#Cc3cccc(C(=O)O)c3-c3ccc4cc[nH]c4c3)c2)n[nH]1]

3-{2-[3-(5-Amino-1H-pyrazol-3-yl)phenyl]ethynyl}-2-(1H-indol-6-yl)benzoic acid was prepared by the same procedure as Example 1. $^1$H NMR (300 MHz, DMSO-d6) δ 11.18 (br s, 1 H), 7.51-7.88 (m, 4 H), 7.27-7.51 (m, 3 H), 7.14 (m, 2 H), 7.01 (br d, J=9.09 Hz, 2 H), 6.46 (br s, 1 H), 6.12 (s, 1 H), 3.60 (br s, 3 H). MS m/z (M+) 418.9.

Example 107

2-(1H-Indol-6-yl)-3-{2-[3-(1,3-oxazol-5-yl)phenyl]ethynyl}benzoic acid

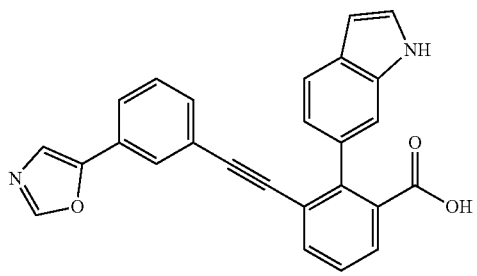 [SMILES: O=C(O)c1cccc(C#Cc2cccc(-c3cnco3)c2)c1-c1ccc2cc[nH]c2c1]

2-(1H-Indol-6-yl)-3-{2-[3-(1,3-oxazol-5-yl)phenyl]ethynyl} benzoic acid was prepared by the same procedure as Example 1. $^1$H NMR (300 MHz, DMSO-d6) δ 12.62-12.97 (bs, 1 H), 11.18 (br s, 1 H), 8.31-8.54 (m, 1 H), 8.23 (br s, 1 H), 7.55-7.77 (m, 4 H), 7.34-7.52 (m, 4 H), 7.10 (br d, J=7.33 Hz, 1 H), 6.70-7.05 (m, 2 H), 6.47 (s, 1 H). MS m/z (M+H) 406.0.

Example 108

2-(1H-Indol-6-yl)-3-{2-[4-(oxane-4-carbonyl)phenyl]ethynyl}benzoic acid

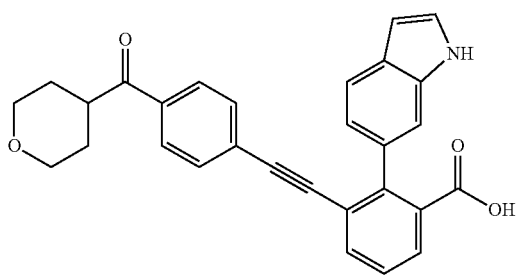 [SMILES: O=C(O)c1cccc(C#Cc2ccc(C(=O)C3CCOCC3)cc2)c1-c1ccc2cc[nH]c2c1]

2-(1H-Indol-6-yl)-3-{2-[4-(oxane-4-carbonyl)phenyl]ethynyl}benzoic acid was prepared by the same procedure as Example 1. $^1$H NMR (300 MHz, DMSO-d6) δ 11.17 (br s, 1 H), 7.63-7.96 (m, 4 H), 7.30-7.60 (m, 4 H), 7.22 (d, J=8.21 Hz, 2 H), 7.02 (d, J=8.21 Hz, 1 H), 6.46 (br s, 1 H), 3.81-3.85 (bs, 1 H), 3.40-3.60 (m, 4 H), 1.39-1.74 (m, 4 H). MS m/z (M+H) 450.1.

Example 109

2-(7-Fluoro-1H-indol-6-yl)-3-(phenylethynyl) benzoic acid

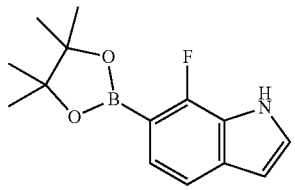 [SMILES: CC1(C)OB(c2ccc3cc[nH]c3c2F)OC1(C)C]

7-Fluoro-6-(4,4,5,5-tetramethyl-[1.3.2]dioxaborolan-2-yl)-1H-indole: A stirring suspension of 6-bromo-7-fluoro-1H-indole (PCT Int. Appl., 2014151005) (1.25 g, 5.8 mmol), potassium acetate (1.14 g, 11.68 mmol), bis(pinacolato) diboron (1.9 g, 7.54 mmol) in dry 1,4-dioxane (18 mL) was deaerated using an argon gas balloon for 15 minutes. To the resulting suspension, [1,1'-bis (diphenylphosphino) ferrocene]palladium (II) dichloride complexed with dichloromethane (473 mg, 0.58 mmol) was added and reaction was heated to 100° C. for 12 hours. The resultant reaction mixture was then allowed to cool to ambient temperature, diluted with ethyl acetate (150 mL) and filtered through celite. The organic layer thus obtained washed with water (2×50 mL), brine (50 mL), dried (anhydrous sodium sulfate), filtered and concentrated under reduced pressure to obtain crude product as a brown liquid. The resultant crude product was taken to next step as such without characterization.

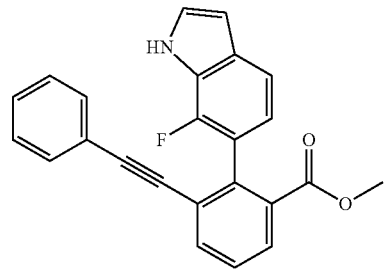 [SMILES: COC(=O)c1cccc(C#Cc2ccccc2)c1-c1ccc2cc[nH]c2c1F]

2-(7-Fluoro-1H-indol-6-yl)-3-(phenylethynyl)benzoic acid methyl ester: A stirring suspension of 7-fluoro-6-(4,4,5,5-tetramethyl-[1,3,2]dioxaborolan-2-yl)-1H-indole (1.2 g, 4.5 mmol), 2-bromo-3-(phenylethynyl)benzoic acid methyl ester (1.4 g, 4.5 mmol) and potassium carbonate (1.2 g, 9.0 mmol) in 1,4-dioxane:water (4:1) (20 mL) was deaerated using an argon gas balloon for 15 minutes. To the resulting suspension, [1,1'-bis (diphenylphosphino) ferrocene]palladium(II) dichloride complexed with dichloromethane (440 mg, 0.45 mmol) was added and reaction mixture was refluxed at 100° C. for 4 hours. The resultant reaction mixture was then allowed to cool to ambient temperature, diluted with ethyl acetate (250 mL) and filtered through celite bed. The organic layer thus obtained washed with water (2×50 mL), brine (50 mL), dried (anhydrous sodium sulfate), filtered and concentrated under reduced pressure to obtain crude product as a brown liquid. The crude product thus obtained was purified by preparative HPLC to give a pale yellow solid with 35% yield. $^1$H NMR (400 MHz, DMSO-d$_6$) δ 11.65 (s, 1H), 7.86 (d, J=7.8 Hz, 2H), 7.58 (t, J=7.8 Hz, 1H), 7.48-7.37 (m, 2H), 7.35-7.20 (m, 3H), 7.05-6.97 (m, 2H), 6.86 (dd, J=8.1, 6.5 Hz, 1H), 6.57 (td, J=3.3, 1.9 Hz, 1H), 3.55 (s, 3H). MS m/z (M−H) 368.2.

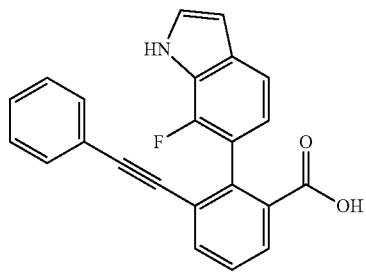 [SMILES: O=C(O)c1cccc(C#Cc2ccccc2)c1-c1ccc2cc[nH]c2c1F]

2-(7-Fluoro-1H-indol-6-yl)-3-(phenylethynyl) benzoic acid: To a solution of 2-(7-fluoro-1H-indol-6-yl)-3-(phenylethynyl) benzoic acid methyl ester (200 mg, 0.42 mmol) in terahydrofuran:methanol (1:1 mL) was added 2 N NaOH (aq) (84 mg, 2.1 mmol) and the resulting solution was stirred for about 24 hours at ambient temperature. The reaction mixture was then concentrated and neutralized to pH 4 using 1 N hydrochloric acid solution. The aqueous layer was then extracted with ethyl acetate (2×25 mL), washed with water (20 mL) and brine (10 mL). The organic layers were combined, dried (sodium sulfate), filtered and concentrated under reduced pressure. The resulting crude product was then purified using reverse phase HPLC to give the 2-(7-fluoro-1H-indol-6-yl)-3-phenylethynyl-benzoic acid as an off-white solid in 70%6 yield. $^1$H NMR (400 MHz, DMSO-d$_6$) δ 11.61 (s, 1H), 7.79 (dd, J=12.9, 7.8 Hz, 2H), 7.52 (t, J=7.8 Hz, 1H), 7.46-7.34 (m, 2H), 7.25 (dt, J=14.7, 7.1 Hz, 3H), 7.02-6.95 (m, 2H), 6.89 (dd, J=8.0, 6.4 Hz, 1H), 6.55 (q, J=2.6 Hz, 1H). MS m/z (M+H) 356.4.

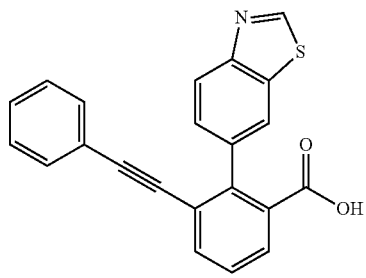 [SMILES: O=C(O)c1cccc(C#Cc2ccccc2)c1-c1ccc2ncsc2c1]

Example 110

2-Benzothiazol-6-yl-3-phenylethynyl-benzoic acid

2-Benzothiazol-6-yl-3-phenylethynyl-benzoic acid was prepared by the same procedure as Example 109. $^1$H NMR (400 MHz, DMSO-d$_6$) δ 12.89 (s, 1H), 9.44 (s, 1H), 8.22-8.11 (m, 2H), 7.83 (dq, J=7.9, 1.4 Hz, 2H), 7.61-7.47 (m, 2H), 7.36-7.22 (m, 3H), 7.05 (dt, J=6.7, 1.6 Hz, 2H). MS m/z (M+H) 356.5.

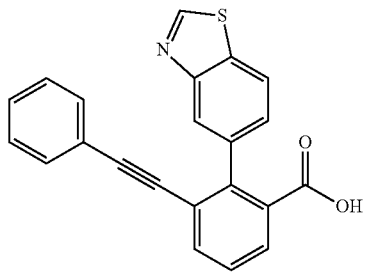 [SMILES: O=C(O)c1cccc(C#Cc2ccccc2)c1-c1ccc2scnc2c1]

Example 111

2-Benzothiazol-5-yl-3-phenylethynyl-benzoic acid

2-Benzothiazol-5-yl-3-phenylethynyl-benzoic acid was prepared by the same procedure as Example 109. $^1$H NMR (400 MHz, DMSO-d$_6$) δ 13.00 (s, 1H), 9.44 (s, 1H), 8.22 (d, J=8.3 Hz, 1H), 8.04 (s, 1H), 7.78 (t, J=6.8 Hz, 2H), 7.57-7.45 (m, 2H), 7.27 (dt, J=14.5, 7.0 Hz, 3H), 7.04 (d, J=7.3 Hz, 2H). MS m/z (M+H) 356.5.

Example 112

2-(2-Methyl-benzothiazol-5-yl)-3-phenylethynyl-benzoic acid

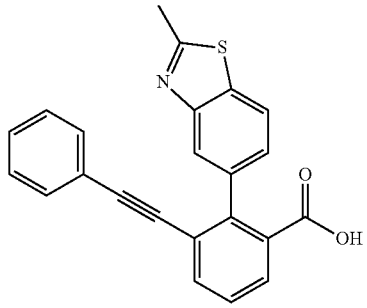 [SMILES: Cc1nc2cc(-c3c(C#Cc4ccccc4)cccc3C(=O)O)ccc2s1]

2-(2-Methyl-benzothiazol-5-yl)-3-phenylethynyl-benzoic acid was prepared by the same procedure as Example 109. $^1$H NMR (400 MHz, DMSO-d$_6$) δ 12.87 (s, 1H), 8.09 (d, J=8.2 Hz, 1H), 7.87-7.77 (m, 3H), 7.55 (t, J=7.8 Hz, 1H), 7.39 (dd, J=8.2, 1.7 Hz, 1H), 7.29 (qd, J=8.7, 7.8, 3.6 Hz, 3H), 7.07 (dt, J=6.5, 1.7 Hz, 2H), 2.82 (s, 3H). MS m/z (M+H) 370.3.

Example 113

2-(5-Fluoro-1H-indol-yl)-3-phenylethynyl-benzoic acid

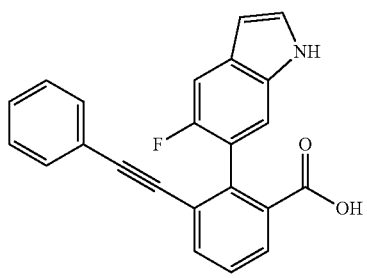 [SMILES: O=C(O)c1cccc(C#Cc2ccccc2)c1-c1cc2[nH]ccc2cc1F]

2-(5-Fluoro-1H-indol-6-yl)-3-phenylethynyl-benzoic acid was prepared by the same procedure as Example 109. ¹H NMR (400 MHz, DMSO-d₆) δ 12.80 (s, 1H), 11.21 (s, 1H), 7.81 (ddd, J=11.9, 7.8, 1.4 Hz, 2H), 7.53 (t, J=7.8 Hz, 1H), 7.44 (t, J=2.8 Hz, 1H), 7.39-7.20 (m, 5H), 7.07-6.98 (m, 2H), 6.47 (s, 1H). MS m/z (M+H) 356.3.

Example 114

2-(6-Fluoro-1H-indol-5-yl)-3-phenylethynyl-benzoic acid

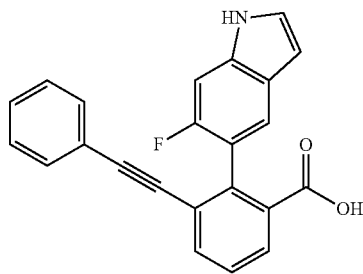 [SMILES: O=C(O)c1cccc(C#Cc2ccccc2)c1-c1cc2cc[nH]c2cc1F]

2-(6-Fluoro-1H-indol-5-yl)-3-phenylethynyl-benzoic acid was prepared by the same procedure as Example 109. ¹H NMR (400 MHz, DMSO-d₆) δ 11.17 (s, 1H), 7.81-7.72 (m, 2H), 7.53-7.42 (m, 2H), 7.35 (t, J=2.7 Hz, 1H), 7.32-7.17 (m, 4H), 7.04 (dt, J=6.7, 1.6 Hz, 2H), 6.46 (d, J=2.5 Hz, 1H). MS m/z (M+H) 356.5.

Example 115

2-[1,8]Naphthyridin-3-yl-3-(phenylethynyl) benzoic acid

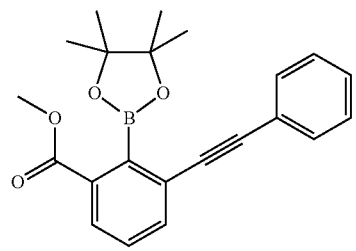 [SMILES: COC(=O)c1cccc(C#Cc2ccccc2)c1B1OC(C)(C)C(C)(C)O1]

3-Phenylethynyl-2-(4,4,5,5-tetramethyl-1,3,2-dioxaborolan-2-yl)-benzoic acid methyl ester: A stirring suspension of 2-iodo-3-phenylethynyl-benzoic acid methyl ester (US 20080153802) (4 g, 11.05 mmol), potassium acetate (2.16 g, 22.1 mmol), bis(pinacolato)diboron (3.06 g, 12.16 mmol) in dry dimethylformamide (40 mL) was deaerated using an argon gas balloon for 15 minutes. To the resulting suspension, [1,1'-bis (diphenylphosphino) ferrocene] palladium (11) dichloride complexed with dichloromethane (897 mg, 1.1 mmol) was added and reaction mixture was heated to 90° C. for 12 hours. The resultant reaction mixture was then allowed to cool to ambient temperature, diluted with ethyl acetate (300 mL) and filtered through pre packed celite pad. The organic layer thus obtained was washed with water (2×100 mL), brine (100 mL), dried (anhydrous sodium sulfate), filtered and concentrated under reduced pressure to obtain crude product as a brown liquid which was purified through silica gel cartridge eluting with hexane/ethyl acetate to give 3-phenylethynyl-2-(4,4,5,5-tetramethyl-[1,3,2]dioxaborolan-2-yl)-benzoic acid methyl ester as a pale yellow solid in 50% yield. ¹H NMR (400 MHz, DMSO-d₆) δ 7.96 (dd, J=7.8, 1.1 Hz, 1H), 7.80 (dd, J=7.7, 1.1 Hz, 1H), 7.64-7.47 (m, 3H), 7.45 (dd, J=5.0, 2.0 Hz, 3H), 3.88 (s, 3H), 1.32 (s, 12H). MS m/z (M+Na) 385.7.

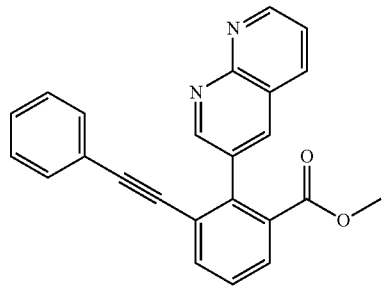 [SMILES: COC(=O)c1cccc(C#Cc2ccccc2)c1-c1cnc2ncccc2c1]

2-1,8-Naphthyridin-3-yl-3-(phenylethynyl) benzoic acid methyl ester: A stirring suspension of 3-phenylethynyl-2-(4, 4,5,5-tetramethyl-1,3,2-dioxaborolan-2-yl)-benzoic acid methyl ester (500 mg, 1.38 mmol), 3-bromo-1,8-naphthyridine (289 mg, 1.38 mmol) and potassium carbonate (380 mg, 2.76 mmol) in 1,4-dioxane:water (4:1) (10 mL) was deaerated using an argon gas balloon for 15 minutes. To the resulting suspension, [1, 1-bis (diphenylphosphino) ferrocene]palladium(II) dichloride complexed with dichloromethane (112 mg, 0.138 mmol) was added and reaction mixture was refluxed at 100° C. for 4 h. The resultant reaction mixture was then allowed to cool to ambient temperature, diluted with ethyl acetate (150 mL) and filtered through celite bed. The organic layer thus obtained washed with water (2×30 mL), brine (30 mL), dried (anhydrous sodium sulfate), filtered and concentrated under reduced pressure to obtain crude product as a brown liquid. The crude product thus obtained was purified using silica gel cartridge eluting with hexane/ethyl acetate to give a pale yellow solid with 40% yield.

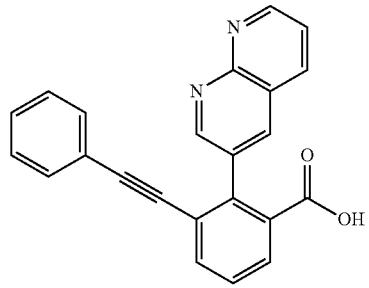 [SMILES: O=C(O)c1cccc(C#Cc2ccccc2)c1-c1cnc2ncccc2c1]

2-1,8-Naphthyridin-3-yl-3-(phenylethynyl) benzoic acid: To a solution of 2-1,8-naphthyridin-3-yl-3-phenylethynyl-benzoic acid methyl ester (200 mg, 0.55 mmol) in terahydrofuran:methanol (1:1 mL) was added 2 N NaOH (aq) (110 mg, 2.75 mmol) and the resulting solution was stirred for about 24 hours at ambient temperature. The reaction mixture was then concentrated and neutralized to pH 4 using 1 N hydrochloric acid solution. The aqueous layer was then extracted using ethyl acetate (2×25 mL) and washed with water (20 mL) and brine (10 mL). The organic layers were combined, dried (sodium sulfate), filtered and concentrated under reduced pressure. The resulting crude product was then purified using reverse phase HPLC to give the product as an off-white solid in 15% yield. $^1$H NMR (400 MHz, DMSO-$d_6$) δ 13.11 (s, 1H), 9.12 (dd. J=4.2, 2.0 Hz, 1H), 9.03 (d, J=2.5 Hz, 1H), 8.59-8.47 (m, 2H), 8.01 (dd, J=7.8, 1.4 Hz, 1H), 7.92 (dd, J=7.8, 1.3 Hz, 1H), 7.73-7.61 (m, 2H), 7.34-7.19 (m, 3H), 7.04-6.96 (m, 2H). MS m/z (M+H) 351.3.

Example 116

2-(1-Methyl-1H-pyrrolo[2,3-b]pyridin-6-yl)-3-phenylethynyl-benzoic acid

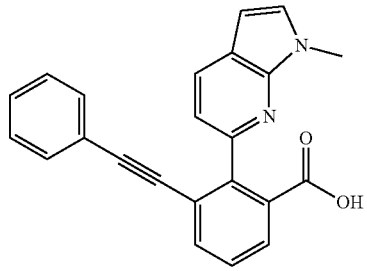 [SMILES: Cn1ccc2ccc(-c3c(C#Cc4ccccc4)cccc3C(=O)O)nc21]

2-(1-Methyl-1H-pyrrolo[2,3-b]pyridin-6-yl)-3-phenylethynyl-benzoic acid was prepared by the same procedure as Example 115. $^1$H NMR (400 MHz, DMSO-$d_6$) δ 12.60 (s., 1H), 8.06 (d, J=8.0 Hz, 1H), 7.78 (ddd, J=15.0, 7.7, 1.4 Hz, 2H), 7.59-7.50 (m, 2H), 7.43 (d, J=8.1 Hz, 1H), 7.39-7.27 (m, 3H), 7.21-7.13 (m, 2H), 6.52 (d, J=3.4 Hz, 1H), 3.77 (s, 3H). MS m/z (M+H) 353.5.

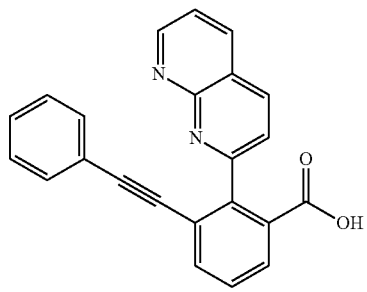 [SMILES: O=C(O)c1cccc(C#Cc2ccccc2)c1-c1ccc2cccnc2n1]

Example 117

2-[1,8]Naphthyridin-2-yl-3-phenylethynyl-benzoic acid

2-[1,8]Naphthyridin-2-yl-3-phenylethynyl-benzoic acid was prepared by the same procedure as Example 115. $^1$H NMR (400 MHz, DMSO-$d_6$) δ 12.85 (s, 1H), 9.08 (dd, J=4.2, 2.0 Hz, 1H), 8.58-8.48 (m, 2H), 7.93 (d, J=7.6 Hz, 1H), 7.82 (t, J=7.8 Hz, 2H), 7.71-7.57 (m, 2H), 7.33-7.24 (m, 1H), 7.27-7.18 (m, 2H), 6.97 (d, J=7.4 Hz, 2H). MS m/z (M+H) 351.4.

Example 118

3-Phenylethynyl-2-(1H-pyrrolo[2,3-b]pyridin-6-yl)-benzoic acid

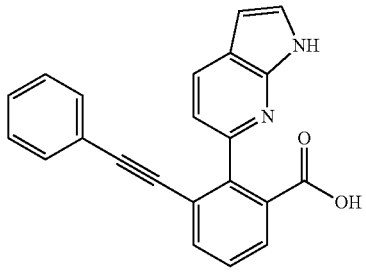 [SMILES: O=C(O)c1cccc(C#Cc2ccccc2)c1-c1ccc2cc[nH]c2n1]

3-Phenylethynyl-2-(1H-pyrrolo[2,3-b]pyridin-6-yl)-benzoic acid was prepared by the same procedure as Example 115. $^1$H NMR (400 MHz, DMSO-$d_6$) δ 12.64 (s, 1H), 11.68 (d, J=2.4 Hz, 1H), 8.04 (d, J=8.1 Hz, 1H), 7.84-7.74 (m, 2H), 7.58-7.45 (m, 2H), 7.37-7.25 (m, 4H), 7.18-7.10 (m, 2H), 6.50 (dd, J=3.4, 1.8 Hz, 1H). MS m/z (M+H) 339.1.

Example 119

2-(4-methoxy-1H-indol-6-yl)-3-(2-phenylethynyl)-benzoic acid

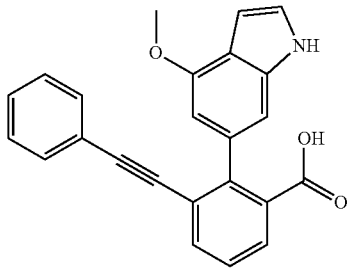 [SMILES: COc1cc(-c2c(C#Cc3ccccc3)cccc2C(=O)O)cc2[nH]ccc12]

2-(4-methoxy-1H-indol-6-yl)-3-(2-phenylethynyl)-benzoic acid was prepared by the same procedure as Example 109. $^1$H NMR (300 MHz, DMSO-$d_6$) δ ppm 11.18 (br, s., 1 H), 7.73 (d, J=6.74 Hz, 1 H), 7.61 (br, s., 1 H), 7.45 (d, J=7.62 Hz, 1 H), 7.29 (s, 2 H), 7.25 (s, 2 H), 7.14 (br, s., 2 H), 7.02 (br, s., 1 H), 6.52 (br, s., 1 H), 6.44 (br, s., 1 H), 3.80 (br, s., 3 H). MS m/z (M+H) 368.4.

Example 120

3-(2-(4-(2-hydroxypropan-2-yl)phenyl)ethynyl)-2-(1H-indol-6-yl)-benzoic acid

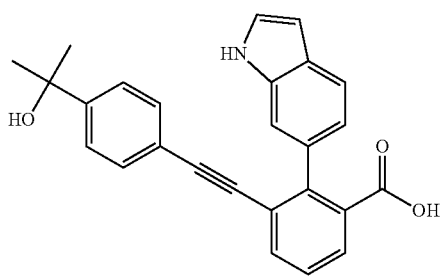 [SMILES: CC(C)(O)c1ccc(C#Cc2cccc(C(=O)O)c2-c2ccc3cc[nH]c3c2)cc1]

3-(2-(4-(2-hydroxypropan-2-yl)phenyl)ethynyl)-2-(1H-indol-6-yl)-benzoic acid was prepared by the same procedure as Example 1. ¹H NMR (300 MHz, DMSO-d₆) δ ppm 11.17 (br, s., 1 H), 7.60-7.74 (m, 2 H), 7.55 (d, J=7.33 Hz, 1 H), 7.30-7.46 (m, 5 H), 6.95-7.09 (m, 3 H), 6.45 (br, s., 1 H), 3.48 (br, s., 2 H), 1.33 (br, s., 5 H) MS m/z (M+H) 396.4.

Example 121

3-(2-(4-(2-aminothiazol-4-yl)phenyl)ethynyl)-2-(1H-indol-6-yl)-benzoic acid

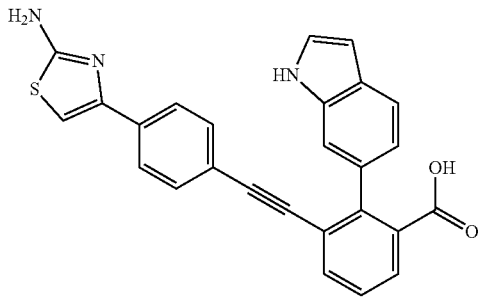 [SMILES: Nc1nc(-c2ccc(C#Cc3cccc(C(=O)O)c3-c3ccc4cc[nH]c4c3)cc2)cs1]

3-(2-(4-(2-aminothiazol-4-yl)phenyl)ethynyl)-2-(1H-indol-6-yl)-benzoic acid was prepared by the same procedure as Example 1. ¹H NMR (300 MHz, DMSO-d₆) δ ppm 11.17 (s, J=3.72 Hz, 1 H), 7.62-7.74 (m, 4 H), 7.55 (d, J=8.21 Hz, 1 H), 7.36-7.47 (m, 3 H), 7.05-7.11 (m, 3 H), 6.99 (dd, J=8.21, 1.47 Hz, 1 H), 6.45 (t, J=3.20 Hz, 1 H). MS m/z (M+H) 436.02.

Example 122

2-(1H-Indol-6-yl)-3-(3-sulfamoyl-phenylethynyl)-benzoic acid

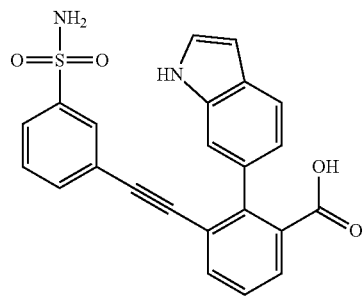 [SMILES: NS(=O)(=O)c1cccc(C#Cc2cccc(C(=O)O)c2-c2ccc3cc[nH]c3c2)c1]

2-(1H-Indol-6-yl)-3-(3-sulfamoyl-phenylethynyl)-benzoic acid was prepared by the same procedure as Example 1. ¹H NMR (300 MHz, DMSO-d₆) δ ppm 12.73 (br, s., 1 H), 11.16 (s, 1 H), 7.67-7.81 (m, 4 H), 7.58 (d, J=8.08 Hz, 1 H), 7.48 (t, J=7.74 Hz; 2 H), 7.36-7.41 (m, 4 H), 7.25 (dt, J=7.62, 1.17 Hz, 1 H), 7.05 (dd, J=8.21, 1.76 Hz, 1 H), 6.45 (t, J=2.05 Hz, 1 H) MS m/z (M+H) 416.9.

Example 123

3-(4-Amino-3-sulfamoyl-phenylethynyl)-2-(1H-indol-6-yl)-benzoic acid

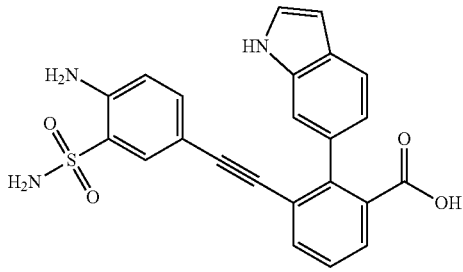 [SMILES: Nc1ccc(C#Cc2cccc(C(=O)O)c2-c2ccc3cc[nH]c3c2)cc1S(N)(=O)=O]

3-(4-Amino-3-sulfamoyl-phenylethynyl)-2-(1H-indol-6-yl)-benzoic acid was prepared by the same procedure as Example 1. ¹H NMR (300 MHz, DMSO-d₆) δ ppm 8.68 (br, s., 1 H), 8.11 (d, J=8.79 Hz, 1 H), 8.00 (dd, J=-7.92, 1.47 Hz, 1 H), 7.78 (d, J=-8.79 Hz, 1 H), 7.62-7.70 (m, 3 H), 7.52-7.58 (m, 1 H), 7.24-7.37 (m, 4 H), 6.96 (d, J=8.21 Hz, 1 H), 6.55 (dd, J=2.78, 1.91 Hz, 1 H). MS m/z (M-H) 431.9.

Example 124

2-(4H-indol-6-yl)-3-(Spiro[2H-1-benzopyran-2,1'-4-piperidine-1-t-butyl carboxylate]-4(3H)-one)ethynyl)benzoic acid

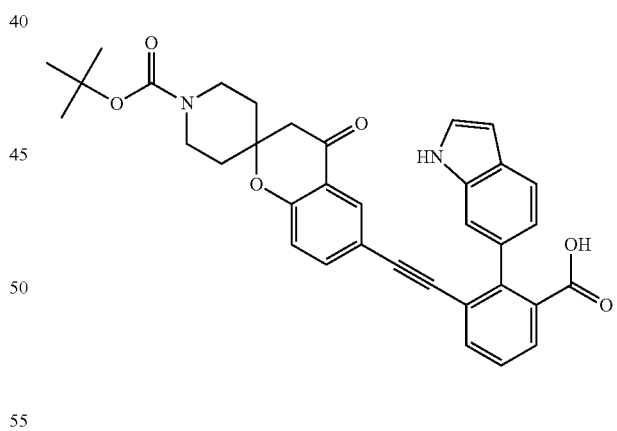

2-(1H-indol-6-yl)-3-(Spiro[2H-1-benzopyran-2,1'-4-piperidine-1-t-Butylcarboxylate]-4(3H)-one)ethynyl)benzoic acid was prepared by the same procedure as Example 1. ¹H NMR (300 MHz, DMSO-d₆) δ ppm 11.00-11.22 (m, 1 H), 7.74 (dd, J=7.77, 1.32 Hz, 1 H), 7.42-7.70 (m, 3 H), 7.34-7.38 (m, 2 H), 7.19-7.32 (m, 1 H), 7.01 (t, J=8.75 Hz, 2 H), 6.30-6.51 (m, 1 H), 3.38-3.71 (m, 4 H), 3.07 (br, s., 2 H), 2.82 (s, 2 H), 1.81 (d, J=13.78 Hz, 2 H), 1.49-1.66 (m, 2 H), 1.37 (s, 9 H) MS m/z (M+H) 577.2.

Example 125

3-(2-(3-(2-aminothiazol-4-yl)phenyl)ethynyl)-2-(1H-indol-6-yl)-benzoic acid

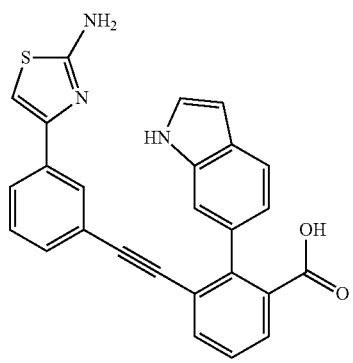 [SMILES: Nc1nc(-c2cccc(C#Cc3cccc(C(=O)O)c3-c3ccc4cc[nH]c4c3)c2)cs1]

3-(2-(3-(2-aminothiazol-4-yl)phenyl)ethynyl)-2-(1H-indol-6-yl)-benzoic acid was prepared by the same procedure as Example 1. $^1$H NMR (300 MHz, DMSO-d$_6$) δ ppm 11.08-11.28 (m, 1 H), 7.72-7.78 (m, 1 H), 7.63-7.72 (m, 2 H), 7.55-7.62 (m, 1 H), 7.39-7.51 (m, 3 H), 7.33-7.38 (m, 1 H), 7.19-7.30 (m, 1 H), 6.93-7.07 (m, 2 H), 6.78-6.85 (m, 1 H), 6.41-6.51 (m, 1 H). MS m/z (M+H) 436.0.

Example 126

3-(2-(4-(5-(methoxycarbonyl)-2-aminothiazol-4-yl)phenyl) ethynyl)-2-(1H-indol-6-yl)-benzoic acid

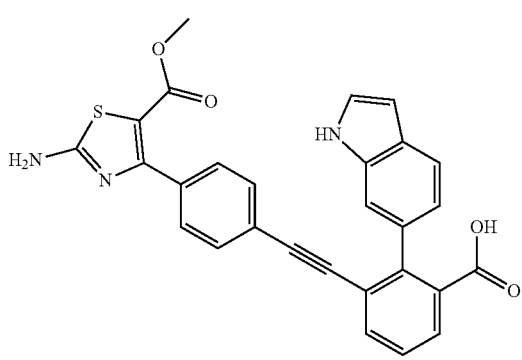 [SMILES: COC(=O)c1sc(N)nc1-c1ccc(C#Cc2cccc(C(=O)O)c2-c2ccc3cc[nH]c3c2)cc1]

3-(2-(4-(5-(methoxy carbonyl)-2-aminothiazol-4-yl)phenyl)ethynyl)-2-(1H-indol-6-yl)-benzoic acid was prepared by the same procedure as Example 1. $^1$H NMR (300 MHz, DMSO-d$_6$) δ ppm 11.05-11.30 (m, 1 H), 7.70-7.75 (m, 1 H), 7.61-7.68 (m, 2 H), 7.53-7.60 (m, 1 H), 7.42-7.49 (m, 3 H), 7.39-7.42 (m, 1 H), 7.35-7.39 (m, 1 H), 7.05-7.11 (m, 1 H), 6.96-7.02 (m, 2 H), 6.42-6.49 (m, 1 H), 2.80-2.92 (m, 3 H). MS m/z (M+H) 479.8.

Example 127

3-(2-(4-(5-amino-1,3,4-thiadiazol-2-yl)phenyl)ethynyl)-2-(1H-indol-6-yl)-benzoic acid

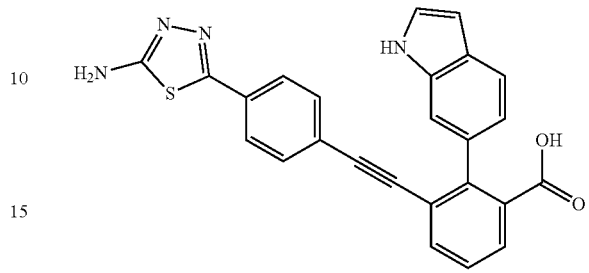

3-(2-(4-(5-amino-1,3,4-thiadiazol-2-yl)phenyl)ethynyl)-2-(1H-indol-6-yl)-benzoic acid was prepared by the same procedure as Example 1. $^1$H NMR (300 MHz, DMSO-d$_6$) δ ppm 12.73 (m, 1 H), 11.17-11.23 (m, 1 H), 7.78 (d, J=7.44 Hz, 1 H), 7.58-7.71 (m, 4 H), 7.39-7.54 (m, 5 H), 7.20 (s, 1 H), 7.18 (s, 1 H), 7.04 (d, J=7.98 Hz, 1 H), 6.49 (m, 1 H). MS m/z (M+H) 437.1.

Example 128

3-(2-(4-(3-amino-1H-pyrazol-5-yl)phenyl)ethynyl)-2-(1H-indol-6-yl)-benzoic acid

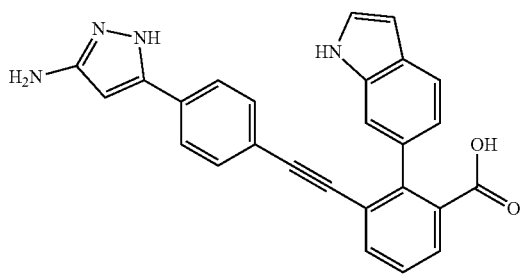 [SMILES: Nc1cc(-c2ccc(C#Cc3cccc(C(=O)O)c3-c3ccc4cc[nH]c4c3)cc2)[nH]n1]

3-(2-(4-(3-amino-1H-pyrazol-5-yl)phenyl)ethynyl)-2-(1H-indol-6-yl)-benzoic acid was prepared by the same procedure as Example 1. $^1$H NMR (300 MHz, DMSO-d$_6$) δ ppm 11.11-11.30 (m, 1 H), 7.73-7.80 (m, 1 H), 7.55-7.72 (m, 4 H), 7.37-7.53 (m, 3 H), 7.10-7.21 (m, 2 H), 6.99-7.08 (m, 1 H), 6.41-6.52 (m, 1 H), 6.06-6.20 (m, 1 H). MS m/z (M+H) 419.2.

Example 129

2-Amino-4-{4-[3-carboxy-2-(1H-indol-6-yl)-phenylethynyl]-phenyl}-thiazole-5-carboxylic acid

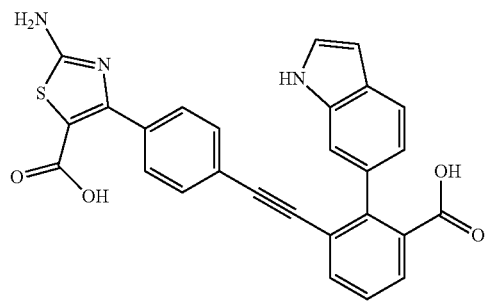 [SMILES: Nc1nc(-c2ccc(C#Cc3cccc(C(=O)O)c3-c3ccc4cc[nH]c4c3)cc2)c(C(=O)O)s1]

2-Amino-4-{4-[3-carboxy-2-(1H-indol-6-yl)-phenylethynyl]-phenyl}-thiazole-5-carboxylic acid was prepared by the same procedure as Example 1. ¹H NMR (300 MHz, DMSO-d₆) δ ppm 11.12-11.33 (m, 1 H), 10.64-10.98 (m, 1 H), 7.74-7.82 (m, 1 H), 7.67-7.74 (m, 1 H), 7.56-7.61 (m, 1 H), 7.36-7.53 (m, 4 H), 7.29-7.34 (m, 1 H), 7.14-7.24 (m, 2 H), 7.00-7.12 (m, 2 H), 6.45-6.50 (m, 1 H). MS m/z (M+H) 558.6.

Example 130

3-(2-(4-(2-aminooxazol-5-yl)phenyl)ethynyl)-2-(1H-indol-6-yl)-benzoic acid

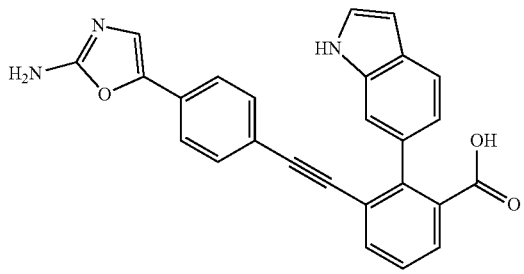 [SMILES: Nc1ncc(-c2ccc(C#Cc3cccc(C(=O)O)c3-c3ccc4cc[nH]c4c3)cc2)o1]

3-(2-(4-(2-aminooxazol-5-yl)phenyl)ethynyl)-2-(1H-indol-6-yl)-benzoic acid was prepared by the same procedure as Example 1. ¹H NMR (300 MHz, DMSO-d₆) δ ppm 12.61-12.76 (m, 1 H), 11.16-11.21 (m, 1 H), 7.74 (d, J=7.55 Hz, 1 H), 7.67 (d, J=-7.70 Hz, 1 H), 7.59 (d, J=-8.09 Hz, 1 H), 7.46-7.50 (m, 1 H), 7.39-7.44 (m, 2 H), 7.31-7.37 (m, 3 H), 7.15-7.28 (m, 2 H), 7.00-7.12 (m, 3 H), 6.48 (m, 1 H). MS m/z (M+H) 420.3.

Example 131

2-(1H-Indol-6-yl)-3-[4-(2-methanesulfonylamino-thiazol-4-yl)-phenylethynyl]-benzoic acid

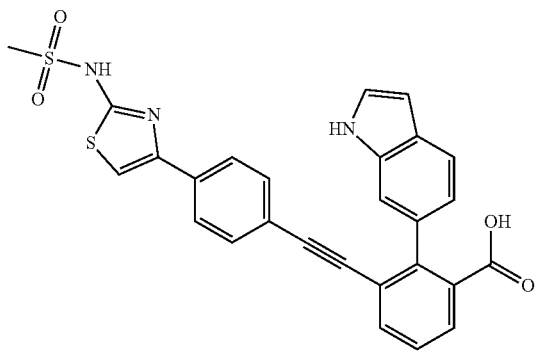 [SMILES: CS(=O)(=O)Nc1nc(-c2ccc(C#Cc3cccc(C(=O)O)c3-c3ccc4cc[nH]c4c3)cc2)cs1]

2-(1H-Indol-6-yl)-3-[4-(2-methanesulfonylamino-thiazol-4-yl)-phenylethynyl]-benzoic acid was prepared by the same procedure as Example 52. ¹H NMR (300 MHz, DMSO-d₆) δ ppm 10.90-11.27 (m, 1 H), 7.59-7.74 (m, 5 H), 7.49-7.56 (m, 1 H), 7.32-7.46 (m, 4 H), 7.18-7.30 (m, 1 H), 7.07-7.15 (m, 2 H), 6.92-7.02 (m, 1 H), 6.38-6.47 (m, 1 H), 2.84-2.99 (m, 3 H). MS m/z (M+H) 514.0.

Example 132

2-(1H-Indol-6-yl)-3-[3-(2-methanesulfonylamino-thiazol-4-yl)-phenylethynyl]-benzoic acid

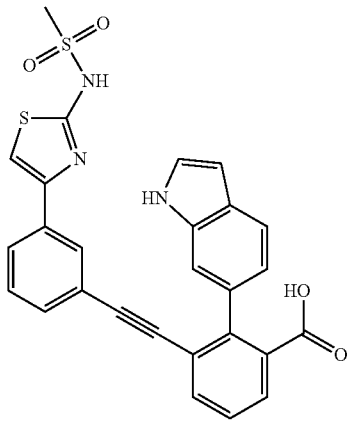 [SMILES: CS(=O)(=O)Nc1nc(-c2cccc(C#Cc3cccc(C(=O)O)c3-c3ccc4cc[nH]c4c3)c2)cs1]

2-(1H-Indol-6-yl)-3-[3-(2-methanesulfonylamino-thiazol-4-yl)-phenylethynyl]-benzoic acid was prepared by the same procedure as Example 52. ¹H NMR (300 MHz, DMSO-d₆) δ ppm 11.09-11.31 (m, 1 H), 7.78-7.84 (m, 1 H), 7.58-7.75 (m, 3 H), 7.48-7.56 (m, 2 H), 7.42-7.46 (m, 1 H), 7.32-7.42 (m, 2 H), 7.07-7.15 (m, 1 H), 6.95-7.01 (m, 1 H), 6.45-6.51 (m, 1 H), 3.49 (s, 3 H). MS m/z (M+H) 514.1.

Example 133

3-(2-(1,4-dihydro-2-((4-methoxypiperidin-1-yl)methyl)-4-oxoquinazolin-6-yl)ethynyl)-2-(1H-indol-6-yl)benzoic acid

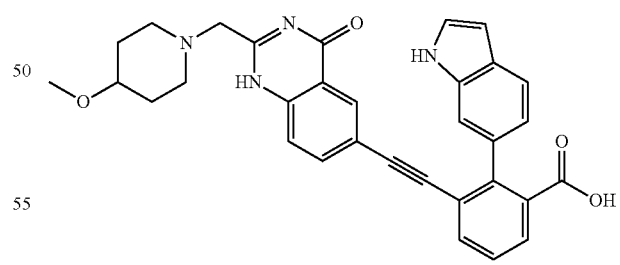

3-(2-(1,4-dihydro-2-((4-methoxypiperidin-1-yl)methyl)-4-oxoquinazolin-6-yl)ethynyl)-2-(1 H-indol-6-yl)benzoic acid was prepared by the same procedure as Example 1. ¹H NMR (300 MHz, CD₃OD) δ ppm 8.02 (d, J=2.05 Hz, 1 H), 7.74-7.86 (m, 2 H), 7.59 (m, 2 H), 7.43-7.50 (m, 2 H), 7.34 (d, J=8.61 Hz, 1 H), 4.86 (s, 153 H), 4.72-4.83 (m, 3 H), 4.34 (s, 2 H), 3.44-3.61 (m, 4 H), 3.38 (s, 3 H), 2.08 (m, 4 H). MS m/z (M+H) 533.1.

Example 134

3-(2-(1,4-dihydro-2-((4-thiomorpholine-1,1dioxide-1-yl)methyl)-4-oxo quinazolin-6-yl)ethynyl)-2-(1H-indol-6-yl)benzoic acid

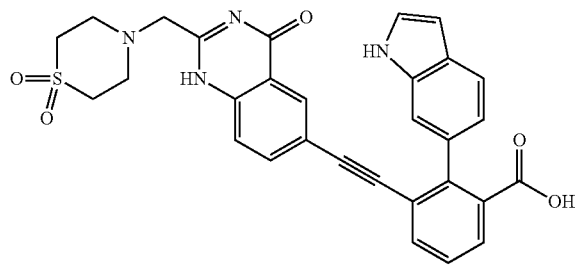 [SMILES: O=C(O)c1cccc(C#Cc2ccc3[nH]c(CN4CCS(=O)(=O)CC4)nc(=O)c3c2)c1-c1ccc2cc[nH]c2c1]

3-(2-(1,4-dihydro-2-((4-thiomorpholine-1,1dioxide-1-yl)methyl)-4-oxoquinazolin-6-yl) ethynyl)-2-(1H-indol-6-yl)benzoic acid was prepared by the same procedure as Example 1. $^1$H NMR (300 MHz, CD$_3$OD) δ 11.66-12.14 (m, 1 H), 8.67-8.72 (m, 1 H), 8.58-8.64 (m, 1 H), 8.46-8.52 (m, 1 H), 8.36-8.43 (m, 1 H), 8.15-8.34 (m, 5 H), 7.84-7.90 (m, 1 H), 7.27 (br, s., 1 H), 4.45 (s, 2 H), 3.95 (br, s., 4 H), 3.83 (br, s., 4 H). MS m/z (M+H) 553.1.

Example 135

3-(2-(2-(trifluoromethyl)-3,4-dihydro-4-oxoquinazolin-6-yl)ethynyl)-2-(1H-indol-6-yl)benzoic acid

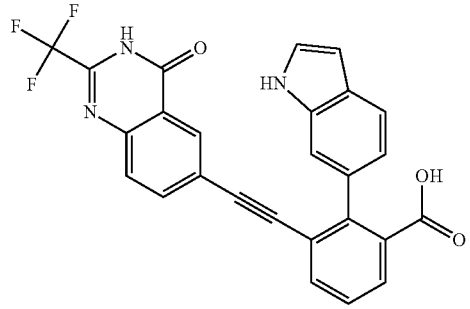 [SMILES: O=C(O)c1cccc(C#Cc2ccc3nc(C(F)(F)F)[nH]c(=O)c3c2)c1-c1ccc2cc[nH]c2c1]

3-(2-(2-(trifluoromethyl)-3,4-dihydro-4-oxoquinazolin-6-yl)ethynyl)-2-(1H-indol-6-yl)benzoic acid was prepared by the same procedure as Example 1. $^1$H NMR (300 MHz, DMSO-d$_6$) δ ppm 7.94 (d, J=1.76 Hz, 1 H), 7.83 (dd, J=7.92, 1.32 Hz, 1 H), 7.68-7.72 (m, 2 H), 7.52-7.61 (m, 2 H), 7.37-7.49 (m, 3 H), 7.07 (dd, J=8.14, 1.54 Hz, 1 H), 6.47 (br, s., 1 H). MS m/z (M+H) 474.1.

Example 136

3-(2-(3,4-dihydro-3-(2-methoxyethyl)-4-oxopyrido[2,3-d]pyrimidin-6-yl)ethynyl)-2-(1H-indol-6-yl)benzoic acid

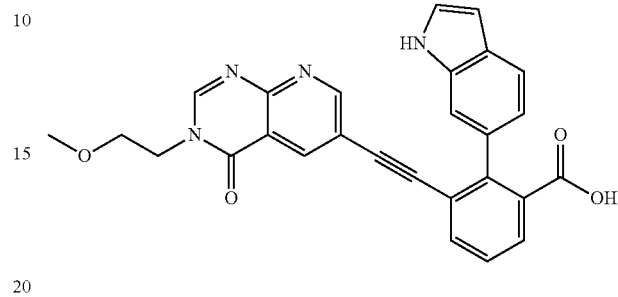

3-(2-(3,4-dihydro-3-(2-methoxyethyl)-4-oxopyrido[2,3-d]pyrimidin-6-yl)ethynyl)-2-(1H-indol-6-yl)benzoic acid was prepared by the same procedure as Example 1. $^1$H NMR (300 MHz, CD$_3$OD) δ ppm 8.18 (s, 1H), 8.03 (d, J=1.76 Hz, 1H), 7.75 (t, J=7.98 Hz, 2H), 7.61 (d, J=8.21 Hz, 1H), 7.41-7.50 (m, 3H), 7.27-7.33 (m, 2H), 7.07 (dd, J=8.21, 1.47 Hz, 1H), 6.50 (d, J=3.27 Hz, 1H), 4.91-5.04 (m, 3H), 4.19 (t, J=4.98 Hz, 3H), 3.65 (t, J=4.98 Hz, 3H), MS m/z (M+H) 464.1.

Example 137

2-(1H-Indol-6-yl)-3-[3-(2-methoxy-6-methyl-phenylcarbamoyl)-phenylethynyl]-benzoic acid

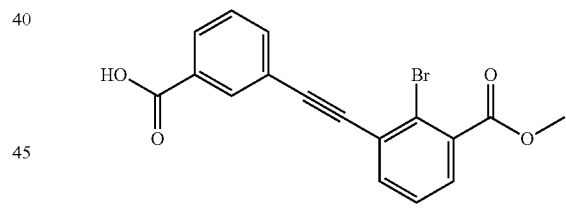

2-Bromo-3-(3-carboxy-phenylethynyl)-benzoic acid methyl ester: A solution of 2-bromo-3-iodo-benzoic acid methyl ester (1.5 g, 4.4 mmol), 3-ethynyl-benzoic acid (0.65 g, 4.4 mmol), potassium carbonate (1.2 g, 8.8 mmol) in dimethoxyethane (15 mL) and water (5 mL) was degassed under N$_2$ for 10 minutes, palladium(II) tetrakis(triphenylphosphine) (254 mg, 0.22 mmol) and copper (I) iodide (84 mg, 0.44 mmol) was added and the reaction mixture was degassed under N$_2$ for 10 minutes and then heated at 45° C. for 4 hours. After cooling to ambient temperature, the crude mixture was partitioned between ethyl acetate (30 mL) and water (20 mL). The organic layer was dried (sodium sulfate), filtered, concentrated and purified through silica gel cartridge eluting with ethyl acetate/dichloromethane to give the product as a white solid in 83% yield.

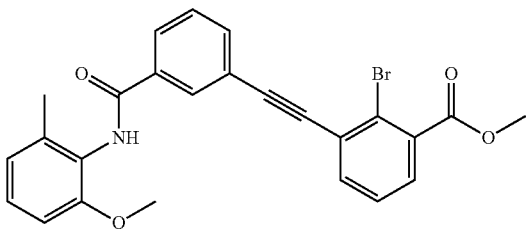 [SMILES: COC(=O)c1cccc(C#Cc2cccc(C(=O)Nc3c(C)cccc3OC)c2)c1Br]

2-Bromo-3-[3-(2-methoxy-6-methyl-phenylcarbamoyl)-phenyl ethynyl]-benzoic acid methyl ester: A mixture of 2-bromo-3-(3-carboxy-phenylethynyl)-benzoic acid methyl ester (150 mg, 0.41 mmol), 2-methoxy-6-methyl-phenylamine (100 mg, 0.73 mmol), 1-[Bis(dimethylamino) methylene]-1H-1,2,3-triazolo[4,5-b]pyridinium 3-oxid hexafluorophosphate (HAT (276 mg, 0.73 mmol) and triethylamine (0.156 ml, 1.12 mmol) in tetrahydrofuran (1 mL) was stirred at room temperature for 24 hours. The reaction mixture was concentrated and purified through preparative thin layered chromatography to give the desired product.

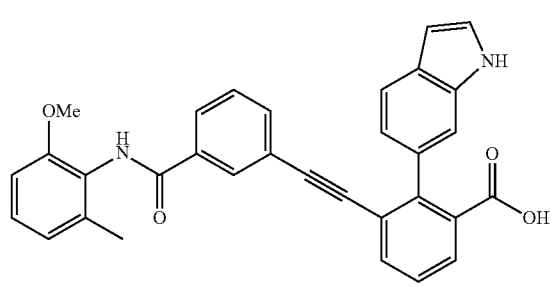 [SMILES: COc1cccc(C)c1NC(=O)c1cccc(C#Cc2cccc(C(=O)O)c2-c2ccc3cc[nH]c3c2)c1]

2-(1H-Indol-6-yl)-3-[3-(2-methoxy-6-methyl-phenyl carbamoyl)-phenylethynyl]-benzoic acid was prepared by the same procedure as Example 1. $^1$H NMR (300 MHz, DMSO-$d_6$) δ=11.16 (s, 1H), 9.59 (s, 1H), 7.91-7.76 (m, 3H), 7.68 (d, J=7.7 Hz, 1H), 7.58 (d, J=8.3 Hz, 1H), 7.51-7.32 (m, 4H), 7.30-7.05 (m, 3H), 6.90-6.82 (m, 2H), 6.21 (s, 1H), 3.65 (s, 3H), 2.05 (s, 3H). MS (ESI) m/z 501.3 (M+1)$^+$.

Example 138

3-{3-[4-(1,1-Dioxo-1-thiomorpholin-4-yl)-phenylcarbamoyl]-phenylethynyl}-2-(1H-indol-6-yl)-benzoic acid

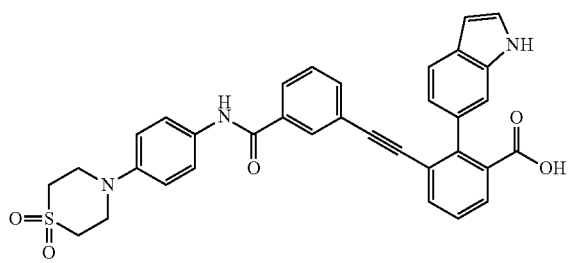 [SMILES: O=C(Nc1ccc(N2CCS(=O)(=O)CC2)cc1)c1cccc(C#Cc2cccc(C(=O)O)c2-c2ccc3cc[nH]c3c2)c1]

3-{3-[4-(1,1-Dioxo-1-thiomorpholin-4-yl)-phenylcarbamoyl]-phenylethynyl}-2-(1H-indol-6-yl)-benzoic acid was prepared by the same procedure as Example 137. $^1$H NMR (300 MHz, CD$_3$OD) δ =11.15 (br, s., 1H), 10.11 (s, 1H), 7.85-7.75 (m, 3H), 7.70-7.56 (m, 3H), 7.51-7.38 (m, 2H), 7.34 (t, J=4.7 Hz, 1H), 7.24 (d, J=7.6 Hz, 1H), 7.03 (t, J=8.7 Hz, 3H), 6.44-6.40 (m, 1H), 3.75-3.70 (m, 4H), 3.19-3.02 (m, 4H). MS (ESI) m/z 590.33 (M+1)$^+$.

Example 139

3-Phenylethynyl-2-(1H-pyrrolo[2,3-b]pyridin-5-yl)-benzoic acid

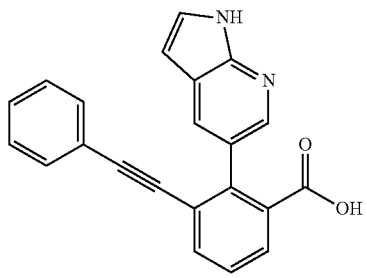 [SMILES: O=C(O)c1cccc(C#Cc2ccccc2)c1-c1cnc2[nH]ccc2c1]

3-Phenylethynyl-2-(1H-pyrrolo[2,3-b]pyridin-5-yl)-benzoic acid was prepared by the same procedure as Example 1. $^1$H NMR (300 MHz, DMSO-$d_6$) δ 8.11 (d, J=0.88 Hz, 1 H), 7.72-7.82 (m, 3 H), 7.46-7.55 (m, 2 H), 7.22-7.32 (m, 3 H), 7.02-7.11 (m, 3 H). MS (ESI) m/z 339 (M+1)$^+$.

Example 140

3-(4-Fluoro-phenylethynyl)-2-(1H-pyrrolo[2,3-b]pyridin-5-yl)-benzoic acid

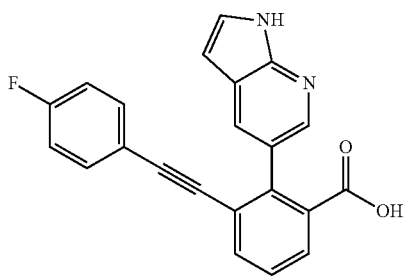 [SMILES: O=C(O)c1cccc(C#Cc2ccc(F)cc2)c1-c1cnc2[nH]ccc2c1]

3-(4-Fluoro-phenylethynyl)-2-(1H-pyrrolo[2,3-b]pyridin-5-yl)-benzoic acid was prepared by the same procedure as Example 1. $^1$H NMR (300 MHz, DMSO-$d_6$) δ 11.73 (br, s., 1 H), 8.17 (d, J=2.05 Hz, 1 H), 7.97 (d, J=2.05 Hz, 1 H), 7.79-7.84 (m, 2 H), 7.51-7.55 (m, 2 H), 7.15-7.17 (m, 4 H), 6.52 (dd, J=3.37, 1.91 Hz, 1 H). MS (ESI) m/z 357 (M+1)$^+$.

Example 141

3-(4-Methoxy-phenylethynyl)-2-(1H-pyrrolo[2,3-b]pyridin-5-yl)-benzoic acid

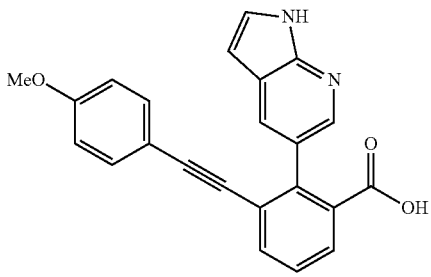 [SMILES: COc1ccc(C#Cc2cccc(C(=O)O)c2-c2cnc3[nH]ccc3c2)cc1]

3-(4-Methoxy-phenylethynyl)-2-(1H-pyrrolo[2,3-b]pyridin-5-yl)-benzoic acid was prepared by the same procedure as Example 1. $^1$H NMR (300 MHz, CD$_3$OD) δ 8.59 (d, J=1.47 Hz, 1 H), 8.39 (d, J=1.47 Hz, 1 H), 8.06 (dd, =7.92, 1.17 Hz, 1 H), 7.85 (dd, J=7.77, 1.32 Hz, 1 H), 7.72 (d, J=3.52 Hz, 1 H), 7.61 (t, J=7.75 Hz, 1 H), 6.94-6.99 (m, 2 H), 6.89 (d, J=3.52 Hz, 1 H), 6.74-6.79 (m, 2 H), 3.75 (s, 3 H). MS (ESI) m/z 369 (M+1)$^+$.

Example 142

2-(1H-Pyrrolo[2,3-b]pyridin-5-yl)-3-[4-(tetrahydro-pyran-4-yloxy)-phenylethynyl]-benzoic acid

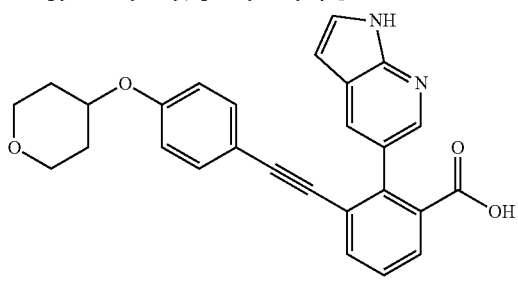

2-(1H-Pyrrolo[2,3-b]pyridin-5-yl)-3-[4-(tetrahydro-pyran-4-yloxy)-phenylethynyl]-benzoic acid was prepared by the same procedure as Example 1. $^1$H NMR (300 MHz, DMSO-d$_6$) δ 11.80 (br s, 2 H), 8.19 (br d, 0.1-2.05 Hz, 1 H), 8.00 (br d, J=1.47 Hz, 1 H), 7.78-7.97 (m, 2 H), 7.51-7.69 (m, 2 H), 6.98-7.30 (m, 3 H), 6.90 (d, J=8.50 Hz, 1 H), 6.55 (dd, J=3.37, 1.61 Hz, 1 H), 4.54-4.75 (m 1 H), 3.75-3.85 (m, 2 H), 3.20-3.40 (m, 2 H), 1.90-1.98 (m, 2 H), 1.49-1.61 (m, 2 H). MS (ESI) m/z 439 (M+1)$^+$.

Example 143

2-(1H-Indol-6-yl)-3-{4-[2-(tetrahydro-pyran-4-yl)-ethoxy]-phenylethynyl}-benzoic acid

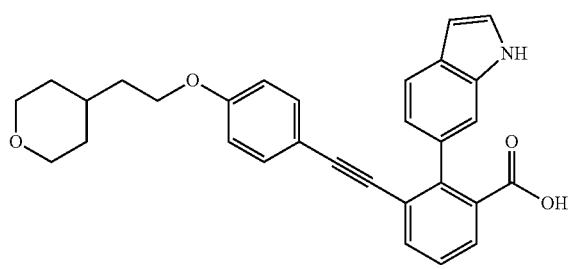 [SMILES: O=C(O)c1cccc(C#Cc2ccc(OCCC3CCOCC3)cc2)c1-c1ccc2cc[nH]c2c1]

2-(1H-Indol-6-yl)-3-({4-[2-(tetrahydro-pyran-4-yl)-ethoxy]-phenylethynyl}-benzoic acid was prepared by the same procedure as Example 1. $^1$H NMR (300 MHz, CD$_3$OD) δ 7.50-7.81 (m, 3 H), 7.32-7.50 (m, 2 H), 7.26 (br s, 1 H), 7.04 (br d, J=8.21 Hz, 1 H), 6.93 (br d, J=8.21 Hz, 2 H), 6.69 (br d, J=8.21 Hz, 2 H), 6.42-6.5 (m, 1 H), 3.67-3.97 (m, 4 H), 3.32-3.62 (m, 2 H), 1.44-1.78 (m, 5 H), 1.07-1.36 (m, 2 H). MS (ESI) m/z 466.3 (M+1)$^+$.

Example 144

3-[4-(1,1-Dioxo-hexahydro-1-thiopyran-4-yloxy)-phenylethynyl]-2-(1H-indol-6-yl)-benzoic acid

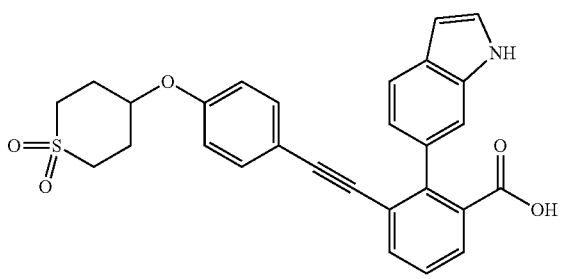 [SMILES: O=C(O)c1cccc(C#Cc2ccc(OC3CCS(=O)(=O)CC3)cc2)c1-c1ccc2cc[nH]c2c1]

3-[4-(1,1-Dioxo-hexahydro-1-thiopyran-4-yloxy)-phenylethynyl]-2-(1H-indol-6-yl)-benzoic acid was prepared by the same procedure as Example 1. $^1$H NMR (300 MHz, CD$_3$OD) δ 7.51-7.70 (m, 3 H), 7.47 (s, 1 H), 7.30-7.43 (m, 1 H), 7.25 (d, J=3.22 Hz, 1 H), 7.09 (br d, J=8.21 Hz, 1 H), 6.90-7.04 (m, 2 H), 6.83 (m, J=8.79 Hz, 2 H), 6.47 (d, J=2.93 Hz, 1 H), 4.62-4.74 (m, 1 H), 3.19-3.34 (m 2 H), 2.92-3.10 (m, 2 H), 2.21-2.38 (m, 4 H). MS (ESI) m/z 486.45 (M+1)$^+$.

Example 145

2-(1H-Indol-6-yl)-3-(4-morpholin-4-ylmethyl-phenylethynyl)-benzoic acid

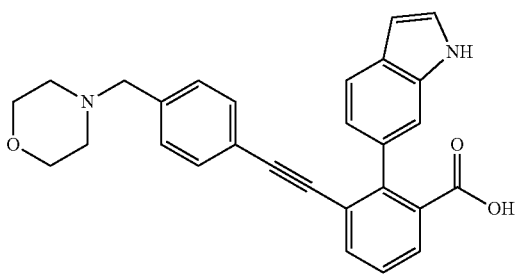 [SMILES: O=C(O)c1cccc(C#Cc2ccc(CN3CCOCC3)cc2)c1-c1ccc2cc[nH]c2c1]

2-(1H-Indol-6-yl)-3-(4-morpholin-4-ylmethyl-phenylethynyl)-benzoic acid; A mixture of 3-(4-formyl-phenylethynyl)-2-(1 H-indol-6-yl)-benzoic acid methyl ester (60 mg, 0.158 mmol), morpholine (28 mg, 0.32 mmol) in tetrahydrofuran (1 mL) was stirred at room temperature for 30 minutes. NaB(OAc)$_3$H (47 mg, 0.22 mmol) was added and the reaction mixture was stirred at room temperature for 24 hours. The reaction mixture was partitioned between ethyl acetate (3 mL) and saturated NaHCO$_3$ solution (3 mL). The organic layer was dried (sodium sulfate), filtered, concentrated and purified over silica gel eluting with ethyl acetate/dichloromethane to give the ester intermediate. To

Example 146

3-[4-(4-Ethyl-piperazin-1-ylmethyl)-phenylethynyl]-2-(1H-indol-6-yl)-benzoic acid

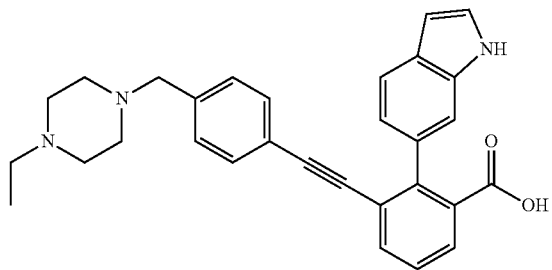 [SMILES: CCN1CCN(Cc2ccc(C#Cc3cccc(C(=O)O)c3-c3ccc4cc[nH]c4c3)cc2)CC1]

3-[4-(4-Ethyl-piperazin-1-ylmethyl)-phenylethynyl]-2-(1H-indol-6-yl)-benzoic acid acid was prepared by same procedure as Example 145. $^1$H NMR (300 MHz, CD$_3$OD) δ=7.67-7.79 (m 2 H), 7.57 (d, J=8.2 Hz, 1 H), 7.38-7.48 (m, 2 H), 7.17-7.29 (m 3 H), 7.01-7.07 (m, 3 H), 6.49 (d, J=3.1 Hz, 1 H), 3.74 (s, 2 H), 3.13-3.28 (m, 6 H), 2.85 (br s, 4 H), 1.31 (t, J=7.2 Hz, 3 H). MS (ESI) m/z 464.63 (M+1)$^+$.

Example 147

2-(1H-Indol-6-yl)-3-[4-(4-methyl-piperazin-1-ylmethyl)-phenylethynyl]-benzoic acid

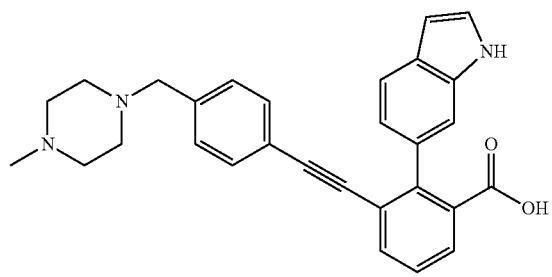 [SMILES: CN1CCN(Cc2ccc(C#Cc3cccc(C(=O)O)c3-c3ccc4cc[nH]c4c3)cc2)CC1]

2-(1H-Indol-6-yl)-3-[4-(4-methyl-piperazin-1-ylmethyl)-phenylethynyl]-benzoic acid was prepared by same procedure as Example 145. $^1$H NMR (300 MHz, CD$_3$OD) δ 7.63-7.80 (m, 2 H), 7.57 (d, J=8.21 Hz, 1 H), 7.34-7.51 (m, 2 H), 7.13-7.34 (m, 3 H), 6.74-7.13 (m, 3 H), 6.49 (d, J=3.22 Hz, 1H), 3.72 (s, 2 H), 3.33-3.54 (m, 4 H), 2.69-3.07 (m, 7 H). MS (ESI) m/z 450.56 (M+1)$^+$.

Example 148

3-[4-(1,1-Dioxo-thiomorpholin-4-ylmethyl)-phenylethynyl]-2-(1H-indol-6-yl)-benzoic acid

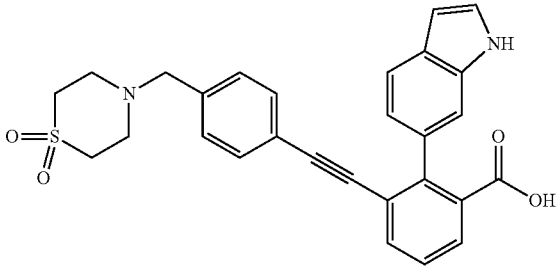 [SMILES: O=C(O)c1cccc(C#Cc2ccc(CN3CCS(=O)(=O)CC3)cc2)c1-c1ccc2cc[nH]c2c1]

3-[4-(1,1-Dioxo-thiomorpholin-4-ylmethyl)-phenylethynyl]-2-(1H-indol-6-yl)-benzoic acid was prepared by same procedure as Example 145. $^1$H NMR (300 MHz, CD$_3$OD) δ 7.64-8.04 (m, 2 H), 7.57 (d, J=8.21 Hz, 1 H), 7.35-7.50 (m, 2 H), 7.18-7.35 (m, 3 H), 6.92-7.18 (m 3 H), 6.49 (d, J=3.17 Hz, 1 H), 4.13 (s, 2 H), 3.45 (dd, J=6.74, 3.52 Hz, 4 H), 3.28-3.33 (m, 4 H). MS (ESI) m/z 495.5 (M+1)$^+$.

Example 149

3-(4-{[(2-Dimethylamino-ethyl)-methyl-amino]-methyl}-phenylethynyl)-2-(1H-indol-6-yl)-benzoic acid

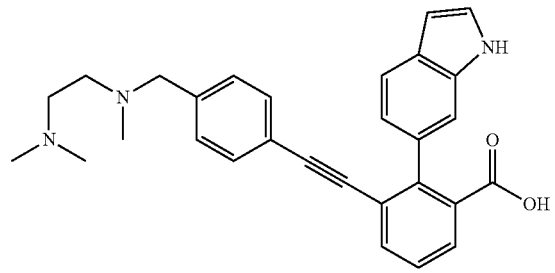 [SMILES: CN(C)CCN(C)Cc1ccc(C#Cc2cccc(C(=O)O)c2-c2ccc3cc[nH]c3c2)cc1]

3-(4-{[(2-Dimethylamino-ethyl)-methyl-amino]-methyl}-phenylethynyl)-2-(1H-indol-6-yl)-benzoic acid was prepared by same procedure as Example 145. $^1$H NMR (300 MHz, CD$_3$OD) δ 7.75-7.69 (min, 2 H), 7.58 (d, J=8.21 Hz, 1 H), 7.50-7.64 (m, 2 H), 7.18-7.46 (m, 3 H), 6.99-7.14 (m, 3 H), 6.34-6.51 (m 1 H), 4.23 (s, 2 H), 3.42-3.58 (m, 4 H), 2.85 (s, 6 H), 2.69 (s, 3 H). MS (ESI) m/z 452.46 (M+1)$^+$.

Example 150

3-{4-[4-(2-Hydroxy-ethyl)-piperidin-1-ylmethyl]-phenylethynyl}-2-(1H-indol-6-yl)-benzoic acid

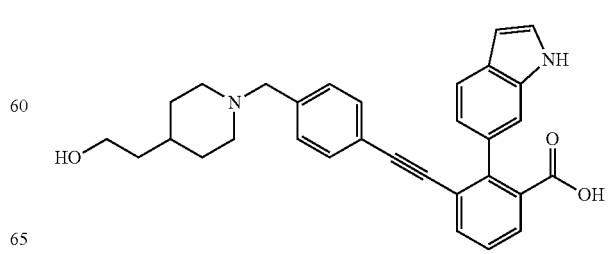

3-{4-[4-(2-Hydroxy-ethyl)-piperidin-1-ylmethyl]-phenylethynyl}-2-(1H-indol-6-yl)-benzoic acid was prepared by same procedure as Example 145. $^1$H NMR (300 MHz, CD$_3$OD) δ 7.66 (ddd, J=7.70, 6.23, 1.32 Hz, 2 H), 7.50 (d, J=8.21 Hz, 1 H), 7.29-7.41 (m, 2 H), 7.14-7.27 (m, 3 H), 6.89-7.11 (m, 3 H), 6.41 (dd, J=−3.22, 0.88 Hz, 1 H), 4.09 (s, 2 H), 3.35-3.66 (m, 2 H), 3.16-3.29 (m, 4 H), 2.72-2.94 (m, 2 H), 1.84 (br d, J=13.78 Hz, 2 H), 1.16-1.50 (m, 3 H). MS (ESI) m/z 479.58 (M+1)$^+$.

Example 151

3-[4-(4-Hydroxymethyl-piperidin-1-ylmethyl)-phenylethynyl]-2-(1H-indol-6-yl)-benzoic acid

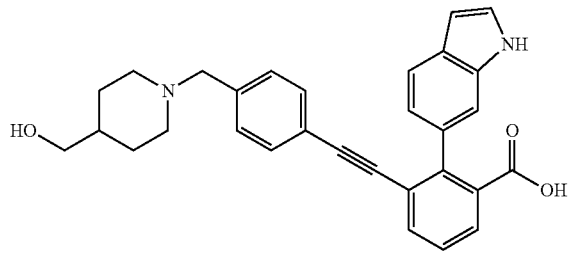 [SMILES: O=C(O)c1cccc(C#Cc2ccc(CN3CCC(CO)CC3)cc2)c1-c1ccc2cc[nH]c2c1]

3-[4-(4-Hydroxymethyl-piperidin-1-ylmethyl)-phenylethynyl]-2-(1H-indol-6-yl)-benzoic acid was prepared by same procedure as Example 145. $^1$H NMR (300 MHz, CD$_3$OD) δ 7.74 (ddd, J=7.48, 5.86, 1.03 Hz, 2 H), 7.58 (d, J=8.21 Hz, 1 H), 7.37-7.49 (m, 2 H), 7.22-7.35 (m, 3 H), 6.94-7.20 (m, 3 H), 6.49 (d, J=3.22 Hz, 1 H), 4.21 (s, 2 H), 3.33-3.59 (m 4 H), 2.86-3.03 (m, 2 H), 1.68-2.04 (m, 2 H), 1.29-1.45 (m, 2 H). MS (ESI) m/z 465.58 (M+1)$^+$.

Example 152

2-(1H-Indol-6-yl)-3-[4-(4-methyl-[1,4]diazepan-1-ylmethyl)-phenylethynyl]-benzoic acid

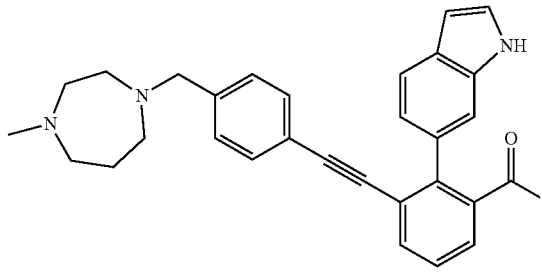

2-(1H-Indol-6-yl)-3-[4-(4-methyl-[1,4]diazepan-1-ylmethyl)-phenylethynyl]-benzoic acid was prepared by same procedure as Example 145. $^1$H NMR (300 MHz, CD$_3$OD) δ 7.65-7.84 (m, 2 H), 7.57 (d, J=7.92 Hz, 1 H), 7.37-7.50 (m, 2 H), 7.19-7.36 (m, 3 H), 6.91-7.19 (m, 3 H), 6.48 (dd, J=3.22, 0.88 Hz, 1 H), 4.18 (s, 2 H), 3.53-3.88 (m, 6 H), 3.38-3.52 (m, 2 H), 2.92 (s, 3 H), 2.11-2.20 (m, 2 H). MS (ESI) m/z 464.56 (M+1)$^+$.

Example 153

3-[4-(3-Hydroxy-azetidin-1-ylmethyl)-phenylethynyl]-2-(1H-indol-6-yl)-benzoic acid

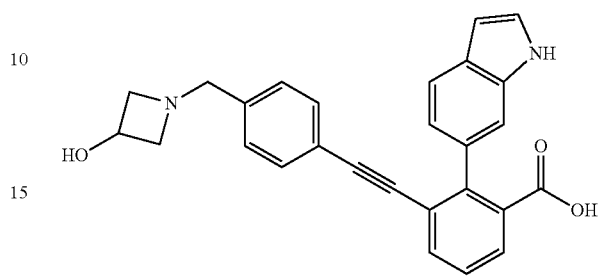

3-[4-(3-Hydroxy-azetidin-1-ylmethyl)-phenylethynyl]-2-(1H-indol-6-yl)-benzoic acid was prepared by same procedure as Example 145. $^1$H NMR (300 MHz, CD$_3$OD) δ 7.69-7.80 (m, 2 H), 7.57 (d, J=7.92 Hz, 1 H), 7.38-7.45 (m, 2 H), 7.21-7.36 (m, 3 H), 6.91-7.19 (m, 3 H), 6.48 (dd, J=3.22, 0.88 Hz, 1 H), 4.62-4.52 (m, 1 H), 4.18-4.30 (m, 4 H), 3.82-3.90 (m, 2 H). MS (ESI) m/z 423 (M+1)$^+$.

Example 154

3-[4-(4-Hydroxy-piperidin-1-ylmethyl)-phenylethynyl]-2-(1H-indol-6-yl)-benzoic acid

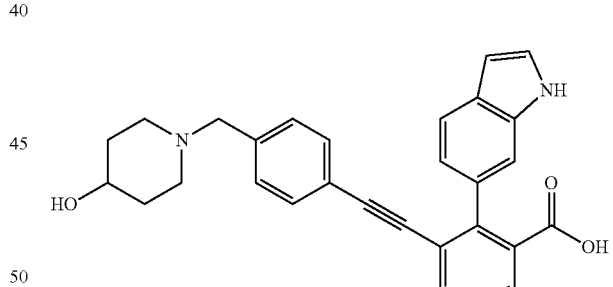

3-[4-(4-Hydroxy-piperidin-1-ylmethyl)-phenylethynyl]-2-(1H-indol-6-yl)-benzoic acid was prepared by same procedure as Example 145. $^1$H NMR (300 MHz, CD$_3$OD) δ 7.65-7.84 (m, 2 H), 7.57 (d, J=7.92 Hz, 1 H), 7.37-7.50 (m, 2 H), 7.19-7.36 (m, 3 H), 6.98-7.19 (m, 3 H), 6.45 (dd, J=−3.22, 0.88 Hz, 1 H), 4.18 (d, J=6.8 Hz, 2 H), 3.98-4.05 (m, 1 H), 3.70-3.81 (m, 1 H), 2.92-3.40 (m, 3 H), 2.10-2.00 (m, 1 H), 1.88-1.80 (m, 2 H), 1.58-1.65 (m, 1 H). MS (ESI) m/z 451.51 (M+1)$^+$.

Example 155

2-(1H-Indol-6-yl)-3-[4-(4-methoxy-piperidin-1-ylmethyl)-phenylethynyl]-benzoic acid

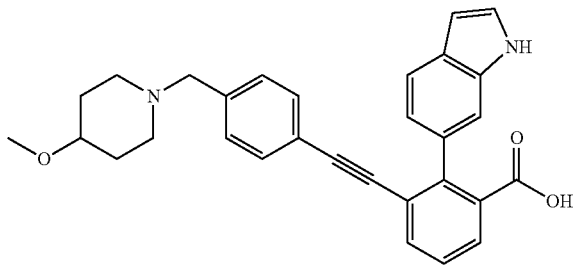 [SMILES: COC1CCN(Cc2ccc(C#Cc3cccc(C(=O)O)c3-c3ccc4cc[nH]c4c3)cc2)CC1]

2-(1H-Indol-6-yl)-3-[4-(4-methoxy-piperidin-1-ylmethyl)-phenylethynyl]-benzoic acid was prepared by same procedure as Example 145. $^1$H NMR (300 MHz, CD$_3$OD) δ 7.66-7.81 (m, 2 H), 7.25-7.59 (m, 6 H), 7.01-7.16 (m, 3 H), 6.48 (d, J=3.11 Hz, 1 H), 4.19 (s, 2 H), 3.52-3.58 (m, 1 H), 3.30-3.38 (m, 4 H), 3.05-3.28 (m, 3 H), 2.79-3.02 (m, 1 H), 1.95-2.23 (m, 2 H), 1.67-1.89 (m, 1 H). MS (ESI) m/z 465.51 (M+1)$^+$.

Example 156

3-(4-Dimethylaminomethyl-phenylethynyl)-2-(1H-indol-6-yl)-benzoic acid

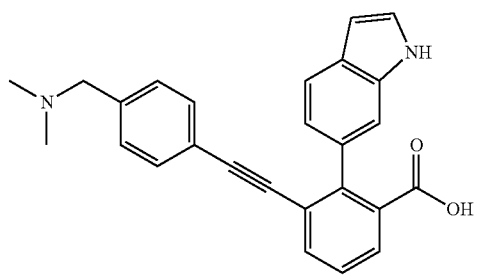 [SMILES: CN(C)Cc1ccc(C#Cc2cccc(C(=O)O)c2-c2ccc3cc[nH]c3c2)cc1]

3-(4-Dimethylaminomethyl-phenylethynyl)-2-(1H-indol-6-yl)-benzoic acid was prepared by same procedure as Example 145. $^1$H NMR (300 MHz, CD$_3$OD) δ 7.66-7.80 (m, 2 H), 7.58 (d, J=8.21 Hz, 1 H), 7.38-7.50 (m, 2 H), 7.22-7.38 (m, 3 H), 7.05-7.18 (m, 3 H), 6.48 (dd, J=3.22, 0.88 Hz, 1 H), 4.15 (s, 2 H), 2.76 (s, 6 H). MS (ESI) m/z 395 (M+1)$^+$.

Example 157

2-(1H-Indol-6-yl)-3-(4-{[(2-methoxy-ethyl)methyl-amino]-methyl}-phenylethynyl)-benzoic acid

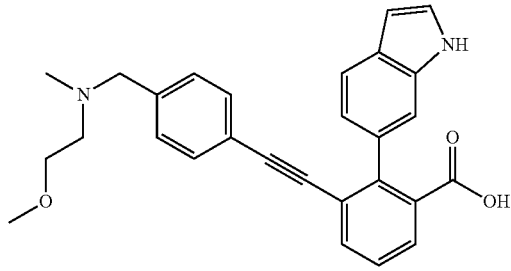 [SMILES: COCCN(C)Cc1ccc(C#Cc2cccc(C(=O)O)c2-c2ccc3cc[nH]c3c2)cc1]

2-(1H-Indol-6-yl)-3-(4-{[(2-methoxy-ethyl)-methyl-amino]-methyl}-phenylethynyl)-benzoic acid was prepared by same procedure as Example 145. $^1$H NMR (300 MHz, CD$_3$OD) δ 7.70-7.77 (m, 2 H), 7.58 (d, J=8.03 Hz, 1 H), 7.38-7.48 (m, 2 H), 7.25-7.34 (m, 3 H), 7.03-7.14 (m, 3 H), 6.48 (dd, J=3.22, 0.88 Hz, 1 H), 4.18-4.34 (m, 2 H), 3.66 (t, J=4.98 Hz, 2 H), 3.48 (s, 3 H), 3.30-3.35 (m, 2 H), 2.76 (s, 3 H). MS (ESI) m/z 439.47 (M+1)$^+$.

Example 158

3-[4-(4,4-Difluoro-piperidin-1-ylmethyl)-phenylethynyl]-2-(1H-indol-6-yl)-benzoic acid

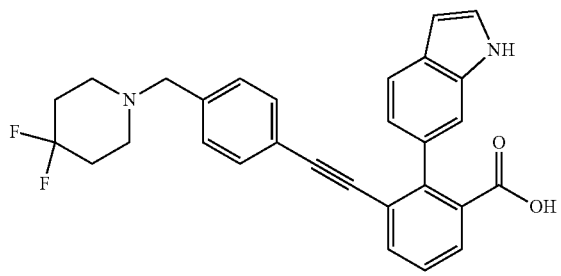 [SMILES: O=C(O)c1cccc(C#Cc2ccc(CN3CCC(F)(F)CC3)cc2)c1-c1ccc2cc[nH]c2c1]

3-[4-(4,4-Difluoro-piperidin-1-ylmethyl)-phenylethynyl]-2-(1H-indol-6-yl)-benzoic acid was prepared by same procedure as Example 145. $^1$H NMR (300 MHz, CD$_3$OD) δ 7.74 (ddd, J=7.77, 6.60, 1.17 Hz, 2 H), 7.57 (d, J=8.21 Hz, 1 H), 7.37-7.51 (m, 2 H), 7.21-7.37 (m, 3 H), 7.11 (d, J=7.92 Hz, 2 H), 7.03 (dd, J=8.06, 1.61 Hz, 1 H), 6.48 (d, J=3.27 Hz, 1 H), 4.29 (s, 2 H), 3.12-3.50 (m, 4 H), 2.14-2.44 (m, 4 H). MS (ESI) m/z 471.49 (M+1)$^+$.

Example 159

3-[4-(3,3-Difluoro-piperidin-1-ylmethyl)-phenylethynyl]-2-(1H-indol-6-yl)-benzoic acid

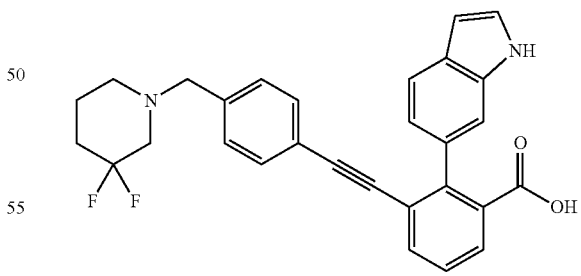

3-[4-(3,3-Difluoro-piperidin-1-ylmethyl)-phenylethynyl]-2-(1H-indol-6-yl)-benzoic acid was prepared by same procedure as Example 145. $^1$H NMR (300 MHz, CD$_3$OD) δ 7.64-7.87 (m, 2 H), 7.51-7.64 (m, 1 H), 7.38-7.51 (m, 2 H), 7.22-7.38 (m 3 H), 7.13 (br d, J=6.45 Hz, 2 H), 7.04 (br d, J=6.74 Hz, 1 H), 6.48 (br s, 1 H), 3.46 (br t, J=10.99 Hz, 2 H), 3.26-3.38 (m 2 H), 3.02-3.26 (m, 2 H), 1.82-2.22 (m, 4 H). MS (ESI) m/z 471.5 (M+1)$^+$.

Example 160

3-[4-(3,4-Dihydro-1H-isoquinolin-2-ylmethyl)-phenylethynyl]-2-(1H-indol-6-yl)-benzoic acid

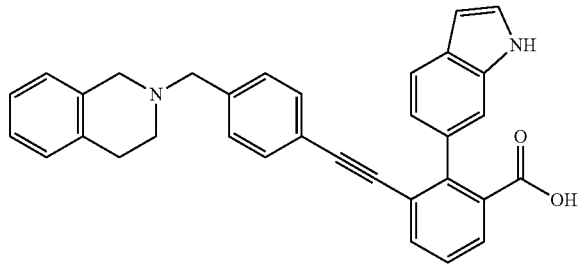 [SMILES: O=C(O)c1cccc(C#Cc2ccc(CN3CCc4ccccc4C3)cc2)c1-c1ccc2cc[nH]c2c1]

3-[4-(3,4-Dihydro-1H-isoquinolin-2-ylmethyl)-phenylethynyl]-2-(1H-indol-6-yl)-benzoic acid was prepared by same procedure as Example 145. $^1$H NMR (300 MHz, CD$_3$OD) δ 7.70-7.80 (m, 2 H), 7.59 (d, J=8.21 Hz, 1 H), 7.32-7.50 (m, 5 H), 7.20-7.32 (m, 4 H), 7.10-7.20 (m 3 H), 7.05 (dd, J=8.21, 1.47 Hz, 1 H), 6.43-6.53 (m, 1 H), 4.41 (s, 2 H), 4.33 (s, 2 H), 3.09-3.21 (m, 2 H). MS (ESI) m/z 483.5 (M+1)$^+$.

Example 161

2-(1H-Indol-6-yl)-3-[4-(4-methanesulfonyl-piperazin-1-ylmethyl)-phenylethynyl]-benzoic acid

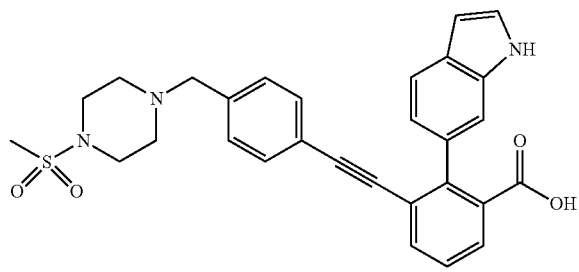 [SMILES: CS(=O)(=O)N1CCN(Cc2ccc(C#Cc3cccc(C(=O)O)c3-c3ccc4cc[nH]c4c3)cc2)CC1]

2-(1H-Indol-6-yl)-3-[4-(4-methanesulfonyl-piperazin-1-ylmethyl)-phenylethynyl]-benzoic acid was prepared by same procedure as Example 145. $^1$H NMR (300 MHz, CD$_3$OD) δ 7.74 (ddd, J=−7.70, 6.38, 1.47 Hz, 2 H), 7.57 (d, J=8.18 Hz, 1 H), 7.39-7.47 (m, 2 H), 7.33 (d, J=7.59 Hz, 2 H), 7.27 (d, J=2.95 Hz, 1 H), 7.12 (d, J=7.68 Hz, 2 H), 7.03 (dd, J=8.21, 1.47 Hz, 1 H), 6.48 (dd, J=3.22, 0.88 Hz, 1 H), 4.31 (s, 2 H), 3.28-3.55 (m 6 H), 2.92 (s, 3 H), 2.65 (s, 2 H). MS (ESI) m/z 514.53 (M+1)$^+$.

Example 162

2-(1H-Indol-6-yl)-3-[4-(3-trifluoromethyl-piperidin-1-ylmethyl)-phenylethynyl]-benzoic acid

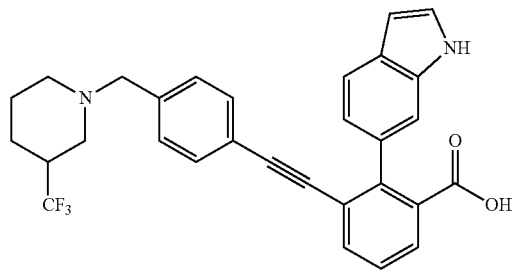 [SMILES: O=C(O)c1cccc(C#Cc2ccc(CN3CCCC(C(F)(F)F)C3)cc2)c1-c1ccc2cc[nH]c2c1]

2-(1H-Indol-6-yl)-3-[4-(3-trifluoromethyl-piperidin-1-yl-methyl)-phenylethynyl]-benzoic acid was prepared by same procedure as Example 145. $^1$H NMR (300 MHz, CD$_3$OD) δ 7.73 (br s, 2 H), 7.52-7.65 (m, 1 H), 7.37-7.51 (m, 2 H), 7.19-7.37 (m, 3 H), 6.93-7.19 (m, 3 H), 6.48 (br s, 1 H), 4.20-4.44 (m, 2 H), 3.58 (br d, J=11.14 Hz, 1 H), 3.16-3.47 (m, 1 H), 2.64-3.10 (m, 3 H), 1.87-2.17 (m, 2 H), 1.46-1.87 (m, 2 H), 1.38-1.66 (m, 2 H). MS (ESI) m/z 503.58 (M+1)$^+$.

Example 163

2-(1H-Indol-6-yl)-3-[4-(3-methoxy-pyrrolidin-1-ylmethyl)-phenylethynyl]-benzoic acid

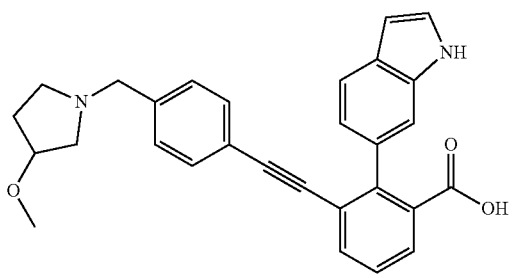 [SMILES: COC1CCN(Cc2ccc(C#Cc3cccc(C(=O)O)c3-c3ccc4cc[nH]c4c3)cc2)C1]

2-(1H-Indol-6-yl)-3-[4-(3-methoxy-pyrrolidin-1-ylmethyl)-phenylethynyl]-benzoic acid was prepared by same procedure as Example 145. $^1$H NMR (300 MHz, CD$_3$OD) δ 7.70-7.75 (m, 2 H), 7.59 (d, J=8.2 Hz, 1 H), 7.39-7.45 (m, 2 H), 7.27-7.35 (m, 3 H), 7.02-7.12 (m, 3 H), 6.48 (dd, J=2.93, 0.88 Hz, 1 H), 4.30 (s, 2 H), 4.08-4.15 (m, 1 H), 3.06-3.60 (m, 7 H), 2.01-2.35 (m, 2 H). MS (ESI) m/z 478.7 (M+1)$^+$. MS (ESI) m/z 451.58 (M+1)$^+$.

Example 164

2-(1H-Indol-6-yl)-3-[4-(4-isopropyl-piperazin-1-ylmethyl)-phenylethynyl]-benzoic acid

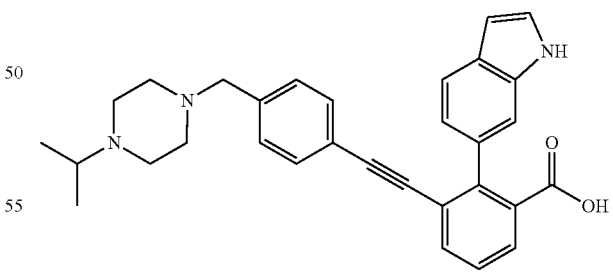

2-(1H-Indol-6-yl)-3-[4-(4-isopropyl-piperazin-1-ylmethyl)-phenylethynyl]-benzoic acid was prepared by same procedure as Example 145. $^1$H NMR (300 MHz, CD$_3$OD) δ 7.64-7.84 (m, 2 H), 7.59 (s, 1 H), 7.35-7.52 (m, 2 H), 7.20-7.35 (m, 3 H), 6.94-7.11 (m, 3 H), 6.48 (dd, J=2.93, 0.88 Hz, 1 H), 3.92 (s, 2 H), 3.30-3.57 (m, 5 H), 3.02-3.15 (m, 4 H), 1.32 (d, J=6.70 Hz, 6 H). MS (ESI) m/z 478.7 (M+1)$^+$.

Example 165

3-[4-(4-cyclohexyl-piperazin-1-ylmethyl)-phenyl-ethynyl]-2-(1H-indol-6-yl)-benzoic acid

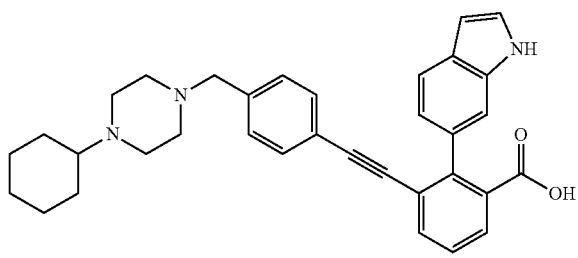 [SMILES: O=C(O)c1cccc(C#Cc2ccc(CN3CCN(C4CCCCC4)CC3)cc2)c1-c1ccc2cc[nH]c2c1]

3-[4-(4-Cyclohexyl-piperazin-1-ylmethyl)-phenylethynyl]-2-(1H-indol-6-yl)-benzoic acid was prepared by same procedure as Example 145. $^1$H NMR (300 MHz; CD$_3$OD) δ 7.68-7.76 (m 2 H), 7.56 (d, J=8.21 Hz, 1 H), 7.34-7.48 (m, 2 H), 7.15-7.32 (m, 3 H), 6.95-7.06 (m, 3 H), 6.42-6.53 (m, 1 H), 3.91 (s, 2 H), 3.32-3.60 (m, 3 H), 2.92-3.27 (m, 5 H), 2.02 (br s, 2 H), 1.81-1.97 (m, 2 H), 1.68 (br d, J=12.02 Hz, 1 H), 1.23-1.49 (m, 5 H), 1.19 (br s, 1 H). MS (ESI) m/z 518.74 (M+1)$^+$.

Example 166

3-[4-(4-Cyclopropanecarbonyl-piperazin-1-ylmethyl)-phenylethynyl]-2-(1H-indol-6-yl)-benzoic acid

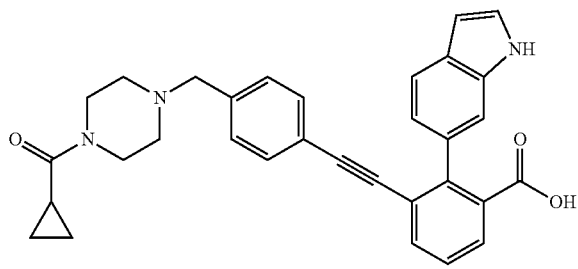 [SMILES: O=C(O)c1cccc(C#Cc2ccc(CN3CCN(C(=O)C4CC4)CC3)cc2)c1-c1ccc2cc[nH]c2c1]

3-[4-(4-Cyclopropanecarbonyl-piperazin-1-ylmethyl)-phenylethynyl]-2-(1H-indol-6-yl)-benzoic acid was prepared by same procedure as Example 145. $^1$H NMR (300 MHz, CD$_3$OD) δ 7.66-7.86 (m, 2 H), 7.57 (d, J=8.21 Hz, 1 H), 7.37-7.51 (m, 2 H), 7.20-7.37 (m, 3 H), 7.12 (d, J=8.21 Hz, 2 H), 7.03 (dd, J=8.21, 1.47 Hz, 1 H), 6.40-6.53 (m, 1 H), 4.27 (s, 2 H), 3.11-3.28 (m, 8 H), 1.92 (ddd, J=7.62, 4.84, 2.79 Hz, 1 H), 0.74-1.02 (m, 4 H). MS (ESI) m/z 504.67 (M+1)$^+$.

Example 167

2-(1H-Indol-6-yl)-3-(4-piperazin-1-ylmethyl-phenylethynyl)-benzoic acid

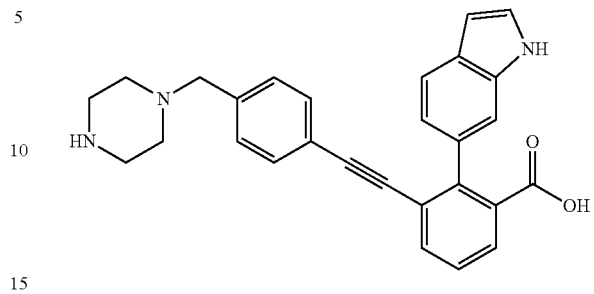

2-(1H-Indol-6-yl)-3-(4-piperazin-1-ylmethyl-phenylethynyl)-benzoic acid was prepared by same procedure as Example 145. $^1$H NMR (300 MHz, CD$_3$OD) δ ppm 7.71-7.77 (m, 2 H), 7.57 (d, J=8.14 Hz, 1 H), 7.39-7.47 (m, 2 H), 7.26-7.35 (m, 3 H), 7.12 (d, J=7.61 Hz, 2 H), 7.03 (dd, J=8.21, 1.47 Hz, 1 H), 6.49 (d, J=3.05 Hz, 1 H), 4.27 (s, 2 H), 3.60-3.98 (m, 4 H), 2.60-2.81 (m, 4 H). MS (ESI) m/z 436.62 (M+1)$^+$.

Example 168

3-[4-(4-Benzenesulfonyl-piperazin-1-ylmethyl)-phenylethynyl]-2-(1H-indol-6-yl)-benzoic acid

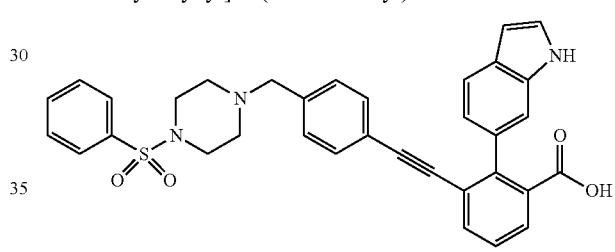

3-[4-(4-Benzenesulfonyl-piperazin-1-ylmethyl)-phenylethynyl]-2-(1H-indol-6-yl)-benzoic acid was prepared by same procedure as Example 145. $^1$H NMR (300 MHz, CD$_3$OD) δ 7.69-7.83 (m, 4 H), 7.62-7.69 (m, 1 H), 7.52-7.62 (m, 3 H), 7.35-7.49 (m, 2 H), 7.18-7.30 (m, 3 H), 7.05-7.11 (m, 2 H), 6.97-7.05 (m, 1 H), 6.48 (dd, J=3.08, 0.88 Hz, 1 H), 4.22 (s, 2 H), 3.11-3.34 (m, 8 H). MS (ESI) m/z 576 (M+1)$^+$.

Example 169

3-{4-[(1,1-Dioxo-hexahydro-1-thiopyran-4-ylamino)-methyl]-phenylethynyl}-2-(1H-indol-6-yl)-benzoic acid

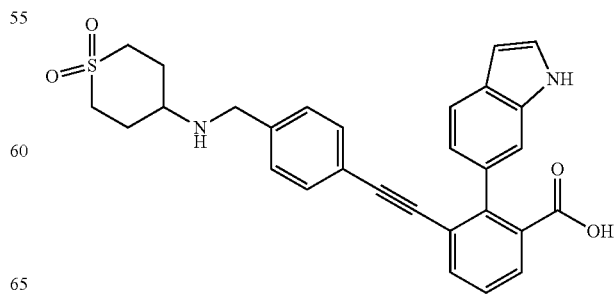

3-{4-[(1,1-Dioxo-hexahydro-1-thiopyran-4-ylamino)-methyl]-phenylethynyl}-2-(1H-indol-6-yl)-benzoic acid was prepared by same procedure as Example 145. ¹H NMR (300 MHz, CD₃OD) δ 7.70-7.79 (m, 2 H), 7.58 (d, J=8.02 Hz, 1 H), 7.45-7.41 (m, 2 H), 7.26-7.35 (m, 3 H), 7.08-7.14 (m, 2 H), 7.04 (dd, J=8.21, 1.47 Hz, 1 H), 6.48 (dd, J=3.22, 0.88 Hz, 1 H), 4.20 (s, 2 H), 3.38-3.53 (m, 1 H), 3.11-3.27 (m, 4 H), 2.46-2.55 (m, 2 H), 2.11-2.26 (m, 2 H). MS (ESI) m/z 499 (M+1)⁺.

Example 170

3-[4-(4-Cyclopentyl-piperazin-1-ylmethyl)-phenyl-ethynyl]-2-(1H-indol-6-yl)-benzoic acid

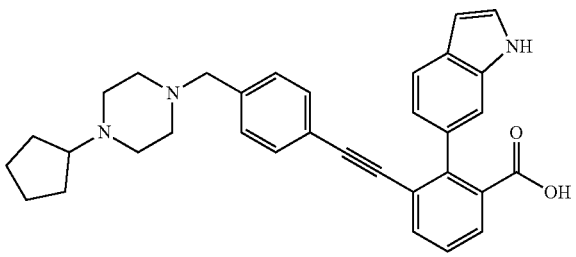 [SMILES: O=C(O)c1cccc(C#Cc2ccc(CN3CCN(C4CCCC4)CC3)cc2)c1-c1ccc2cc[nH]c2c1]

3-[4-(4-Cyclopentyl-piperazin-1-ylmethyl)-phenylethynyl]-2-(1H-indol-6-yl)-benzoic acid was prepared by the same procedure as Example 145. ¹H NMR (300 MHz, CD₃OD) δ 7.64-7.84 (m, 2 H), 7.59 (s, 1 H), 7.35-7.52 (m, 2 H), 7.24-7.35 (m, 1 H), 7.19 (d, J=7.92 Hz, 2 H), 6.94-7.11 (m, 3 H), 6.48 (dd, =-2.93, 0.88 Hz, 1 H), 3.63 (s, 2 H), 3.39-3.57 (m, 3 H), 2.55-2.95 (m, 4 H), 1.99-2.27 (m, 2 H), 1.54-1.91 (m, 8 H). MS (ESI) m/z 504 (M+1)⁺.

Example 171

3-[4-(4-Dimethylcarbamoyl-piperazin-1-ylmethyl)-phenylethynyl]-2-(1H-indol-6-yl)-benzoic acid

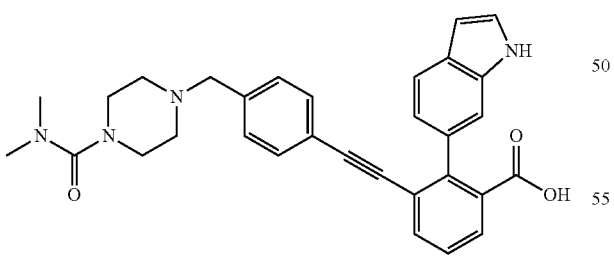

3-[4-(4-Dimethylcarbamoyl-piperazin-1-ylmethyl)-phenylethynyl]-2-(1H-indol-6-yl)-benzoic acid was prepared by same procedure as Example 145. ¹H NMR (300 MHz, CD₃OD) δ 7.63-7.77 (m, 2 H), 7.58 (d, J=7.33 Hz, 1 H), 7.38-7.45 (m, 2 H), 7.25-7.32 (m, 3 H), 7.16 (d, J=8.21 Hz, 2 H), 6.96-7.12 (m, 1 H), 6.49 (dd, J=3.22, 0.88 Hz, 1 H), 4.21 (s, 2 H), 3.11-3.30 (m, 8 H), 2.83 (s, 6 H). MS (ESI) m/z 507 (M+1)⁺.

Example 172

2-(1H-Indol-6-yl)-3-[4-(2,3,5,6-tetrahydro-[1,2']bipyrazinyl-4-ylmethyl)-phenylethynyl]-benzoic acid

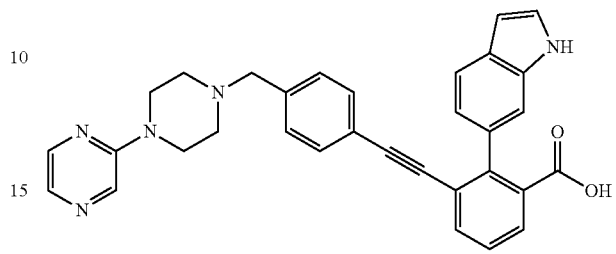

2-(1H-Indol-6-yl)-3-[4-(2,3,5,6-tetrahydro-[1,2']bipyrazinyl-4-ylmethyl)-phenylethynyl]-benzoic acid was prepared by same procedure as Example 145. ¹H NMR (300 MHz, CD₃OD) δ 8.24 (s, 1 H), 8.16 (dd, J=2.49, 1.32 Hz, 1 H), 7.90 (br d, J=2.05 Hz, 1 H), 7.74 (ddd, J=7.70, 6.08, 1.47 Hz, 2 H), 7.57 (d, J=8.21 Hz; 1 H), 7.36-7.49 (m, 2 H), 7.23-7.36 (m, 3 H), 7.11 (d, J=8.21 Hz, 2 H), 7.02 (dd, J=8.06, 1.61 Hz, 1 H), 6.48 (dd, J=3.22, 0.88 Hz, 1 H), 4.26 (s, 2 H), 3.14-3.34 (m, 8 H). MS (ESI) m/z 514 (M+1)⁺.

Example 173

2-(1H-Indol-6-yl)-3-[4-(4-thiazol-2-yl-piperazin-1-ylmethyl)-phenylethynyl]-benzoic acid

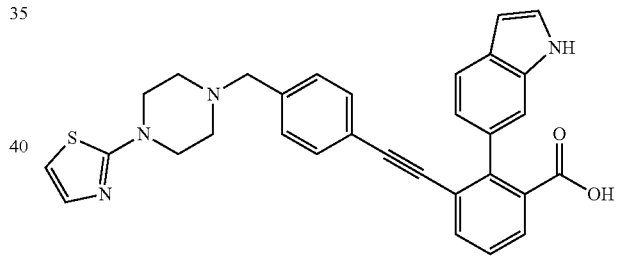

2-(1H-Indol-6-yl)-3-[4-(4-thiazol-2-yl-piperazin-1-ylmethyl)-phenylethynyl]-benzoic acid was prepared by same procedure as Example 145. MS (ESI) m/z 519 (M+1)⁺.

Example 174

3-(4-[(2-Amino-4,5,6,7-tetrahydro-benzothiazol-6-ylamino)-methyl]-phenylethynyl-2-(1H-indol-6-yl)-benzoic acid

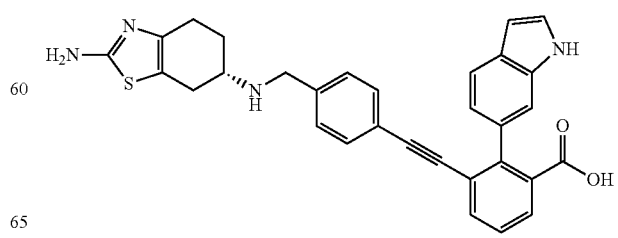

3-{4-[(2-Amino-4,5,6,7-tetrahydro-benzothiazol-6-ylamino)-methyl]-phenylethynyl}-2-(1H-indol-6-yl)-benzoic acid was prepared by same procedure as Example 145. $^1$H NMR (300 MHz, CD$_3$OD) δ 7.73 (ddd, =7.70, 5.94, 1.32 Hz, 2 H), 7.57 (d, J=8.79 Hz, 1 H), 7.38-7.51 (m, 2 H), 7.35 (d, J=8.21 Hz, 2 H), 7.26 (d, J=2.93 Hz, 1 H), 6.99-7.20 (m, 3 H), 6.48 (dd, J=3.22, 0.88 Hz, 1 H), 4.25 (s, 2 H), 2.57-2.84 (m, 5 H), 1.90-1.95 (m, 2 H). MS (ESI) m/z 519.13 (M+1)$^+$.

Example 175

3-(4-[(2-Amino-4,5,6,7-tetrahydro-benzothiazol-6-ylamino)-methyl]-phenylethynyl)-2-(1H-indol-6-yl)-benzoic acid

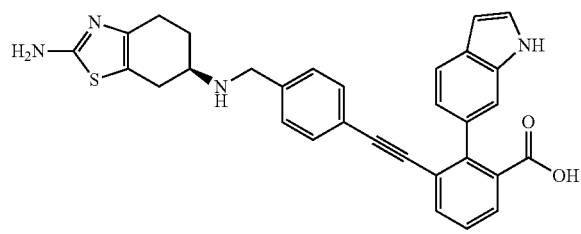 [SMILES: Nc1nc2c(s1)C[C@H](NCc1ccc(C#Cc3cccc(C(=O)O)c3-c3ccc4cc[nH]c4c3)cc1)CC2]

3-{4-[(2-Amino-4,5,6,7-tetrahydro-benzothiazol-6-ylamino)-methyl]-phenylethynyl}-2-(1H-indol-6-yl)-benzoic acid was prepared by same procedure as Example 145. $^1$H NMR (300 MHz, CD$_3$OD) δ 7.63-7.81 (m, 2 H), 7.51-7.63 (m, 1 H), 7.38-7.51 (m, 2 H), 7.33 (d, J=7.92 Hz, 2 H), 7.17-7.29 (m, 1 H), 6.93-7.17 (m, 3 H), 6.47 (d, J=2.93 Hz, 1 H), 4.22 (s, 2 H), 3.46-3.73 (m, 1 H), 2.98-3.23 (m, 1 H), 2.53-2.88 (m, 3 H), 2.25-2.49 (m, 1 H), 1.82-2.15 (m, 1 H). MS (ESI) m/z 519.14 (M+1)$^+$.

Example 176

3-[4-(4-Methyl-piperazin-1-ylmethyl)-phenylethynyl]-2-(1H-pyrrolo[2,3-b]pyridin-5-yl)-benzoic acid

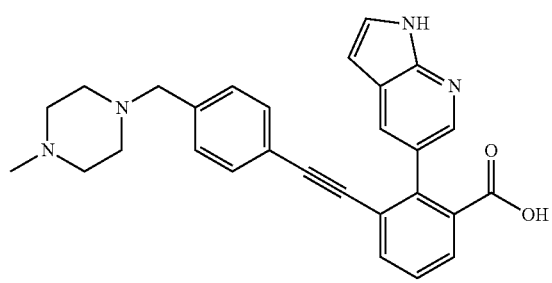

3-[4-(4-Methyl-piperazin-1-ylmethyl)-phenylethynyl]-2-(1H-pyrrolo[2,3-b]pyridin-5-yl)-benzoic acid was prepared by same procedure as Example 145. $^1$H NMR (300 MHz, CDCl$_3$) δ 8.40 (d, J=1.17 Hz, 1 H), 8.18 (d, J=1.47 Hz, 1 H), 8.02 (dd, J=7.62, 1.17 Hz, 1 H), 7.70-7.84 (m, 1 H), 7.42-7.58 (m, 2 H), 7.13 (d, J=8.21 Hz, 2 H), 6.98 (d, J=7.92 Hz, 2 H), 6.69 (d, J=3.52 Hz, 1 H), 3.66 (s, 2 H), 3.07-3.47 (m, 4 H), 2.87 (br s, 4 H), 2.74 (s, 3 H). MS (ESI) m/z 451 (M+1)$^+$.

Example 177

3-[4-(4-Methoxy-piperidin-1-ylmethyl)-phenylethynyl]-2-(1H-pyrrolo[2,3-b]pyridin-5-yl)-benzoic acid

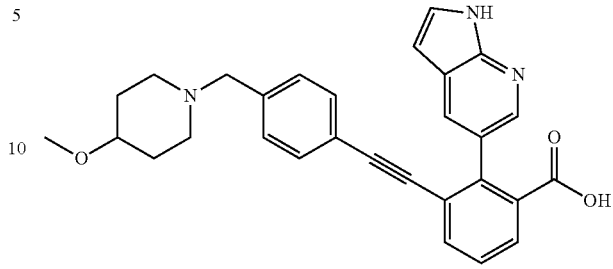

3-[4-(4-Methoxy-piperidin-1-ylmethyl)-phenylethynyl]-2-(1H-pyrrolo[2,3-b]pyridin-5-yl)-benzoic acid was prepared by same procedure as Example 145. $^1$H NMR (300 MHz, CDCl$_3$) δ 8.43 (d, J=1.47 Hz, 1 H), 8.11-8.23 (m, 1 H), 8.05 (dd, J=7.92, 1.17 Hz, 1 H), 7.79 (dd, J=7.62, 1.17 Hz, 1 H), 7.40-7.60 (m, 2 H), 7.13-7.32 (m, 2 H), 7.04 (d, J=8.21 Hz, 2 H), 6.71 (d, J=3.22 Hz, 1 H), 4.03 (s, 2 H), 3.70-3.81 (m, 4 H), 3.05-3.29 (m, 4 H), 1.79-2.09 (m, 4 H). MS (ESI) m/z 466.1 (M+1)$^+$.

Example 178

2-(1H-Indol-5-yl)-3-[4-(4-methoxy-piperidin-1-ylmethyl)-phenylethynyl]-benzoic acid

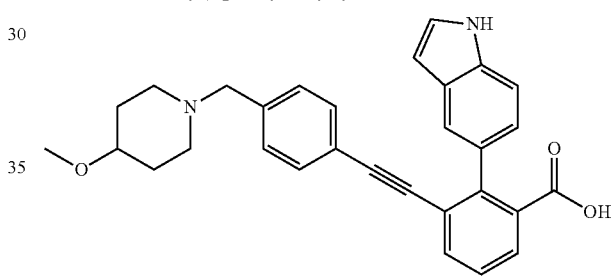

2-(1H-Indol-5-yl)-3-[4-(4-methoxy-piperidin-1-ylmethyl)-phenylethynyl]-benzoic acid was prepared by same procedure as Example 145. $^1$H NMR (300 MHz, CDCl$_3$) δ 7.77-7.88 (m, 1 H), 7.63-7.74 (m, 1 H), 7.59 (d, J=0.88 Hz, 1 H), 7.30-7.42 (m, 2 H), 7.05-7.22 (m, 4 H), 6.98 (d, J=8.21 Hz, 2 H), 6.47 (br d, J=3.22 Hz, 1 H), 3.96 (s, 2 H), 3.47 (br d, J=1.47 Hz, 1 H), 3.05-3.31 (m, 5 H), 2.60-2.95 (m, 2H), 1.73-2.06 (m, 4 H). MS (ESI) m/z 465.23 (M+1)$^+$.

Example 179

2-(1H-Indol-5-yl)-3-[4-(4-methanesulfonyl-piperazin-1-ylmethyl)-phenylethynyl]-benzoic acid

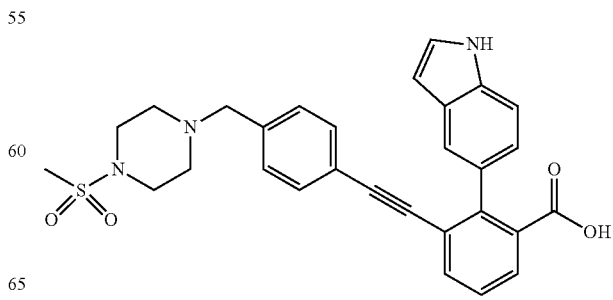

2-1H-Indol-5-yl)-3-[4-(4-methanesulfonyl-piperazin-1-ylmethyl)-phenylethynyl]-benzoic acid was prepared by same procedure as Example 145. ¹H NMR (300 MHz, CDCl₃) δ 7.81 (dd, J=7.77, 1.32 Hz, 1 H), 7.68 (dd, J=7.77, 1.32 Hz, 1 H), 7.53 (d, J=1.17 Hz, 1 H), 7.27-7.41 (m, 2 H), 7.17 (t, J=1.47 Hz, 1 H), 7.02-7.12 (m, 3 H), 6.92-7.02 (m, 2 H), 6.44 (d, J=2.64 Hz, 1 H), 3.95 (s, 2 H), 3.34 (br dd, J=3.22, 1.47 Hz, 2 H), 2.86-3.07 (m, 2 H), 2.47-2.86 (m, 7 H). MS (ESI) m/z 514.10 (M+1)⁺.

Example 180

3-[4-(4-Methanesulfonyl-piperazin-1-ylmethyl)-phenylethynyl]-2-(1H-pyrrolo[2,3-b]pyridin-5-yl)-benzoic acid

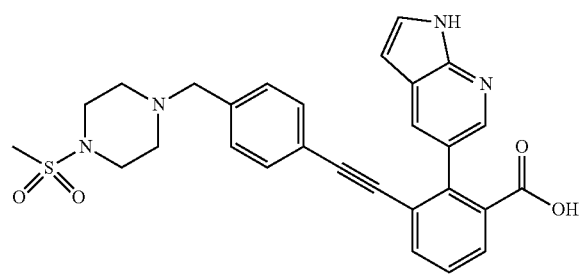 [SMILES: CS(=O)(=O)N1CCN(Cc2ccc(C#Cc3cccc(C(=O)O)c3-c3cnc4[nH]ccc4c3)cc2)CC1]

3-[4-(4-Methanesulfonyl-piperazin-1-ylmethyl)-phenyl-ethynyl]-2-(1H-pyrrolo[2,3-b]pyridin-5-yl)-benzoic acid was prepared by same procedure as Example 145. ¹H NMR (300 MHz, CDCl₃) δ ppm 8.37-8.54 (m, 1 H), 8.21 (s, 1 H), 8.02-8.15 (m, 1 H), 7.82 (dd, J=7.77, 1.32 Hz, 1 H), 7.44-7.64 (m, 2 H), 7.17-7.32 (m, 2 H), 7.08 (d, J=7.92 Hz, 2 H), 6.73 (d, J=3.52 Hz, 1 H), 4.11 (s, 2 H), 3.53 (br s, 4 H), 3.00-3.31 (m, 4 H), 2.82 (s, 3 H). MS (ESI) m/z 515.17 (M+1)⁺.

Example 181

3-[4-(4,4-Difluoro-piperidin-1-ylmethyl)-phenyl-ethynyl]-2-(1H-indol-5-yl)-benzoic acid

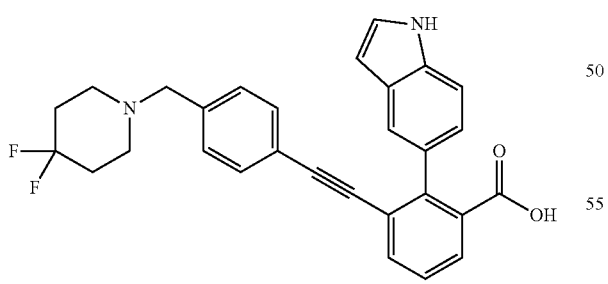

3-[4-(4,4-Difluoro-piperidin-1-ylmethyl)-phenylethy-nyl]-2-(1H-indol-5-yl)-benzoic acid was prepared by same procedure as Example 145. ¹H NMR (300 MHz, CDCl₃) δ 7.78 (dd, J=7.77, 1.03 Hz, 1 H), 7.67 (dd, J=7.77, 1.03 Hz, 1 H), 7.57 (d, J=1.47 Hz, 1 H), 7.30-7.41 (m, 2 H), 7.05-7.21 (m, 4 H), 6.95-7.05 (m, 2 H), 6.44 (d, J=3.22 Hz, 1 H), 3.99 (s, 2 H), 3.18-3.55 (m, 4 H), 2.81-3.17 (m, 2 H), 2.04-2.43 (m, 2 H). MS (ESI) m/z 471.08 (M+1)⁺.

Example 182

2-(1H-Indol-5-yl)-3-[4-(4-methyl-piperazin-1-ylm-ethyl)-phenylethynyl]-benzoic acid

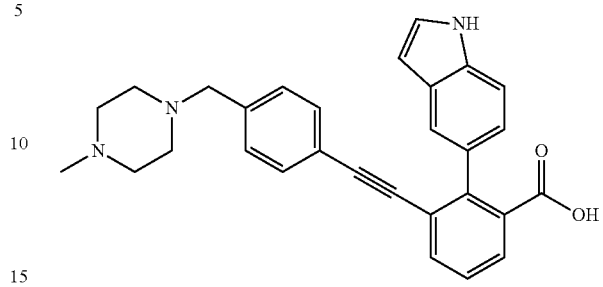

2-(1H-Indol-5-yl)-3-[4-(4-methyl-piperazin-1-ylmethyl)-phenylethynyl]-benzoic acid was prepared by same procedure as Example 145. ¹H NMR (300 MHz, CDCl₃) δ 7.89 (dd, J=7.77, 1.32 Hz, 1 H), 7.72 (dd. J=7.62, 1.47 Hz, 1 H), 7.33-7.50 (m, 2 H), 7.19 (d, J=8.50 Hz, 1 H), 7.02-7.15 (m, 3 H), 6.83-6.97 (m, 3 H), 6.36 (dd, J=3.22, 0.88 Hz, 1 H), 3.87 (s, 2 H), 2.97 (br d, J=5.86 Hz, 8 H), 2.62 (s, 3 H). MS (ESI) m/z 450.17 (M+1)⁺.

Example 183

3-[4-(4-Ethanesulfonyl-piperazin-1-ylmethyl)-phe-nylethynyl]-2-(1H-indol-6-yl)-benzoic acid

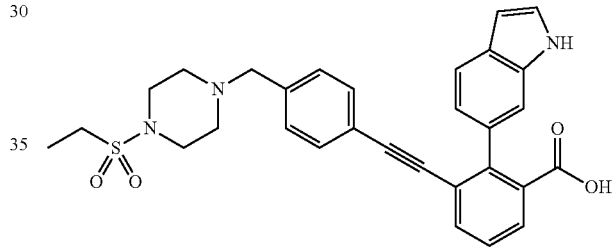

3-[4-(4-Ethanesulfonyl-piperazin-1-ylmethyl)-phenyl-ethynyl]-2-(1H-indol-6-yl)-benzoic acid was prepared by same procedure as Example 145. ¹H NMR (300 MHz, CDCl₃) δ=7.85 (d, J=7.9 Hz, 1 H), 7.74 (td, J=1.2, 7.8 Hz, 1 H), 7.66 (d, J=7.8 Hz, 1 H), 7.37-7.49 (m, 2 H), 7.13-7.25 (m, 4 H), 7.03-7.10 (m, 2 H), 6.45-6.49 (m, 1 H), 4.10 (s, 2 H), 3.56-3.69 (m, 4 H), 2.96-3.12 (m, 6 H), 1.38 (t, J=7.6 Hz, 3 H). MS (ESI) m/z 528.33 (M+1)⁺.

Example 184

3-[4-(1,1-Dioxo-hexahydro-1-thiopyran-4-yloxy)-phenylethynyl]-2-(1H-indol-5-yl)-benzoic acid

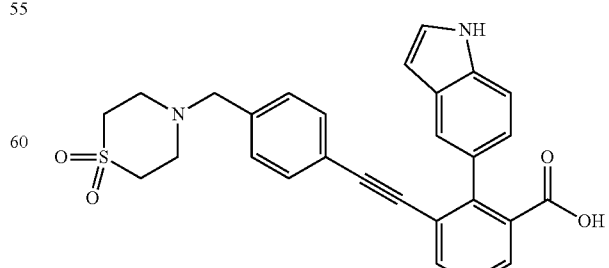

3-[4-(1,1-Dioxo-hexahydro-1-thiopyran-4-yloxy)-phenylethynyl]-2-(1H-indol-5-yl)-benzoic acid was prepared by same procedure as Example 1. ¹H NMR (300 MHz, CDCl₃) δ 8.22 (br s, 1 H), 7.62-7.81 (m, 3 H), 7.30-7.46 (m, 2 H), 7.18-7.30 (m, 2 H), 6.98-7.18 (m, 2 H), 6.63-6.82 (m, 2 H), 6.57 (br s, 1 H), 4.52-4.65 (m, 1 H), 3.25-3.41 (m, 2 H), 2.82-2.90 (m, 2 H), 2.20-2.49 (m, 4 H). MS (ESI) m/z 486.14 (M+1)⁺.

Example 185

3-[4-(1,1-Dioxo-hexahydro-thiopyran-4-yloxy)-phenylethynyl]-2-(1H-indazol-6-yl)-benzoic acid

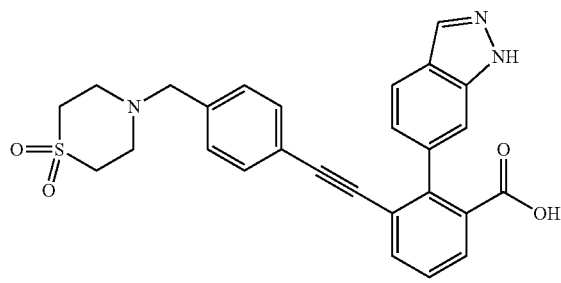 [SMILES: O=C(O)c1cccc(C#Cc2ccc(CN3CCS(=O)(=O)CC3)cc2)c1-c1ccc2cn[nH]c2c1]

3-[4-(1,1-Dioxo-hexahydro-thiopyran-4-yloxy)-phenylethynyl]-2-(1H-indazol-6-yl)-benzoic acid was prepared by the same procedure as Example 1. ¹H NMR (300 MHz, CD₃OD) δ=8.08 (s, 1 H), 7.67-7.81 (m, 3 H), 7.42-7.55 (m, 2 H), 7.18 (d, J=8.2 Hz, 1 H), 6.91-6.96 (m, 2 H), 6.81-6.86 (m, 2 H), 4.62-4.70 (m, 1 H), 3.20-3.26 (m, 2 H), 2.95-3.06 (m, 2 H), 2.22-2.36 (m, 4 H). MS (ESI) m/z 487.08 (M+1)⁺.

Example 186

3-[2-Fluoro-4-(tetrahydro-pyran-4-yloxymethyl)-phenylethynyl]-2-(1H-indol-6-yl)-benzoic acid

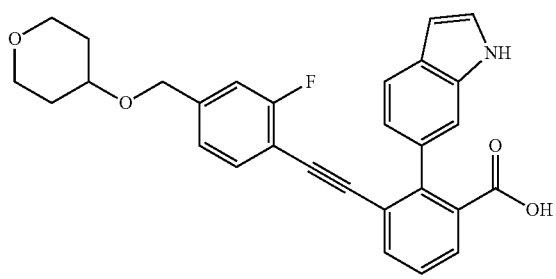 [SMILES: O=C(O)c1cccc(C#Cc2ccc(COC3CCOCC3)cc2F)c1-c1ccc2cc[nH]c2c1]

3-[2-Fluoro-4-(tetrahydro-pyran-4-yloxymethyl)-phenylethynyl]-2-(1H-indol-6-yl)-benzoic acid was prepared by the same procedure as Example 1. ¹H NMR (300 MHz, CDCl₃) δ 8.25 (br s, 1 H), 7.89 (dd, J=7.77, 1.32 Hz, 1 H), 7.81 (dd, J=7.92, 1.47 Hz, 1 H), 7.67 (d, J=7.92 Hz, 1 H), 7.34-7.55 (m, 2 H), 7.25-7.21 (m, 1 H), 7.15 (dd, J=8.06, 1.61 Hz, 1 H), 6.98 (br d, J=10.26 Hz, 1 H), 6.83-6.93 (m, 2 H), 6.58 (dt, J=2.05, 1.03 Hz, 1 H), 4.47 (s, 2 H), 3.96 (dt, J=11.87, 4.32 Hz, 2 H), 3.37-3.64 (m, 3 H), 1.77-1.98 (m, 2 H), 1.48-1.77 (m, 2 H). MS (ESI) m/z 470 (M+1)⁺.

Example 187

3-[4-(1,1-Dioxo-hexahydro-1-thiopyran-4-yloxymethyl)-2-fluoro-phenylethynyl]-2-(1H-indol-6-yl)-benzoic acid

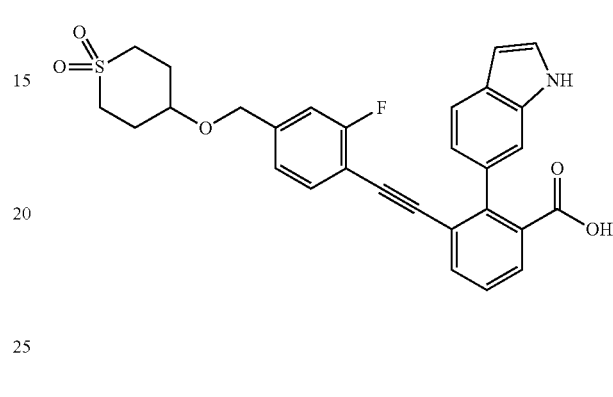

3-[4-(1,1-Dioxo-hexahydro-1-thiopyran-4-yloxymethyl)-2-fluoro-phenylethynyl]-2-(1H-indol-6-yl)-benzoic acid was prepared by the same procedure as Example 1. ¹H NMR (300 MHz, CDCl₃) 7.79 (dd, J=10.41, 7.77 Hz, 2 H), 7.65 (d, J=8.21 Hz, 1 H), 7.48 (d, J=1.47 Hz, 1 H), 7.40 (t, J=7.77 Hz, 1 H), 7.13-7.28 (m, 2 H), 6.83-7.02 (m, 3 H), 6.48 (dt, J=2.05, 1.03 Hz, 1 H), 4.46 (s, 2 H), 3.61-3.80 (m, 1 H), 3.20-3.40 (m, 2 H), 2.80-2.99 (m, 2 H), 2.06-2.44 (m, 4 H). MS (ESI) m/z 518 (M+1)⁺.

Example 188

2-(1H-Indol-6-yl)-3-[4-(2-methanesulfonyl-2,7-diaza-spiro[3.5]non-7-ylmethyl)-phenylethynyl]-benzoic acid

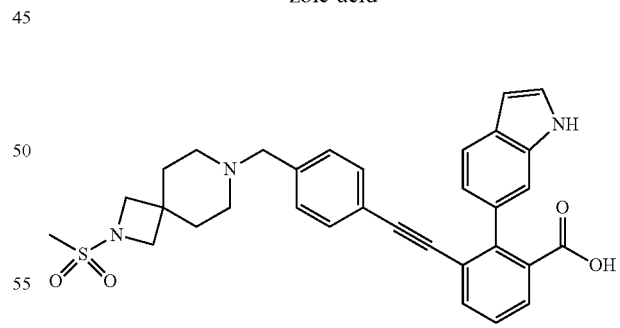

2-(1H-Indol-6-yl)-3-[4-(2-methanesulfonyl-2,7-diaza-spiro[3.5]non-7-ylmethyl)-phenyl ethynyl]-benzoic acid was prepared by the same procedure as Example 58. ¹H NMR (300 MHz, CDCl₃) δ 7.84 (dd, J=7.62, 1.47 Hz, 2 H), 7.74 (dd, J=7.77, 1.32 Hz, 1 H), 7.64 (d, J=8.21 Hz, 1 H), 7.34-7.52 (m, 2 H), 7.04-7.32 (m, 5 H), 6.49 (dd, J=3.22, 0.88 Hz, 1 H), 4.05 (s, 2 H), 3.61-3.68 (m, 2 H), 3.41 (dt, J=3.22, 1.61 Hz, 2 H), 2.86 (s, 3 H), 2.13-2.44 (m, 4 H), 1.77-2.13 (m, 4 H). MS (ESI) m/z 554.2 (M+1)⁺.

Example 189

2-(1H-Indol-6-yl)-3-[4-(5-methanesulfonyl-hexahydro-pyrrolo[3,4-c]pyrrol-2-ylmethyl)-phenylethynyl]-benzoic acid

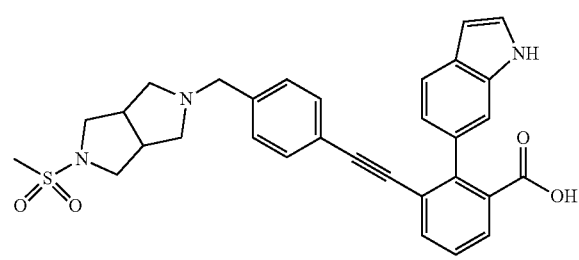 [SMILES: CS(=O)(=O)N1CC2CN(Cc3ccc(C#Cc4cccc(C(=O)O)c4-c4ccc5cc[nH]c5c4)cc3)CC2C1]

2-(1H-Indol-6-yl)-3-[4-(5-methanesulfonyl-hexahydro-pyrrolo[3,4-c]pyrrol-2-ylmethyl)-phenylethynyl]-benzoic acid was prepared by same procedure as Example 58. $^1$H NMR (300 MHz, CD$_3$OD) δ 7.74 (ddd, J=7.84, 6.38, 1.32 Hz, 2 H), 7.58 (d, J=8.21 Hz, 1 H), 7.37-7.50 (m, 2 H), 7.34 (d, J=8.21 Hz, 2 H), 7.27 (d, J=2.93 Hz, 1 H), 7.09-7.19 (m, 2 H), 7.01-7.09 (m, 1 H), 6.49 (dd, J=3.22, 0.88 Hz, 1 H), 4.33 (s, 2 H), 3.75-3.63 (m, 2 H) 3.28-3.42 (m, 6 H), 3.15-3.00 (m, 2 H), 2.87 (s, 3 H). MS (ESI) m/z 540.2 (M+1)$^+$.

Example 190

3-[4-(4-Cyclopropanesulfonyl-piperazin-1-ylmethyl)-phenyl ethynyl]-2-(1H-indol-6-yl)-benzoic acid

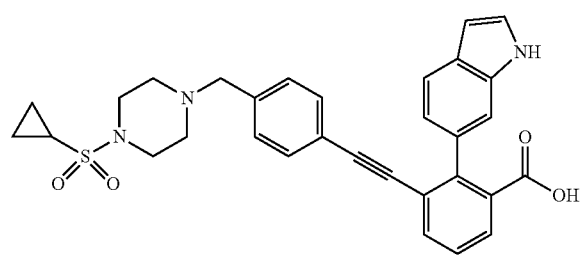 [SMILES: O=C(O)c1cccc(C#Cc2ccc(CN3CCN(S(=O)(=O)C4CC4)CC3)cc2)c1-c1ccc2cc[nH]c2c1]

3-[4-(4-Cyclopropanesulfonyl-piperazin-1-ylmethyl)-phenylethynyl]-2-(1H-indol-6-yl)-benzoic acid was prepared by same procedure as Example 58. $^1$H NMR (300 MHz, CD$_3$OD) δ 7.65-7.88 (m, 2 H), 7.58 (dd, J=8.21, 0.88 Hz, 1 H), 7.38-7.51 (m, 2 H), 7.21-7.38 (m, 3 H), 7.09-7.21 (m, 2 H), 7.04 (dd, J=8.21, 1.76 Hz, 1 H), 6.49 (dd, J=3.22, 0.88 Hz, 1 H), 4.28 (s, 2 H), 3.60-3.42 (m, 2 H), 3.17-3.12 (m, 6 H), 2.56-2.49 (m, 1 H), 1.05-1.11 (m, 4 H). MS (ESI) m/z 540.24 (M+1)$^+$.

Example 191

2-(1H-Indol-6-yl)-3-(4-[4-(propane-2-sulfonyl)-piperazin-1-ylmethyl]-phenylethynyl)-benzoic acid

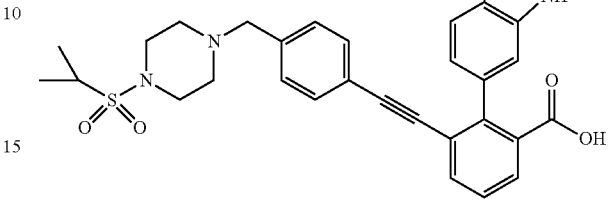

2-(1H-Indol-6-yl)-3-{4-[4-(propane-2-sulfonyl)-piperazin-1-ylmethyl]-phenylethynyl}-benzoic acid was prepared by same procedure as Example 58. $^1$H NMR (300 MHz, CD$_3$OD) δ 7.74 (ddd, J=7.84, 6.52, 1.17 Hz, 2 H), 7.49-7.65 (m, 1 H), 7.38-7.49 (m, 2 H), 7.30-7.38 (m, 2 H), 7.24-7.30 (m, 1 H), 7.08-7.19 (m, 2 H), 7.04 (dd, J=8.21, 1.47 Hz, 1 H), 6.49 (dd, J=3.22, 0.88 Hz, 1 H), 4.30 (s, 2 H), 3.62-3.45 (m, 4 H), 3.29-3.36 (m, 1 H), 3.13-3.29 (m, 4 H), 1.31 (d, J=6.74 Hz, 6 H). MS (ESI) m/z 542.13 (M+1)$^+$.

Example 192

2-(1H-Indol-6-yl)-3-[4-(7-methanesulfonyl-2,7-diaza-spiro[3.5]non-2-ylmethyl)-phenylethynyl]-benzoic acid 2-(1H-Indol-6-yl)-3-[4-(7-methanesulfonyl-2,7-diaza-spiro[3.5]non-2-ylmethyl)-phenyl ethynyl]-benzoic acid was prepared by same procedure as Example 58. $^1$H NMR (300 MHz, CD$_3$OD) δ 7.74 (td, J=−7.62, 1.47 Hz, 2 H), 7.57 (d, J=8.21 Hz, 1 H), 7.37-7.51 (m, 3 H), 7.21-7.37 (m, 2 H), 7.08-7.21 (m, 2 H), 7.04 (dd, =8.06, 1.61 Hz, 1 H), 6.48 (dd, J=3.22, 0.88 Hz, 1 H), 4.33 (s, 2 H), 3.94 (s, 4 H), 3.10-3.24 (m, 4 H), 2.80 (s, 3 H), 1.86-2.05 (m, 4 H). MS (ESI) m/z 554.16 (M+1)$^+$.

Example 193

2-(1H-Indol-5-yl)-3-[4-(tetrahydro-pyran-4-yloxy)-phenylethynyl]-benzoic acid

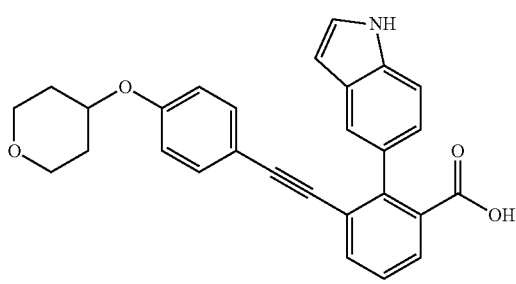

2-(1H-Indol-5-yl)-3-[4-(tetrahydro-pyran-4-yloxy)-phenylethynyl]-benzoic acid was prepared by same procedure as Example 1. H NMR (300 MHz, CD$_3$OD) 7.53-7.74 (m, 3H), 7.30-7.49 (m, 2 H), 7.25 (t, J=1.61 Hz, 1 H), 7.14 (dd, J=8.35, 1.61 Hz, 1 H), 6.91-7.05 (m, 2 H), 6.67-6.77 (m, 2 H), 6.47 (dd, J=3.22, 0.88 Hz, 1 H), 4.45 (tt, J=8.03, 3.99 Hz, 1 H), 3.76-3.97 (m, 2 H), 3.51 (ddd, J=11.73, 8.65, 3.08 Hz, 2 H), 1.79-2.03 (m, 2 H), 1.61 (dtd, J=12.94, 8.56, 8.56, 3.96 Hz, 2 H). MS (ESI) m/z 438.15 (M+1)$^+$.

Example 194

-(N,N-dimethylsulfamoyl)-2-(1H-indol-6-yl)-3-((4-(((tetrahydro-2H-pyran-4-yl)oxy)methyl)phenyl) ethynyl)benzamide

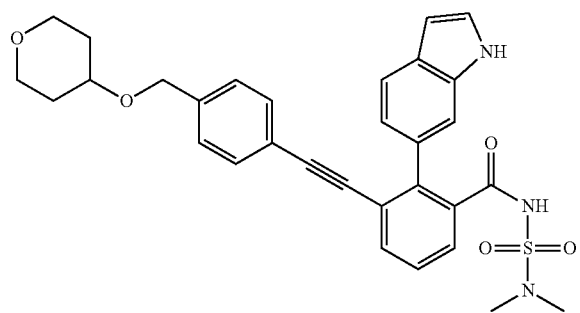 [SMILES: CN(C)S(=O)(=O)NC(=O)c1cccc(C#Cc2ccc(COC3CCOCC3)cc2)c1-c1ccc2cc[nH]c2c1]

2-(1H-Indol-6-yl)-3-[4-(tetrahydro-pyran-4-yloxymethyl)-phenylethynyl]-benzoic acid (45.1 mg, 0.1 mmol) and dimethylsulfamoyl amine (149 mg, 0.14 mmol) were dissolved in N,N-dimethylformamide (1 mL), followed by the addition of 1-ethyl-3-(3-dimethylaminopropyl) carbodiimide hydrochloride (1.2 eq), 4-dimethylaminopyridine (2 eq) and hydroxybenzotriazole (1.2 eq). The reaction was stirred at room temperature for 16 hours. The solvent was then evaporated to dryness and reaction mixture was purified by preparative HPLC to give product as an off-white solid in 68% yield. $^1$H NMR (300 MHz, CDCl$_3$) δ ppm 8.39 (br, s., 1 H) 7.71-7.86 (m, 3 H) 7.54 (s, 1 H) 7.39-7.51 (m, 2 H) 7.20-7.33 (m, 4 H) 7.16 (d, J=7.92 Hz, 2 H) 7.01 (d, J=8.21 Hz, 2 H) 6.63 (br, s., 1 H) 4.49 (s, 2 H) 3.88-4.06 (m, 2 H) 3.37-3.61 (m, 3 H) 2.56 (s, 6 H) 1.82-1.99 (m, 2 H) 1.54-1.75 (m, 2 H). MS m/z (M+H) 558.2.

Example 195

2-(1H-indol-6-yl)-N-(methylsulfonyl)-3-((4-(((tetrahydro-2H-pyran-4-yl)oxy)methyl)phenyl)ethynyl) benzamide

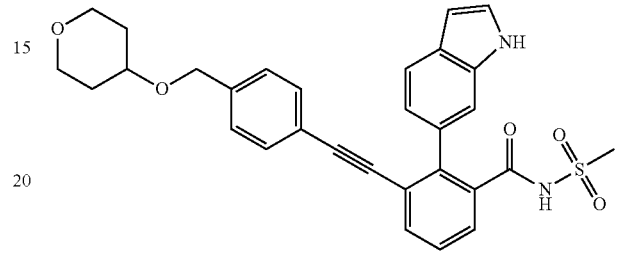

2-(1H-indol-6-yl)-N-(methylsulfonyl)-3-((4-(((tetrahydro-2H-pyran-4-yl)oxy)methyl)phenyl) ethynyl)benzamide was prepared by same procedure as Example 194. $^1$H NMR (300 MHz, DMSO-d$_6$) δ ppm 12.18 (br, s., 1 H) 11.34 (br, s., 1 H) 7.84 (dd, J=7.48, 1.32 Hz, 1 H) 7.68 (d, J=7.92 Hz, 1 H) 7.52-7.64 (m, 3 H) 7.48 (t, J=2.64 Hz, 1 H) 7.29-7.37 (m, 2 H) 7.14-7.27 (m, 3 H) 6.54 (br, s., 1 H) 4.55 (s, 2 H) 3.85 (dt, J=11.58, 4.18 Hz, 2 H) 3.58 (tt, J=8.80, 4.25 Hz, 1 H) 3.31-3.45 (m, 2 H) 2.95 (s, 3 H) 1.91 (dd, J=12.90, 3.52 Hz, 2 H) 1.40-1.60 (m, 2 H). MS m/z (M+H) 529.2

Example 196

6-[2-[4-(Tetrahydro-pyran-4-yloxymethyl)-phenylethynyl]-6-(1H-tetrazol-5-yl)-phenyl]-1H-indole

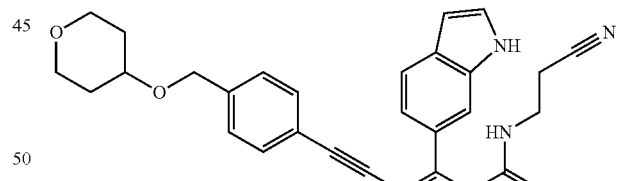

N-(2-Cyanoethyl)-2-(1H-indol-6-yl)-3-((4-(((tetra hydro-2H-pyran-4-yl)oxy)methyl) phenyl)ethynyl)benzamide: 2-(1H-Indol-6-yl)-3-[4-(tetrahydro-pyran-4-yloxymethyl)-phenylethynyl] benzoic acid (451 mg, 1 mmol) and 3-aminopropanenitrile (77 mg, 1.1 mmol) were dissolved in DMF, followed by the addition of 1-ethyl-3-(3-dirmethyl-amino propyl) carbodiimide hydrochloride (1.2 eq), N,N-diisopropylethylamine (2 eq) and hydroxybenzo triazole (1.2 eq). The reaction was stirred at room temperature for 16 hours. The solvent was evaporated and reaction mixture was purified by preparative HPLC to give product as a white solid in 98% yield.

227

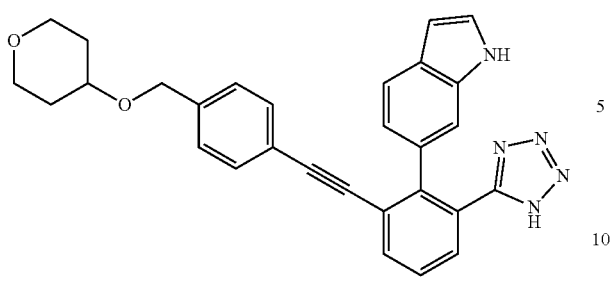

6-[2-[4-(Tetrahydro-pyran-4-yloxymethyl)-phenyl ethynyl]-6-(1H-tetrazol-5-yl)-phenyl]-1H-indole: N-(2-cyanoethyl)-2-(1H-indol-6-yl)-3-((4-(((tetrahydro-2H-pyran-4-yl)oxy) methyl)phenyl) ethynyl)benzamide (500 mg, 1 mmol), diisopropyl azodicarboxylate (808 mg, 4 mmol) triphenylphosphine (1048 mg, 4 mmol) and trimethylsilyl azide (460 mg, 4 mmol) and tetrahydrofuran (5 mL) were added to a vial under nitrogen. After stirring for 24 hours at ambient temperature, 4 additional equivalents of diisopropyl azodicarboxylate (808 mg, 4 mmol) triphenylphosphine (1048 mg, 4 mmol) and trimethylsilyl azide were added to reaction mixture and stirred for an additional 24 hours. The reaction was concentrated at reduced pressure behind a shield. Tetrahydrofuran (5 mL) and 2 M aqueous sodium hydroxide (5 mL) was added to the reaction mixture and stirred for 4 hours. The tetrahydrofuran was removed by evaporation. 10 ml water and 10 ml diethyl ether were added and layer is separated. The aqueous layer was washed with 3×2 mL diethyl ether. 2 M aqueous hydrogen chloride (5 mL) was added to the aqueous layer to acidify the solution. Water was removed by evaporation and the resulting material was dissolved in N,N-dimethylformamide and purified via preparative HPLC to yield product as white foam in 48% yield. $^1$H NMR (300 MHz, CDCl$_3$) δ ppm 9.71 (br, s., 1 H) 8.50 (br, s., 1 H) 8.30 (d, J=7.92 Hz, 1 H) 7.81 (t, J=-8.06 Hz, 2 H) 7.46-7.60 (m, 1 H) 7.31-7.38 (m, 2 H) 7.06-7.22 (m, 3 H) 6.93 (d, J=8.21 Hz, 2 H) 6.68 (br, s., 1 H) 4.48 (s, 2 H) 3.86-4.13 (m, 2 H) 3.31-3.72 (m, 3 H) 1.82-1.98 (m, 2 H) 1.53-1.73 (m, 2 H). MS m/z (M+H) 476.2

Example 197

3-[4-(Benzoylamino-methyl)-phenylethynyl]-2-(1H-indol-6-yl)-benzoic acid

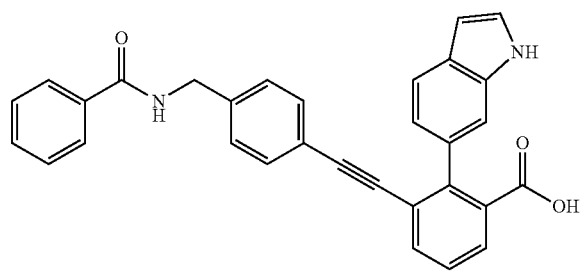 [SMILES: O=C(NCc1ccc(C#Cc2cccc(C(=O)O)c2-c2ccc3cc[nH]c3c2)cc1)c1ccccc1]

3-[4-(Benzoylamino-methyl)-phenylethynyl]-2-(1H-indol-6-yl)-benzoic acid was prepared by same procedure as Example 1. $^1$H NMR (300 MHz, CD$_3$OD) δ 7.75-7.85 (m, 2 H), 7.70 (d, J=7.62 Hz, 2 H), 7.30-7.60 (m, 6 H), 7.23-7.28

228

(m 1 H), 7.17 (d, J=7.92 Hz, 2 H), 6.95-7.10 (m, 3 H), 6.48 (d, J=3.15 Hz, 1 H), 4.49 (s, 2 H). MS (ESI) m/z 471.49 (M+1)$^+$.

Example 198

2-(1H-Indol-6-yl)-3-(4-{[(4-oxo-cyclohexanecarbonyl)-amino]-methyl}-phenylethynyl)-benzoic acid

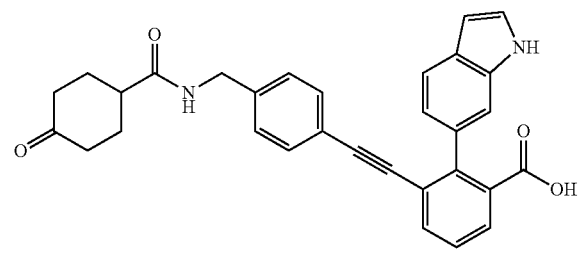 [SMILES: O=C1CCC(C(=O)NCc2ccc(C#Cc3cccc(C(=O)O)c3-c3ccc4cc[nH]c4c3)cc2)CC1]

2-(1H-Indol-6-yl)-3-(4-{[(4-oxo-cyclohexanecarbonyl)-amino]-methyl}-phenylethynyl)-benzoic acid; A was prepared by same procedure as Example 1. $^1$H NMR (300 MHz, CD$_3$OD) δ 7.69 (d, J=7.62 Hz, 2 H), 7.57 (d, J=7.92 Hz, 1 H), 7.33-7.48 (m, 2 H), 7.26 (t, J=1.61 Hz, 1 H), 6.91-7.13 (m, 5 H), 6.48 (d, J=2.93 Hz, 1 H), 4.26 (s, 2 H), 2.18-2.25 (m, 1 H), 1.97-2.12 (m, 2 H), 1.54-1.75 (m, 4 H), 1.18-1.44 (m, 2 H). MS (ESI) m/z 490.86 (M+H)$^+$.

Example 199

2-(1H-Indol-6-yl)-3-[4-(4-oxo-cyclohexylcarbamoyl)-phenyl ethynyl]-benzoic acid

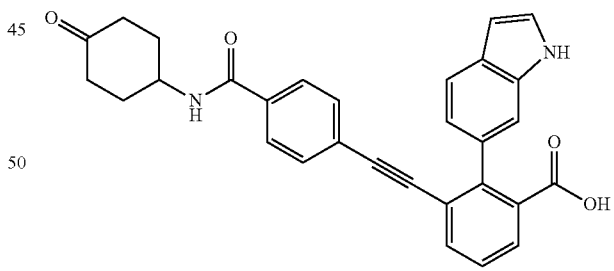

2-(1H-Indol-6-yl)-3-[4-(4-oxo-cyclohexylcarbamoyl)-phenylethynyl]-benzoic acid was prepared by same procedure as Example 1. $^1$H NMR (300 MHz, CD$_3$OD) δ 7.67-7.82 (m, 2 H), 7.50-7.67 (m, 3 H), 7.36-7.50 (m, 2 H), 7.21-7.31 (m, 1 H), 6.94-7.14 (m, 3 H), 6.41-6.56 (m, 1 H), 3.80-3.94 (m, 1 H), 2.44-2.67 (m, 1 H), 2.09-2.44 (m, 2 H), 1.67-2.07 (m 3 H), 1.36-1.67 (m, 2 H). MS (ESI) m/z 477.19 (M+1)$^+$.

Example 200

3-[4-(2-Amino-4,5,6,7-tetrahydro-benzothiazol-6-ylcarbamoyl)-phenylethynyl]-2-(1H-indol-6-yl)-benzoic acid

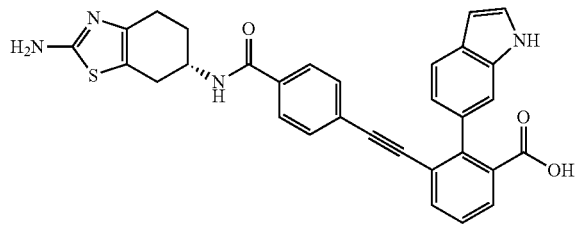 [SMILES: Nc1nc2c(s1)C[C@@H](NC(=O)c1ccc(C#Cc3cccc(C(=O)O)c3-c3ccc4cc[nH]c4c3)cc1)CC2]

3-[4-(2-Amino-4,5,6,7-tetrahydro-benzothiazol-6-ylcarbamoyl)-phenylethynyl]-2-(1H-indol-6-yl)-benzoic acid was prepared by same procedure as Example 1. ¹H NMR (300 MHz, CD₃OD) δ 7.67-7.82 (m, 2 H), 7.53-7.67 (m, 3 H), 7.37-7.53 (m, 2 H), 7.22-7.33 (m, 1 H), 6.98-7.16 (m, 3 H), 6.49 (d, J=3.21 Hz, 1 H), 4.18-4.45 (m, 1 H), 2.90 (br dd, J=15.83, 5.28 Hz, 1 H), 2.65 (br s, 2 H), 2.42

Example 201

3-[4-(2-Amino-4,5,6,7-tetrahydro-benzothiazol-6-ylcarbamoyl)-phenylethynyl]-2-(1H-indol-6-yl)-benzoic acid

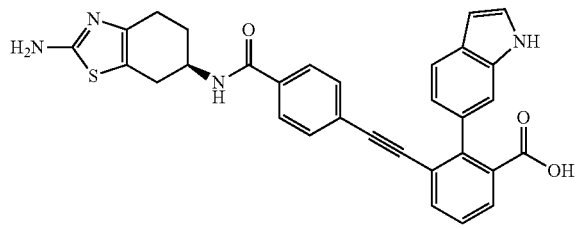 [SMILES: Nc1nc2c(s1)C[C@H](NC(=O)c1ccc(C#Cc3cccc(C(=O)O)c3-c3ccc4cc[nH]c4c3)cc1)CC2]

3-[4-(2-Amino-4,5,6,7-tetrahydro-benzothiazol-6-ylcarbamoyl)-phenylethynyl 1]-2-(1H-indol-6-yl)-benzoic acid was prepared by same procedure as Example 1. ¹H NMR (300 MHz, CD₃OD) δ 7.68-7.80 (m, 2 H), 7.54-7.67 (m, 3 H), 7.32-7.50 (m, 2 H), 7.21-7.32 (m, 1 H), 6.98-7.15 (m, 3 H), 6.49 (dd, J=3.22, 0.88 Hz, 1 H), 4.26-4.42 (m, 1 H), 2.87 (br dd, J=15.98, 5.13 Hz, 1 H), 2.63 (br s, 2 H), 2.51 (br dd, J=15.83, 8.79 Hz, 1 H), 2.02-2.19 (m, 1 H), 1.81-2.02 (m, 1 H). MS (ESI) m/z 533.18 (M+1)⁺.

Example 202

2-(1H-Indol-6-yl)-3-[4-(4-methyl-piperazine-1-carbonyl)-phenylethynyl]-benzoic acid

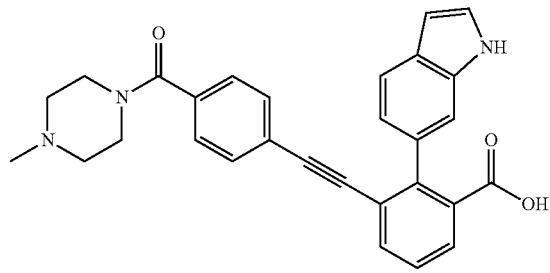 [SMILES: CN1CCN(C(=O)c2ccc(C#Cc3cccc(C(=O)O)c3-c3ccc4cc[nH]c4c3)cc2)CC1]

2-(1H-Indol-6-yl)-3-[4-(4-methyl-piperazine-1-carbonyl)-phenylethynyl]-benzoic acid was prepared by same procedure as Example 1. ¹H NMR (300 MHz, CDCl₃) δ 7.85 (dt, J=7.55, 1.21 Hz, 1 H), 7.70-7.81 (m, 1 H), 7.55-7.70 (m, 1 H), 7.37-7.50 (m, 2 H), 7.14-7.26 (m 4 H), 7.09 (d, J=-7.33 Hz, 2 H), 6.52 (br d, J=2.93 Hz, 1 H), 3.62-3.97 (m, 2 H), 3.41-3.45 (m, 2 H), 2.88-3.26 (m, 4 H), 2.80 (s, 3 H). MS (ESI) m/z 464.28 (M+1)⁺.

Example 203

2-(1H-Indol-6-yl)-3-[4-(4-methoxy-piperidine-1-carbonyl)-phenylethynyl]-benzoic acid

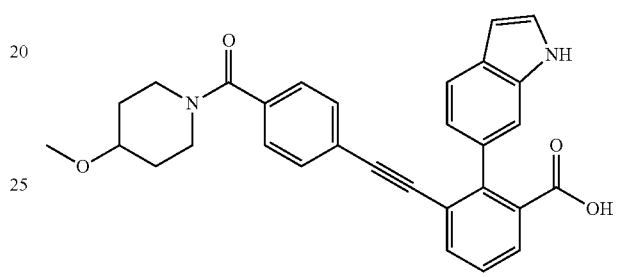

2-(1H-Indol-6-yl)-3-[4-(4-methoxy-piperidine-1-carbonyl)-phenylethynyl]-benzoic acid was prepared by same procedure as Example 1. ¹H NMR (300 MHz, CDCl₃) δ 8.25 (br s, 1 H), 7.83-7.98 (m 1 H), 7.77 (dt, J=7.48, 1.10 Hz; 1 H), 7.68 (d, J=8.21 Hz; 1 H), 7.33-7.50 (m, 2 H), 7.09-7.23 (m, 4 H), 6.92-7.09 (m, 2 H), 6.58 (ddd, J=3.22, 2.05, 0.88 Hz, 1 H), 3.50-3.41 (m 3 H), 3.35 (s, 3 H), 2.38-2.53 (m, 6 H). MS (ESI) m/z 479.4 (M+1)⁺.

Example 204

2-(1H-Indazol-6-yl)-3-[4-(4-methanesulfonyl-piperazin-1-ylmethyl)-phenylethynyl]-benzoic acid

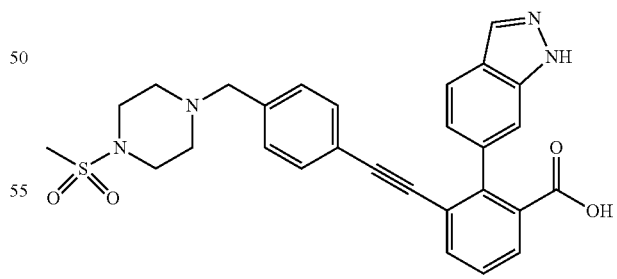

2-(1H-Indazol-6-yl)-3-[4-(4-methanesulfonyl-piperazin-1-ylmethyl)-phenylethynyl]-benzoic acid was prepared by same procedure as Example 145. ¹H NMR (300 MHz, CDCl₃) δ 8.12 (br d, J=2.05 Hz, 1 H), 7.70-7.94 (m, 3 H), 7.37-7.55 (m, 2 H), 7.09-7.26 (m, 3 H), 7.04 (d, J=8.21 Hz, 2 H), 4.12 (s, 2 H), 3.52-3.67 (m, 4 H), 3.04-3.31 (m, 4 H), 2.87 (s, 3 H). MS (ESI) m/z 515.2 (M+1)*.

Example 205

2-(1H-Indol-6-yl)-3-[4-(4-sulfamoyl-piperazin-1-ylmethyl)-phenylethynyl]-benzoic acid

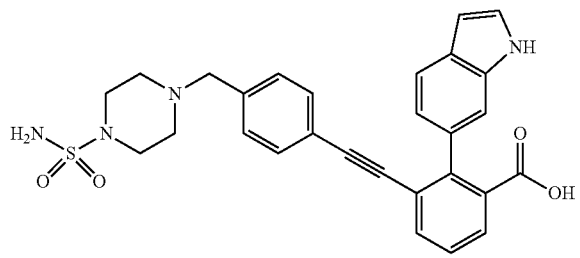 [SMILES: NS(=O)(=O)N1CCN(Cc2ccc(C#Cc3cccc(C(=O)O)c3-c3ccc4cc[nH]c4c3)cc2)CC1]

2-(1H-Indol-6-yl)-3-[4-(4-sulfamoyl-piperazin-1-ylmethyl)-phenylethynyl]-benzoic acid was prepared by same procedure as Example 145. $^1$H NMR (300 MHz, CD$_3$OD) δ 7.74 (ddd, J=7.62, 6.16, 1.17 Hz, 2 H), 7.58 (d, J=7.92 Hz, 1 H), 7.39-7.49 (m, 2 H), 7.26-7.37 (m, 3 H), 7.11-7.17 (m, 2 H), 7.05 (dd, J=8.21, 1.47 Hz, 1 H), 6.49 (dd, J=3.08, 1.03 Hz, 1 H), 4.30 (s, 3 H). MS (ESI) m/z 515.23 (M+1)$^+$.

Example 206

Inhibition of 5'-Biotin-oPL4624 Binding to his-EBNA1 Using Alpha Screen Technology Assays were performed using the DNA binding domain of EBNA1 (amino acids 459-607), which was His-tagged (His-EBNA1) and the self-complementary biotinylated (bt) oligonucleotide with the sequence 5'-bt-GGGTAGCATAT-GCTATCTAGATAGCAT-ATGCTACCC-3' (bt-oPL4624; or 5'-bt-SEQ ID NO: 1). The protein was expressed in E. coli and purified according to Barwell, et al., 1995, J Biol Chem. 270:20556-9.). The bt-oPL4624 oligonucleotide was purchased from Integrated DNA Technologies, Inc (IDT). AlphaScreen donor, acceptor beads and white, opaque 384-well assay plates were purchased from PerkinElmer, Inc.

Assays contained 15 nM His-EBNA1, 0.2 nM bt-oPL4624, 5 µg/mL AlphaScreen streptavidin donor beads and nickel chelate acceptor beads, and a series of concentrations of test compound ranging from 3.2 nM to 100 µM in a total volume of 40 µL assay buffer (25 mM Tris, pH 7.2, 160 mM NaCl, 1 mM MgCl$_2$). His-EBNA1 (30 nM) and bt-oPL4624 (0.4 nM) were preincubated with 10 µg/mL nickel chelate AlphaScreen acceptor bead, or 10 µg/mL streptavidin AlphaScreen donor bead, respectively, for 30 minutes at room temperature in assay buffer. Twenty microliters of His-EBNA1/acceptor bead mix and bt-oPL4624/donor bead mix were transferred to assay plates containing 0.4 µL of 1:3 serial dilutions of test compounds previously prepared in DMSO at concentrations ranging from 0.32 µM to 10 mM. Non-specific binding was determined with 5 µg/mL AlphaScreen acceptor bead in the absence of His-EBNA1. After 2 hr incubation at room temperature, the AlphaScreen signal was measured on the Envision plate reader (PerkinElmer, Inc.) at 680 nm excitation and 570 nm emission. Inhibition values at each concentration of test compound were determined by setting 100% equal to raw data values in the absence of EBNA1 and 0% equal to the raw data values in the presence of EBNA1. Nonlinear regression fits of the inhibition values to a one-site dose-response equation were performed using GraphPad Prism.

Example 207

Cell Based Luciferase Assay of EBNA1 Inhibition

In vivo inhibition of EBNA1 was determined for compounds of the disclosure using a cell based luciferase reporter assay. EBNA1 binding to the Family of Repeat (FR) region is essential for EBV latent infection and host-cell viability, thus providing a physiologically meaningful cell-based readout. A derivative of EBNA1, which is functionally equivalent to full-length EBNA1 and lacks the GGA repeats (90-325), was cloned into p3×FLAG-Myc-CMV™-24 (Sigma-Aldrich Co., LLC) (N803). To make the assay more sensitive by reducing the expression levels of EBNA1, the CMV promoter was excised and the TK promoter inserted upstream of EBNA1. To enhance the EBNA1-driven luciferase signal, the activation domain of herpes virus VP16 (411-490) was fused to the C-terminus of EBNA1 using SacII and BamHI restriction sites, resulting in the plasmid pTK-3×FLAG-Myc-EBNA1-VP16AD. Empty vector p3×FLAG-Myc-CMV-24 was used as a control. To create luciferase reporter plasmid, the FR region, a locus of 21 contiguous EBNA1 binding sites (7421-8042), was PCR amplified from EBV genomic DNA and cloned into the pGLuc-Basic 2 (New England Biolabs) using the KpnI and HindIII restriction sites, resulting in plasmid pGLuc2-21× FR.

For the transient transfection assay. HEK293T cells were seeded at a concentration of 4-8×10$^6$ cells in a 10 cm plate in Delbecco's Modified Eagle Medium (DMEM) (Life Technologies Corp.) supplemented with 10% Fetal Bovine Serum (FBS) (Gemini Bio-Products). After overnight incubation, the transfection was performed using Lipofectamine 2000 (Life Technologies). 3 µg of pGLuc2-21×FR and 0.6 µg of pTK-3×FLAG-Myc-EBNA1-VP16AD or p3×FLAG-Myc-CMV-24 (empty vector) were added to 0.5 ml Optimem buffer (Life Technologies Corp.). 30 µl Lipofectamine was added to a separate 0.5 ml Optimem buffer and incubated for 5 minutes. The DNA and lipofectamine mixtures were combined and incubated for 20 minutes at room temperature and added drop wise to the 10 cm plate. The cells were then incubated for 6 hours at 37° C. The cells were harvested, counted and re-suspended at a concentration of 2×10$^5$ cells/ml and distributed using a MicroFlo dispenser (BioTek) in 384-well tissue culture plate (Greiner BioOne), 40 µl (8000 cells) per well. 160 nl of solutions of compounds of the disclosure in DMSO at concentrations ranging from 50 mM to 976 µM were added to the cells (10-point 2-fold dilution series, final concentration 200 uM-390 nM) using a Janus modular Nanohead dispenser (PerkinElmer, Inc.). Compounds and transfected cells were incubated overnight at 37° C. Gaussia luciferase is secreted into the medium. The top 10 µl of cell media from the 384-well tranfected HEK293T cells is transferred to a white opaque 384-well development plate. 10 µl of substrate is added to each well and incubated for 5 minutes. Bioluminescence is then measured using the Envision Multiplate Reader (Perkin Elmer, Inc.). To normalize the activity of the compounds of the disclosure and to filter toxic compound, the remaining 30 µl of cell media (including the cells) are incubated with 6 µl resazurin, incubated for 4-6 hours at 37° C., and measured using the Envision Multiplate Reader. Data analysis and IC$_{50}$ curves are generated using Prism (GraphPad).

Example 208

Cell Viability Assay

To further evaluate the cell-based efficacy of EBNA1 inhibitors, a cell cytotoxicity assay was performed. EBNA1 inhibitors selectively kill EBV-positive cell lines (Raji, LCL, C666-1) relative to EBV-negative cell lines (Bjab, DG75, HNE-1). Raji, Bjab, and DG75 were obtained from American Type Tissue Culture (ATCC), C666-1 and HNE-1 were a gift from Anne Lee (Hong Kong University) and the Lymphoblastic Cell Line (LCL) was obtained by in vitro infection of B-cells with the B95.8 strain of EBV.

To perform this assay, 40 µl of the different cell lines were seeded at a concentration of 1×10$^5$ cells in a clear 384-well plate (4000 cell/well). 160 nl of compound at concentrations ranging from 50 mM to 976 µM were added to each well (10-point, 2-fold dilution series, final concentration 200 uM-390 nM) using a Janus modular Nanohead dispenser (PerkinElmer, Inc.). Cells were incubated for 72 hours in a humidified 37° C. incubator 5% CO$_2$. The cell viability is inferred using the oxidation-reduction indicator, resazurin. 8 ul of resazurin was added to each well and after 4-6 hours incubation at 37° C., the fluorescent signal was monitored using 530-560 nm excitation wavelength and 590 nm emission wavelength using the Envision Multiplate Reader.

Data analysis and CC$_{50}$ (Cytotoxicity Concentration) curves are generated using Prism (GraphPad). A selectivity index is calculated by determining the ratio of the CC$_{50}$ from the EBV-negative cell line over the CC$_{50}$ from the EBV-positive cell line.

TABLE 2

Inhibition of 5'-biotin-oPL4624 binding to His-EBNA1 of representative compounds of the disclosure using Alpha Screen technology:

| Entry | Compound | Alpha Screen Activity |
|---|---|---|
| 1 | 2-(1H-indol-6-yl)-3-[1-(2-morpholin-4-yl-ethyl)-1H-indol-6-ylethynyl]-benzoic acid | ++ |
| 2 | 3-[3-Acetylamino-4-(tetrahydro-pyran-4-yloxy)-phenylethynyl]-2-(1H-indol-6-yl)-benzoic acid | ++ |
| 3 | 3-[4-(8-Acetyl-8-aza-bicyclo[3.2.1]oct-3-yl)-phenylethynyl]-2-(1H-indol-6-yl)-benzoic acid | ++ |
| 4 | 3-[1-(2-Dimethylamino-ethyl)-1H-pyrrolo(2,3-b]pyridin-5-ylethynyl]-2-(1H-indol-6-yl)-benzoic acid | +++ |
| 5 | 3-[1-(3-Dimethylamino-propyl)-1H-pyrrolo(2,3-b]pyridin-5-ylethynyl]-2-(1H-indol-6-yl)-benzoic acid | ++ |
| 6 | 2-(1H-indol-6-yl)-3-[1-(3-morpholin-4-yl-propyl)-1H-pyrrolo[2,3-b]pyridin-5-ylethynyl]-benzoic acid | +++ |
| 7 | 2-(1H-indol-6-yl)-3-[1-(3-morpholin-4-yl-propyl)-1H-pyrrolo[2,3-b]pyridin-3-ylethynyl]-benzoic acid | ++ |
| 8 | 2-(1H-indol-6-yl)-3-[1-(2-morpholin-4-yl-ethyl)-1H-pyrrolo[2,3-b]pyridin-5-ylethynyl]-benzoic acid | +++ |
| 9 | 3-{2-[3-(3,3-dimethyl-2-oxoazetidin-1-yl)phenyl]ethynyl}-2-(1H-pyrrol-1-yl)benzoic acid3-[1-(2-Dimethylamino-ethyl)-1H-pyrrolo[2,3-b]pyridin-3-ylethynyl]-2-(1H-indol-6-yl)-benzoic acid | + |
| 10 | 2-(1H-indol-6-yl)-3-[1-(2-morpholin-4-yl-ethyl)-1H-pyrrolo[2,3-b]pyridin-3-ylethynyl]-benzoic acid | ++ |
| 11 | 3-[1-(3-Dimethylamino-propyl)-1H-pyrrolo[2,3-b]pyridin-3-ylethynyl]-2-(1H-indol-6-yl)-benzoic acid | + |
| 12 | 3-{1-[2-(1,1-Dioxo-1$\lambda^6$-thiomorpholin-4-yl)-ethyl]-1H-pyrrolo[2,3-b]pyridin-5-ylethynyl}-2-(1H-indol-6-yl)-benzoic acid | ++ |
| 13 | 2-(1H-indol-6-yl)-3-[1-(2-morpholin-4-yl-ethyl)-1H-indol-5-ylethynyl]-benzoic acid | ++ |
| 14 | 2-(1H-indol-6-yl)-3-[1-(3-morpholin-4-yl-propyl)-1H-indol-5-ylethynyl]-benzoic acid | ++ |
| 15 | 2-(1H-indol-6-yl)-3-[1-(3-morpholin-4-yl-propyl)-1H-indol-6-ylethynyl]-benzoic acid | ++ |
| 16 | 2-(1H-Indol-6-yl)-3-(5,6,7,8-tetrahydro-[1,8]naphthyridin-3-ylethynyl)-benzoic acid | +++ |
| 17 | 2-(1H-indol-6-yl)-3-[1-(tetrahydro-pyran-4-ylmethyl)-1H-pyrrolo[2,3-b]pyridin-5-ylethynyl]-benzoic acid | +++ |
| 18 | 2-(1H-Indol-6-yl)-3-[1-(tetrahydro-pyran-4-ylmethyl)-1H-indol-5-ylethynyl]-benzoic acid | +++ |
| 19 | 2-(1H-Indol-6-yl)-3-[1-(1-methanesulfonyl-piperidin-4-ylmethyl)-1H-indol-5-ylethynyl]-benzoic acid | +++ |
| 20 | 2-(1H-Indol-6-yl)-3-[1-(1-methanesulfonyl-piperidin-4-ylmethyl)-1H-pyrrolo [2,3-b]pyridin-5-ylethynyl]-benzoic acid | +++ |
| 21 | 3-[1-(1,1-Dioxo-hexahydro-1$\lambda^6$-thiopyran-4-ylmethyl)-1H-pyrrolo [2,3-b]pyridin-5-ylethynyl]-2-(1H-indol-6-yl)-benzoic acid | +++ |
| 22 | 3-{1-[2-(1,1-Dioxo-1$\lambda^6$-thiomorpholin-4-yl)-ethyl]-1H-indol-5-yl-ethynyl}-2-(1H-indol-6-yl)-benzoic acid | +++ |
| 23 | 3-{1-[2-(1,1-Dioxo-1$\lambda^6$-thiomorpholin-4-yl)-ethyl]-1H-indol-6-ylethynyl}-2-(1H-indol-6-yl)-benzoic acid | ++ |
| 24 | 3-{1-[3-(1,1-Dioxo-1$\lambda^6$-thiomorpholin-4-yl)-propyl]-1H-indol-5-yl-ethynyl}-2-(1H-indol-6-yl)-benzoic acid | ++ |
| 25 | 3-{1-[3-(1,1-Dioxo-1$\lambda^6$-thiomorpholin-4-yl)-propyl]-1H-indol-6-yl-ethynyl}-2-(1H-indol-6-yl)-benzoic acid | +++ |

TABLE 2-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 26 | 3-[4-(1,1-Dioxo-hexahydro-1λ$^6$-thiopyran-4-yloxymethyl)-phenyethynyl]-2-(1H-indol-6-yl)-benzoic acid | ++ |
| 27 | 2-(1H-Indol-6-yl)-3-[4-(tetrahydro-pyran-4-yloxymethyl)-phenylethynyl]-benzoic acid | ++ |
| 28 | 2-(1H-Indol-6-yl)-3-(4-isopropoxymethyl-phenylethynyl)-benzoic acid | +++ |
| 29 | 2-(1H-Indol-6-yl)-3-[4-(1-oxo-hexahydro-1λ$^4$-thiopyran-4-yloxy)-phenylethynyl]-benzoic acid | ++ |
| 30 | 2-(1H-indol-6-yl)-3-(3-morpholin-4-ylmethyl-1H-indol-6-ylethynyl)-benzoic acid | ++ |
| 31 | 2-(1H-indol-6-yl)-3-[3-(4-methanesulfonyl-piperazin-1-ylmethyl)-1H-indol-6-ylethynyl]-benzoic acid | +++ |
| 32 | 3-[3-(1,1-Dioxo-1λ$^6$-thiomorpholin-4-ylmethyl)-1H-indol-6-ylethynyl]-2-(1H-indol-6-yl)-benzoic acid | +++ |
| 33 | 2-(1H-indol-6-yl)-3-(2-morpholin-4-ylmethyl-1H-indol-6-ylethynyl)-benzoic acid | ++ |
| 34 | 3-[2-(1,1-Dioxo-1λ$^6$-thiomorpholin-4-ylmethyl)-1H-indol-6-ylethynyl]-2-(1H-indol-6-yl)-benzoic acid | +++ |
| 35 | 3-[1-(4-ethoxy-2-methyl-butyl)-6-fluoro-1H-indol-5-ylethynyl]-2-(1H-indol-6-yl)-benzoic acid | +++ |
| 36 | 3-[7-fluoro-1-(tetrahydro-pyran-4-ylmethyl)-1H-indol-6-ylethynyl]-2-(1H-indol-6-yl)-benzoic acid | +++ |
| 37 | 3-[1-(1,1-dioxo-hexahydro-1λ$^6$-thiopyran-4-ylmethyl)-7-fluoro-1H-indol-6-ylethynyl]-2-(1H-indol-1)-benzoic acid | +++ |
| 38 | 3-[1-(1,1-dioxo-hexahydro-1λ$^6$-thiopyran-4-ylmethyl)-6-fluoro-1H-indol-5-ylethynyl]-2-(1H-indol-6-yl)-benzoic acid | +++ |
| 39 | 3-(7-fluoro-3-morpholin-4-ylmethyl-1H-indol-6-ylethynyl)-2-(1H-indol-6-yl)-benzoic acid | +++ |
| 40 | 3-(6-fluoro-3-morpholin-4-ylmethyl-1H-indol-5-ylethynyl)-2-(1H-indol-6-yl)-benzoic acid | ++ |
| 41 | 3-((4-(2H-tetrazol-5-yl)phenyl)ethynyl)-2-(1H-indol-6-yl)benzoic acid | ++++ |
| 42 | 3-((3-(2H-tetrazol-5-yl)phenyl)ethynyl)-2-(1H-indol-6-yl)benzoic acid | ++++ |
| 43 | 2-(1H-indol-6-yl)-3-((4-(oxazol-5-yl)phenyl)ethynyl)benzoic acid | +++ |
| 44 | 2-(1H-indol-6-yl)-3-((4-(6-oxo-1,6-dihydropyridazin-3-yl)phenyl)ethynyl)benzoic acid | +++ |
| 45 | 2-(1H-indol-6-yl)-3-((3-methoxy-4-(morpholinomethyl)phenyl)ethynyl)benzoic acid | ++ |
| 46 | 3-((3-hydroxy-4-(morpholine-4-carbonyl)phenyl)ethynyl)-2-(1H-indol-6-yl)benzoic acid | ++ |
| 47 | 2-(1H-Indol-6-yl)-3-{3-methoxy-4-(4-morpholin-4-yl-piperidin-1-ylmethyl)-phenylethynyl]-benzoic acid | + |
| 48 | 3-((4-((4,4-difluoropiperidin-1-yl)methyl)-3-methoxyphenyl)ethynyl)-2-(1H-indol-6-yl)benzoic acid | +++ |
| 49 | 3-((4-((4-(dimethylcarbamoyl)piperidin-1-yl)methyl)-3-methoxyphenyl)ethynyl)-2-(1H-indol-6-yl)benzoic acid | |
| 50 | 3-((3-hydroxy-4-(4-morpholinopiperidine-1-carbonyl)phenyl)ethynyl)-2-(1H-indol-6-yl)benzoic acid | +++ |
| 51 | 3-((4-(4,4-difluoropiperidine-1-carbonyl)-3-hydroxyphenyl)ethynyl)-2-(1H-indol-6-yl)benzoic acid | +++ |
| 52 | 2-(1H-indol-6-yl)-3-((4-((1-(methylsulfonyl)piperidin-4-yl)methyl)phenyl)ethynyl) benzoic acid | +++ |
| 53 | 2-(1H-indol-6-yl)-3-((4-((1-((trifluoromethyl)sulfonyl)piperidin-4-yl)methyl)phenyl)ethynyl)benzoic acid | +++ |
| 54 | 2-(1H-indol-6-yl)-3-((4-((1-(isopropylsulfonyl)piperidin-4-yl)methyl)phenyl)ethynyl) benzoic acid | +++ |
| 55 | 3-((4-((1-acetylpiperidin-4-yl)methyl)phenyl)ethynyl)-2-(1H-indol-6-yl)benzoic acid | +++ |
| 56 | 3-((2-acetylisoindolin-5-yl)ethynyl)-2-(1H-indol-6-yl)benzoic acid | +++ |
| 57 | 2-(1H-indol-6-yl)-3-((2-(isopropylsulfonyl)isoindolin-5-yl)ethynyl)benzoic acid | +++ |
| 58 | 2-(1H-indol-6-yl)-3-((2-(1-(methylsulfonyl)pyrrolidin-3-yl)-1,2,3,4-tetrahydroisoquinolin-7-yl)ethynyl)benzoic acid | ++ |
| 59 | 2-(1H-indol-6-yl)-3-((2-((1-(methylsulfonyl)piperidin-4-yl)methyl)-1,2,3,4-tetrahydroisoquinolin-6-yl)ethynyl)benzoic acid | ++ |
| 60 | 2-(1H-indol-6-yl)-3-((2-(1-(methylsulfonyl)azetidin-3-yl)-1,2,3,4-tetrahydroisoquinolin-6-yl) ethynyl)benzoic acid | ++ |
| 61 | 2-(1H-indol-6-yl)-3-((2-((1-(methylsulfonyl)pyrrolidin-3-yl)methyl)-1,2,3,4-tetrahydroisoquinolin-6-yl)ethynyl)benzoic acid | ++ |
| 62 | 2-(1H-indol-6-yl)-3-((2-((1-(methylsulfonyl)pyrrolidin-3-yl)methyl)-1,2,3,4-tetrahydroisoquinolin-7-yl)ethynyl)benzoic acid | ++ |
| 63 | 3-((2-((1-acetylpyrrolidin-3-yl)methyl)-1,2,3,4-tetrahydroisoquinolin-7-yl)ethynyl)-2-(1H-indol-6-yl)benzoic acid | ++ |
| 64 | 2-(1H-indol-6-yl)-3-((2-((1-(methylsulfonyl)azetidin-3-yl)methyl)-1,2,3,4-tetrahydroisoquinolin-6-yl)ethynyl)benzoic acid | ++ |

TABLE 2-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 65 | 2-(1H-indol-6-yl)-3-((2-((1-(methylsulfonyl)azetidin-3-yl)methyl)-1,2,3,4-tetrahydroisoquinolin-7-yl)ethynyl)benzoic acid | ++ |
| 66 | 2-(1H-indol-6-yl)-3-((2-(3-(methylsulfonamido)benzyl)-1,2,3,4-tetrahydroisoquinolin-6-yl)ethynyl)benzoic acid | +++ |
| 67 | 2-(1H-indol-6-yl)-3-((2-(3-(methylsulfonamido)benzyl)-1,2,3,4-tetrahydroisoquinolin-7-yl)ethynyl)benzoic acid | +++ |
| 68 | 2-(1H-indol-6-yl)-3-((2-(1-(methylsulfonyl)pyrrolidin-3-yl)isoindolin-5-yl)ethynyl)benzoic acid | +++ |
| 69 | 2-(1H-indol-6-yl)-3-((2-(1-(methylsulfonyl)azetidin-3-yl)isoindolin-5-yl)ethynyl)benzoic acid | +++ |
| 70 | 2-(1H-indol-6-yl)-3-((2-((1-(methylsulfonyl)pyrrolidin-3-yl)methyl)isoindolin-5-yl)ethynyl)benzoic acid | +++ |
| 71 | 2-(1H-indol-6-yl)-3-((2-((1-(methylsulfonyl)azetidin-3-yl)methyl)isoindolin-5-yl)ethynyl)benzoic acid | ++ |
| 72 | 2-(1H-indol-6-yl)-3-((2-((1-(methylsulfonyl)piperidin-4-yl)methyl)isoindolin-5-yl)ethynyl)benzoic acid | ++ |
| 73 | 2-(1H-indol-6-yl)-3-((2-(methylsulfonyl)-1,2,3,4-tetrahydroisoquinolin-7-yl)ethynyl)benzoic acid | +++ |
| 74 | 2-(1H-indol-6-yl)-3-((2-(isopropylsulfonyl)-1,2,3,4-tetrahydroisoquinolin-7-yl)ethynyl)benzoic acid | +++ |
| 75 | 2-(1H-indol-6-yl)-3-((2-propionyl-1,2,3,4-tetrahydroisoquinolin-7-yl)ethynyl) benzoic acid | ++ |
| 76 | 2-(1H-indol-6-yl)-3-((2-(methylsulfonyl)-1,2,3,4-tetrahydroisoquinolin-6-yl)ethynyl)benzoic acid | +++ |
| 77 | 2-(1H-indol-6-yl)-3-((2-(isopropylsulfonyl)-1,2,3,4-tetrahydroisoquinolin-6-yl)ethynyl)benzoic acid | +++ |
| 78 | 3-((2-acetyl-1,2,3,4-tetrahydroisoquinolin-6-yl)ethynyl)-2-(1H-indol-6-yl)benzoic acid | +++ |
| 79 | 2-(1H-indol-6-yl)-3-((2-propionyl-1,2,3,4-tetrahydroisoquinolin-6-yl)ethynyl)benzoic acid | +++ |
| 80 | 3-[4-(4-cyano-phenoxymethyl)-phenylethynyl]-2-(1H-indol-6-yl)-benzoic acid | +++ |
| 81 | 3-[4-(3-cyano-phenoxymethyl)-phenylethynyl]-2-(1H-indol-6-yl)-benzoic acid | +++ |
| 82 | 3-[4-(3-carbamoyl-phenoxymethyl)-phenylethynyl]-2-(1H-indol-6-yl)-benzoic acid | +++ |
| 83 | 2-(1H-indol-6-yl)-3-[4-(4-trifluoromethyl-phenoxymethyl)-phenylethynyl]-benzoic acid | +++ |
| 84 | 2-(1H-indol-6-yl)-3-[4-(3-trifluoromethyl-phenoxymethyl)-phenylethynyl]-benzoic acid | +++ |
| 85 | 2-(1H-indol-6-yl)-3-[4-(4-methoxy-phenoxylmethyl)-phenylethynyl]-benzoic acid | +++ |
| 86 | 3-[4-(4-carbamoyl-phenoxymethyl)-phenylethynyl]-2-(1H-indol-6-yl)-benzoic acid | +++ |
| 87 | 2-(1H-indol-6-yl)-3-[4-(3-methoxy-phenoxymethyl)-phenylethynyl]-benzoic acid | +++ |
| 88 | 2-(1H-indol-6-yl)-3-(4-phenoxymethyl-phenylethynyl)-benzoic acid | +++ |
| 89 | 3-[4-(2-fluoro-phenoxymethyl)-phenylethynyl]-2-(1H-indol-6-yl)-benzoic acid | +++ |
| 90 | 2-(1H-indol-6-yl)-3-[4-(pyridin-3-yloxymethyl)-phenylethynyl]-benzoic acid | +++ |
| 91 | 3-[4-(3-chloro-phenoxymethyl)-phenylethynyl]-2-(1H-indol-6-yl)-benzoic acid | +++ |
| 92 | 3-[4-(3,4-dichloro-phenoxymethyl)-phenylethynyl]-2-(1H-indol-6-yl)-benzoic acid | +++ |
| 93 | 2-(1H-indol-6-yl)-3-[4-(2-trifluoromethyl-phenoxymethyl)-phenylethynyl]-benzoic acid | +++ |
| 94 | 3-[4-(2-cyano-phenoxymethyl)-phenylethynyl]-2-(1H-indol-6-yl)-benzoic acid | +++ |
| 95 | 2-(1H-indol-6-yl)-3-[4-(4-methanesulfonyl-phenoxymethyl)-phenylethynyl]-benzoic acid | +++ |
| 96 | 2-(1H-indol-6-yl)-3-[4-(pyrimidin-5-yloxymethyl)-phenylethynyl]-benzoic acid | +++ |
| 97 | 2-(1H-indol-6-yl)-3-[4-(2-methanesulfonyl-phenoxymethyl)-phenylethynyl]-benzoic acid | +++ |
| 98 | 2-(1H-indol-6-yl)-3-[4-(3-methanesulfonyl-phenoxymethyl)-phenylethynyl]-benzoic acid | +++ |
| 99 | 2-(1H-Indol-6-yl)-3-{2-[3-(3-methanesulfonamidophenyl)phenyl]ethynyl}benzoic acid | +++ |
| 100 | 2-(1H-Indol-6-yl)-3-{2-[6-(oxan-4-yloxy)pyridin-3-yl]ethynyl}benzoic acid | +++ |
| 101 | 2-(1H-Indol-6-yl)-3-{2-[2-(propylcarbamoyl)-1H-indol-6-yl]ethynyl}benzoic acid | +++ |

TABLE 2-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 102 | 2-(1H-Indol-6-yl)-3-{2-[3-(1,2,3,4-tetrahydroisoquinolin-2-ylmethyl)phenyl]ethynyl}benzoic acid | +++ |
| 103 | 3-{2-[3-Cyano-4-(oxan-4-yloxy)phenyl]ethynyl}-2-(1H-indol-6-yl)benzoic acid | +++ |
| 104 | 3-[2-(3-{[4-(Ethoxycarbonyl)piperazin-1-yl]methyl}phenyl)ethynyl]-2-(1H-indol-6-yl)benzoic acid | ++ |
| 105 | 3-(2-{4-[3-(Hydroxymethyl)oxetan-3-yl]phenyl}ethynyl)-2-(1H-indol-6-yl)benzoic acid | +++ |
| 106 | 3-{2-[3-(5-Amino-1H-pyrazol-3-yl)phenyl]ethynyl}-2-(1H-indol-6-yl)benzoic acid | +++ |
| 107 | 2-(1H-Indol-6-yl)-3-{2-[3-(1,3-oxazol-5-yl)phenyl]ethynyl}benzoic acid | +++ |
| 108 | 2-(1H-Indol-6-yl)-3-{2-[4-(oxane-4-carbonyl)phenyl]ethynyl} benzoic acid | +++ |
| 109 | 2-(7-Fluoro-1H-indol-6-yl)-3-phenylethynyl-benzoic acid | ++ |
| 110 | 2-Benzothiazol-6-yl-3-phenylethynyl-benzoic acid | ++ |
| 111 | 2-Benzothiazol-5-yl-3-phenylethynyl-benzoic acid | ++ |
| 112 | 2-(2-Methyl-benzothiazol-5-yl)-3-phenylethynyl-benzoic acid | ++ |
| 113 | 2-(5-Fluoro-1H-indol-6-yl)-3-phenylethynyl-benzoic acid | +++ |
| 114 | 2-(6-Fluoro-1H-indol-5-yl)-3-phenylethynyl-benzoic acid | ++ |
| 115 | 2-[1,8]Naphthyridin-3-yl-3-phenylethynyl-benzoic acid | + |
| 116 | 2-(1-Methyl-1H-pyrrolo [2,3-b]pyridin-6-yl)-3-phenylethynyl-benzoic acid | ++ |
| 117 | 2-[1,8]Naphthyridin-2-yl-3-phenylethynyl-benzoic acid | ++ |
| 118 | 3-Phenylethynyl-2-(1H-pyrrolo [2,3-b]pyridin-6-yl)-benzoic acid | + |
| 119 | 2-(4-methoxy-1H-indol-6-yl)-3-(2-phenylethynyl)-benzoic acid | +++ |
| 120 | 3-(2-(4-(2-hydroxypropan-2-yl)phenyl)ethynyl)-2-(1H-indol-6-yl)-benzoic acid | +++ |
| 121 | 3-(2-(4-(2-aminothiazol-4-yl)phenyl)ethynyl)-2-(1H-indol-6-yl)-benzoic acid | +++ |
| 122 | 2-(1H-Indol-6-yl)-3-(3-sulfamoyl-phenylethynyl)-benzoic acid | ++ |
| 123 | 3-(4-Amino-3-sulfamoyl-phenylethynyl)-2-(1H-indol-6-yl)-benzoic acid | ++ |
| 124 | 2-(1H-indol-6-yl)-3-(Spiro[2H-1-benzopyran-2,1'-4-piperidine-1-t-butylcarboxylate]-4(3H)-one)ethynyl)benzoic acid | +++ |
| 125 | 3-(2-(3-(2-aminothiazol-4-yl)phenyl)ethynyl)-2-(1H-indol-6-yl)-benzoic acid | +++ |
| 126 | 3-(2-(4-(5-(methoxycarbonyl)-2-aminothiazol-4-yl)phenyl)ethynyl)-2-(1H-indol-6-yl)-benzoic acid | ++++ |
| 127 | 3-(2-(4-(5-amino-1,3,4-thiadiazol-2-yl)phenyl)ethynyl)-2-(1H-indol-6-yl)-benzoic acid | +++ |
| 128 | 3-(2-(4-(3-amino-1H-pyrazol-5-yl)phenyl)ethynyl)-2-(1H-indol-6-yl)-benzoic acid | +++ |
| 129 | 2-Amino-4-{4-[3-carboxy-2-(1H-indol-6-yl)-phenylethynyl]-phenyl}-thiazole-5-carboxylic acid | ++++ |
| 130 | 3-(2-(4-(2-aminooxazol-5-yl)phenyl)ethynyl)-2-(1H-indol-6-yl)-benzoic acid | +++ |
| 131 | 2-(1H-Indol-6-yl)-3-[4-(2-methanesulfonylamino-thiazol-4-yl)-phenylethynyl]-benzoic acid | ++++ |
| 132 | 2-(1H-Indol-6-yl)-3-[3-(2-methanesulfonylamino-thiazol-4-yl)-phenylethynyl]-benzoic acid | ++++ |
| 133 | 3-(2-(1,4-dihydro-2-((4-methoxypiperidin-1-yl)methyl)-4-oxoquinazolin-6-yl)ethynyl)-2-(1H-indol-6-yl)benzoic acid | ++ |
| 134 | 3-(2-(1,4-dihydro-2-((4-thiomorpholine-1,1dioxide-1-yl)methyl)-4-oxoquinazolin-6-yl)ethynyl)-2-(1H-indol-6-yl)benzoic acid | +++ |
| 135 | 3-(2-(2-(trifluoromethyl)-3,4-dihydro-4-oxoquinazolin-6-yl)ethynyl)-2-(1H-indol-6-yl)benzoic acid | +++ |
| 136 | 3-(2-(3,4-dihydro-3-(2-methoxyethyl)-4-oxopyrido[2,3-d]pyrimidin-6-yl)ethynyl)-2-(1H-indol-6-yl)benzoic acid | +++ |
| 137 | 2-(1H-Indol-6-yl)-3-[3-(2-methoxy-6-methyl-phenylcarbamoyl)-phenylethynyl]-benzoic acid | +++ |
| 138 | 3-{3-[4-(1,1-Dioxo-1-thiomorpholin-4-yl)-phenylcarbamoyl]-phenylethynyl}-2-(1H-indol-6-yl)-benzoic acid | +++ |
| 139 | 3-Phenylethynyl-2-(1H-pyrrolo[2,3-b]pyridin-5-yl)-benzoic acid | ++++ |
| 140 | 3-(4-Fluoro-phenylethynyl)-2-(1H-pyrrolo[2,3-b]pyridin-5-yl)-benzoic acid | ++ |
| 141 | 3-(4-Methoxy-phenylethynyl)-2-(1H-pyrrolo[2,3-b]pyridin-5-yl)-benzoic acid | ++ |
| 142 | 2-(1H-Pyrrolo[2,3-b]pyridin-5-yl)-3-[4-(tetrahydro-pyran-4-yloxy)-phenylethynyl]-benzoic acid | ++ |
| 143 | 2-(1H-Indol-6-yl)-3-{4-[2-(tetrahydro-pyran-4-yl)-ethoxy]-phenylethynyl}-benzoic acid | +++ |
| 144 | 3-[4-(1,1-Dioxo-hexahydro-1-thiopyran-4-yloxy)-phenylethynyl]-2-(1H-indol-6-yl)-benzoic acid | ++ |
| 145 | 2-(1H-Indol-6-yl)-3-(4-morpholin-4-ylmethyl-phenylethynyl)-benzoic acid | +++ |
| 146 | 3-[4-(4-Ethyl-piperazin-1-ylmethyl)-phenylethynyl]-2-(1H-indol-6-yl)-benzoic acid | ++ |

TABLE 2-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 147 | 2-(1H-Indol-6-yl)-3-[4-(4-methyl-piperazin-1-yimethyl)-phenylethynyl]-benzoic acid | ++ |
| 148 | 3-[4-(1,1-Dioxo-thiomorpholin-4-ylmethyl)-phenylethynyl]-2-(1H-indol-6-yl)-benzoic acid | +++ |
| 149 | 3-(4-{[(2-Dimethylamino-ethyl)-methyl-amino]-methyl}-phenylethynyl)-2-(1H-indol-6-yl)-benzoic acid | ++ |
| 150 | 3-{4-[4-(2-Hydroxy-ethyl)-piperidin-1-ylmethyl]-phenylethynyl}-2-(1H-indol-6-yl)-benzoic acid | +++ |
| 151 | 3-[4-(4-Hydroxymethyl-piperidin-1-ylmethyl)-phenylethynyl]-2-(1H-indol-6-yl)-benzoic acid | ++ |
| 152 | 2-(1H-Indol-6-yl)-3-[4-(4-methyl-[1,4]diazepan-1-ylmethyl)-phenylethynyl]-benzoic acid | +++ |
| 153 | 3-[4-(3-Hydroxy-azetidin-1-ylmethyl)-phenylethynyl]-2-(1H-indol-6-yl)-benzoic acid | ++ |
| 154 | 3-[4-(4-Hydroxy-piperidin-1-ylmethyl)-phenylethynyl]-2-(1H-indol-6-yl)-benzoic acid | ++ |
| 155 | 2-(1H-Indol-6-yl)-3-[4-(4-methoxy-piperidin-1-ylmethyl)-phenylethynyl]-benzoic acid | ++ |
| 156 | 3-(4-Dimethylaminomethyl-phenylethynyl)-2-(1H-indol-6-yl)-benzoic acid | ++ |
| 157 | 2-(1H-Indol-6-yl)-3-(4-{[(2-methoxy-ethyl)-methyl-amino]-methyl}-phenylethynyl)-benzoic acid | ++ |
| 158 | 3-[4-(4,4-Difluoro-piperidin-1-ylmethyl)-phenylethynyl]-2-(1H-indol-6-yl)-benzoic acid | +++ |
| 159 | 3-[4-(3,3-Difluoro-piperidin-1-ylmethyl)-phenylethynyl]-2-(1H-indol-6-yl)-benzoic acid | +++ |
| 160 | 3-[4-(3,4-Dihydro-1H-isoquinolin-2-ylmethyl)-phenylethynyl]-2-(1H-indol-6-yl)-benzoic acid | +++ |
| 161 | 2-(1H-Indol-6-yl)-3-[4-(4-methanesulfonyl-piperazin-1-ylmethyl)-phenylethynyl]-benzoic acid | ++ |
| 162 | 2-(1H-Indol-6-yl)-3-[4-(3-trifluoromethyl-piperidin-1-ylmethyl)-phenylethynyl]-benzoic acid | +++ |
| 163 | 2-(1H-Indol-6-yl)-3-[4-(3-methoxy-pyrrolidin-1-ylmethyl)-phenylethynyl]-benzoic acid | ++ |
| 164 | 2-(1H-Indol-6-yl)-3-[4-(4-isopropyl-piperazin-1-ylmethyl)-phenylethynyl]-benzoic acid | ++ |
| 165 | 3-[4-(4-Cyclohexyl-piperazin-1-ylmethyl)-phenylethynyl]-2-(1H-indol-6-yl)-benzoic acid | ++ |
| 166 | 3-[4-(4-Cyclopropanecarbonyl-piperazin-1-ylmethyl)-phenylethynyl]-2-(1H-indol-6-yl)-benzoic acid | +++ |
| 167 | 2-(1H-Indol-6-yl)-3-(4-piperazin-1-ylmethyl-phenylethynyl)-benzoic acid | ++ |
| 168 | 3-[4-(4-Benzenesulfonyl-piperazin-1-ylmethyl)-phenylethynyl]-2-(1H-indol-6-yl)-benzoic acid | +++ |
| 169 | 3-{4-[(1,1-Dioxo-hexahydro-1-thiopyran-4-ylamino)-methyl]-phenylethynyl}-2-(1H-indol-6-yl)-benzoic acid | ++ |
| 170 | 3-[4-(4-Cyclopentyl-piperazin-1-ylmethyl)-phenylethynyl]-2-(1H-indol-6-yl)-benzoic acid | ++ |
| 171 | 3-[4-(4-Dimethylcarbamoyl-piperazin-1-ylmethyl)-phenylethynyl]-2-(1H-indol-6-yl)-benzoic acid | ++ |
| 172 | 2-(1H-Indol-6-yl)-3-[4-(2,3,5,6-tetrahydro-[1,2']bipyrazinyl-4-ylmethyl)-phenylethynyl]-benzoic acid | +++ |
| 173 | 2-(1H-Indol-6-yl)-3-[4-(4-thiazol-2-yl-piperazin-1-ylmethyl)-phenylethynyl]-benzoic acid | +++ |
| 174 | 3-{4-[(2-Amino-4,5,6,7-tetrahydro-benzothiazol-6-ylamino)-methyl]-phenylethynyl}-2-(1H-indol-6-yl)-benzoic acid | +++ |
| 175 | 3-{4-[(2-Amino-4,5,6,7-tetrahydro-benzothiazol-6-ylamino)-methyl]-phenylethynyl}-2-(1H-indol-6-yl)-benzoic acid | +++ |
| 176 | 3-[4-(4-Methyl-piperazin-1-ylmethyl)-phenylethynyl]-2-(1H-pyrrolo[2,3-b]pyridin-5-yl)-benzoic acid | ++ |
| 177 | 3-[4-(4-Methoxy-piperidin-1-ylmethyl)-phenylethynyl]-2-(1H-pyrrolo[2,3-b]pyridin-5-yl)-benzoic acid | + |
| 178 | 2-(1H-Indol-5-yl)-3-[4-(4-methoxy-piperidin-1-ylmethyl)-phenylethynyl]-benzoic acid | ++ |
| 179 | 2-(1H-Indol-5-yl)-3-[4-(4-methanesulfonyl-piperazin-1-ylmethyl)-phenylethynyl]-benzoic acid | ++ |
| 180 | 3-[4-(4-Methanesulfonyl-piperazin-1-ylmethyl)-phenylethynyl]-2-(1H-pyrrolo[2,3-b]pyridin-5-yl)-benzoic acid | +++ |
| 181 | 3-[4-(4,4-Difluoro-piperidin-1-ylmethyl)-phenylethynyl]-2-(1H-indol-5-yl)-benzoic acid | +++ |
| 182 | 2-(1H-Indol-5-yl)-3-[4-(4-methyl-piperazin-1-ylmethyl)-phenylethynyl]-benzoic acid | +++ |
| 183 | 3-[4-(4-Ethanesulfonyl-piperazin-1-ylmethyl)-phenylethyhyl]-2-(1H-indol-6-yl)-benzoic acid | ++ |

TABLE 2-continued

Inhibition of 5'-biotin-oPL4624 binding to His-EBNA1 of representative compounds of the disclosure using Alpha Screen technology:

| Entry | Compound | Alpha Screen Activity |
|---|---|---|
| 184 | 3-[4-(1,1-Dioxo-hexahydro-1-thiopyran-4-yloxy)-phenylethynyl]-2-(1H-indol-5-yl)-benzoic acid | +++ |
| 185 | 3-[4-(1,1-Dioxo-hexahydro-thiopyran-4-yloxy)-phenylethynyl]-2-(1H-indazol-6-yl)-benzoic acid | ++ |
| 186 | 3-[2-Fluoro-4-(tetrahydro-pyran-4-yloxymethyl)-phenylethynyl]-2-(1H-indol-6-yl)-benzoic acid | +++ |
| 187 | 3-[4-(1,1-Dioxo-hexahydro-1-thiopyran-4-yloxymethyl)-2-fluoro-phenylethynyl]-2-(1H-indol-6-yl)-benzoic acid | ++ |
| 188 | 2-(1H-Indol-6-yl)-3-[4-(2-methanesulfonyl-2,7-diaza-spiro[3.5]non-7-ylmethyl)phenylethynyl]-benzoic acid | ++ |
| 189 | 2-(1H-Indol-6-yl)-3-[4-(5-methanesulfonyl-hexahydro-pyrrolo[3,4-c]pyrrol-2-ylmethyl)-phenylethynyl]-benzoic acid | ++ |
| 190 | 3-[4-(4-Cyclopropanesulfonyl-piperazin-1-ylmethyl)-phenylethynyl]-2-(1H-indol-6-yl)-benzoic acid | ++ |
| 191 | 2-(1H-Indol-6-yl)-3-{4-[4-(propane-2-sulfonyl)-piperazin-1-ylmethyl]-phenylethynyl}-benzoic acid | +++ |
| 192 | 2-(1H-Indol-6-yl)-3-[4-(7-methanesulfonyl-2,7-diaza-spiro[3.5]non-2-ylmethyl)-phenylethynyl]-benzoic acid | ++ |
| 193 | 2-(1H-Indol-5-yl)-3-[4-(tetrahydro-pyran-4-yloxy)-phenylethynyl]-benzoic acid | +++ |
| 194 | N-(N,N-dimethylsulfamoyl)-2-(1H-indol-6-yl)-3-((4-(((tetrahydro-2H-pyran-4-yl)oxy)methyl)phenyl)ethynyl)benzamide | +++ |
| 195 | 2-(1H-indol-6-yl)-N-(methylsulfonyl)-3-((4-(((tetrahydro-2H-pyran-4-yl)oxy)methyl)phenyl)ethynyl)benzamide | ++ |
| 196 | 6-[2-[4-(Tetrahydro-pyran-4-yloxymethyl)-phenylethynyl]-6-(1H-tetrazol-5-yl)-phenyl]-1H-indole | +++ |
| 197 | 3-[4-(Benzoylamino-methyl)-phenylethynyl]-2-(1H-indol-6-yl)-benzoic acid | +++ |
| 198 | 2-(1H-Indol-6-yl)-3-(4-{[(4-oxo-cyclohexanecarbonyl)-amino]-methyl}-phenylethynyl)-benzoic acid | ++++ |
| 199 | 2-(1H-Indol-6-yl)-3-[4-(4-oxo-cyclohexylcarbamoyl)-phenylethynyl]-benzoic acid | ++++ |
| 200 | 3-[4-(2-Amino-4,5,6,7-tetrahydro-benzothiazol-6-ylcarbamoyl)-phenylethynyl]-2-(1H-indol-6-yl)-benzoic acid | +++ |
| 201 | 3-[4-(2-Amino-4,5,6,7-tetrahydro-benzothiazol-6-ylcarbamoyl)-phenylethynyl]-2-(1H-indol-6-yl)-benzoic acid | +++ |
| 202 | 2-(1H-Indol-6-yl)-3-[4-(4-methyl-piperazine-1-carbonyl)-phenylethynyl]-benzoic acid | ++ |
| 203 | 2-(1H-Indol-6-yl)-3-[4-(4-methoxy-piperidine-1-carbonyl)-phenylethynyl]-benzoic acid | +++ |
| 204 | 2-(1H-Indazol-6-yl)-3-[4-(4-methanesulfonyl-piperazin-1-ylmethyl)-phenylethynyl]-benzoic acid | ++ |
| 205 | 2-(1H-Indol-6-yl)-3-[4-(4-sulfamoyl-piperazin-1-ylmethyl)-phenylethynyl]-benzoic acid | +++ |

Alpha Screen Activity: $IC_{50} < 1$ uM = ++++; 1 uM $< IC_{50} <$ 10 uM = +++; 10 uM $< IC_{50} <$ 100 uM = ++; 100 uM $< IC_{50} <$ 1 mM = +.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. 2-(1H-Indol-6-yl)-3-[4-(tetrahydro-pyran-4-yloxymethyl)-phenylethynyl]-benzoic acid; or a salt thereof.

2. A pharmaceutical composition comprising 2-(1H-Indol-6-yl)-3-[4-(tetrahydro-pyran-4-yloxymethyl)-phenylethynyl]-benzoic acid, or a salt thereof, and at least one pharmaceutically acceptable carrier.

3. The pharmaceutical composition of claim 2, further comprising at least one additional antiviral or anticancer agent.

4. 2-(1H-Indol-6-yl)-3-[4-(tetrahydro-pyran-4-yloxymethyl)-phenylethynyl]-benzoic acid.

5. A pharmaceutical composition comprising 2-(1H-Indol-6-yl)-3-[4-(tetrahydro-pyran-4-yloxymethyl)-phenylethynyl]-benzoic acid and at least one pharmaceutically acceptable carrier.

* * * * *